United States Patent
Mizutani et al.

(10) Patent No.: US 9,847,501 B2
(45) Date of Patent: Dec. 19, 2017

(54) AROMATIC HETEROCYCLIC DERIVATIVE, MATERIAL FOR ORGANIC ELECTROLUMINESCENT ELEMENT, AND ORGANIC ELECTROLUMINESCENT ELEMENT

(71) Applicant: IDEMITSU KOSAN CO., LTD., Chiyoda-ku (JP)

(72) Inventors: Sayaka Mizutani, Sodegaura (JP); Takayasu Sado, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 630 days.

(21) Appl. No.: 14/358,043

(22) PCT Filed: Nov. 21, 2012

(86) PCT No.: PCT/JP2012/080190
§ 371 (c)(1),
(2) Date: May 14, 2014

(87) PCT Pub. No.: WO2013/077362
PCT Pub. Date: May 30, 2013

(65) Prior Publication Data
US 2014/0312338 A1    Oct. 23, 2014

(30) Foreign Application Priority Data

Nov. 22, 2011   (JP) .................. 2011-255473

(51) Int. Cl.
*H01L 51/50*   (2006.01)
*C07D 405/14*  (2006.01)
(Continued)

(52) U.S. Cl.
CPC ........ *H01L 51/5016* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS

| | | | |
|---|---|---|---|
| 2004/0086745 A1 | 5/2004 | Iwakuma et al. | |
| 2005/0158578 A1 | 7/2005 | Iwakuma et al. | |
| (Continued) | | | |

FOREIGN PATENT DOCUMENTS

| | | |
|---|---|---|
| CN | 102503938 A | 6/2012 |
| JP | 2003-45662 A | 2/2003 |
| (Continued) | | |

OTHER PUBLICATIONS

Office Action dated May 24, 2016 in Japanese Patent Application No. 2013-545948 (with English language translation).
(Continued)

*Primary Examiner* — Gregory Clark
(74) *Attorney, Agent, or Firm* — Oblon, McClelland, Maier & Neustadt, L.L.P.

(57) ABSTRACT

An aromatic heterocyclic derivative is represented by a formula (1) below.

(1)

(Continued)

In the formula (1), $X_1$ to $X_3$ each are a nitrogen atom or $CR_1$, with a proviso that at least one of $X_1$ to $X_3$ is a nitrogen atom. A is represented by a formula (2) and B is represented by a formula (4) below.

$$(HAr)_a\text{—}L_1\text{—} \quad (2)$$

$$(Cz)_b\text{—}L_2\text{—} \quad (4)$$

23 Claims, 14 Drawing Sheets

(51) Int. Cl.
  *C07D 409/14*  (2006.01)
  *C07D 491/048*  (2006.01)
  *C09K 11/06*  (2006.01)
  *H05B 33/14*  (2006.01)
  *C07D 471/04*  (2006.01)
  *C07D 487/06*  (2006.01)
  *C07F 7/08*  (2006.01)
  *C07D 519/00*  (2006.01)
  *C09B 57/00*  (2006.01)
  *H01L 51/00*  (2006.01)

(52) U.S. Cl.
  CPC ......... *C07D 471/04* (2013.01); *C07D 487/06* (2013.01); *C07D 491/048* (2013.01); *C07D 519/00* (2013.01); *C07F 7/0812* (2013.01); *C09B 57/00* (2013.01); *C09K 11/06* (2013.01); *H01L 51/0067* (2013.01); *H01L 51/0072* (2013.01); *H01L 51/0073* (2013.01); *H01L 51/0074* (2013.01); *H01L 51/5056* (2013.01); *H01L 51/5072* (2013.01); *H01L 51/5088* (2013.01); *H01L 51/5092* (2013.01); *H01L 51/5096* (2013.01); *H05B 33/14* (2013.01); *C09K 2211/1007* (2013.01); *C09K 2211/1011* (2013.01); *H01L 51/006* (2013.01); *H01L 51/0055* (2013.01); *H01L 51/0059* (2013.01)

(56) References Cited

U.S. PATENT DOCUMENTS

| | | |
|---|---|---|
| 2006/0041126 A1 | 2/2006 | Schafer et al. |
| 2006/0141284 A1 | 6/2006 | Tomita et al. |
| 2006/0180806 A1 | 8/2006 | Arakane et al. |
| 2007/0051944 A1 | 3/2007 | Vestweber et al. |
| 2007/0069638 A1 | 3/2007 | Matsuura et al. |
| 2007/0159083 A1 | 7/2007 | Matsuura et al. |
| 2007/0190355 A1 | 8/2007 | Ikeda et al. |
| 2007/0224448 A1 | 9/2007 | Ikeda et al. |
| 2008/0145699 A1 | 6/2008 | Yabe et al. |
| 2009/0236973 A1 | 9/2009 | Yabe et al. |
| 2009/0243473 A1 | 10/2009 | Iwakuma et al. |
| 2009/0284138 A1 | 11/2009 | Yasukawa et al. |
| 2010/0039026 A1 | 2/2010 | Yang et al. |
| 2010/0084966 A1 | 4/2010 | Otsu et al. |
| 2010/0163857 A1 | 7/2010 | Kim et al. |
| 2010/0327738 A1 | 12/2010 | Toba et al. |
| 2011/0006670 A1 | 1/2011 | Katakura et al. |
| 2011/0156014 A1 | 6/2011 | Kim et al. |
| 2011/0248257 A1 | 10/2011 | Kim et al. |
| 2011/0291081 A1 | 12/2011 | Inoue et al. |
| 2012/0104941 A1 | 5/2012 | Jung et al. |
| 2012/0119197 A1 | 5/2012 | Nishimura et al. |
| 2012/0126208 A1* | 5/2012 | Kawamura ......... H01L 51/0061 257/40 |
| 2012/0126221 A1 | 5/2012 | Kitamura et al. |
| 2012/0126690 A1 | 5/2012 | Ise et al. |
| 2012/0126691 A1 | 5/2012 | Ise et al. |
| 2012/0126692 A1 | 5/2012 | Ise et al. |
| 2012/0193619 A1 | 8/2012 | Taka et al. |
| 2012/0211735 A1 | 8/2012 | Imada et al. |
| 2012/0223276 A1 | 9/2012 | Parham et al. |
| 2012/0238105 A1 | 9/2012 | Anémian et al. |
| 2012/0273771 A1 | 11/2012 | Jung et al. |
| 2012/0326601 A1 | 12/2012 | Yasukawa et al. |
| 2013/0200357 A1 | 8/2013 | Ludemann et al. |
| 2013/0207540 A1 | 8/2013 | Itai et al. |
| 2013/0256644 A1 | 10/2013 | Kim et al. |
| 2013/0256646 A1 | 10/2013 | Fennimore et al. |
| 2013/0293094 A1 | 11/2013 | Dyatkin et al. |
| 2013/0306962 A1 | 11/2013 | Yamamoto et al. |
| 2013/0313542 A1 | 11/2013 | Hakii et al. |
| 2014/0001456 A1 | 1/2014 | Mizutani et al. |
| 2014/0054564 A1 | 2/2014 | Kim et al. |
| 2014/0159023 A1 | 6/2014 | Matsumoto et al. |
| 2014/0272398 A1 | 9/2014 | Hakii et al. |
| 2014/0299865 A1 | 10/2014 | Nishimura et al. |
| 2014/0312338 A1 | 10/2014 | Mizutani et al. |

FOREIGN PATENT DOCUMENTS

| | | |
|---|---|---|
| JP | 2004-171808 A | 6/2004 |
| JP | 2005-213188 A | 8/2005 |
| JP | 2005-276801 A | 10/2005 |
| JP | 2008-205488 A | 9/2008 |
| JP | 2008-252094 A | 10/2008 |
| JP | 2009-21336 A | 1/2009 |
| JP | 2009-114370 A | 5/2009 |
| JP | 2010-040830 | 2/2010 |
| JP | 2010-114180 A | 5/2010 |
| JP | 2010-141353 A | 6/2010 |
| JP | 2010-165830 A | 7/2010 |
| JP | 2010-185047 A | 8/2010 |
| JP | 2011-8991 A | 1/2011 |
| JP | 2011-86442 A | 4/2011 |
| JP | 2012-97006 A | 5/2012 |
| JP | 2012-142613 A | 7/2012 |
| JP | 2013-4245 A | 1/2013 |
| JP | 2013-48192 A | 3/2013 |
| JP | 2013-84965 A | 5/2013 |
| JP | 2013-110262 A | 6/2013 |
| JP | 2013-206649 A | 10/2013 |
| JP | 2013-242988 A | 12/2013 |
| JP | 2014-17077 A | 1/2014 |
| JP | 2014-17389 A | 1/2014 |
| JP | 2014-45101 A | 3/2014 |
| JP | 5795896 B2 | 10/2015 |
| KR | 10-2014-0094408 A | 7/2014 |
| WO | WO 03-080760 | 10/2003 |
| WO | WO 2006/013739 A1 | 2/2006 |
| WO | WO 2009-008099 | 1/2009 |
| WO | WO 2010/044342 A1 | 4/2010 |
| WO | WO 2010/079678 A1 | 7/2010 |
| WO | WO 2010-134350 | 11/2010 |
| WO | WO 2011/055912 * | 5/2011 |
| WO | WO 2011-055912 | 5/2011 |
| WO | WO 2011-055934 | 5/2011 |
| WO | WO 2011-071255 | 6/2011 |
| WO | WO 2011/132550 A1 | 10/2011 |
| WO | WO 2012/005360 A1 | 1/2012 |
| WO | WO 2012-086170 | 6/2012 |
| WO | WO 2012/099038 A1 | 7/2012 |
| WO | WO 2012/105310 A1 | 8/2012 |
| WO | WO 2012/115034 A1 | 8/2012 |
| WO | WO 2012/145173 A1 | 10/2012 |
| WO | WO 2013/032297 A1 | 3/2013 |
| WO | WO 2013/035275 A1 | 3/2013 |
| WO | WO 2013/038804 A1 | 3/2013 |
| WO | WO 2013/038843 A1 | 3/2013 |
| WO | WO 2013/073874 A1 | 5/2013 |
| WO | WO 2013/100538 A1 | 7/2013 |
| WO | WO 2013/100539 A1 | 7/2013 |
| WO | WO 2013/100540 A1 | 7/2013 |
| WO | WO 2013/157420 A1 | 10/2013 |

(56) References Cited

FOREIGN PATENT DOCUMENTS

| WO | WO 2013/157515 A1 | 10/2013 |
|---|---|---|
| WO | WO 2013/168516 A1 | 11/2013 |
| WO | WO 2013/168534 A1 | 11/2013 |
| WO | WO 2013/175746 A1 | 11/2013 |
| WO | WO 2013/175747 A1 | 11/2013 |
| WO | WO 2013/180020 A1 | 12/2013 |
| WO | WO 2014/014310 A1 | 1/2014 |
| WO | WO 2014/097711 A1 | 6/2014 |
| WO | WO 2014/122933 A1 | 8/2014 |
| WO | WO 2014/166584 A1 | 10/2014 |
| WO | WO 2014/166585 A1 | 10/2014 |
| WO | WO 2014/166586 A1 | 10/2014 |

OTHER PUBLICATIONS

Combined Taiwanese Office Action and Search Report dated Jun. 21, 2016 in Patent Application No. 101143761 (with English language translation).

International Search Report for corresponding International Application No. PCT/JP2012/080190, dated Feb. 5, 2013.

International Preliminary Report on Patentability and Written Opinion for International Application No. PCT/JP2012/080190, dated May 27, 2014, 6 pages.

\* cited by examiner

AROMATIC HETEROCYCLIC DERIVATIVE, MATERIAL FOR ORGANIC ELECTROLUMINESCENT ELEMENT, AND ORGANIC ELECTROLUMINESCENT ELEMENT

TECHNICAL FIELD

The present invention relates to an aromatic heterocyclic derivative, a material for an organic electroluminescence device, and an organic electroluminescence device.

BACKGROUND ART

An organic electroluminescence device (hereinafter, also referred to as organic EL device) can be classified by the emission principle into two types: a fluorescent EL device and a phosphorescent EL device. When a voltage is applied to the organic EL device, holes are injected from an anode and electrons are injected from a cathode. The holes and the electrons are recombined in an emitting layer to form excitons. According to the electron spin statistics theory, singlet excitons and triplet excitons are generated at a ratio of 25%:75%. In a fluorescent EL device which uses emission caused by singlet excitons, the limited value of an internal quantum efficiency is believed to be 25%. A technology for extending a lifetime of a fluorescent EL device using a fluorescent material has recently been improved and applied to a full-color display of a mobile phone, TV and the like. However, as compared with a phosphorescent device, a fluorescent EL device is required to be improved in efficiency.

To cope with this problem, in association with a technology of improving an efficiency of a fluorescent device, a technology of obtaining emission derived from triplet excitons by a phenomenon in which singlet excitons are generated by collision and fusion of two triplet excitons, (i.e., a TTF (Triplet-Triplet Fusion) phenomenon) is disclosed. A blocking layer for effectively causing the TTF phenomenon is required to have a wide gap so as to increase triplet energy. Moreover, since an electron transporting layer is required to be a compound having a high electron tolerance, the electron transporting layer is considered to be preferably a compound formed of a hydrocarbon ring.

Patent Literature 1 discloses an organic EL device in which a host material including an azine ring and a carbazole skeleton is used in a fluorescent emitting layer and BAlq is used in an electron injecting layer adjacent to the emitting layer.

Patent Literature 2 discloses an organic EL device in which a blocking layer is provided adjacently to the emitting layer so as to effectively cause the TTF phenomenon and a fluoranthene derivative is used in the blocking layer.

CITATION LIST

Patent Literature(s)

Patent Literature 1: International Publication No. WO2003/080760
Patent Literature 2: International Publication No. WO2010/134350

SUMMARY OF THE INVENTION

Problems to be Solved by the Invention

An object of the invention is to provide an organic electroluminescence device exhibiting a highly efficient emission and driven at a lower voltage, an aromatic heterocyclic derivative usable in the organic electroluminescence device, a material for an organic electroluminescence device (an organic-electroluminescence-device material) containing the aromatic heterocyclic derivative.

Means for Solving the Problems

The invention provides an aromatic heterocyclic derivative, an organic-electroluminescence-device material, and an organic electroluminescence device as follows.

[1] According to an aspect of the invention, the aromatic heterocyclic derivative is represented by a formula (1) below.

[Formula 1]

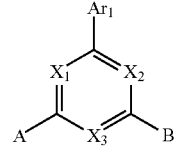

(1)

In the formula (1), $X_1$ to $X_3$ each are a nitrogen atom or $CR_1$, with a proviso that at least one of $X_1$ to $X_3$ is a nitrogen atom.

$R_1$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms.

In the formula (1), A is represented by a formula (2) below.

[Formula 2]

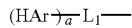

(2)

In the formula (2), HAr is represented by a formula (3) below.

In the formula (2), a is an integer of 1 to 5.

When a is 1, $L_1$ is a single bond or a divalent linking group.

When a is in a range of 2 to 5, $L_1$ is a trivalent to hexavalent linking group. HAr is the same or different.

The linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups.

The groups to be mutually bonded are mutually the same or different.

[Formula 3]

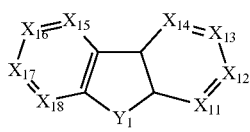
(3)

In the formula (3), $X_{11}$ to $X_{18}$ each independently represent a nitrogen atom, $CR_{13}$ or a carbon atom to be bonded to $L_1$ by a single bond.

In the formula (3), $Y_1$ represent an oxygen atom, a sulfur atom, $SiR_{11}R_{12}$ or a silicon atom to be bonded to $R_{11}$ and $L_1$ by a single bond.

However, the atom bonded to $L_1$ is one of the carbon atom at $X_{11}$ to $X_{18}$ and $R_{11}$ to $R_{12}$ and the silicon atom at $Y_1$.

$R_{11}$ and $R_{12}$ represent the same as $R_1$ of the formula (1). $R_{11}$ and $R_{12}$ are the same or different.

$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms.

A plurality of $R_{13}$ are the same or different. Adjacent ones of $R_{13}$ may be bonded to each other to form a ring.

In the formula (1), B is represented by a formula (4) below.

[Formula 4]

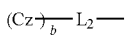
(4)

In the formula (4), Cz is represented by a formula (5) or (6) below.

In the formula (4), b is an integer of 1 to 5.

When b is 1, $L_2$ is a single bond or a divalent linking group.

When b is in a range of 2 to 5, $L_2$ is a trivalent to hexavalent linking group. Cz is the same or different.

The linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups.

The groups to be mutually bonded are mutually the same or different.

[Formula 5]

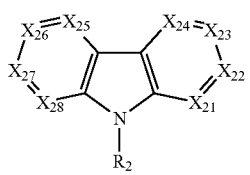
(5)

In the formula (5), $R_2$ represents the same as $R_1$ of the formula (1).

One of $X_{21}$ to $X_{28}$ is a carbon atom to be bonded to $L_2$ by a single bond. Each of the rest of $X_{21}$ to $X_{28}$ is a nitrogen atom or $CR_{21}$.

$R_{21}$ represents the same as $R_{13}$ of the formula (3).

However, when at least one of $X_{21}$ and $X_{28}$ is $CR_{21}$, $R_2$ may be bonded to one of $R_{21}$ to form a ring, or alternatively, N may be directly bonded to one of $R_{21}$ to form a ring.

[Formula 6]

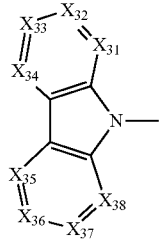
(6)

In the formula (6), $X_{31}$ to $X_{38}$ each are a nitrogen atom or $CR_{31}$.

$R_{31}$ represents the same as $R_{13}$ of the formula (3).

In the formula (6), a nitrogen atom at a position 9 is bonded to $L_2$ by a single bond.

In the formula (1), $Ar_1$ is represented by the formula (2) or (4), or $Ar_1$ represents a substituted or unsubstituted aryl group having 6 to 30 ring carbon atoms, or a substituted or unsubstituted heterocyclic group having 5 to 30 ring atoms.

[2] In the aromatic heterocyclic derivative according to the above aspect of the invention, in the formula (3), one of $X_{13}$ and $X_{16}$ or one of $X_{11}$ and $X_{18}$ is a carbon atom to be bonded to $L_1$ by a single bond.

[3] In the aromatic heterocyclic derivative according to the above aspect of the invention, a is an integer of 1 to 3 in the formula (2).

[4] In the aromatic heterocyclic derivative according to the above aspect of the invention, a is 1 or 2 in the formula (2).

[5] In the aromatic heterocyclic derivative according to the above aspect of the invention, a is 1 and $L_1$ is a linking group in the formula (2), and the linking group is a divalent residue of a substituted or unsubstituted aryl group having 6 to 30 ring carbon atoms, or a divalent residue of a substituted or unsubstituted heterocyclic group having 5 to 30 ring atoms.

[6] In the aromatic heterocyclic derivative according to the above aspect of the invention, a is 2 and $L_1$ is a linking group in the formula (2), and the linking group is a trivalent residue of a substituted or unsubstituted aryl group having 6 to 30 ring carbon atoms or a trivalent residue of a substituted or unsubstituted heterocyclic group having 5 to 30 ring atoms.

[7] In the aromatic heterocyclic derivative according to the above aspect of the invention, b is an integer of 1 to 3 in the formula (4).

[8] In the aromatic heterocyclic derivative according to the above aspect of the invention, b is 1 or 2 in the formula (2).

[9] In the aromatic heterocyclic derivative according to the above aspect of the invention, b is 1 and $L_2$ is a linking group in the formula (4), and the linking group is a divalent residue of a substituted or unsubstituted aryl group having 6 to 30 ring carbon atoms, or a divalent residue of a substituted or unsubstituted heterocyclic group having 5 to 30 ring atoms.

[10] In the aromatic heterocyclic derivative according to the above aspect of the invention, n is 2 and $L_1$ is a linking group in the formula (2), and $L_2$ is a trivalent residue of a substituted or unsubstituted aryl group having 6 to 30 ring carbon atoms, or a trivalent residue of a substituted or unsubstituted heterocyclic group having 5 to 30 ring atoms.

[11] In the aromatic heterocyclic derivative according to the above aspect of the invention, $Y_1$ is an oxygen atom or a sulfur atom in the formula (3).

[12] In the aromatic heterocyclic derivative according to the above aspect of the invention, $Y_1$ is an oxygen atom or a sulfur atom in the formula (3), and one of $X_{21}$ to $X_{28}$ is a carbon atom to be bonded to $L_1$ by a single bond and each of the rest of $X_{21}$ to $X_{28}$ is $CR_{13}$.

[13] In the aromatic heterocyclic derivative according to the above aspect of the invention, two or three of $X_1$ to $X_3$ are nitrogen atoms in the formula (1).

[14] In the aromatic heterocyclic derivative according to the above aspect of the invention, at least one of $L_1$ in the formula (2) and $L_2$ in the formula (4) is a divalent or trivalent residue derived from one of benzene, biphenyl, terphenyl, naphthalene and phenanthrene.

[15] A material for an organic electroluminescence device including the aromatic heterocyclic derivative according to the above aspect of the invention.

[16] In the material for an organic electroluminescence device according to the above aspect of the invention, the material is used for a blocking layer.

[17] An organic electroluminescence device comprising: an anode, an emitting layer, an electron transporting zone, and a cathode in this sequential order, the electron transporting zone contains the aromatic heterocyclic derivative according to the above aspect of the invention.

[18] In the organic electroluminescence device according to the above aspect of the invention, the electron transporting zone includes a blocking layer, and the blocking layer contains the aromatic heterocyclic derivative according to the above aspect of the invention.

[19] In the organic electroluminescence device according to the above aspect of the invention, at least one of an electron injecting layer and an electron transporting layer is provided between the blocking layer and the cathode and contains at least one of an electron-donating material and an organic metal complex.

[20] In the organic electroluminescence device according to the above aspect of the invention, the electron-donating material is at least one material selected from a group of alkali metal, alkaline earth metal, rare earth metal, oxide of alkali metal, halide of alkali metal, oxide of alkaline earth metal, halide of alkaline earth metal, oxide of rare earth metal, and halide of rare earth metal, and the organic metal complex is at least one selected from an organic metal complex including an alkali metal, an organic metal complex including an alkaline earth metal, and an organic metal complex including rare earth metal.

[21] In the organic electroluminescence device according to the above aspect of the invention, the emitting layer is adjacent to the electron transporting zone.

[22] In the organic electroluminescence device according to the above aspect of the invention, the emitting layer contains an anthracene derivative represented by a formula (20D) below.

[Formula 7]

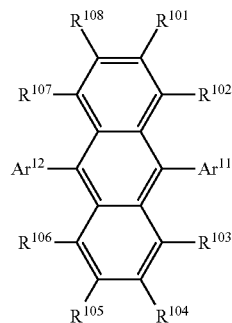

(20D)

In the formula (20D), $Ar^{11}$ and $Ar^{12}$ each independently represent a substituted or unsubstituted monocyclic group having 5 to 30 ring atoms, a substituted or unsubstituted fused ring group having 10 to 30 ring atoms, or a group provided by combining the monocyclic group and the fused ring group.

In the formula (20D), $R^{101}$ to $R^{108}$ each independently represent a hydrogen atom, a halogen atom, a cyano group, a substituted or unsubstituted monocyclic group having 5 to 30 ring atoms, a substituted or unsubstituted fused ring group having 10 to 30 ring atoms, a group provided by combining the monocyclic group and the fused ring group, a substituted or unsubstituted alkyl group having 1 to 30 carbon atoms, a substituted or unsubstituted cycloalkyl group having 3 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, or a substituted or unsubstituted silyl group.

[23] In the organic electroluminescence device according to the above aspect of the invention, the emitting layer contains a dopant material that exhibits fluorescence emission having a main peak wavelength of 500 nm or less.

According to the invention, an organic electroluminescence device exhibiting a highly efficient emission and driven at a lower voltage, an aromatic heterocyclic derivative usable in the organic electroluminescence device, an organic-electroluminescence-device material containing the aromatic heterocyclic derivative can be provided.

DESCRIPTION OF EMBODIMENT(S)

Aromatic Heterocyclic Derivative

Figure 1:
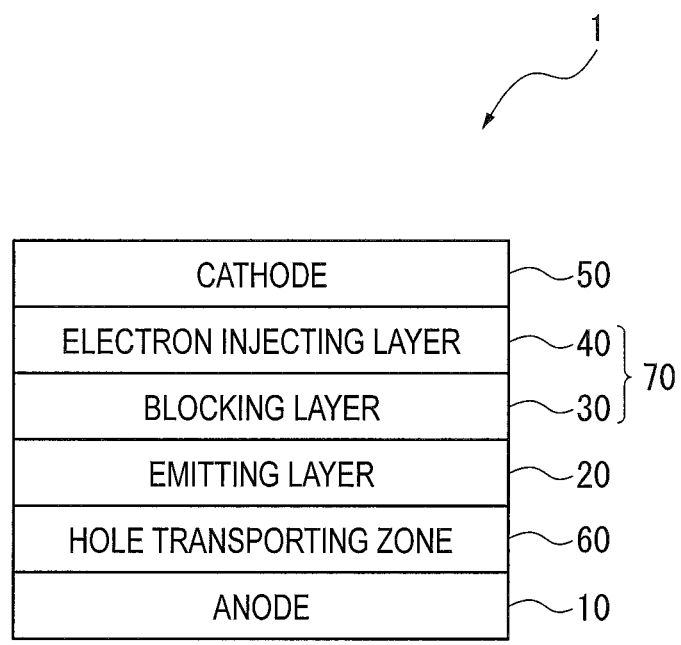
FIG. 1 is a view showing an example of an organic EL device according to a first exemplary embodiment of the invention.

An aromatic heterocyclic derivative of the invention is represented by a formula (1) below.

[Formula 8]

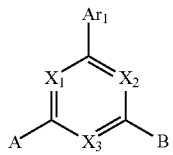

(1)

In the formula (1), $X_1$ to $X_3$ each are a nitrogen atom or $CR_1$, with a proviso that at least one of $X_1$ to $X_3$ is a nitrogen atom.

$R_1$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms.

In the formula (1), A is represented by a formula (2) below.

[Formula 9]

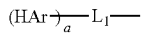

(2)

In the formula (2), HAr is represented by a formula (3) below.

In the formula (2), a is an integer of 1 to 5.

When a is 1, $L_1$ is a single bond or a divalent linking group.

When a is in a range of 2 to 5, $L_1$ is a trivalent to hexavalent linking group. HAr is the same or different.

The linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups.

The groups to be mutually bonded are mutually the same or different.

[Formula 10]

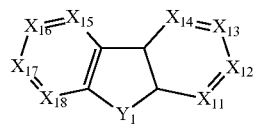

(3)

In the formula (3), $X_{11}$ to $X_{18}$ each independently represent a nitrogen atom, $CR_{13}$ or a carbon atom to be bonded to $L_1$ by a single bond.

In the formula (3), $Y_1$ represent an oxygen atom, a sulfur atom, $SiR_{11}R_{12}$ or a silicon atom to be bonded to $R_{11}$ and $L_1$ by a single bond.

However, the atom bonded to $L_1$ is one of the carbon atom at $X_{11}$ to $X_{18}$ and $R_{11}$ to $R_{12}$ and the silicon atom at $Y_1$.

$R_{11}$ and $R_{12}$ represent the same as $R_1$ of the formula (1). $R_{11}$ and $R_{12}$ are the same or different.

$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms.

A plurality of $R_{13}$ are the same or different. Adjacent ones of $R_{13}$ may be bonded to each other to form a ring.

In the formula (1), B is represented by a formula (4) below.

[Formula 11]

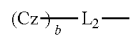

(4)

In the formula (4), Cz is represented by a formula (5) or (6) below.

In the formula (4), b is an integer of 1 to 5.

When b is 1, $L_2$ is a single bond or a divalent linking group.

When b is in a range of 2 to 5, $L_2$ is a trivalent to hexavalent linking group. Cz is the same or different.

The linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups.

The groups to be mutually bonded are mutually the same or different.

[Formula 12]

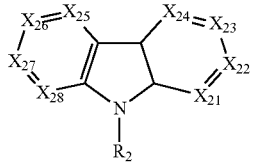

(5)

In the formula (5), $R_2$ represents the same as $R_1$ of the formula (1).

One of $X_{21}$ to $X_{28}$ is a carbon atom to be bonded to $L_2$ by a single bond. Each of the rest of $X_{21}$ to $X_{28}$ is a nitrogen atom or $CR_{21}$.

$R_{21}$ represents the same as $R_{13}$ of the formula (3).

However, when at least one of $X_{21}$ and $X_{28}$ is $CR_{21}$, $R_2$ may be bonded to one of $R_{21}$ to form a ring, or alternatively, N may be directly bonded to one of $R_{21}$ to form a ring.

[Formula 13]

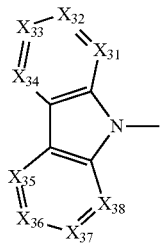

(6)

In the formula (6), $X_{31}$ to $X_{38}$ each are a nitrogen atom or $CR_{31}$.

$R_{31}$ represents the same as $R_{13}$ of the formula (3).

In the formula (6), a nitrogen atom at a position 9 is bonded to $L_2$ by a single bond.

In the formula (1), $Ar_1$ is represented by the formula (2) or (4), or $Ar_1$ represents a substituted or unsubstituted aryl group having 6 to 30 ring carbon atoms, or a substituted or unsubstituted heterocyclic group having 5 to 30 ring atoms.

Groups for $R_1$, $R_2$, $R_{11}$ to $R_{13}$, $R_{21}$, $R_{31}$, $L_1$, $L_2$ and $Ar_1$ will be described below.

Examples of the aryl group having 6 to 30 ring carbon atoms in the formulae (1) to (6) are a phenyl group, 1-naphthyl group, 2-naphthyl group, 1-anthryl group, 2-anthryl group, 9-anthryl group, benzanthryl group, 1-phenanthryl group, 2-phenanthryl group, 3-phenanthryl group, 4-phenanthryl group, 9-phenanthryl group, naphthacenyl group, pyrenyl group, 1-chrysenyl group, 2-chrysenyl group, 3-chrysenyl group, 4-chrysenyl group, 5-chrysenyl group, 6-chrysenyl group, benzo[c]phenanthryl group, benzo[g]chrysenyl group, 1-triphenylenyl group, 2-triphenylenyl group, 3-triphenylenyl group, 4-triphenylenyl group, 1-fluorenyl group, 2-fluorenyl group, 3-fluorenyl group, 4-fluorenyl group, 9-fluorenyl group, benzofluorenyl group, dibenzofluorenyl group, 2-biphenylyl group, 3-biphenylyl group, 4-biphenylyl group, o-terphenyl group, m-terphenyl-4-yl group, m-terphenyl-3-yl group, m-terphenyl-2-yl group, p-terphenyl-4-yl group, p-terphenyl-3-yl group, p-terphenyl-2-yl group, m-quarterphenyl group, 3-fluoranthenyl group, 4-fluoranthenyl group, 8-fluoranthenyl group, 9-fluoranthenyl group, benzofluoranthenyl group, o-tolyl group, m-tolyl group, p-tolyl group, 2,3-xylyl group, 3,4-xylyl group, 2,5-xylyl group, mesityl group, o-cumenyl group, m-cumenyl group, p-cumenyl group, p-t-butylphenyl group, p-(2-phenylpropyl)phenyl group, 4'-methylbiphenylyl group, and 4''-t-butyl-p-terphenyl-4-yl group.

The aryl group of the formula (1) is preferably an aryl group having 6 to 20 ring carbon atoms, more preferably having 6 to 12 ring carbon atoms. Among the aryl group, a phenyl group, biphenyl group, naphthyl group, phenanthryl group, terphenyl group, fluorenyl group, and triphenylenyl group are particularly preferable. In a 1-fluorenyl group, 2-fluorenyl group, 3-fluorenyl group and 4-fluorenyl group, a carbon atom at a position 9 is preferably substituted by the substituted or unsubstituted alkyl group having 1 to 30 carbon atoms in the formula (1).

Examples of the heterocyclic group having 5 to 30 ring atoms in the formulae (1) to (6) are a pyrrolyl group, pyrazinyl group, pyridinyl group, indolyl group, isoindolyl group, imidazolyl group, furyl group, benzofuranyl group, isobenzofuranyl group, dibenzofuranyl group, dibenzothiophenyl group, quinolyl group, isoquinolyl group, quinoxalinyl group, carbazolyl group, phenanthridinyl group, acridinyl group, phenanthrolinyl group, phenazinyl group, phenothiazinyl group, phenoxazinyl group, oxazolyl group, oxadiazolyl group, furazanyl group, thienyl group, benzothiophenyl group, and a group formed from a pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiazole ring, benzothiazole ring, triazole ring, imidazole ring, benzimidazole ring, pyrane ring and dibenzofuran ring.

More specifically, the examples of the heterocyclic group having 5 to 30 ring atoms in the formulae (1) to (6) are a 1-pyrrolyl group, 2-pyrrolyl group, 3-pyrrolyl group, pyrazinyl group, 2-pyridinyl group, 2-pyrimidinyl group, 4-pyrimidinyl group, 5-pyrimidinyl group, 6-pyrimidinyl group, 1,2,3-triazine-4-yl group, 1,2,4-triazine-3-yl group, 1,3,5-triazine-2-yl group, 1-imidazolyl group, 2-imidazolyl group, 1-pyrazolyl group, 1-indolizinyl group, 2-indolizinyl group, 3-indolizinyl group, 5-indolizinyl group, 6-indolizinyl group, 7-indolizinyl group, 8-indolizinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl, 4-pyridinyl, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl, 5-quinoxalinyl, 6-quinoxalinyl, 1-carbazolyl group, 2-carbazolyl group, 3-carbazolyl group, 4-carbazolyl group, 9-carbazolyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, azacarbazolyl-9-yl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl, 5-oxadiazolyl, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

The heterocyclic group of the formulae (1) to (6) preferably has 5 to 20 ring atoms, more preferably 5 to 14 ring atoms. Among the heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, 9-carbazolyl group, 2-pyridinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl, 4-pyridinyl, 1-imidazolyl group, 2-imidazolyl group, 2-quinolyl group, 3-quinolyl group, 4-quinolyl group, 5-quinolyl group, 6-quinolyl group, 7-quinolyl group, 8-quinolyl group, phenanthrolinyl group, or a group formed from a triazine ring or a benzimidazole ring are preferable. In the 1-carbazolyl group, 2-carbazolyl group, 3-carbazolyl group, and 4-carbazolyl group, a nitrogen atom at a position 9 is preferably substituted by a substituted or unsubstituted aryl group having 6 to 30 ring carbon atoms or a substituted or unsubstituted heterocyclic group having 5 to 30 ring atoms in the formula (1).

The alkyl group having 1 to 30 carbon atoms in the formulae (1), (3), (5) and (6) may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group and 1,2,3-trinitropropyl group.

Examples of the cyclic alkyl group (cycloalkyl group) are a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The linear or branched alkyl group of the formulae (1), (3), (5) and (6) preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group and n-hexyl group are preferable.

The cycloalkyl group of the formulae (1), (3), (5) and (6) preferably has 3 to 10 ring carbon atoms, more preferably 5 to 8 ring carbon atoms. Among the cycloalkyl group, a cyclopentyl group and a cyclohexyl group are preferable.

The halogenated alkyl group provided by substituting an alkyl group with a halogen atom is exemplified by a halogenated alkyl group provided by substituting the above alkyl group having 1 to 30 carbon atoms with one or more halogen groups. Specific examples of the above halogenated alkyl group are a fluoromethyl group, difluoromethyl group, trifluoromethyl group, fluoroethyl group and trifluoromethylmethyl group.

The alkenyl group having 2 to 30 carbon atoms in the formulae (1), (3), (5) and (6) may be linear, branched or cyclic. Examples of the alkenyl group are vinyl, propenyl, butenyl, oleyl, eicosapentaenyl, docosahexaenyl, styryl, 2,2-diphenylvinyl, 1,2,2-triphenylvinyl and 2-phenyl-2-propenyl. Among the above alkenyl group, a vinyl group is preferable.

The alkynyl group having 2 to 30 carbon atoms in the formulae (1), (3), (5) and (6) may be linear, branched or cyclic. Examples of the alkynyl group are ethynyl, propynyl and 2-phenylethynyl. Among the above alkynyl group, an ethynyl group is preferable.

The alkylsilyl group having 3 to 30 carbon atoms in the formulae (1), (3), (5) and (6) is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyl dimethylsilyl group, and triisopropylsilyl group. Three alkyl groups may be the same or different.

Examples of the arylsilyl group having 6 to 30 ring carbon atoms in the formulae (1), (3), (5) and (6) are a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the examples of the aryl group having 6 to 30 ring carbon atoms. The dialkylarylsilyl group preferably has 8 to 30 carbon atoms. Two alkyl groups may be the same or different.

The alkyldiarylsilyl group is exemplified by an alkyldiarylsilyl group having one of the examples of the alkyl group having 1 to 30 carbon atoms and two of the examples of the aryl group having 6 to 30 ring carbon atoms. The dialkylarylsilyl group preferably has 13 to 30 carbon atoms. Two aryl groups may be the same or different.

The triarylsilyl group is exemplified by a triarylsilyl group having three of the examples of the aryl group having 6 to 30 ring carbon atoms. The dialkylarylsilyl group preferably has 18 to 30 carbon atoms. Three aryl groups may be the same or different.

The alkoxy group having 1 to 30 carbon atoms in the formulae (1), (3), (5) and (6) is represented by —OY. Y is exemplified by the above alkyl group having 1 to 30 carbon atoms. Examples of the alkoxy group are a methoxy group, ethoxy group, propoxy group, butoxy group, pentyloxy group and hexyloxy group.

The halogenated alkoxy group provided by substituting an alkoxy group with a halogen atom is exemplified by a halogenated alkoxy group provided by substituting the above alkoxy group having 1 to 30 carbon atoms with one or more halogen groups.

The aralkyl group having 6 to 30 ring carbon atoms in the formulae (1), (3), (5) and (6) is represented by —Y—Z. Y is exemplified by an alkylene group corresponding to the above alkyl group having 1 to 30 carbon atoms. Z is exemplified by the above aryl group having 6 to 30 ring carbon atoms. The aralkyl group is preferably an aralkyl having 7 to 30 carbon atoms in which an aryl portion has 6 to 30 carbon atoms, preferably 6 to 20 carbon atoms, more preferably 6 to 12 carbon atoms and an alkyl portion has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxy group having 6 to 30 ring carbon atoms in the formulae (1), (3), (5) and (6) is represented by —OZ. Z is exemplified by the above aryl group having 6 to 30 ring carbon atoms or a later-described monocyclic group and fused ring group. The aryloxy group is exemplified by a phenoxy group.

Examples of the halogen atom in the formulae (1), (3), (5) and (6) are fluorine, chlorine, bromine, and iodine, among which a fluorine atom is preferable.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring and aromatic ring.

Examples of a substituent used for a "substituted or unsubstituted" group are a hydroxyl group, nitro group, and carboxy group in addition to the above-described aryl group, heterocyclic group, alkyl group (linear or branched alkyl group, cycloalkyl group, halogenated alkyl group), alkenyl group, alkynyl group, alkylsilyl group, arylsilyl group, alkoxy group, halogenated alkoxy group, aralkyl group, aryloxy group, halogen atom and cyano group. Among the above substituents, the aryl group, heterocyclic group, alkyl group, halogen atom, alkylsilyl group, arylsilyl group and cyano group are preferable and the specific preferable substituents described in each of the substituents are further preferable. Moreover, the substituents may be further substituted by the above-described substituents.

Herein, "unsubstituted" in "substituted or unsubstituted" means substitution by a hydrogen atom.

The same description as the above applies to "substituted or unsubstituted" in a later-described compound or moieties thereof.

In the invention, a hydrogen atom includes isotope having different numbers of neutrons, specifically, protium, deuterium and tritium.

In the aromatic heterocyclic derivative of the invention, $X_{13}$ or $X_{16}$ in the formula (3) is preferably a carbon atom to be bonded to $L_1$ by a single bond.

Moreover, in the aromatic heterocyclic derivative of the invention, $X_{11}$ or $X_{18}$ in the formula (3) is preferably a carbon atom to be bonded to $L_1$ by a single bond.

In the aromatic heterocyclic derivative of the invention, a in the formula (2) is preferably an integer of 1 to 5, more preferably an integer of 1 to 3, particularly preferably 1 or 2.

When a is 1, $L_1$ is a single bond or a divalent linking group and the formula (2) is represented by a formula (2-1) below.

When a is 2, $L_1$ is a trivalent linking group and the formula (2) is represented by a formula (2-2) below. Herein, HAr is the same or different.

[Formula 14]

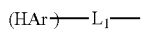
(2-1)

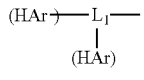
(2-2)

The linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups.

In the linking group, the group provided by bonding two or three of the above groups is a group provided by bonding with a single bond two or three of the divalent or trivalent group derived from the aryl group having 6 to 30 ring carbon atoms and the heterocyclic group having 5 to 30 ring atoms. In the linking group, the groups to be mutually bonded are mutually the same or different.

In the formulae (2), (2-1) and (2-2), $L_1$ is preferably a linking group, which is preferably a substituted or unsubstituted aryl group having 6 to 30 ring carbon atoms and a substituted or unsubstituted heterocyclic group having 5 to 30 ring atoms.

In the aromatic heterocyclic derivative of the invention, it is preferable that a is 1 and $L_1$ is a linking group in the formula (2), the linking group being a divalent residue of a substituted or unsubstituted aryl group having 6 to 30 ring carbon atoms or a divalent residue of a substituted or unsubstituted heterocyclic group having 5 to 30 ring atoms.

Moreover, in the aromatic heterocyclic derivative of the invention, it is preferable that a is 2 and $L_1$ is a linking group in the formula (2), the linking group being a divalent residue of a substituted or unsubstituted aryl group having 6 to 30 ring carbon atoms or a divalent residue of a substituted or unsubstituted heterocyclic group having 5 to 30 ring atoms.

In the aromatic heterocyclic derivative of the invention, b in the formula (4) is preferably an integer of 1 to 5, more preferably an integer of 1 to 3, particularly preferably an integer of 1 or 2.

When b is 1, $L_2$ is a single bond or a divalent linking group and the formula (4) is represented by a formula (4-1) below.

When b is 2, $L_2$ is a trivalent linking group and the formula (4) is represented by a formula (4-2) below. Herein, Cz is the same or different.

[Formula 15]

(4-1)

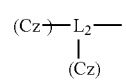
(4-2)

In the formulae (4), (4-1) and (4-2), the same description as the above in relation to $L_1$ applies to $L_2$.

In the formulae (4), (4-1) and (4-2), $L_2$ is preferably a linking group, which is preferably a substituted or unsubstituted aryl group having 6 to 30 ring carbon atoms and a substituted or unsubstituted heterocyclic group having 5 to 30 ring atoms.

In the formulae (4), (4-1) and (4-2), Cz is represented by the formula (5) or (6).

In the aromatic heterocyclic derivative of the invention, it is preferable that b is 1 and $L_2$ is a linking group in the formula (4), the linking group being a divalent residue of a substituted or unsubstituted aryl group having 6 to 30 ring carbon atoms or a divalent residue of a substituted or unsubstituted heterocyclic group having 5 to 30 ring atoms.

Moreover, in the aromatic heterocyclic derivative of the invention, it is preferable in the formula (4) that b is 2 and $L_2$ is a divalent residue of a substituted or unsubstituted aryl group having 6 to 30 ring carbon atoms or a divalent residue of a substituted or unsubstituted heterocyclic group having 5 to 30 ring atoms.

Moreover, in the aromatic heterocyclic derivative of the invention, $Y_1$ in the formula (3) is preferably an oxygen atom or a sulfur atom.

Moreover, in the aromatic heterocyclic derivative of the invention, it is preferable in the formula (3) that $Y_1$ is an oxygen atom or a sulfur atom, one of $X_{11}$ to $X_{18}$ is a carbon atom to be bonded to $L_1$ by a single bond, and the rest of $X_{11}$ to $X_{18}$ are $CR_{13}$.

Moreover, two or three of $X_1$ to $X_3$ are preferably a nitrogen atom in the formula (1).

In the aromatic heterocyclic derivative of the invention, at least one of $L_1$ in the formula (2) and $L_2$ in the formula (4) is preferably a divalent or trivalent residue derived from one of benzene, biphenyl, terphenyl, naphthalene and phenanthrene.

Specific examples of each of the groups in $L_1$ and $L_2$ in the formulae (2-1), (2-1), (4-1) and (4-2) may be the groups described for each of the groups in $L_1$ and $L_2$ in the formulae (2) and (4).

Examples of a specific structure of the aromatic heterocyclic derivative of the invention are as follows. However, the invention is not limited by the aromatic heterocyclic derivative having these structures.

[Formula 16]
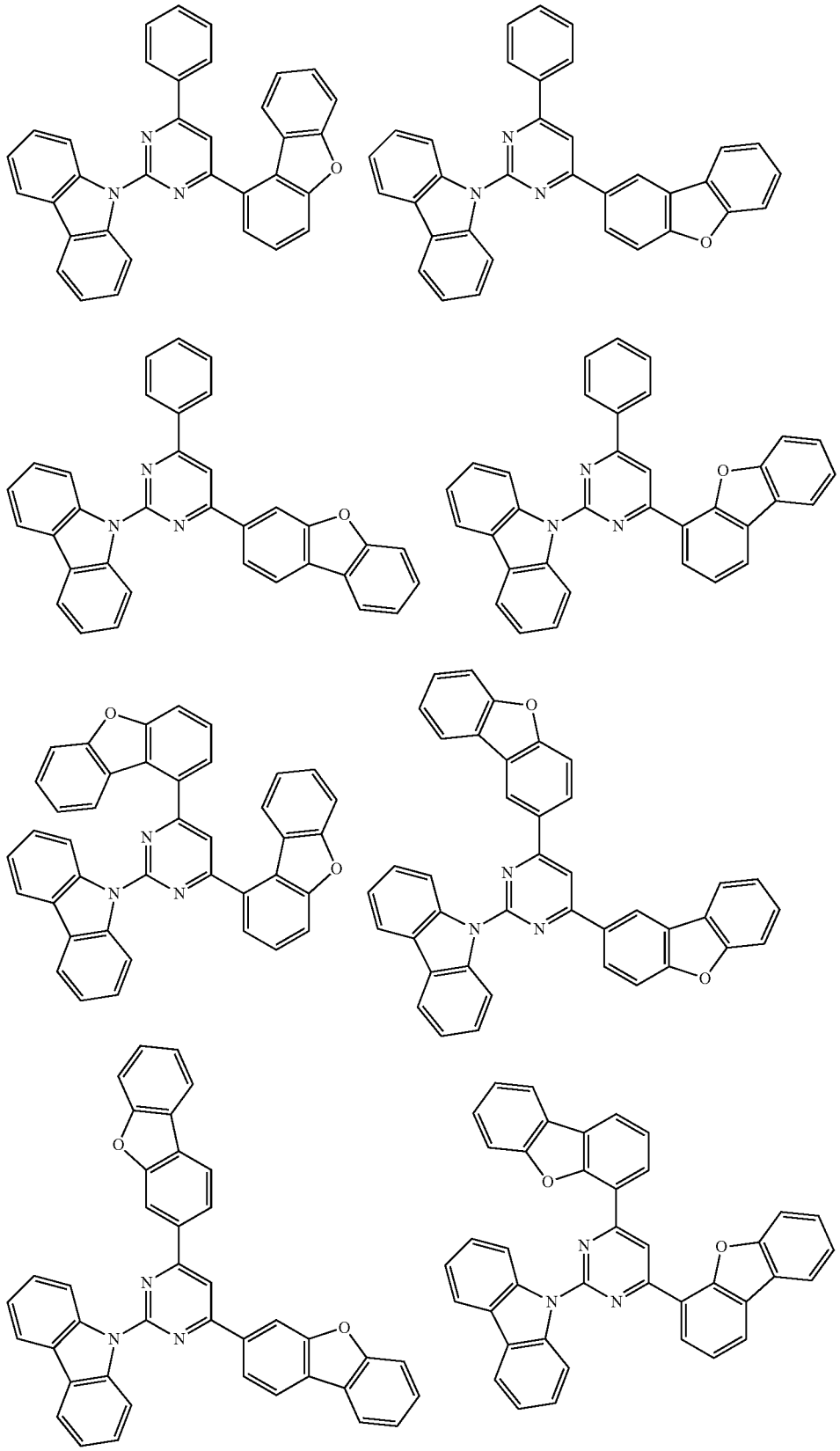

-continued
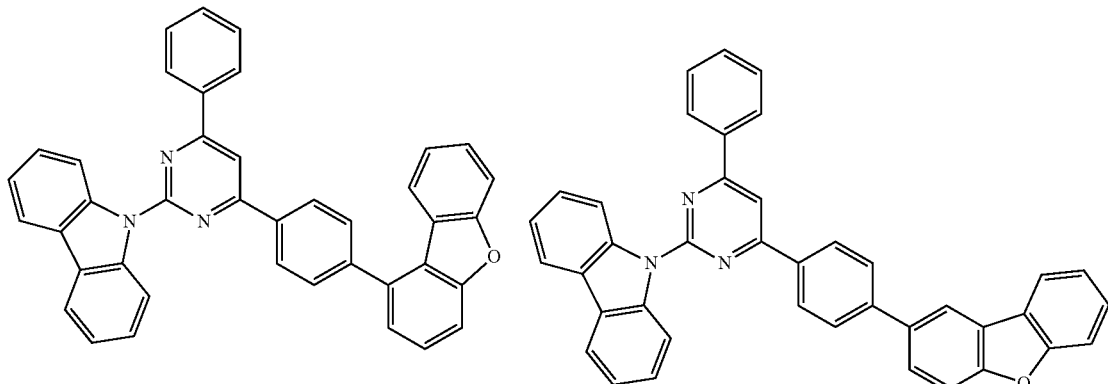
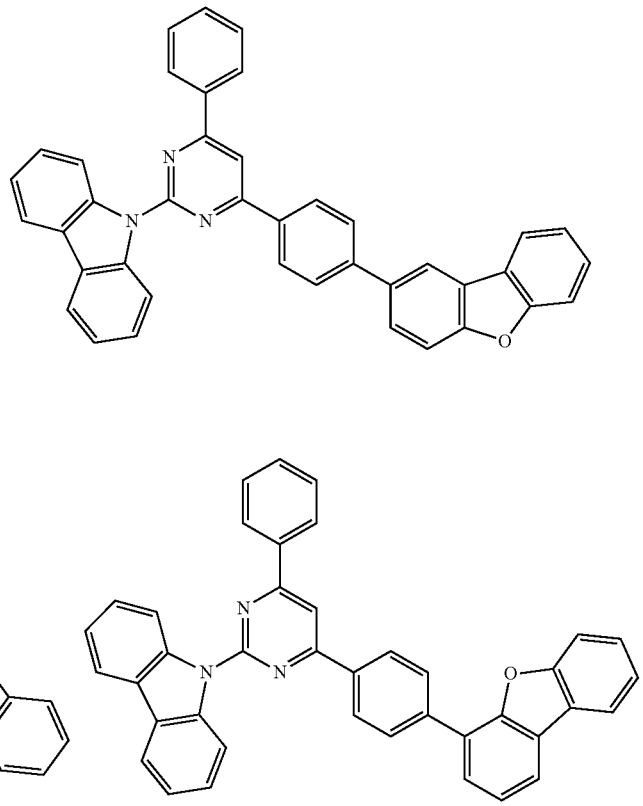
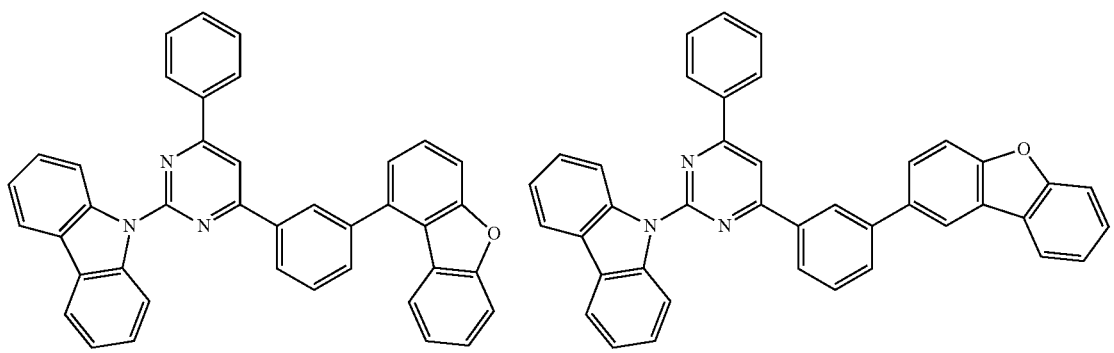
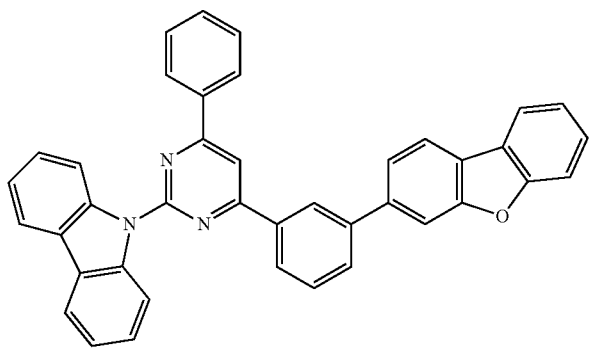

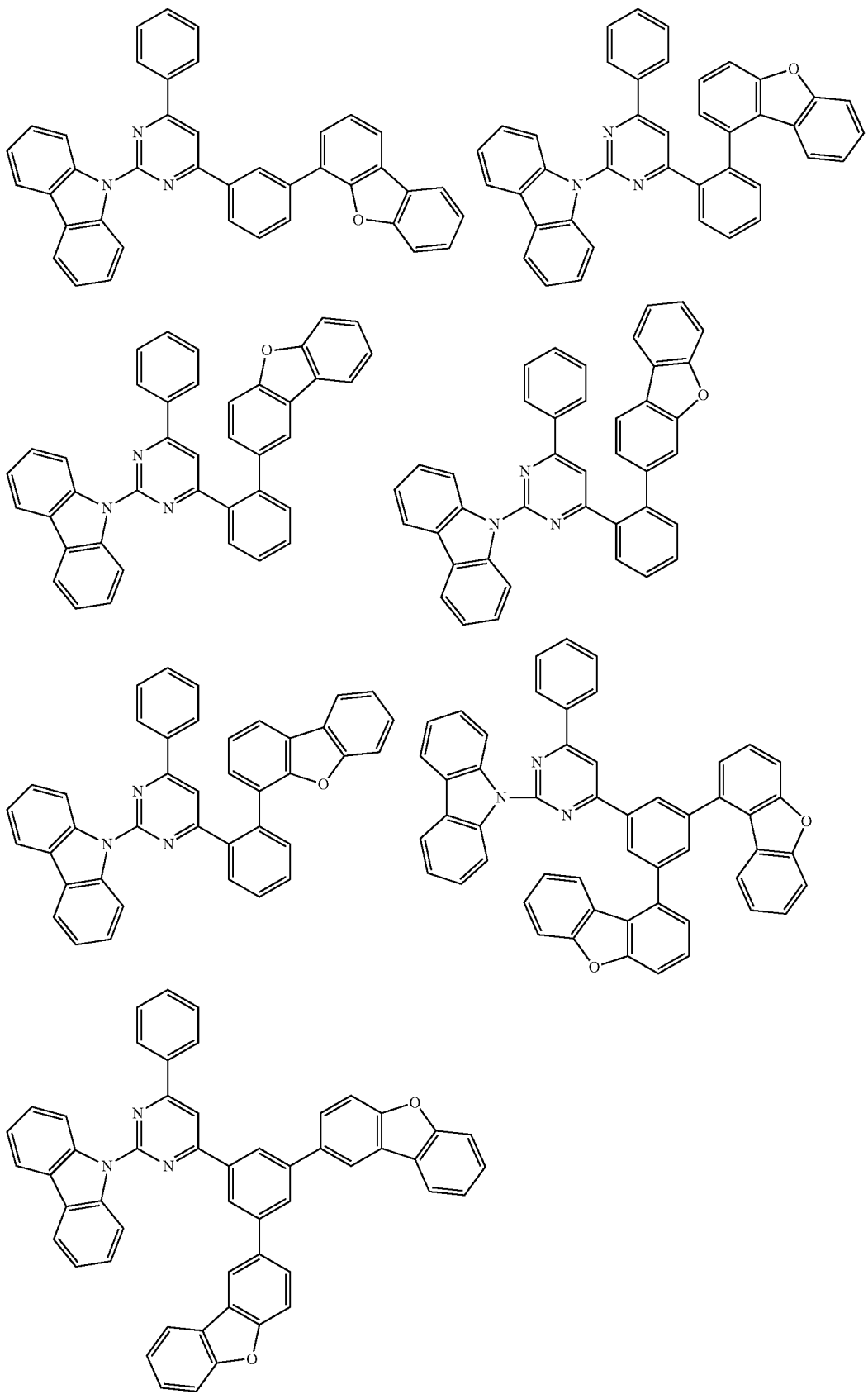

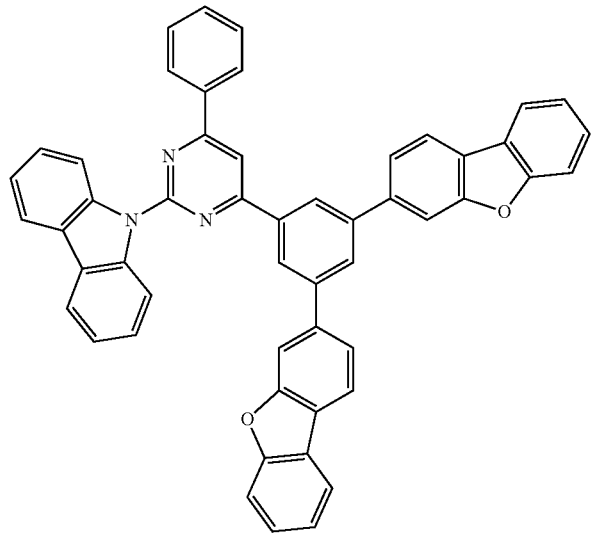
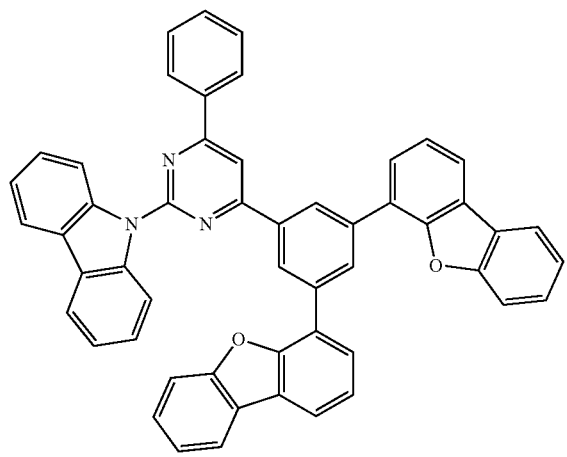
[Formula 17]
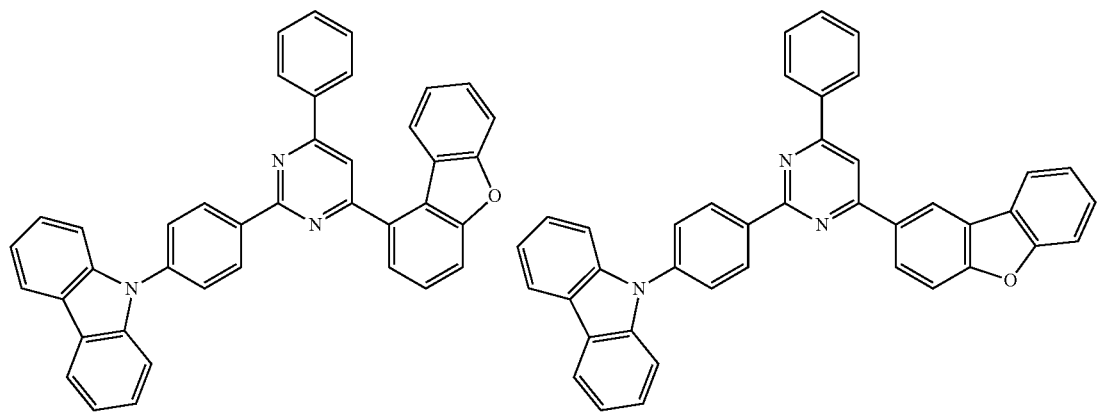

-continued
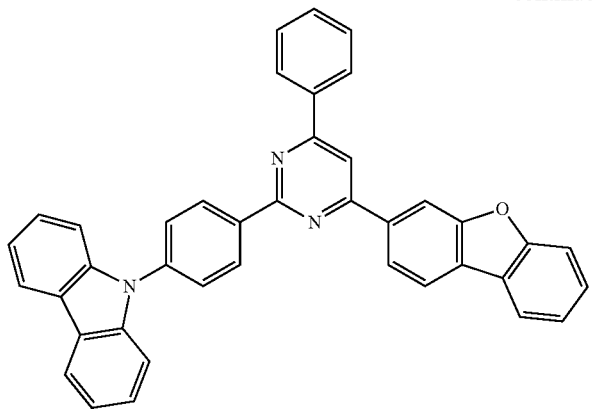
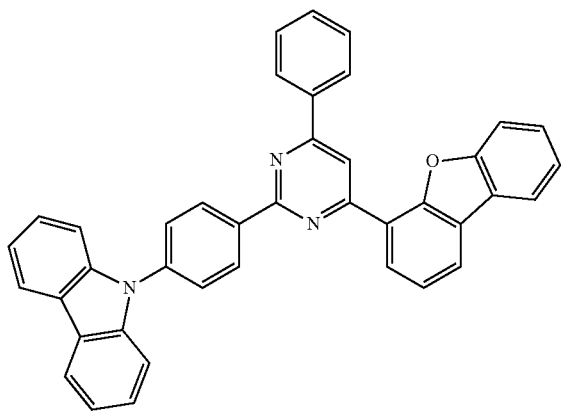
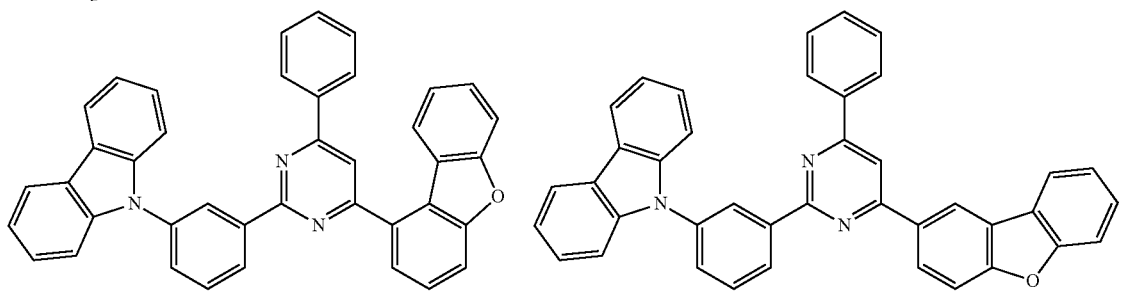
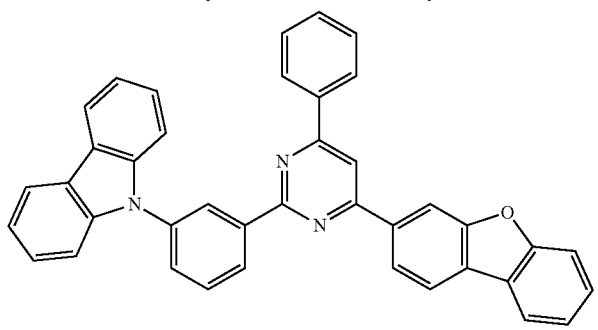
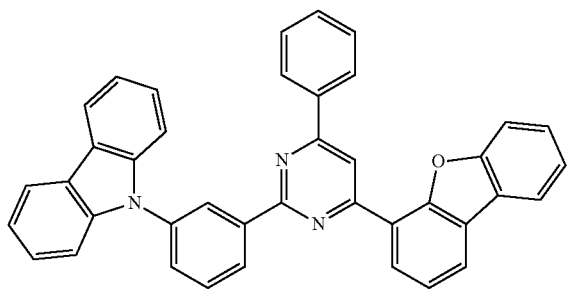

-continued
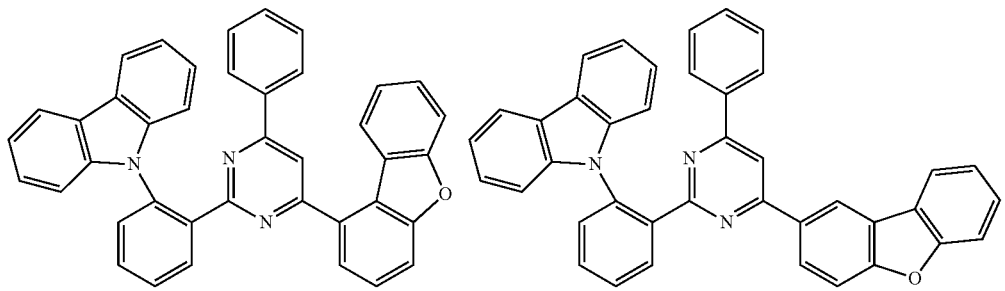
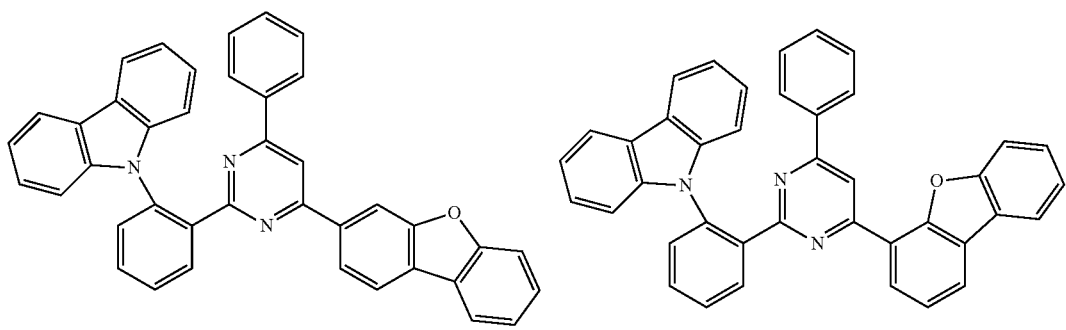
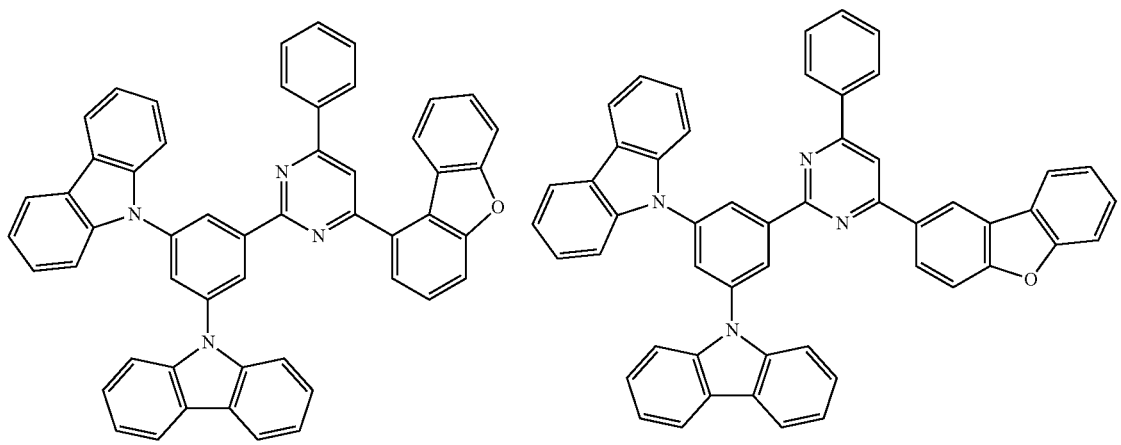
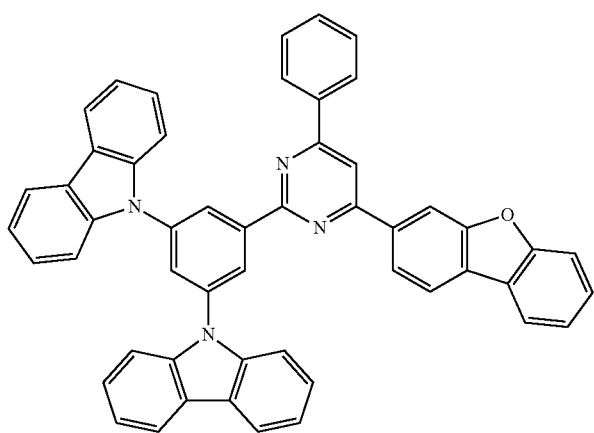

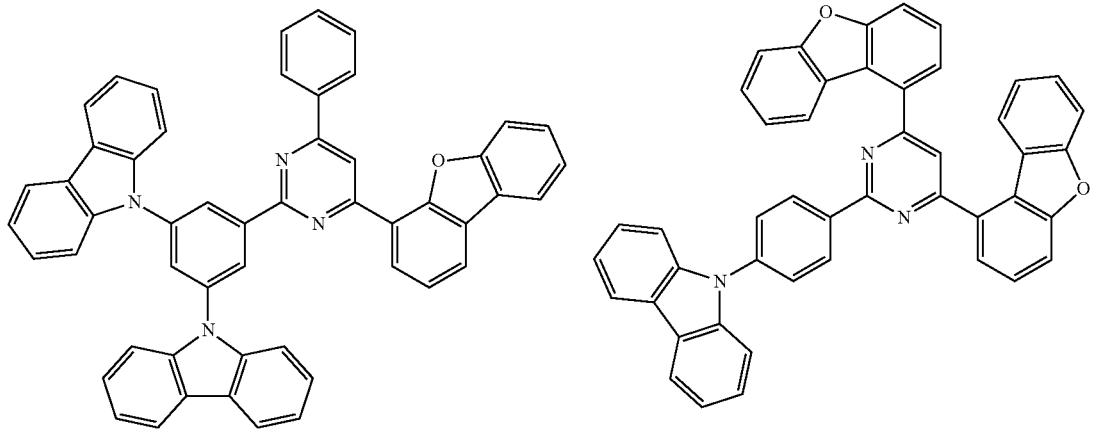
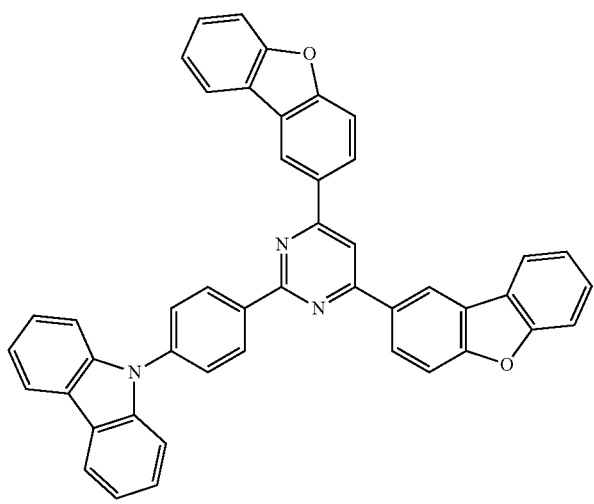
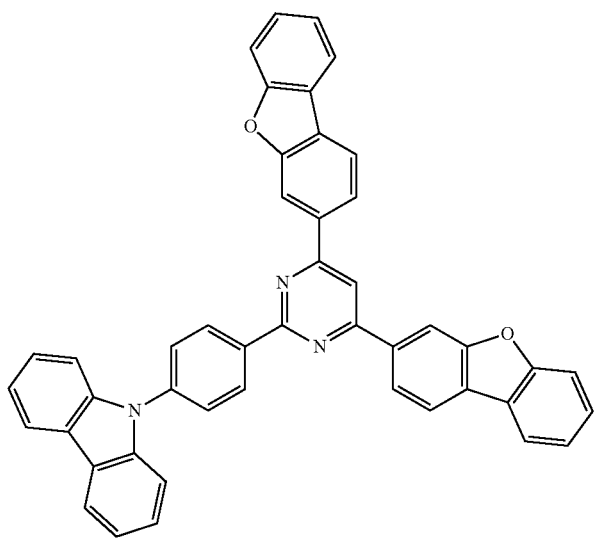

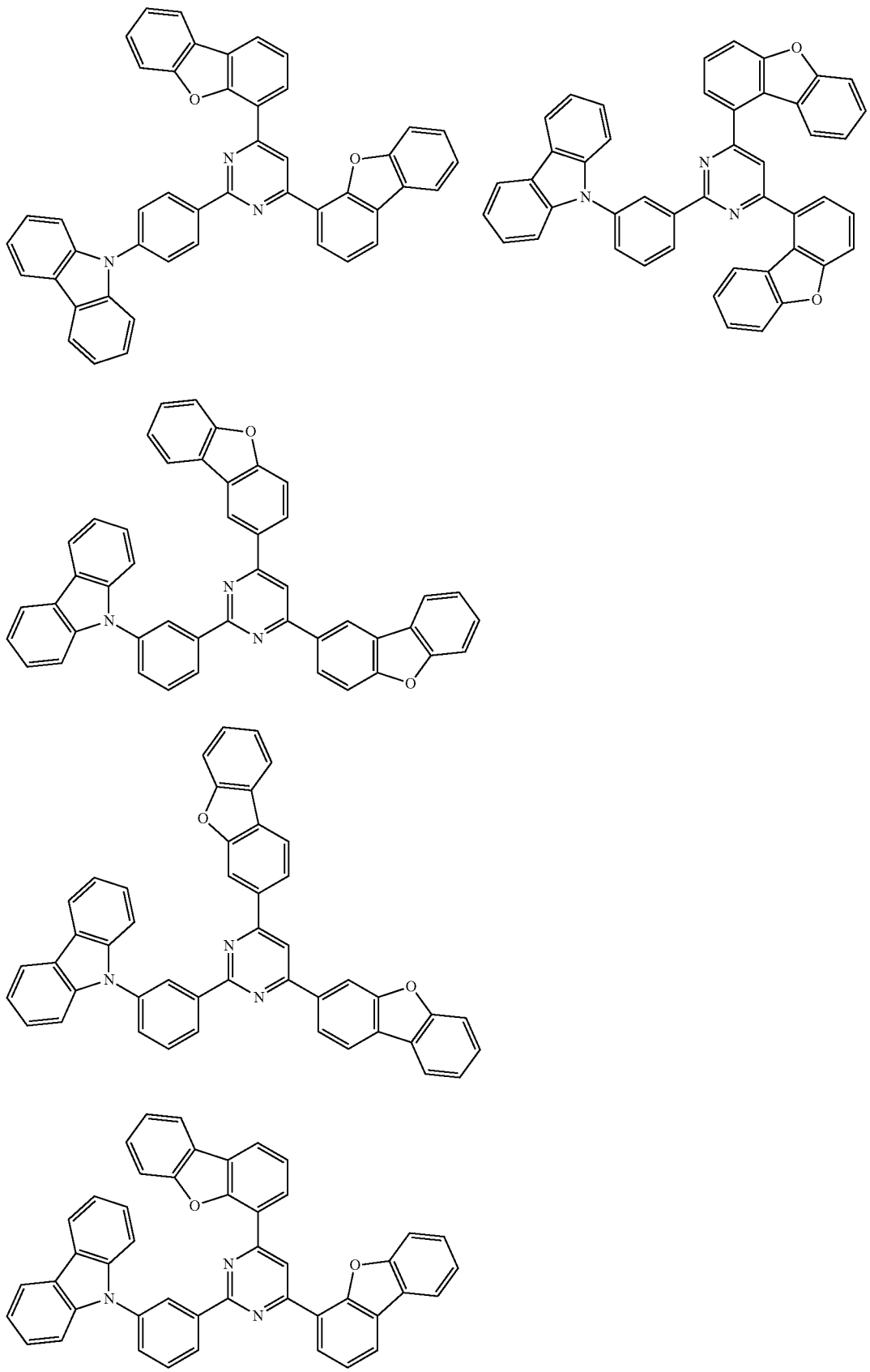

-continued
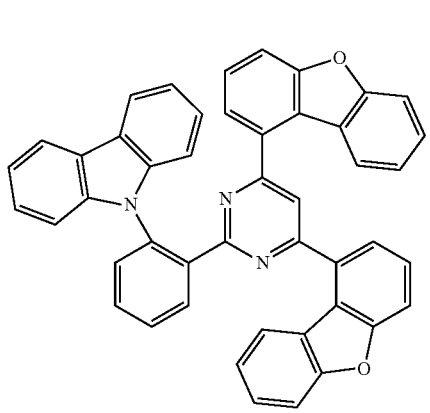 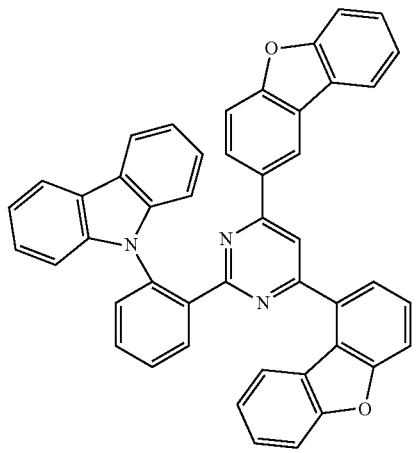
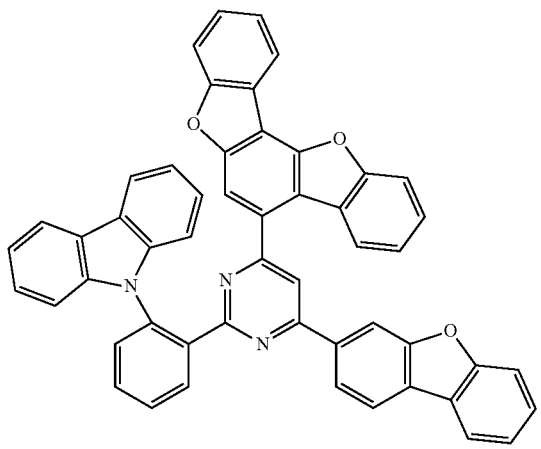 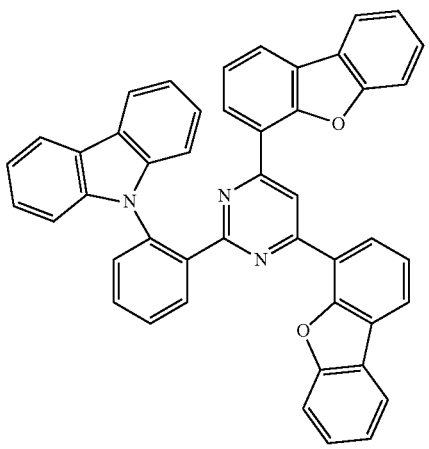
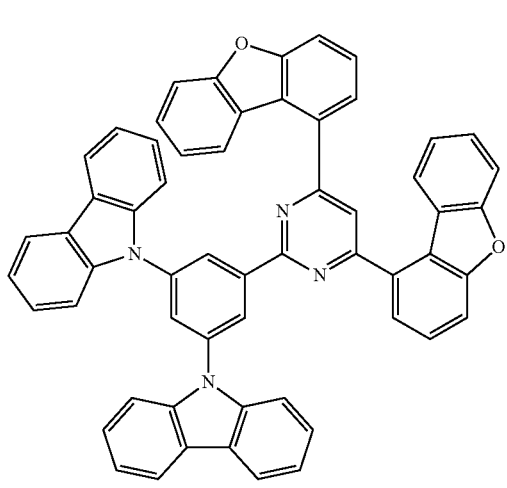 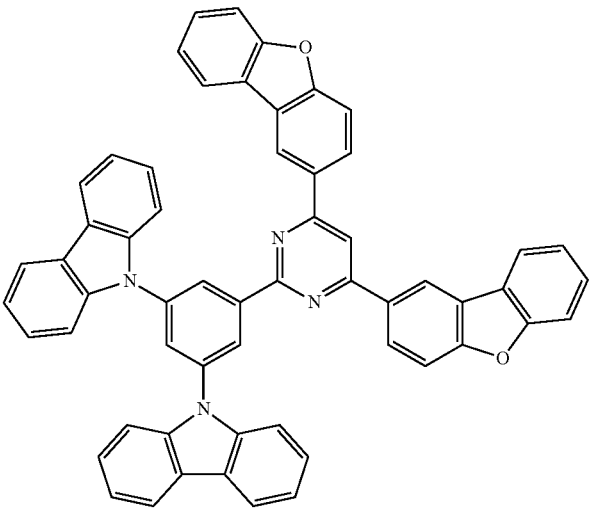

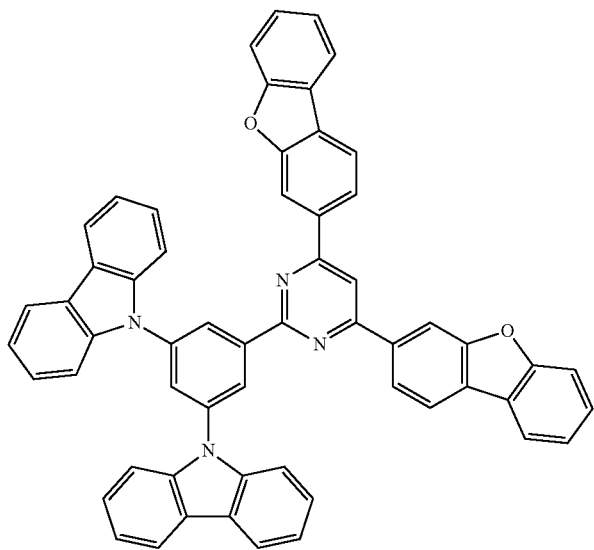
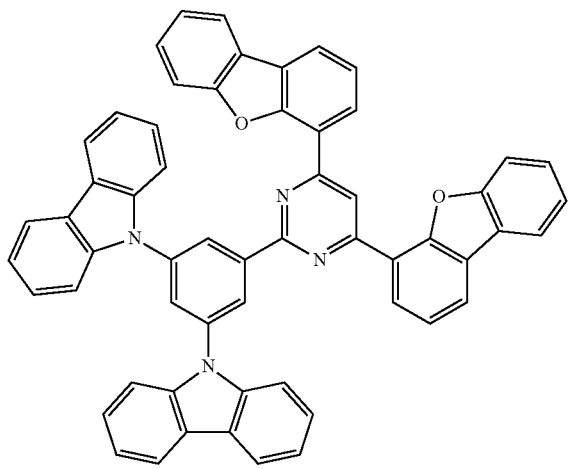
[Formula 18]
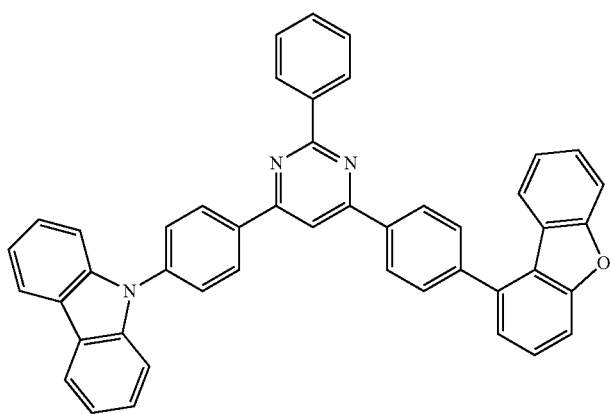

-continued
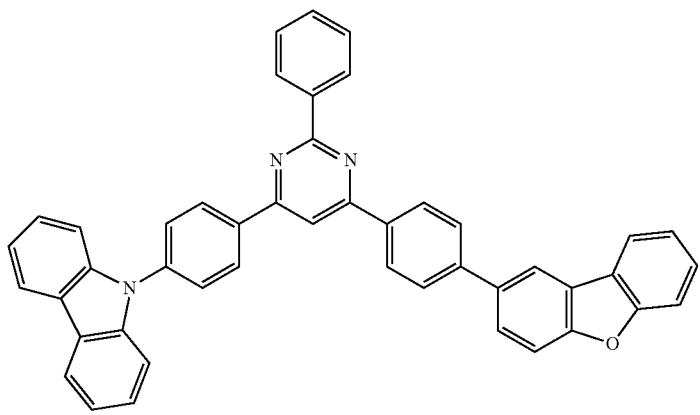
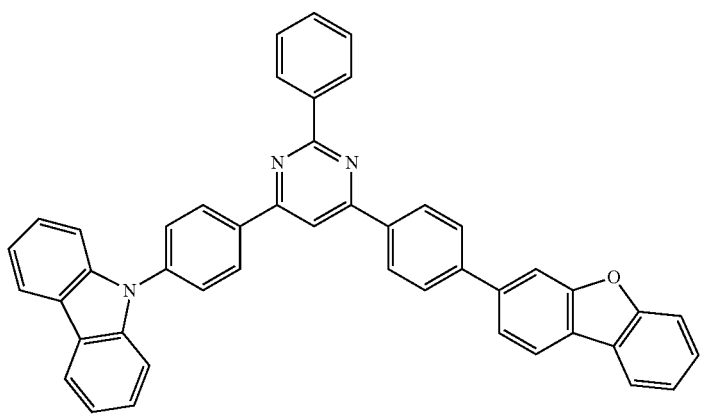
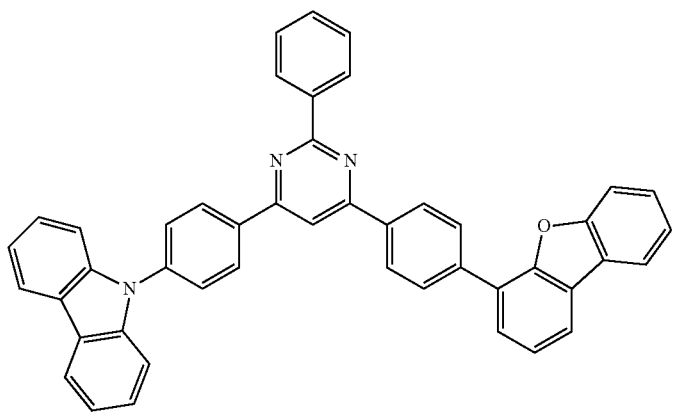
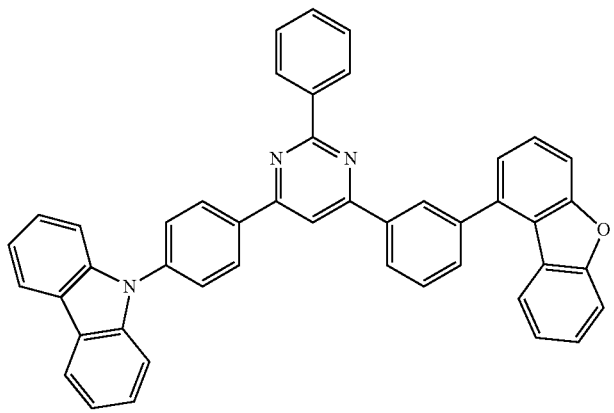

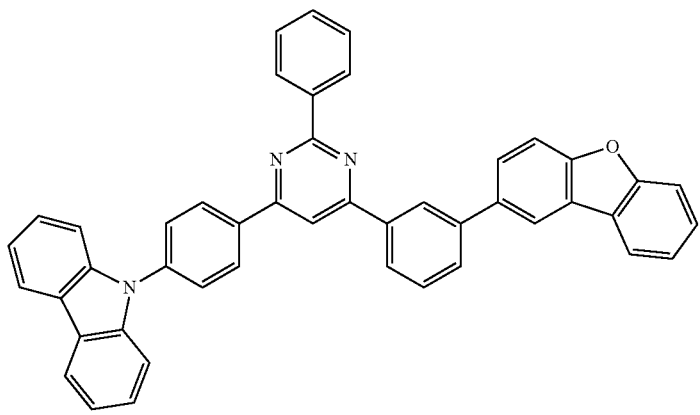
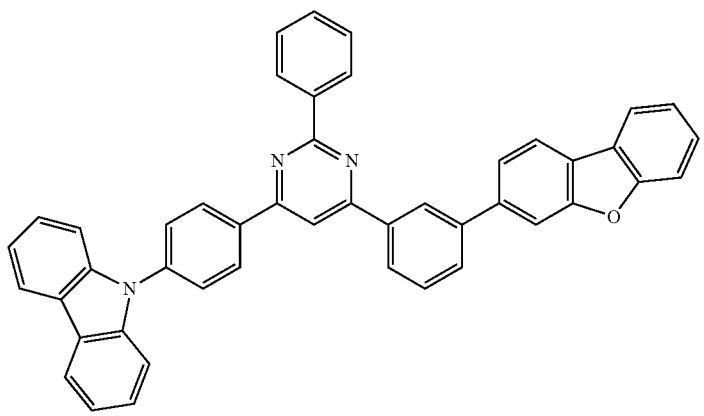
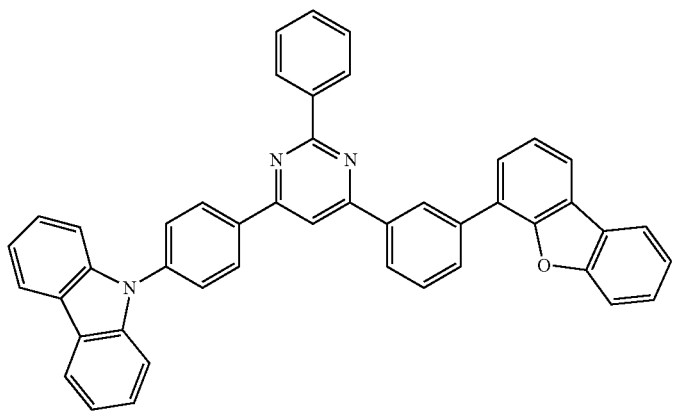
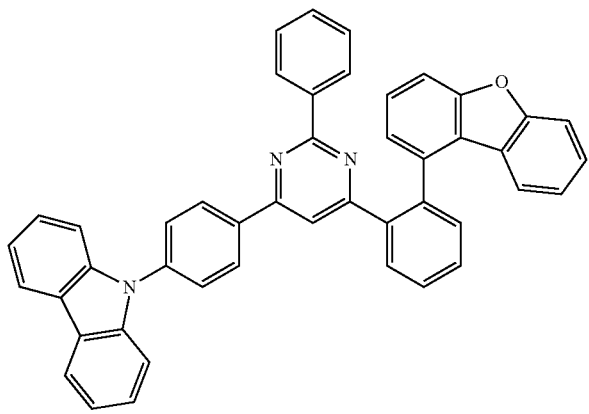

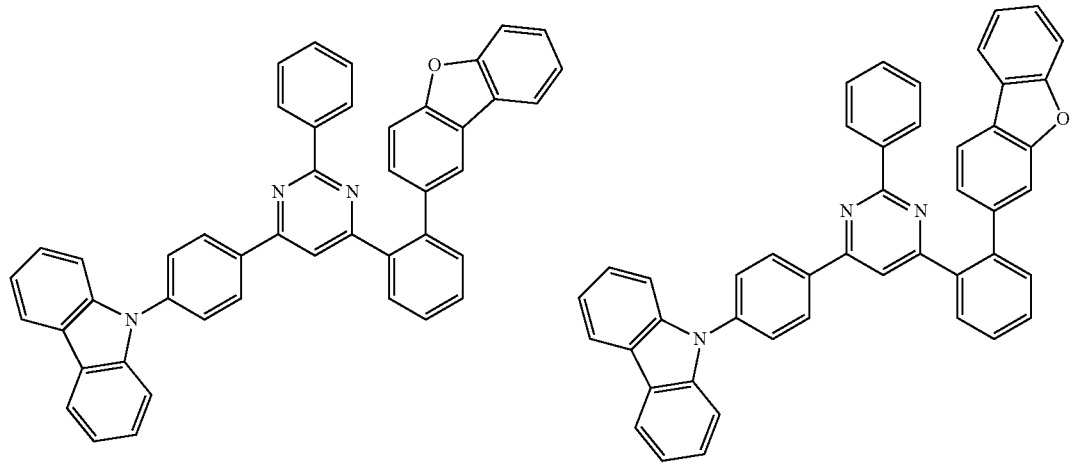
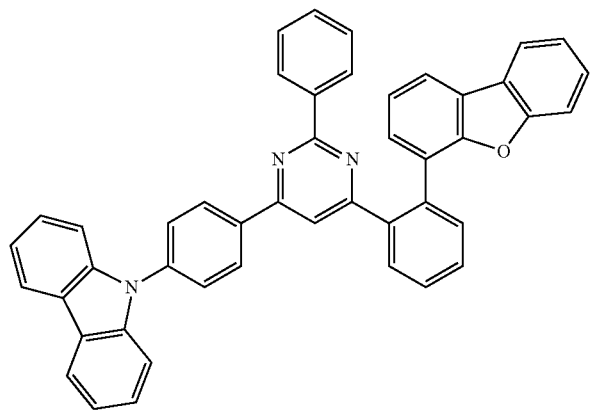
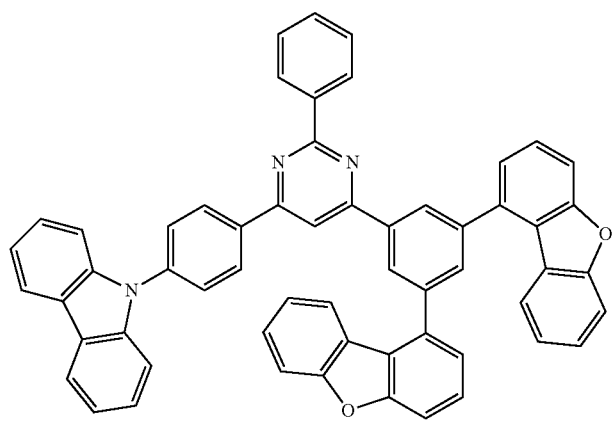

-continued
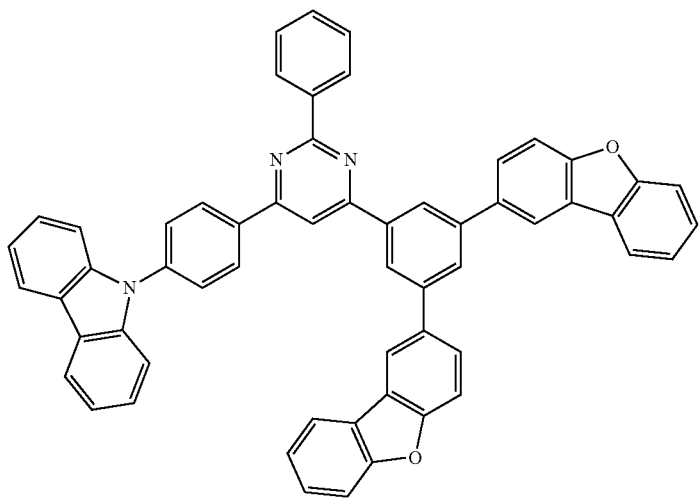
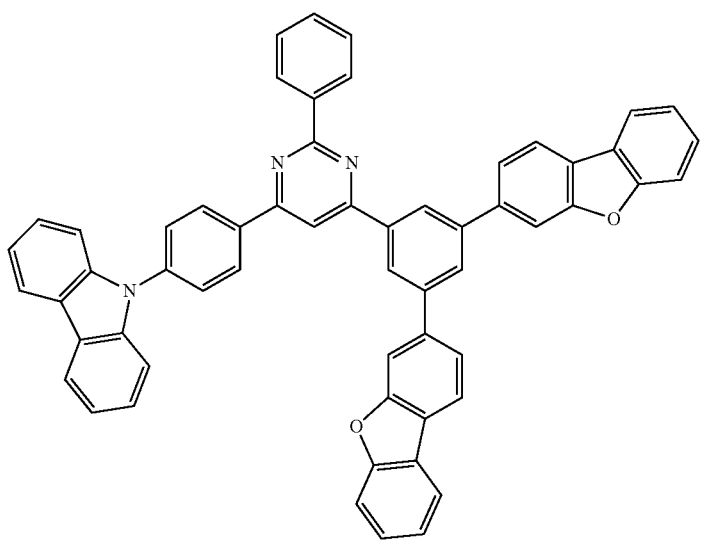
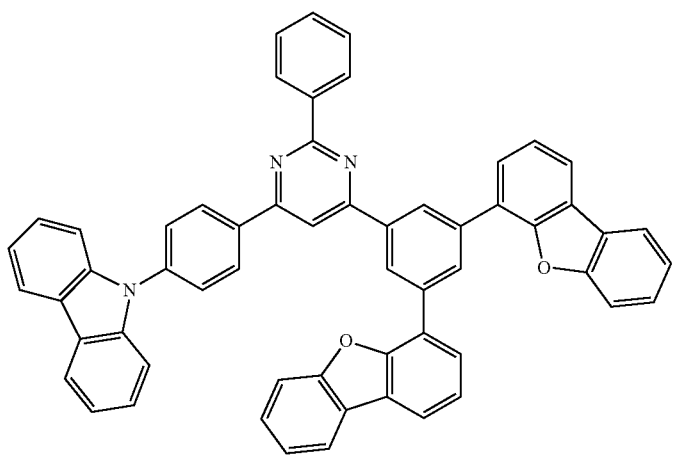

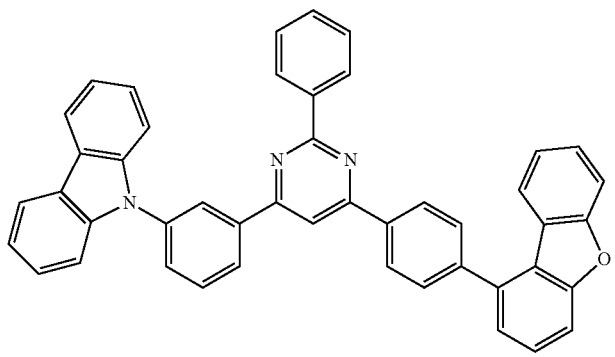
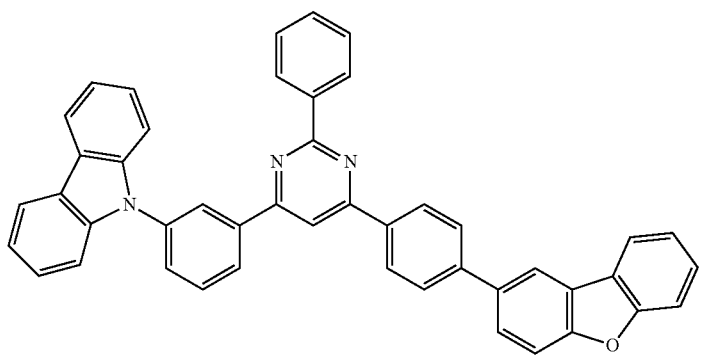
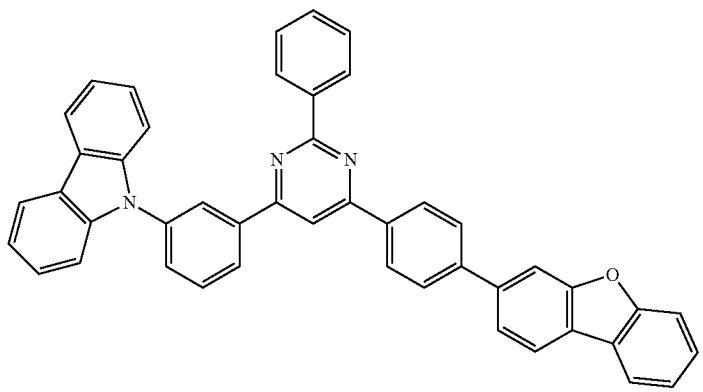
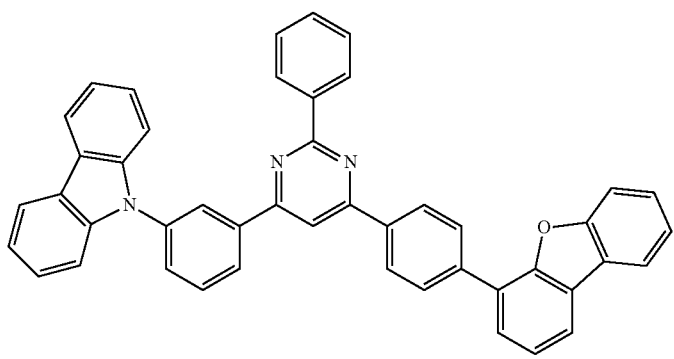

-continued
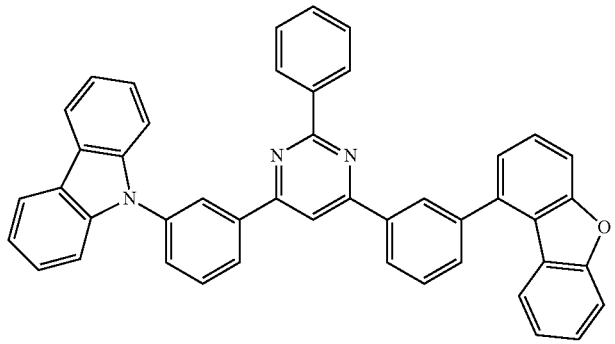
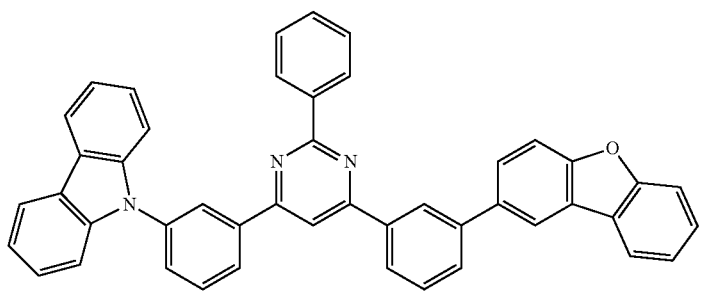
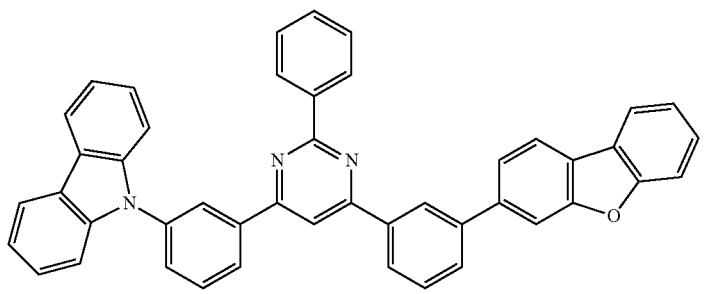
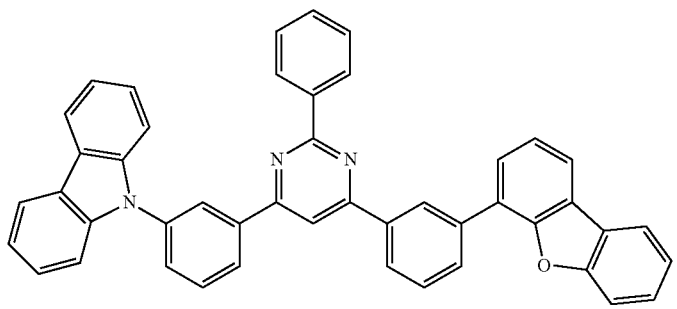
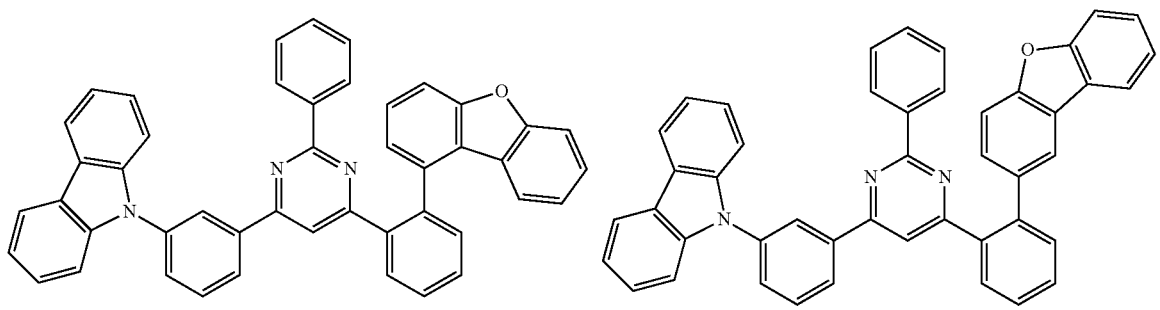

-continued
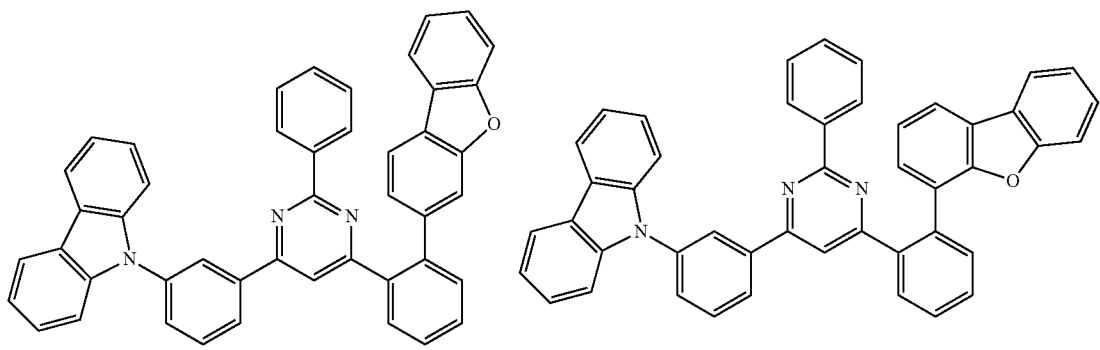
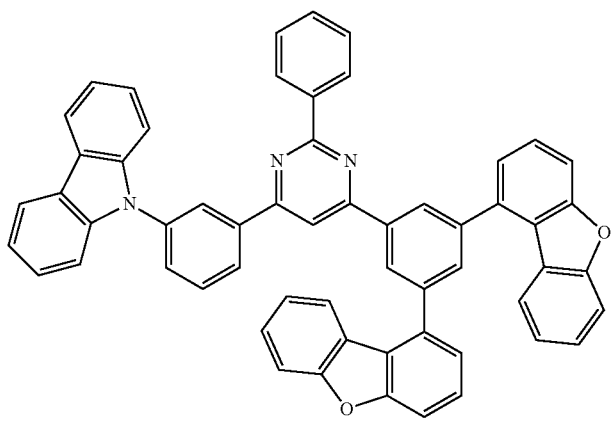
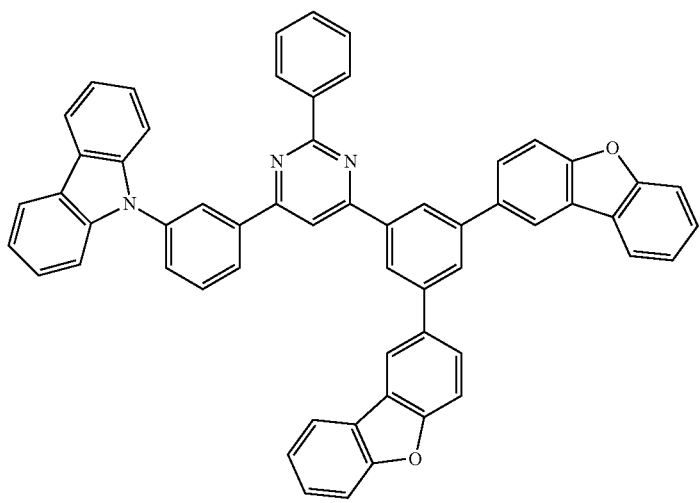

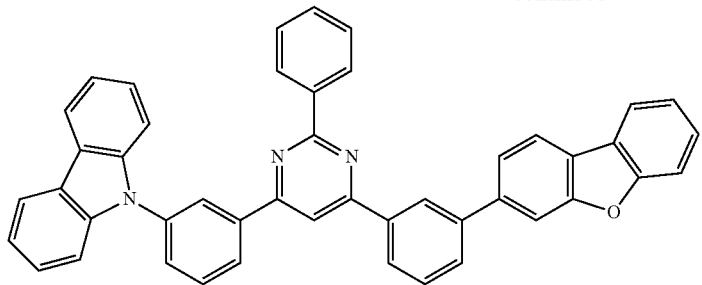
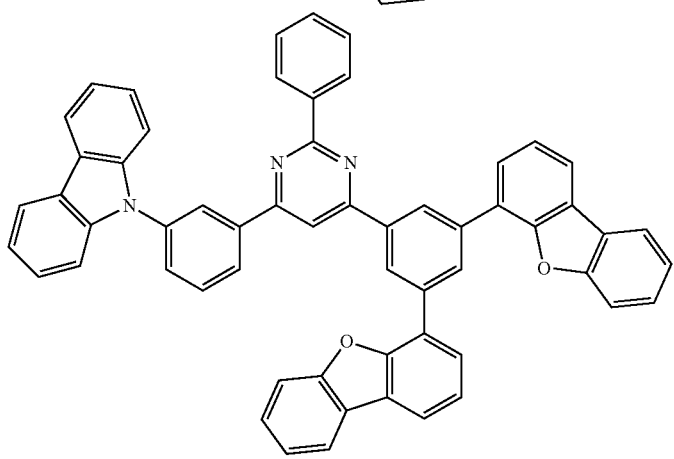
[Formula 19]
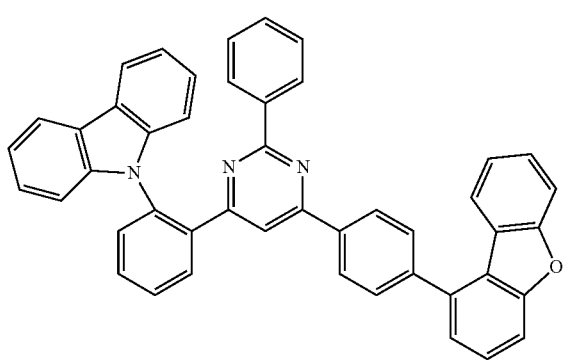
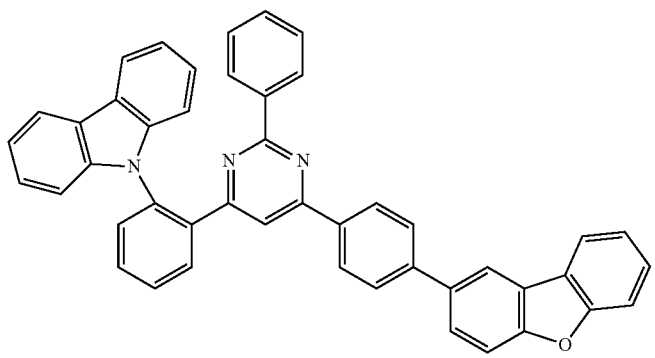

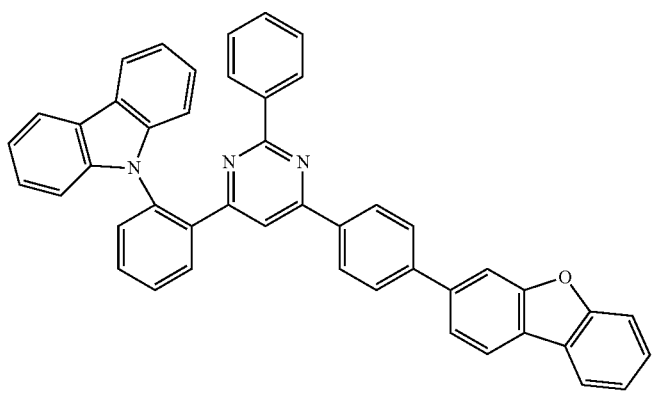
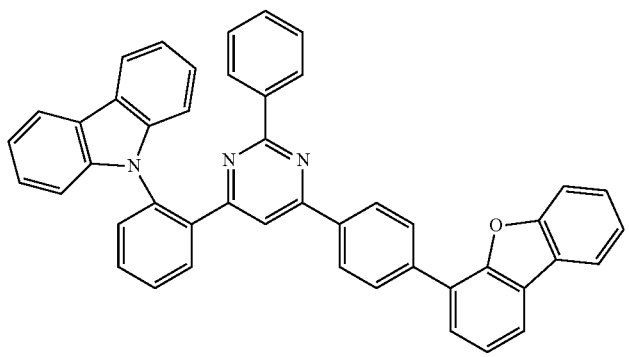
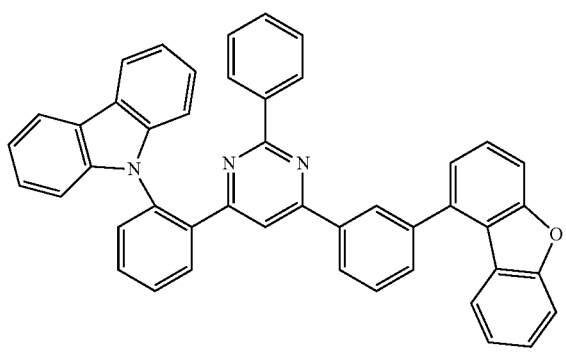
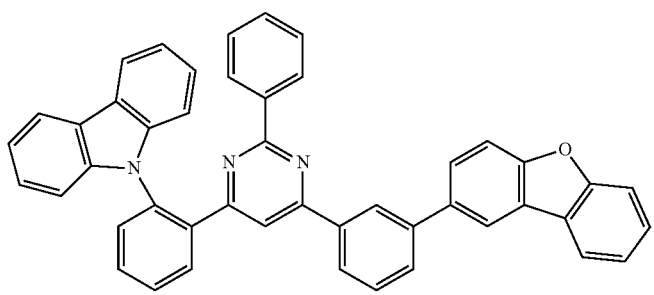
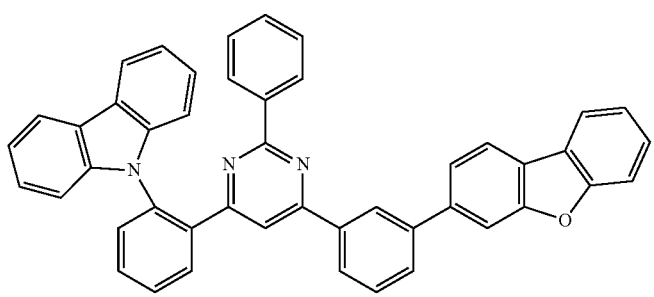

-continued
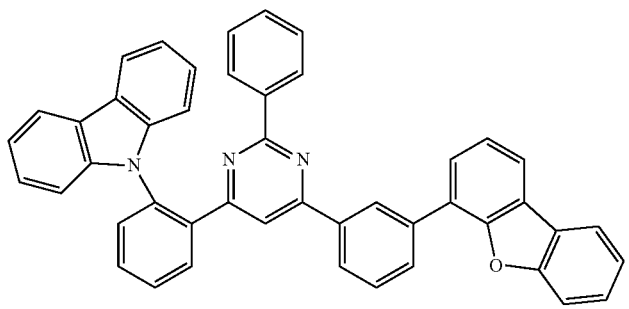
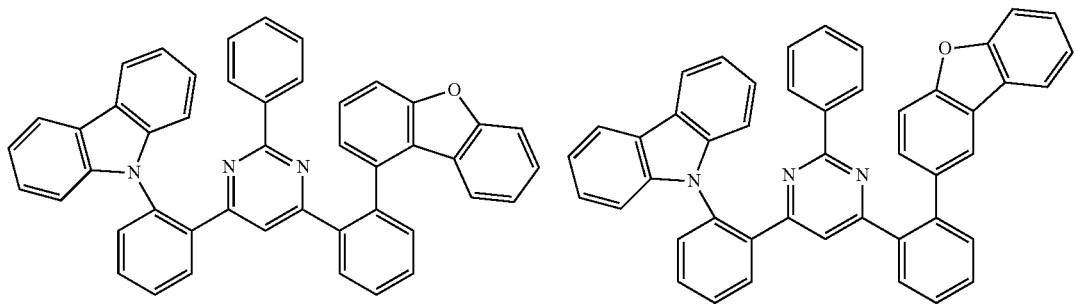
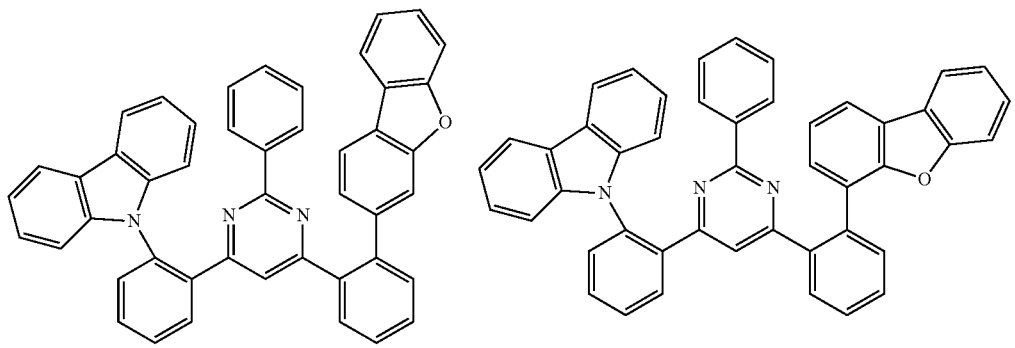
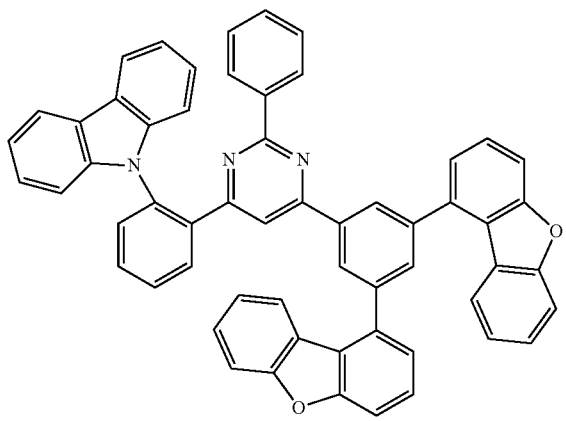

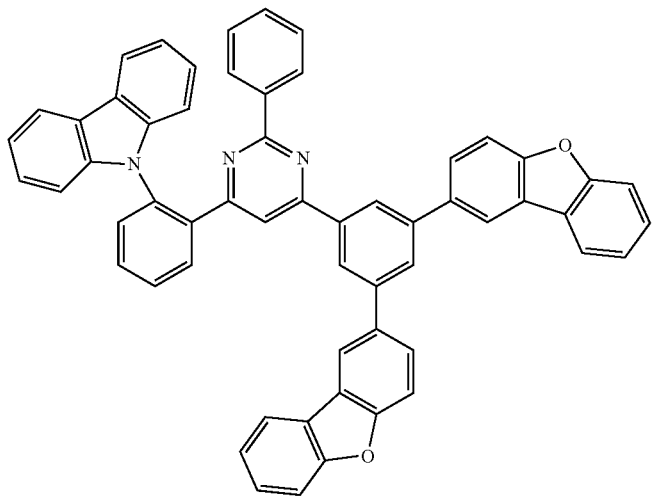
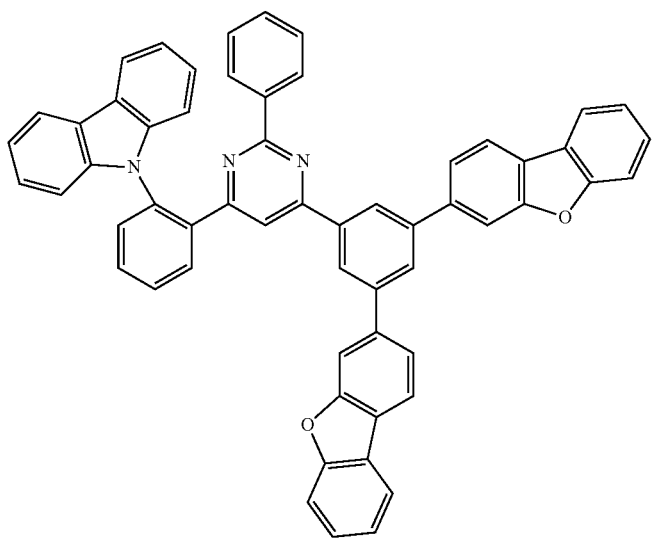
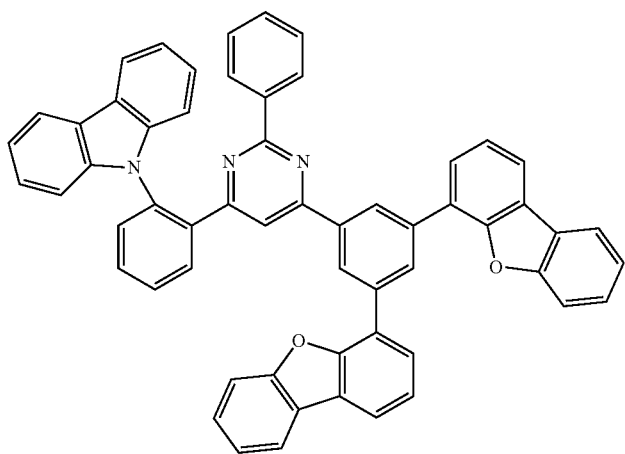

-continued
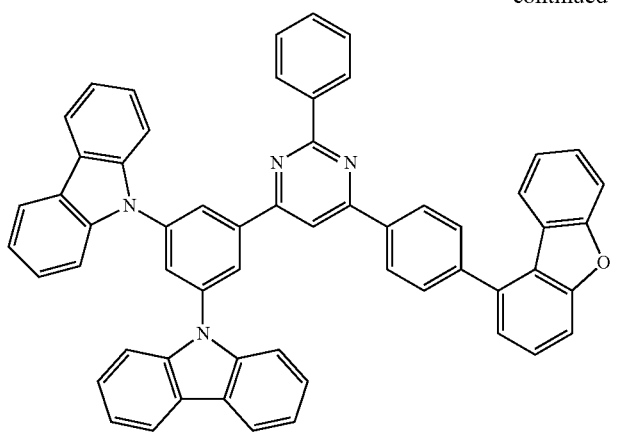
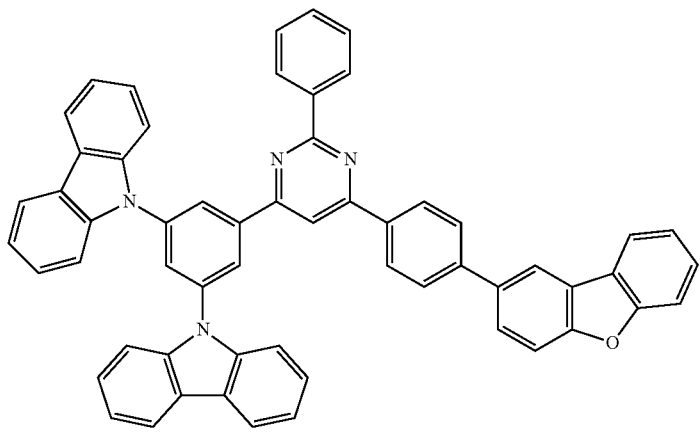
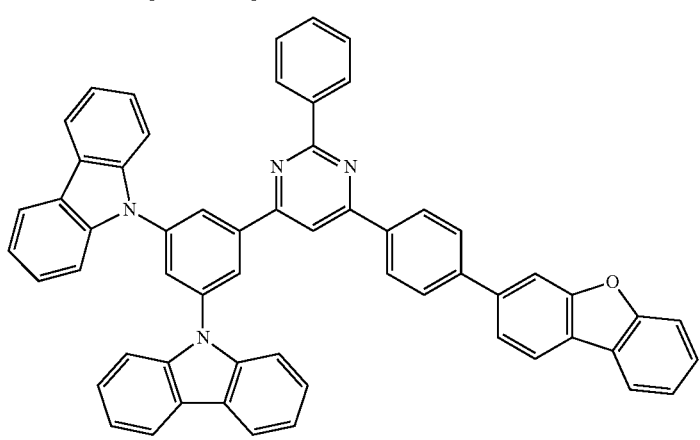
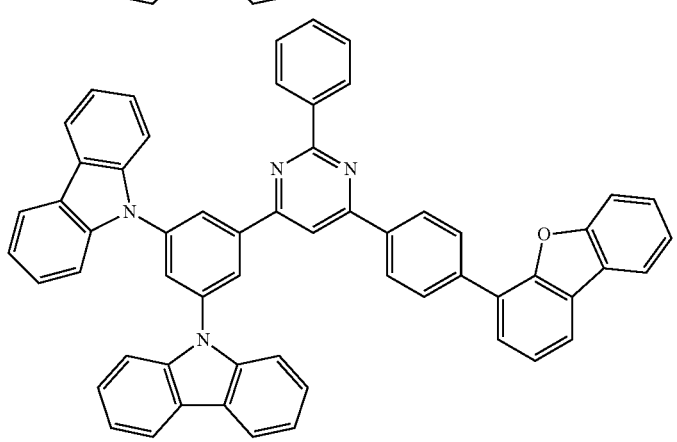

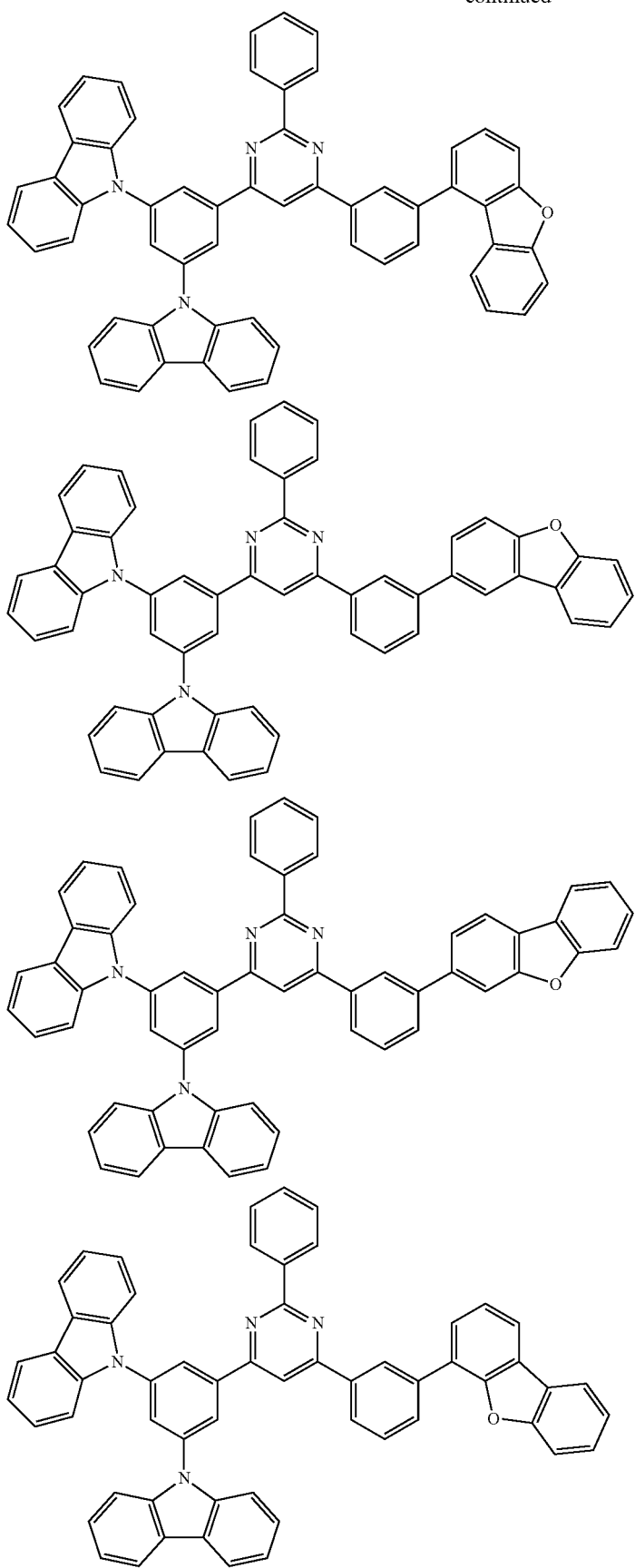

-continued
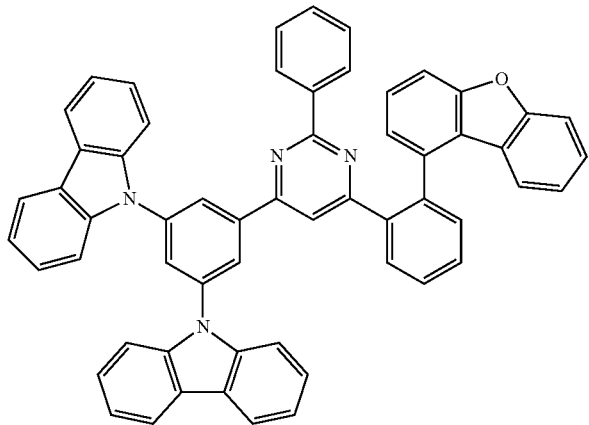
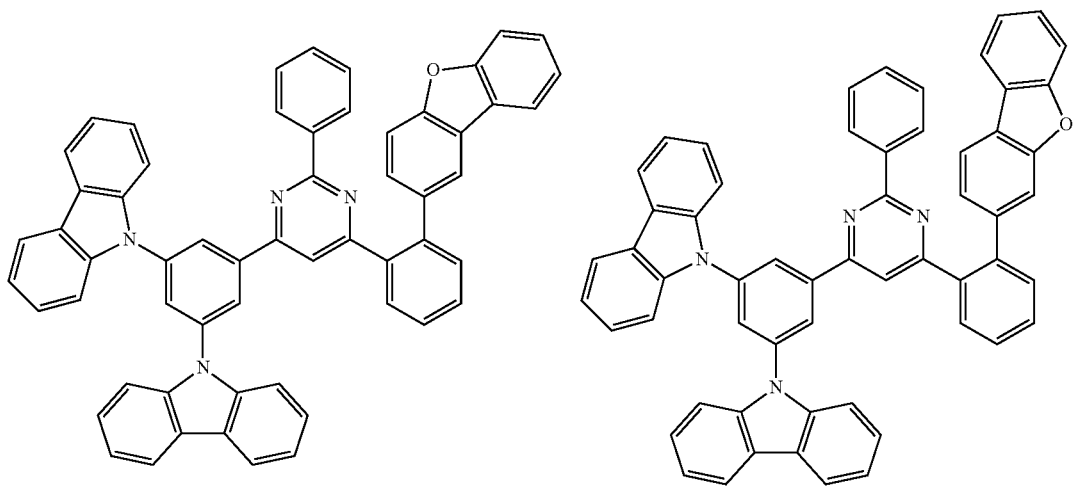
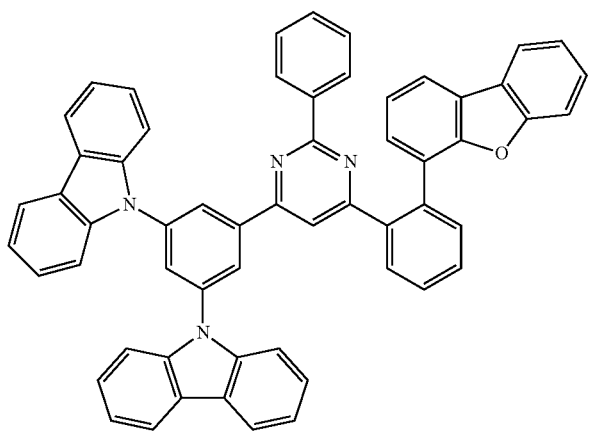

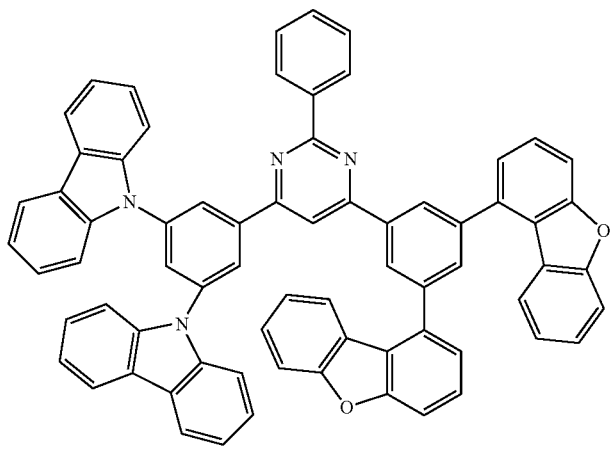
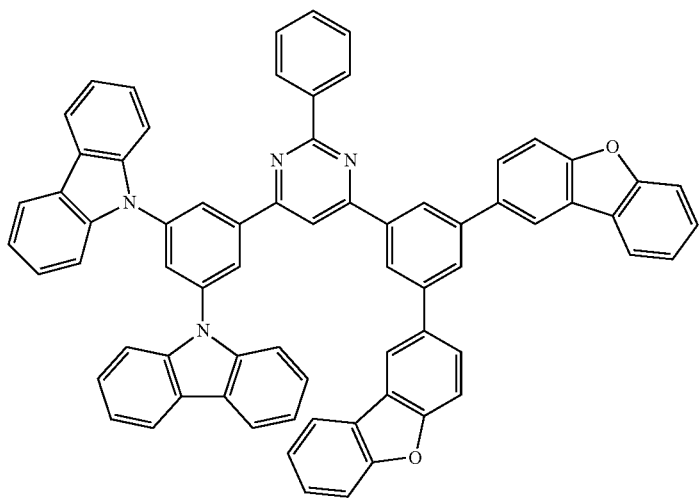
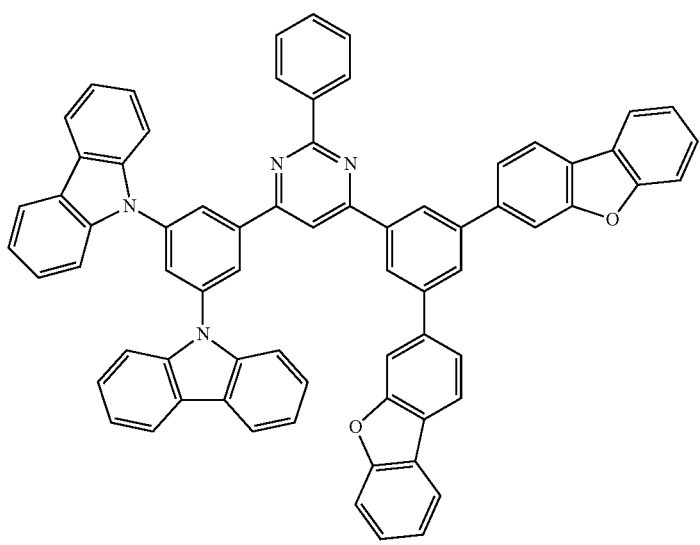

-continued
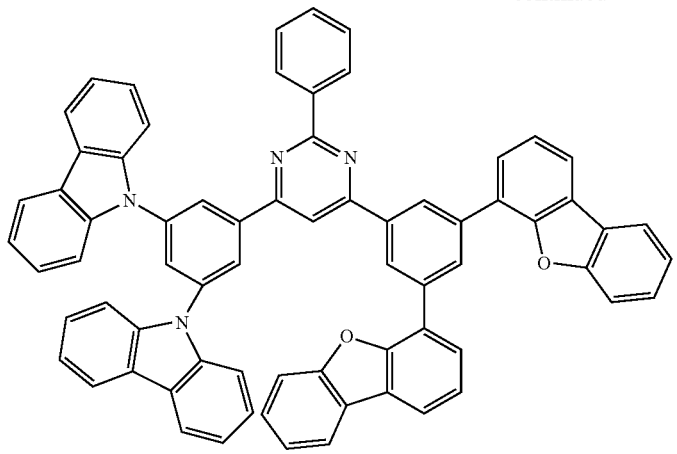
[Formula 20]
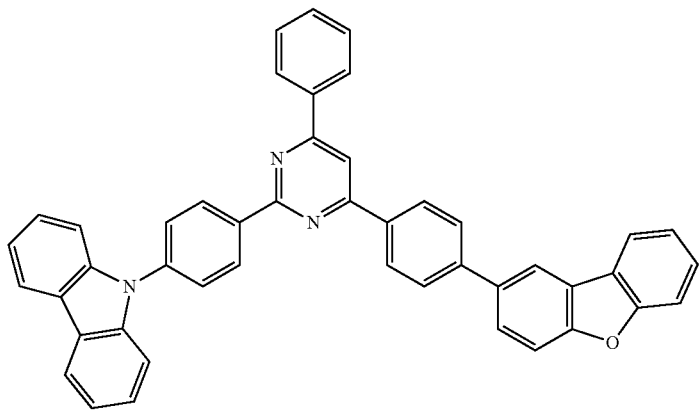
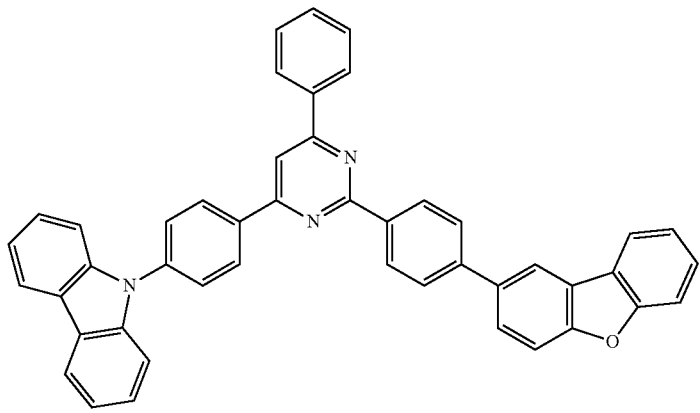
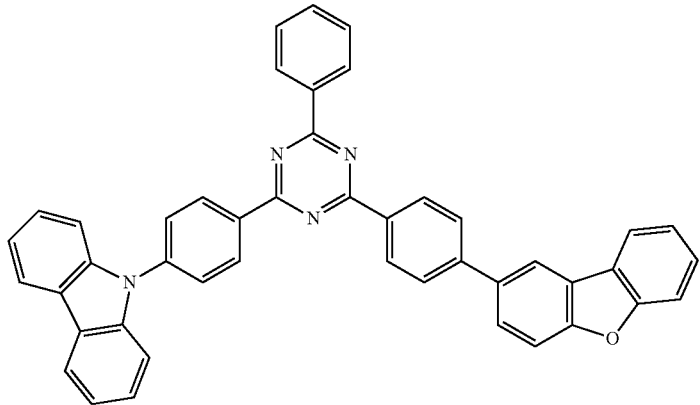

-continued
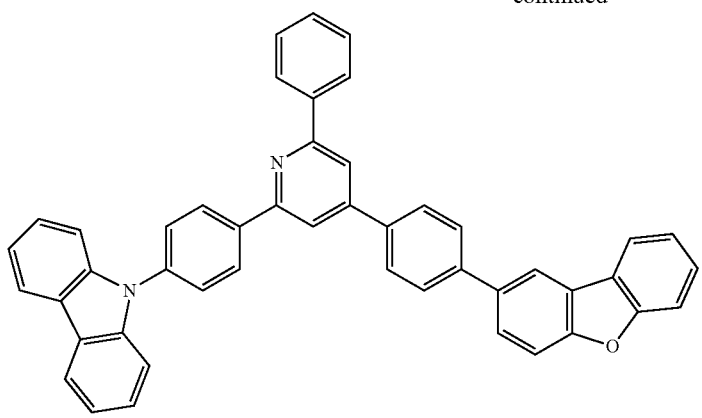
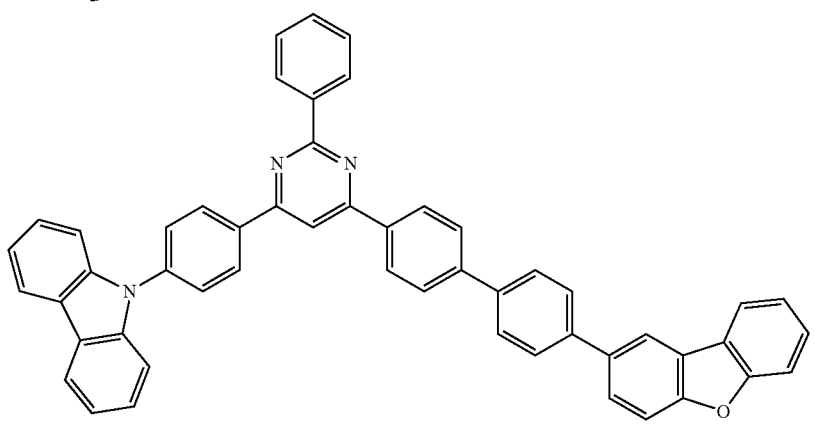
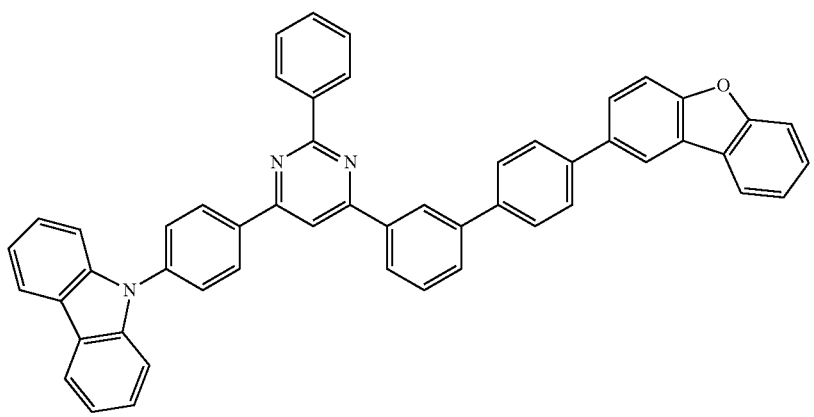
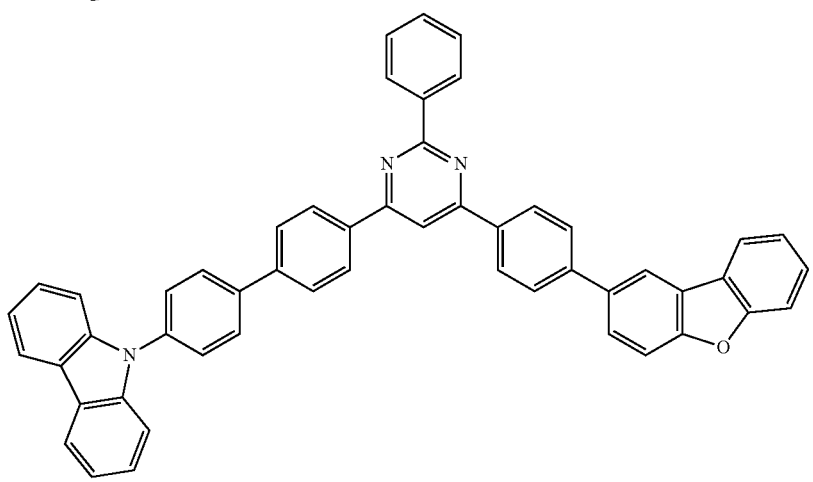

-continued
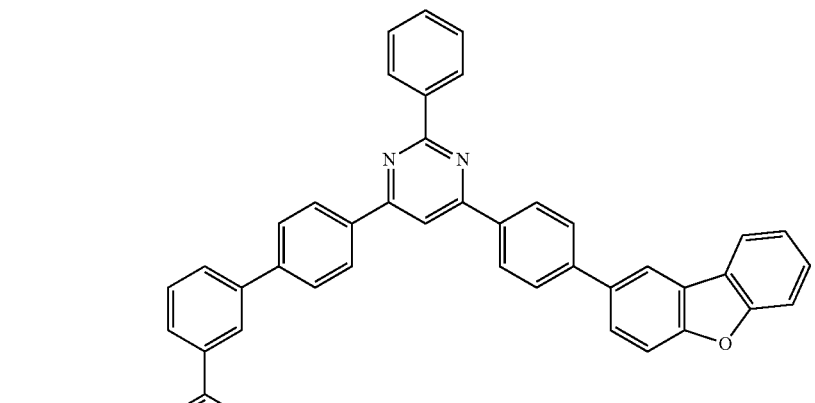
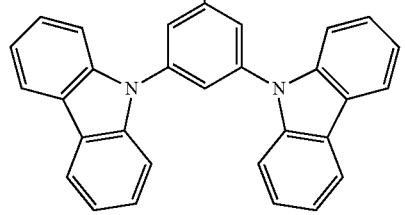
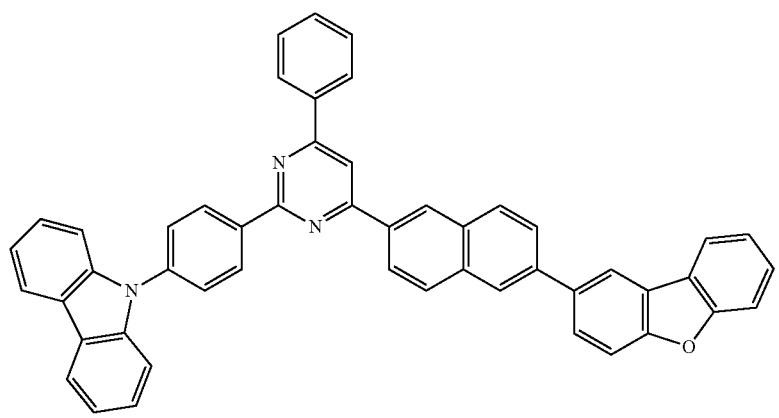
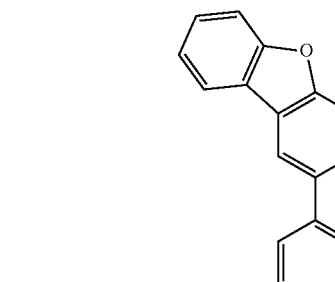
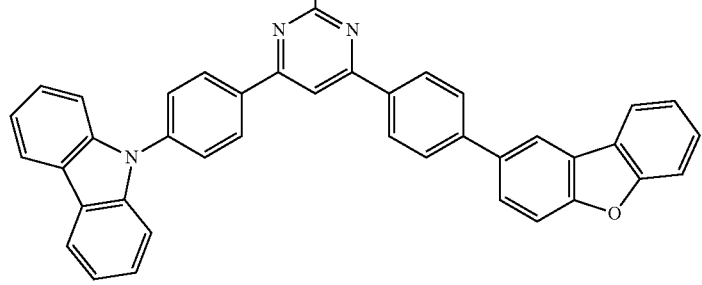

-continued
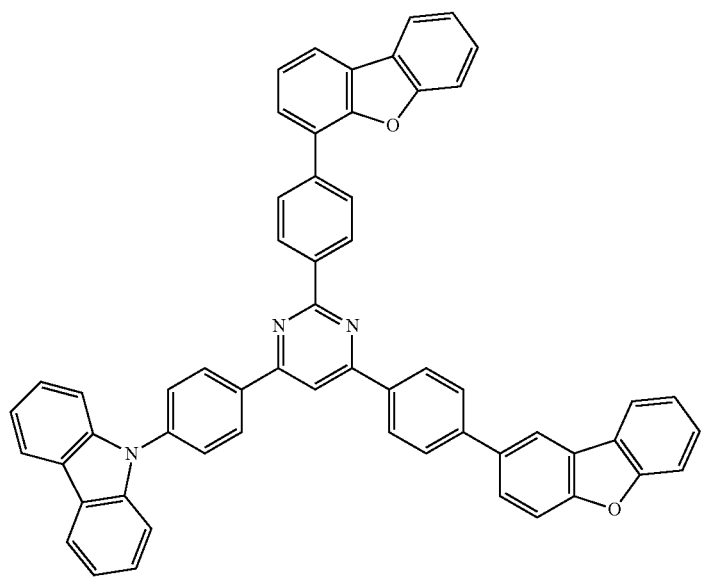
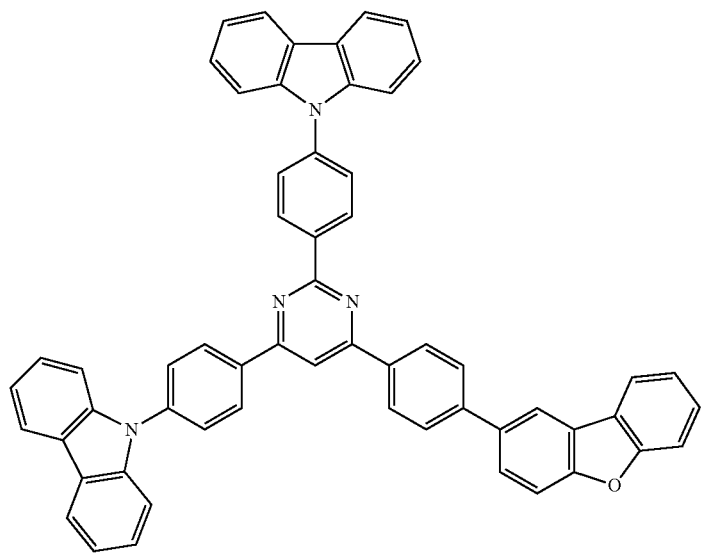

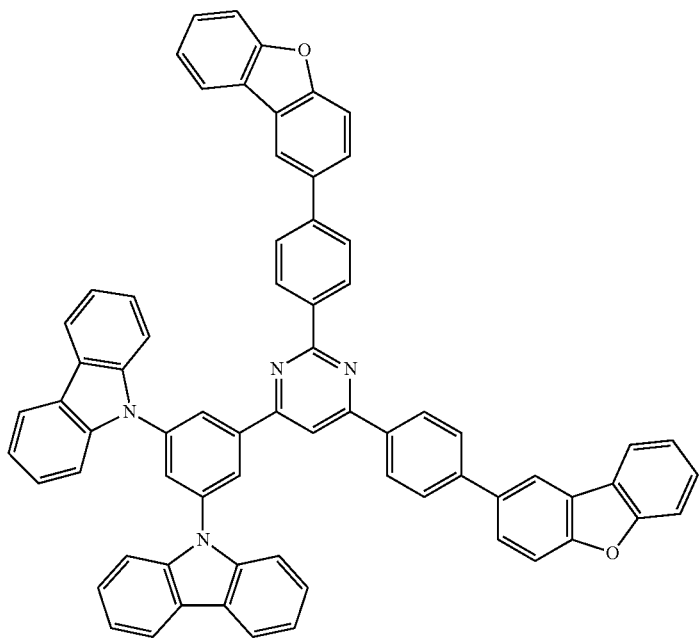
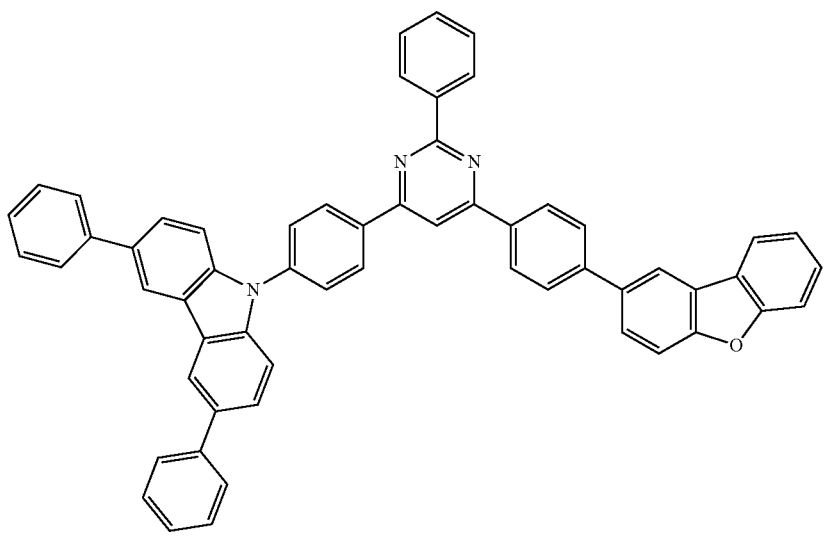
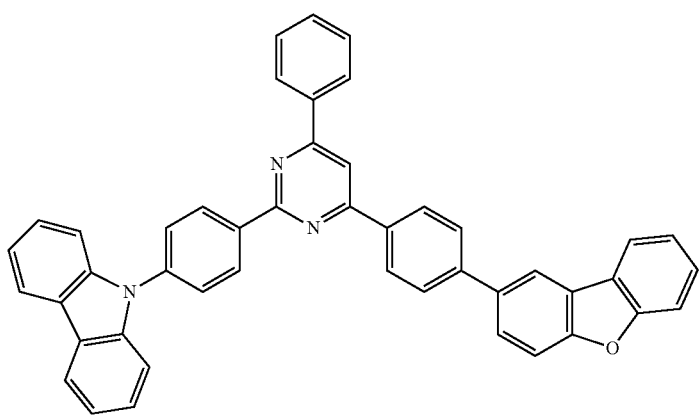

-continued
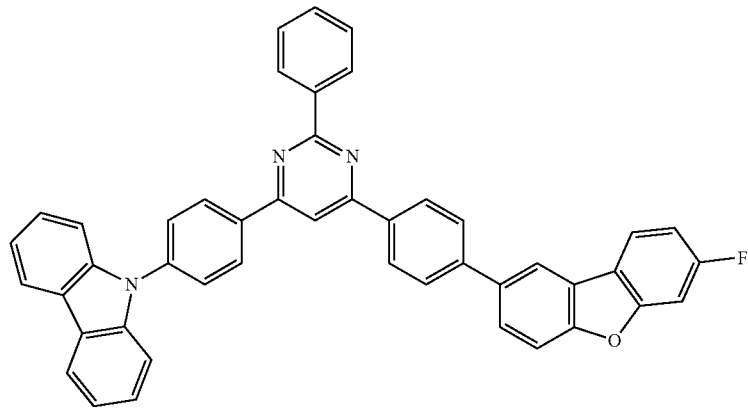
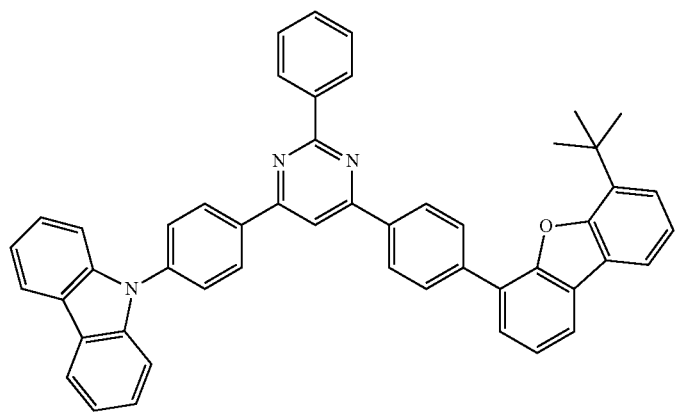
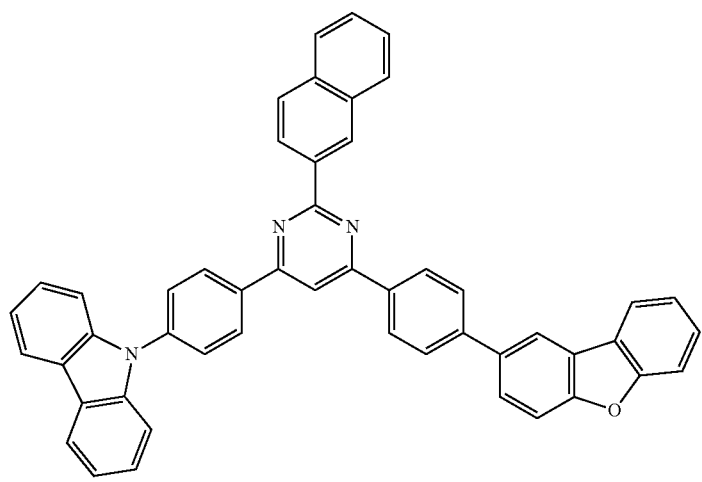

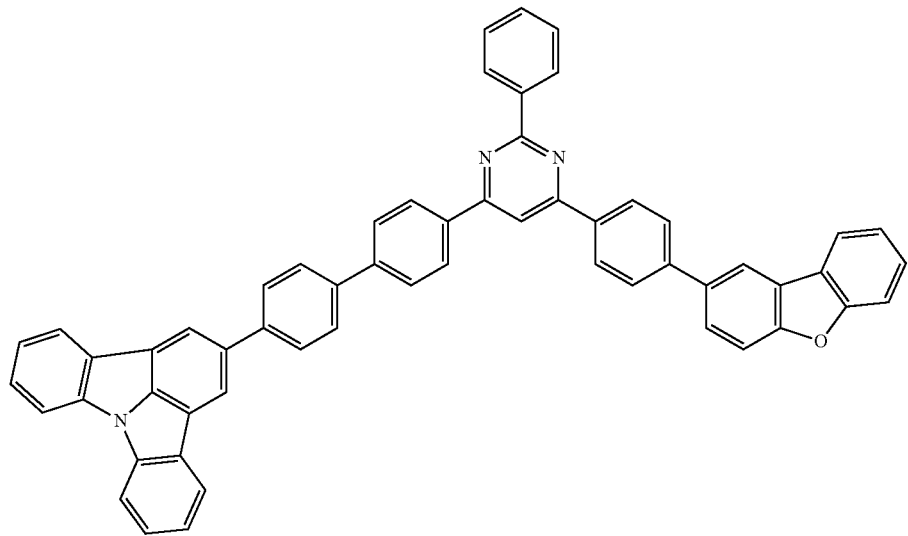
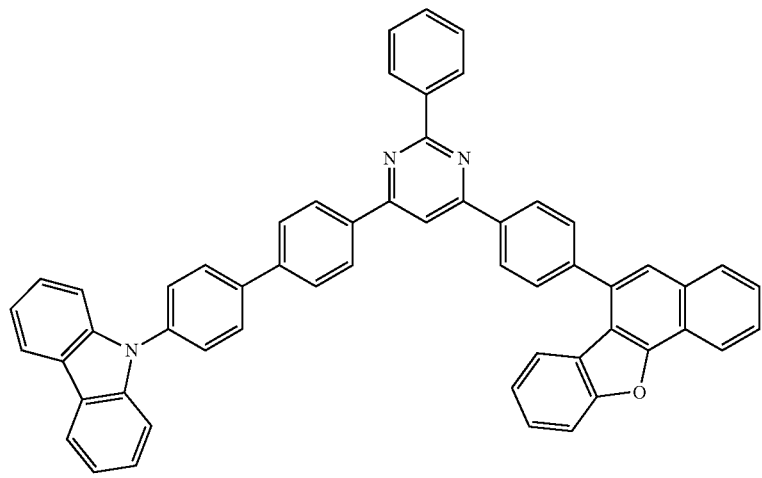
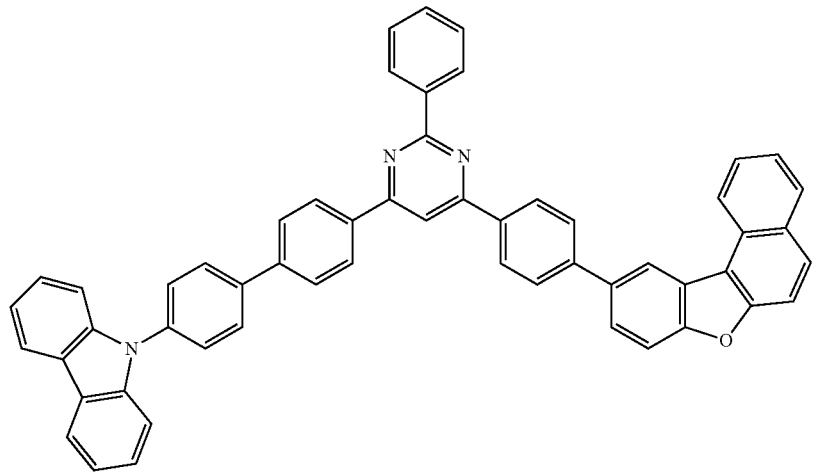

-continued
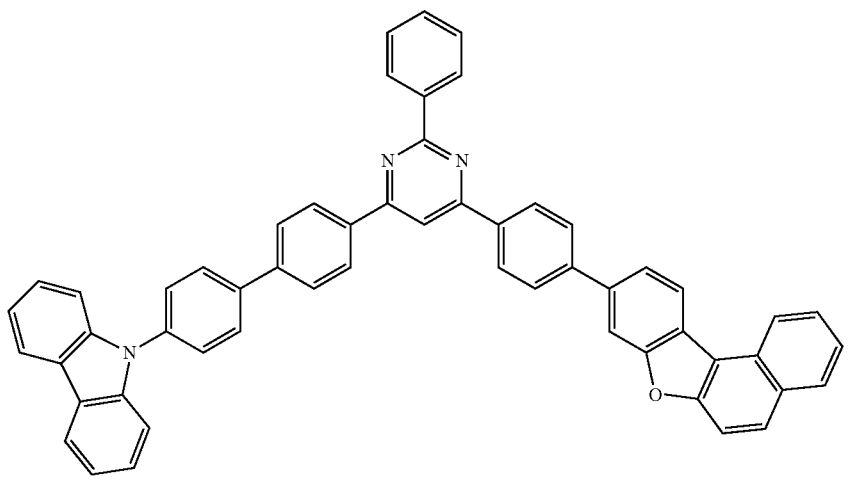
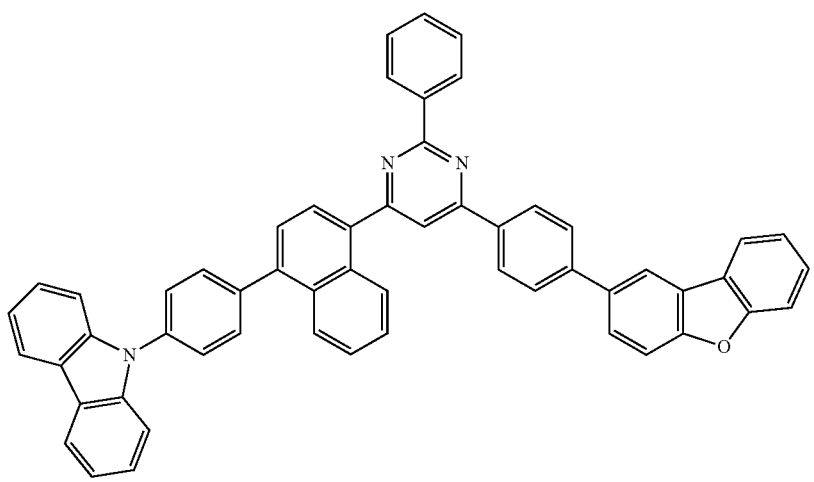
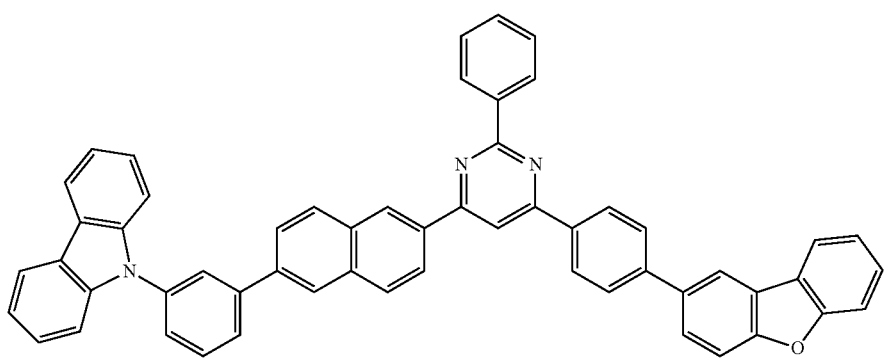
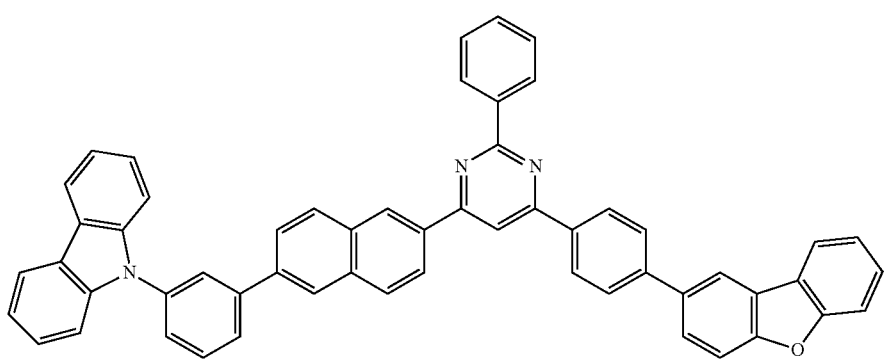

-continued
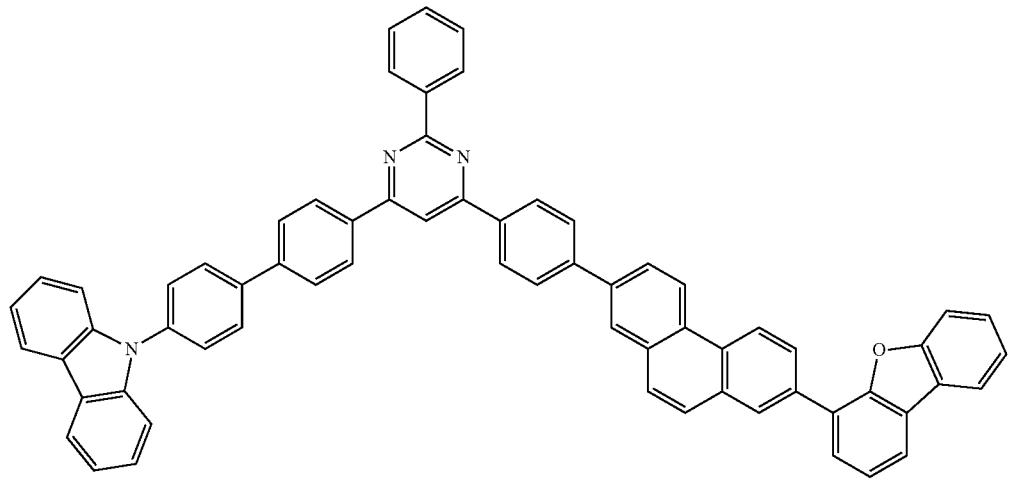
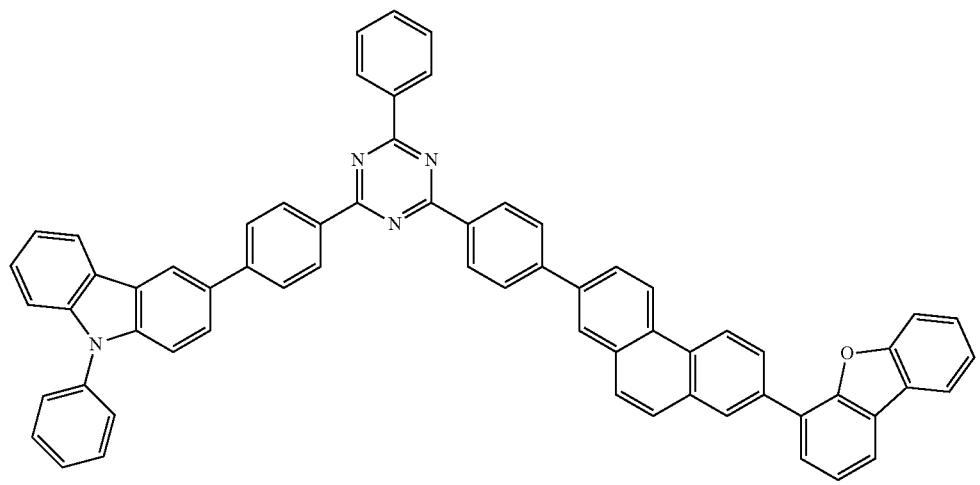
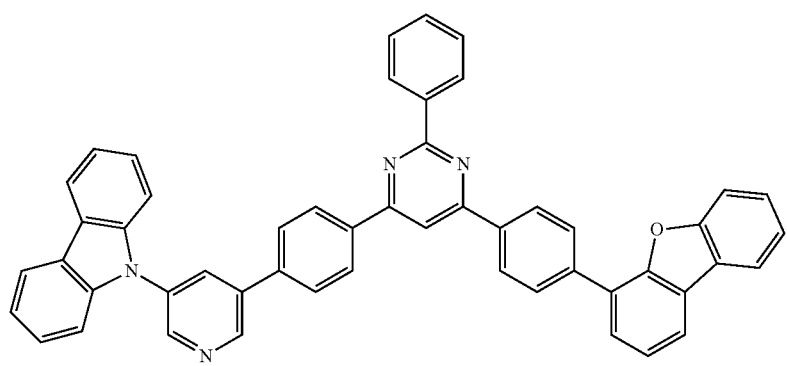

-continued
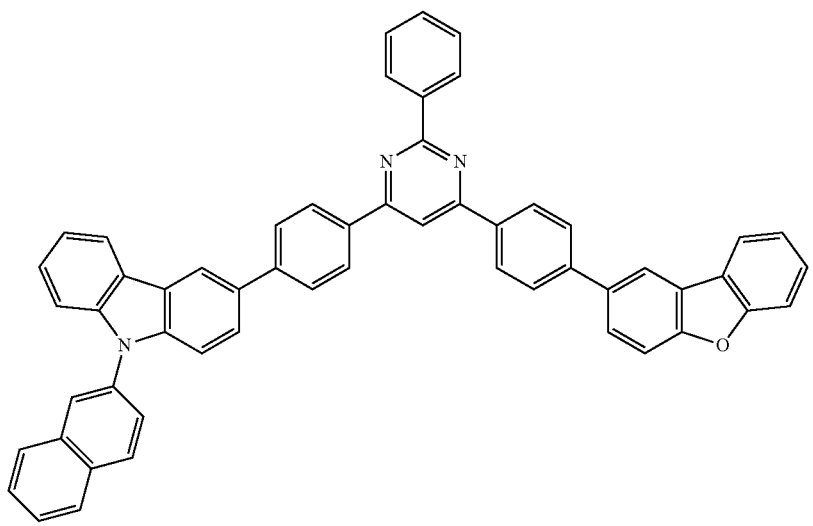
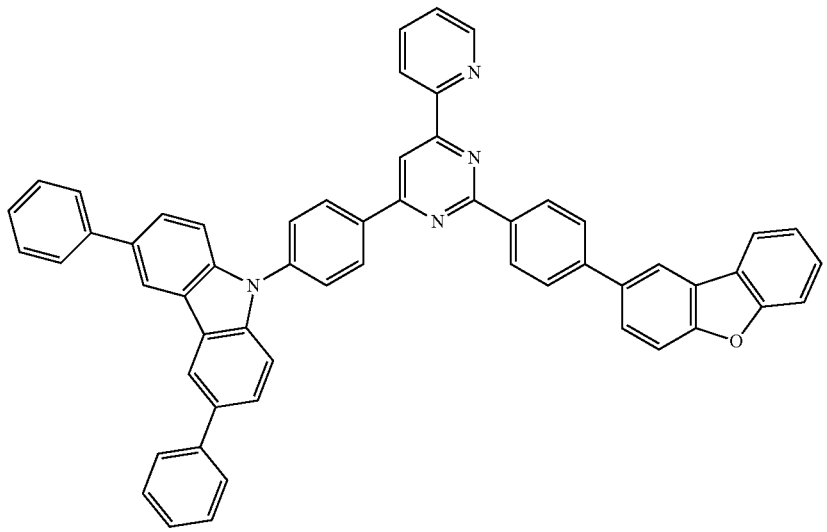
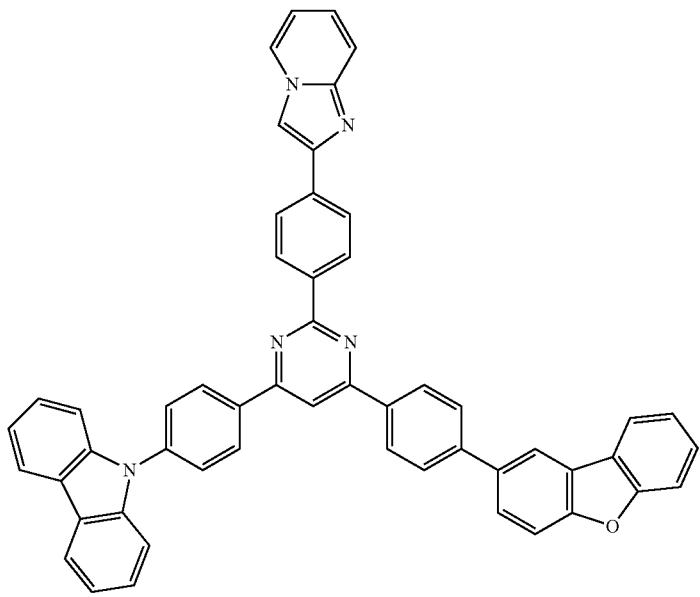

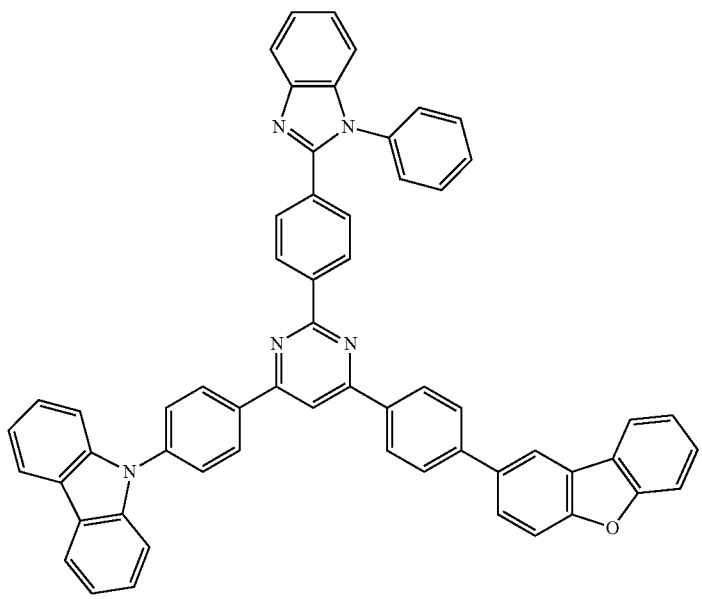
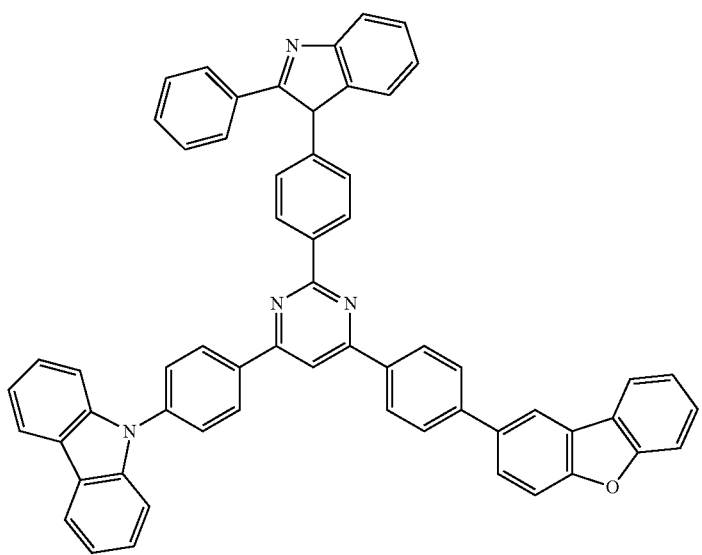

-continued
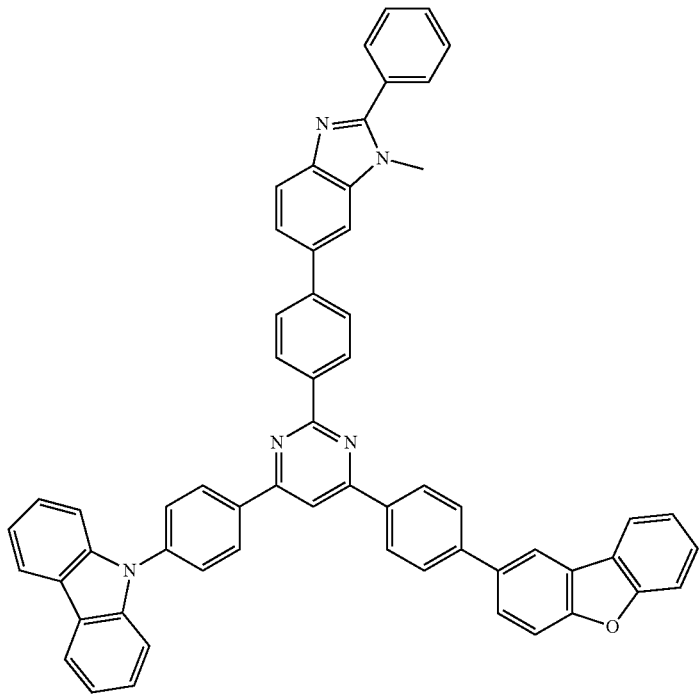
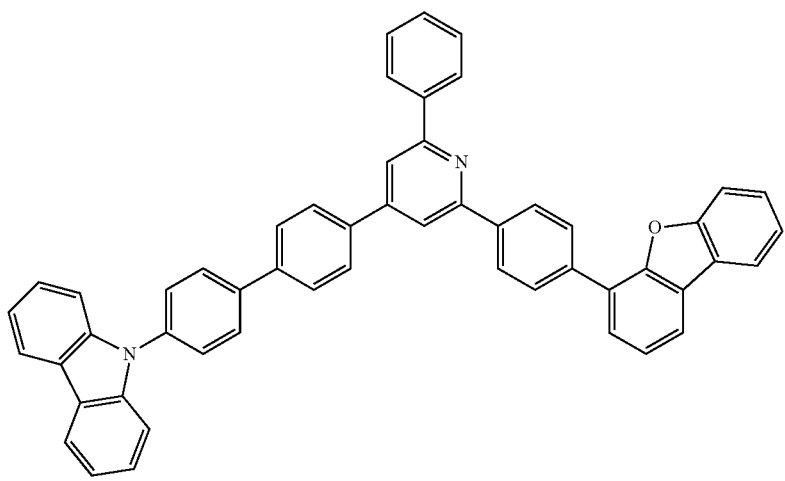
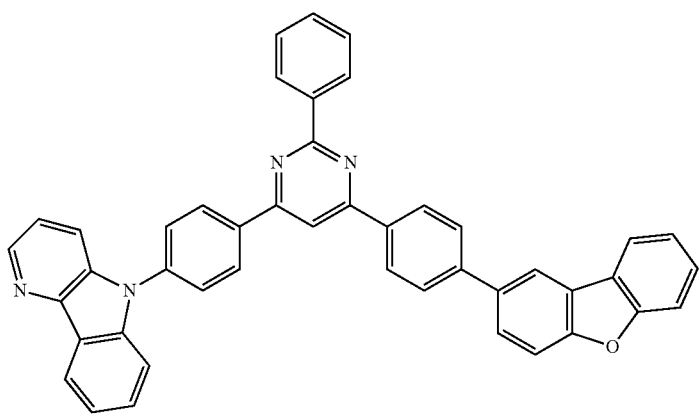

-continued
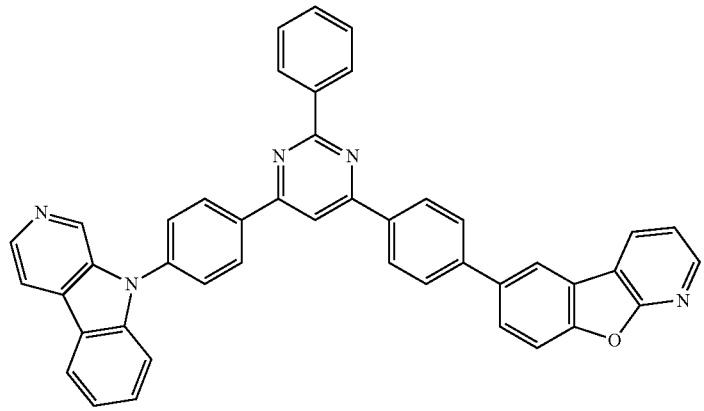
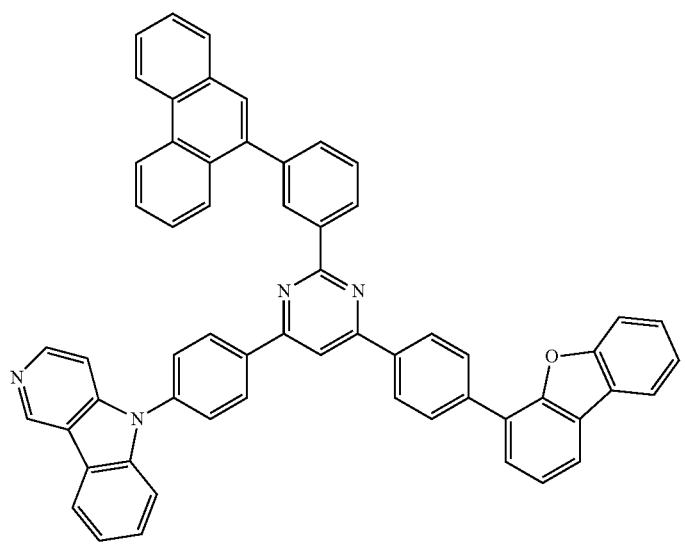
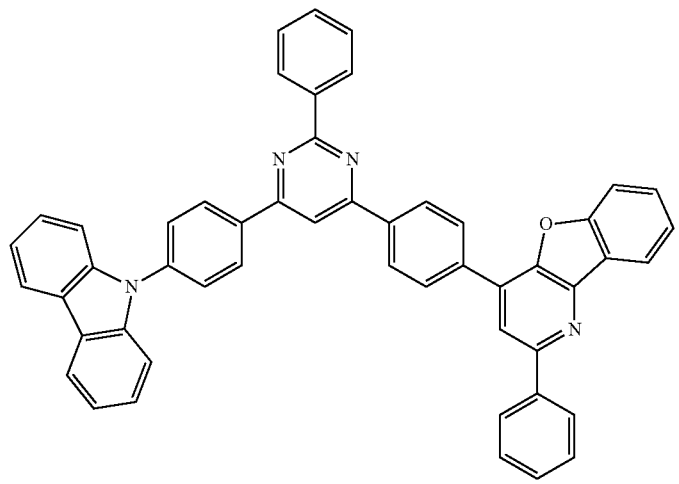

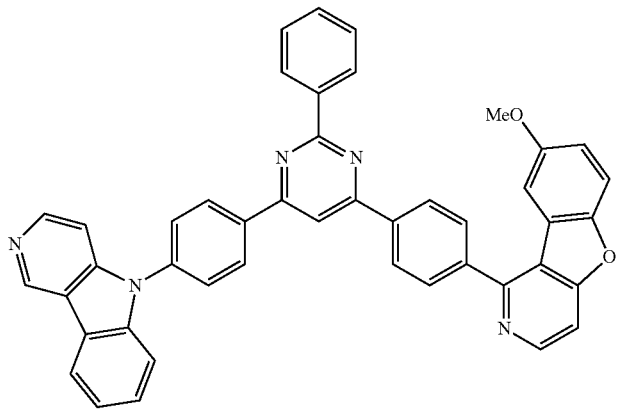
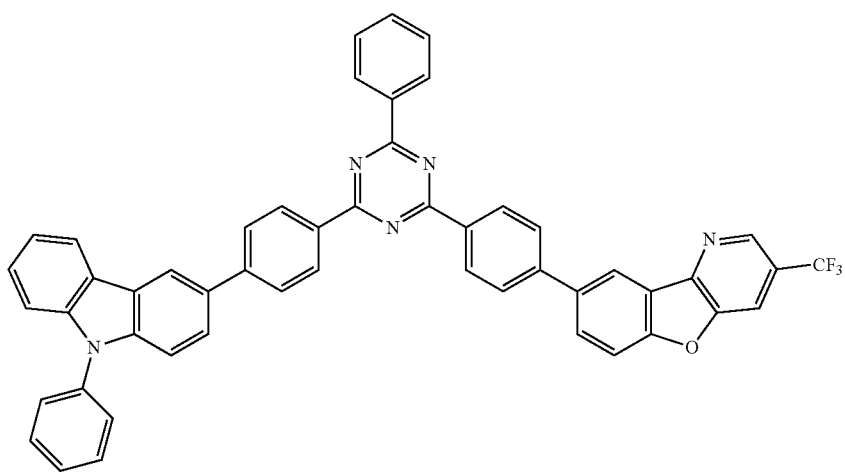
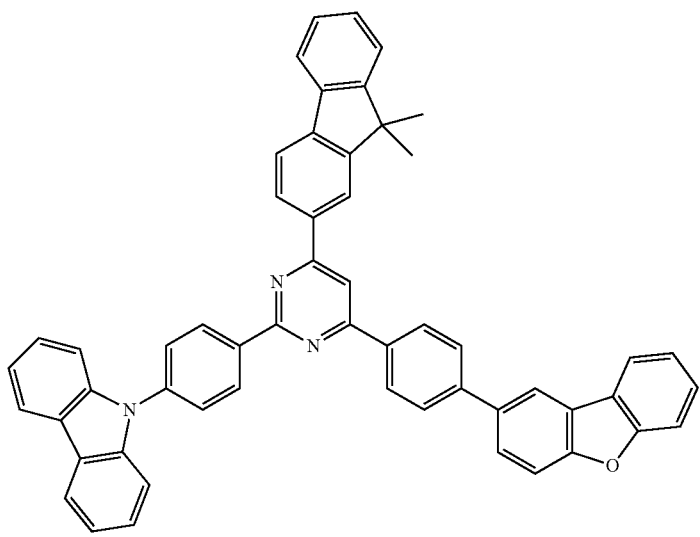

[Formula 22]
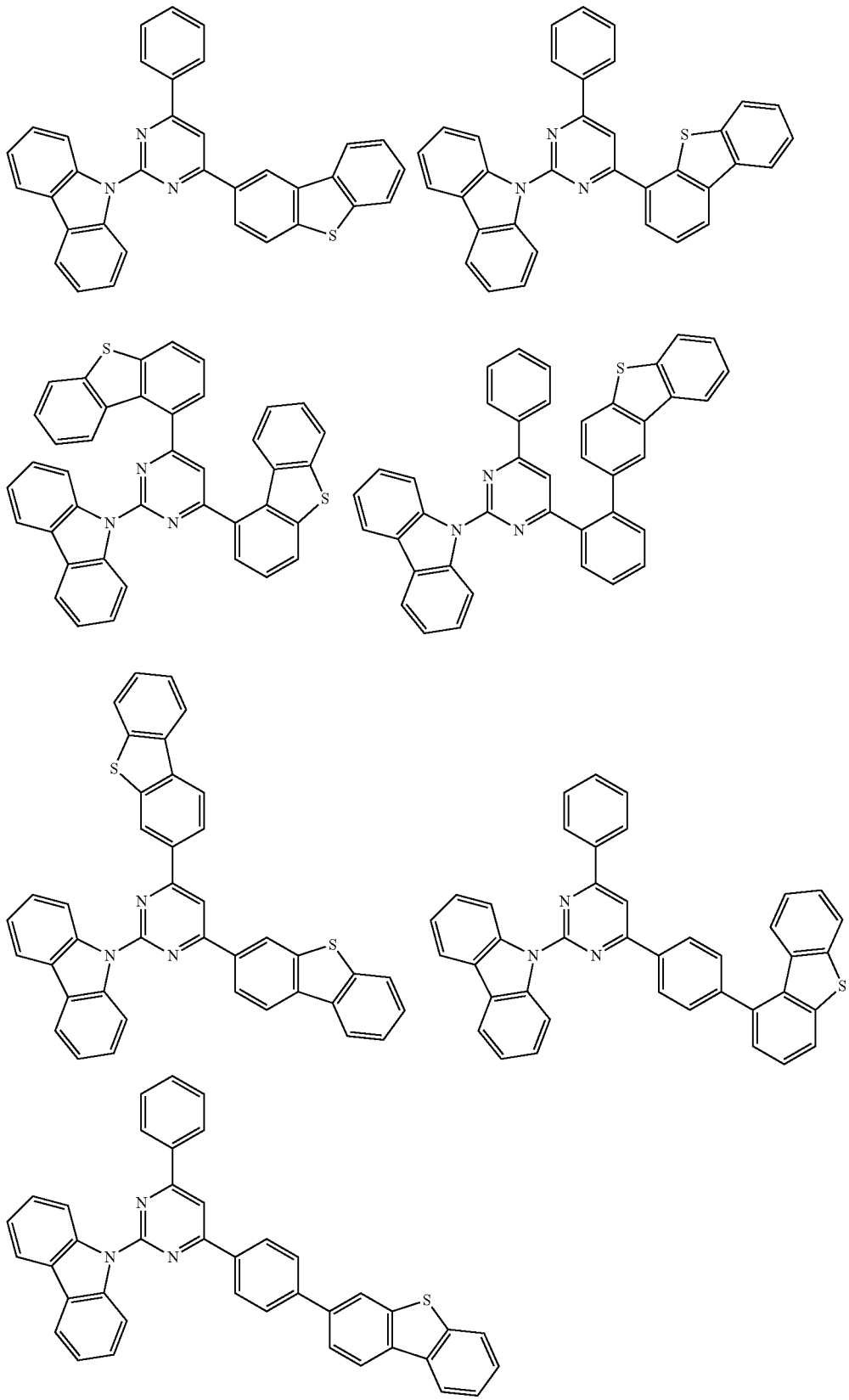

-continued
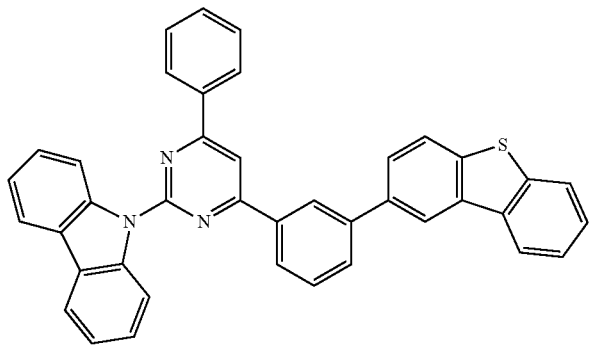
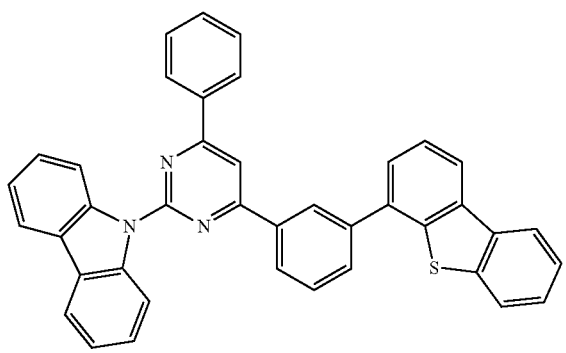
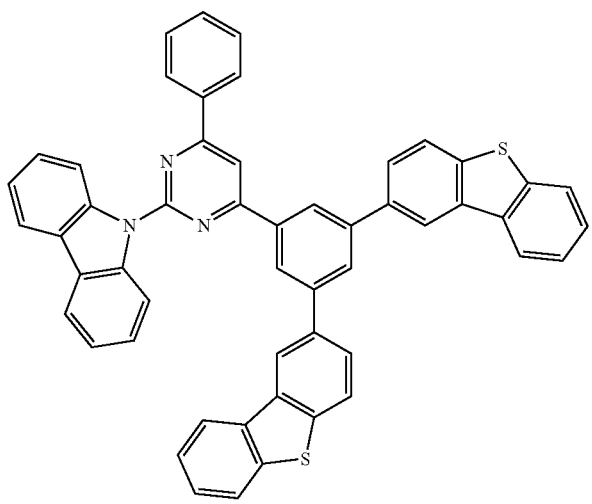
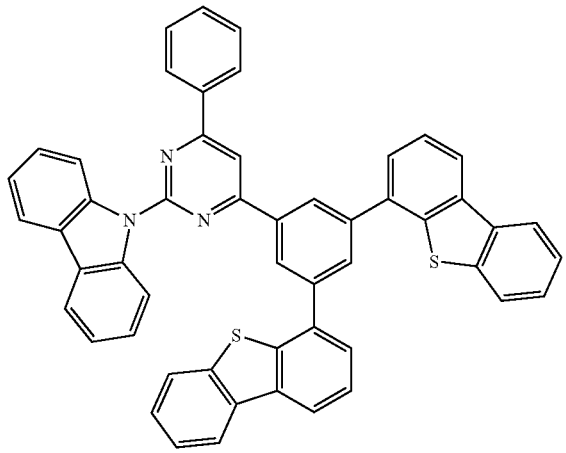

-continued
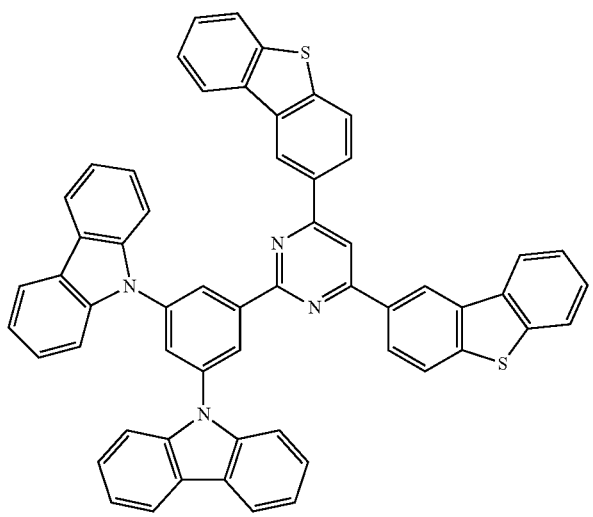
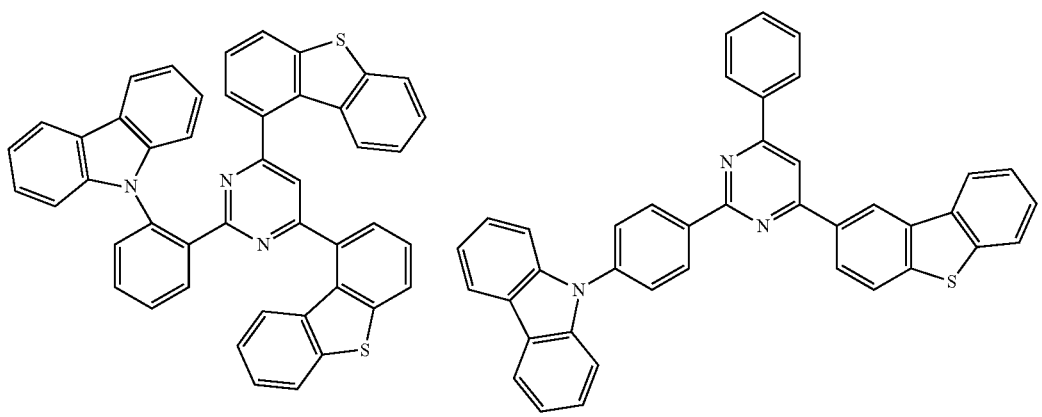
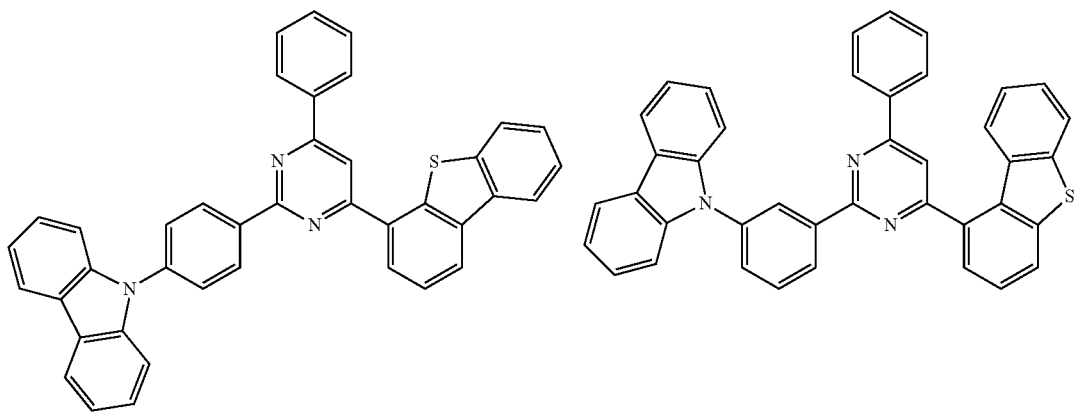
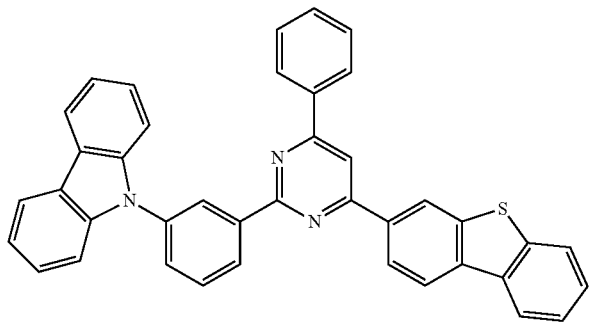

101
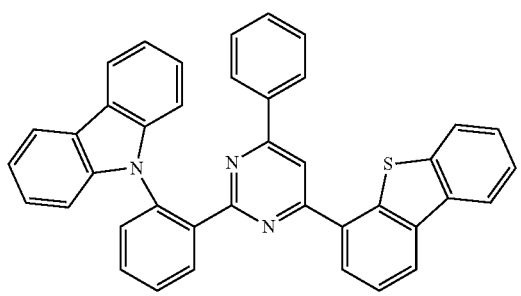
102
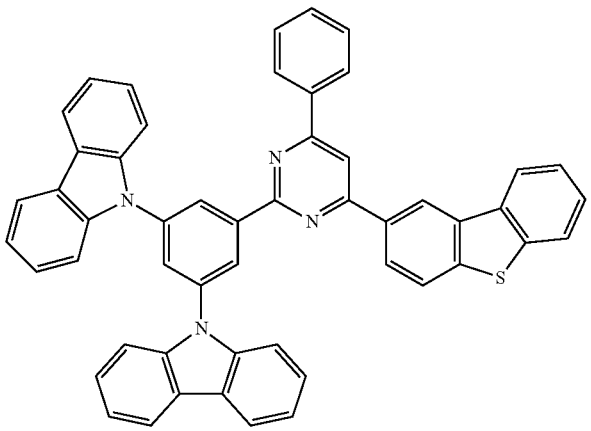
-continued
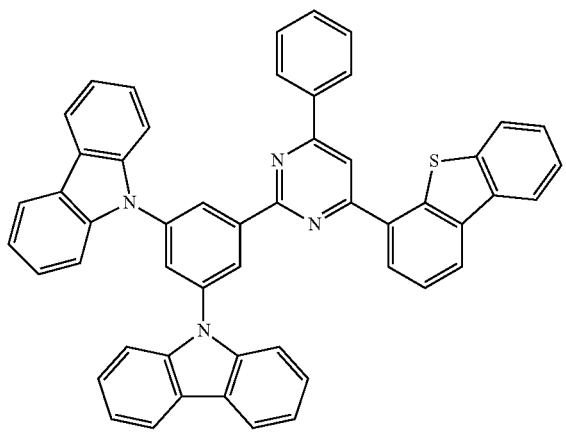
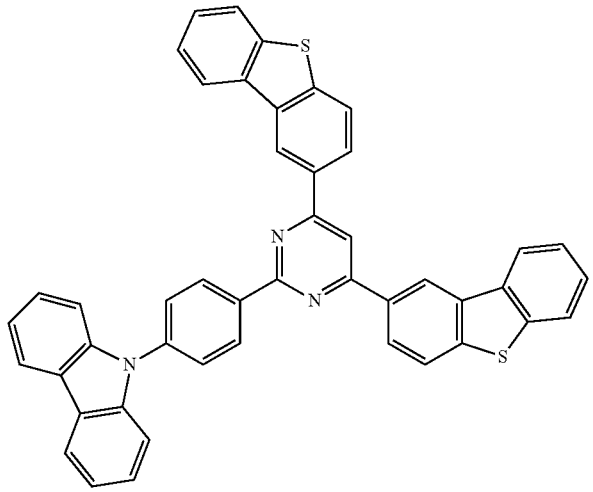
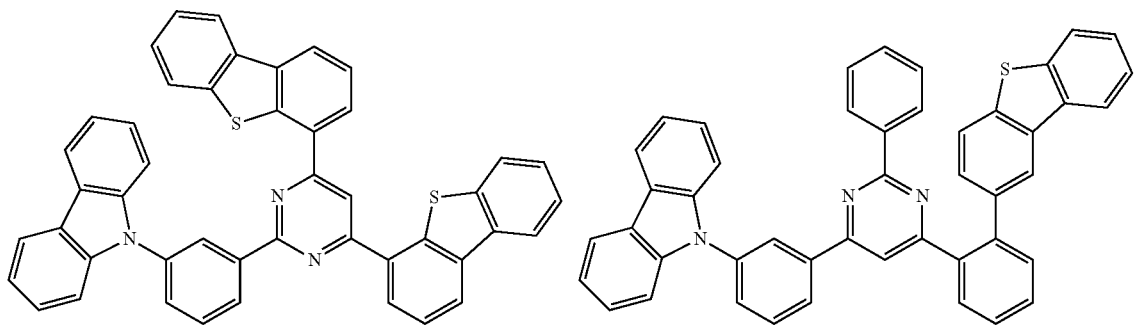

-continued
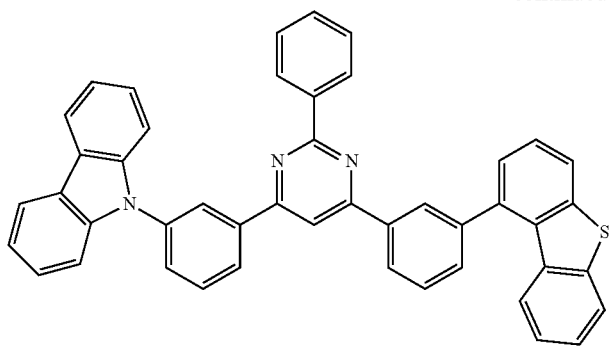
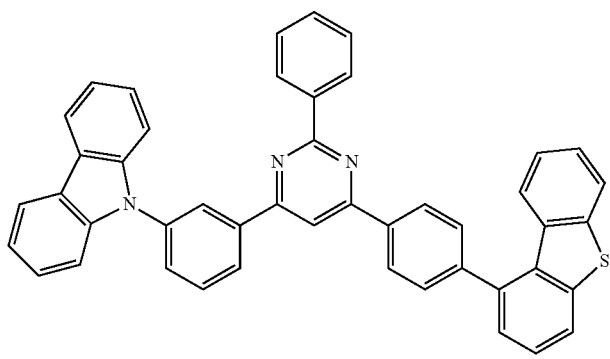
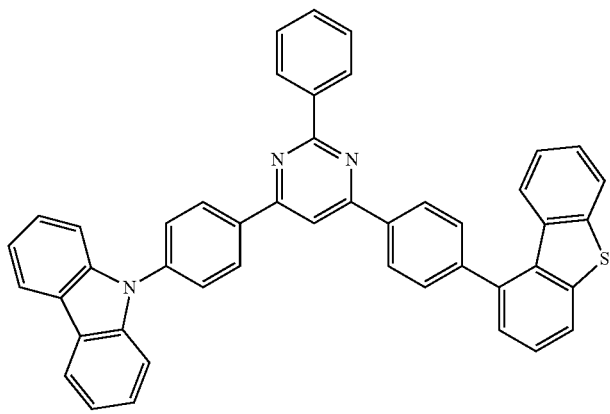
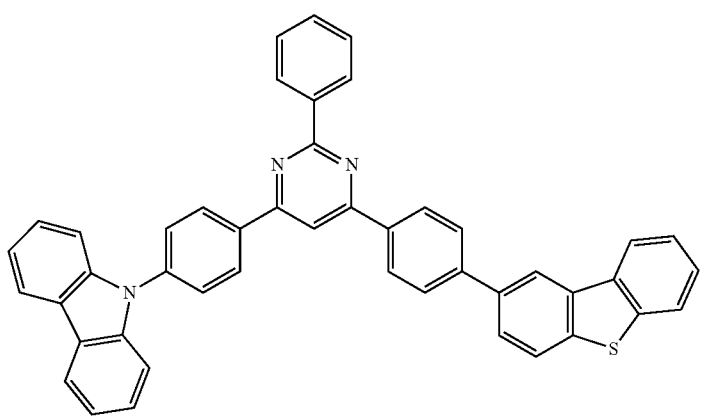

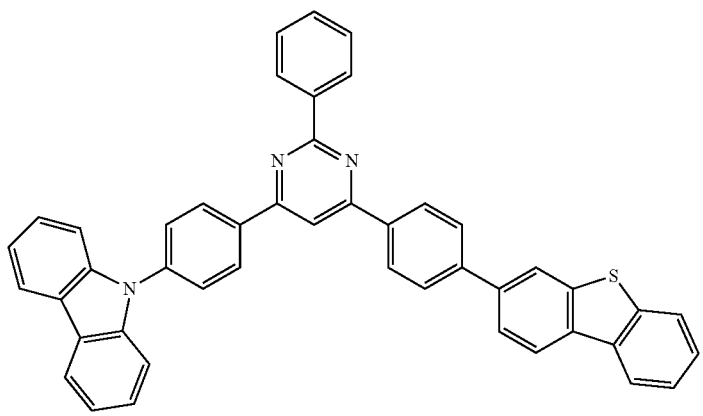
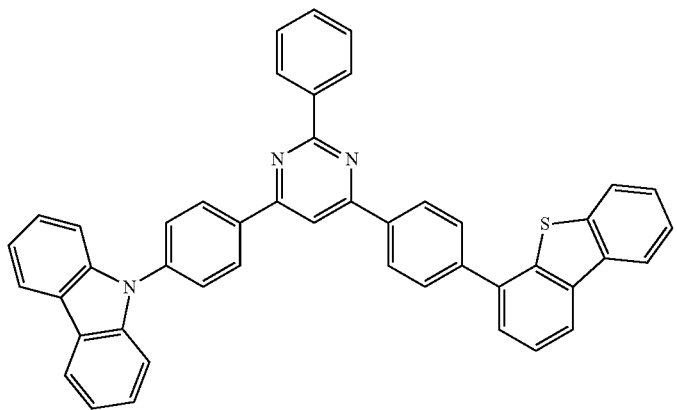
[Formula 23]
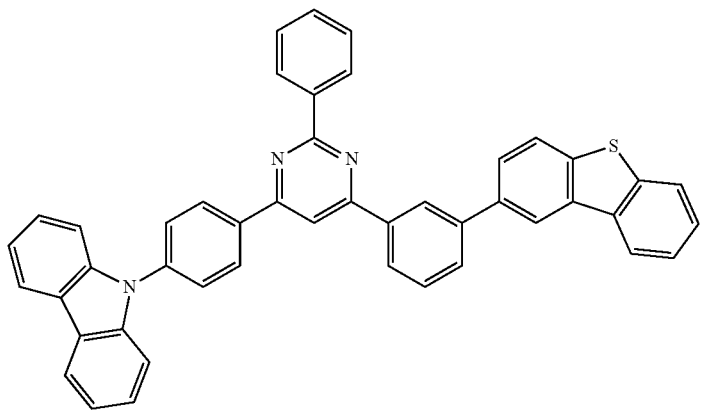
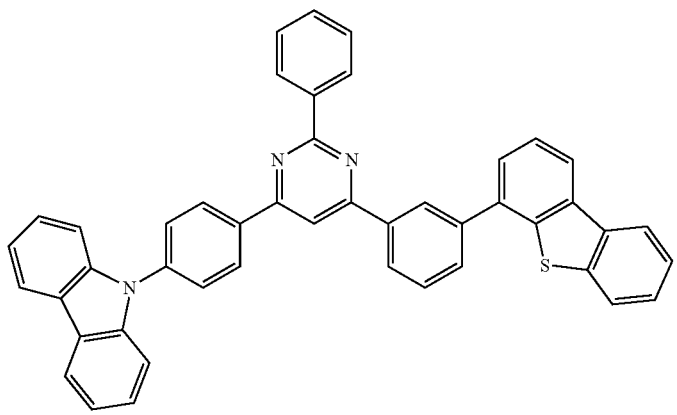

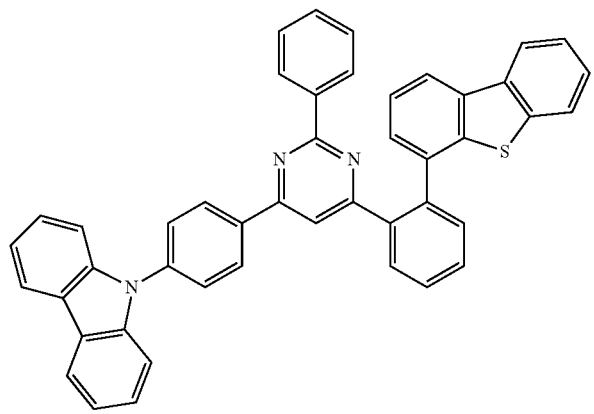
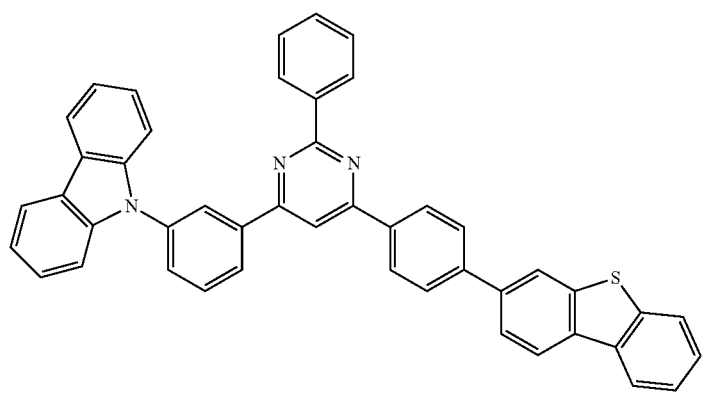
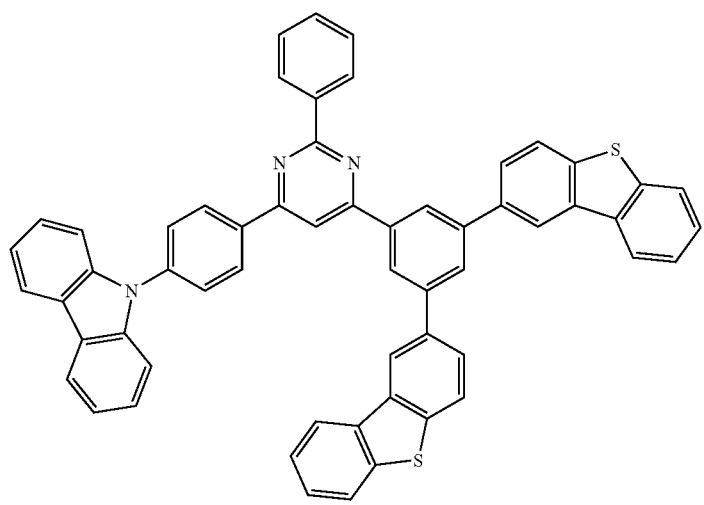

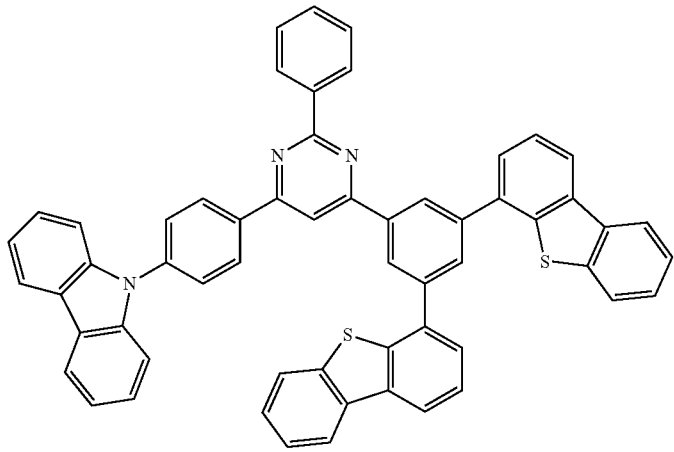
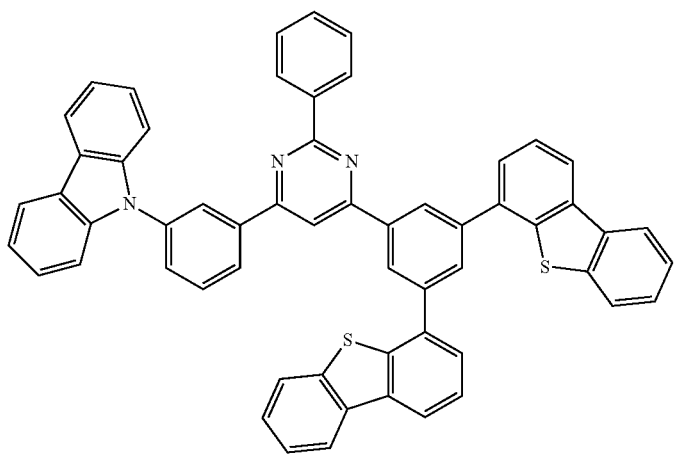
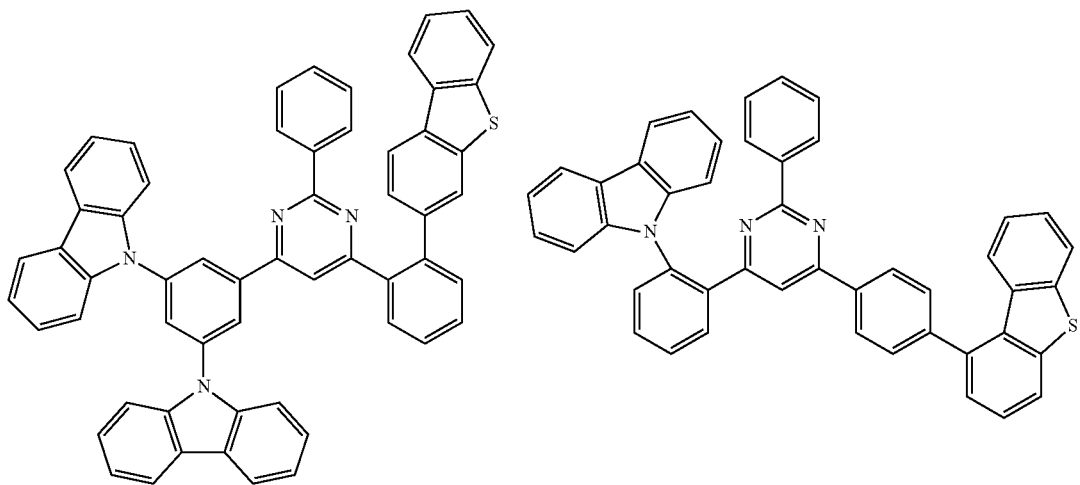

-continued
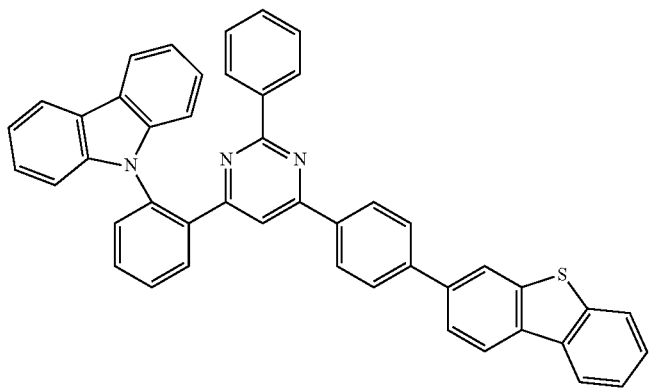
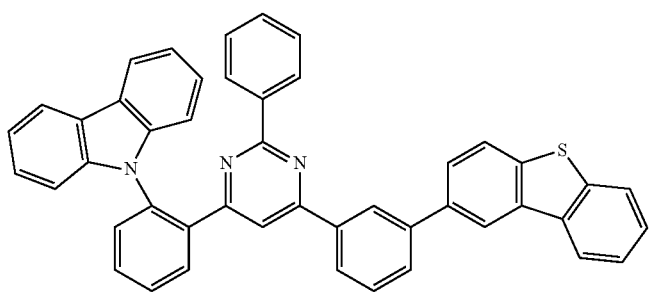
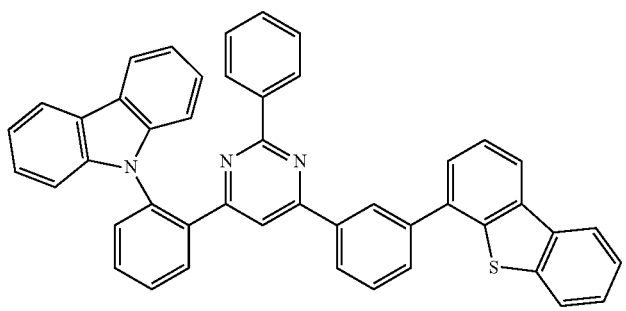
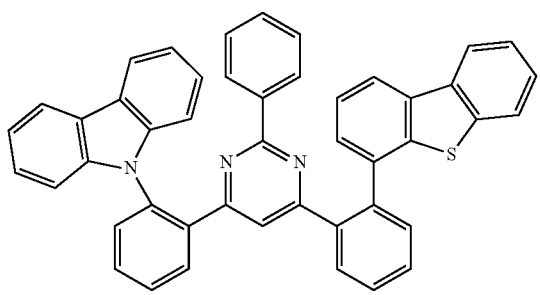

-continued
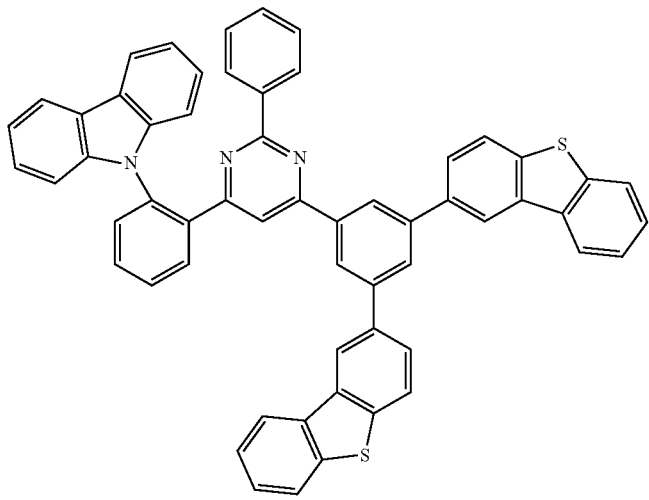
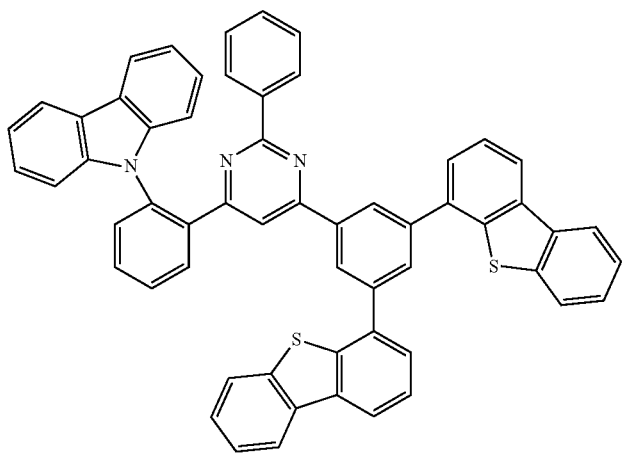
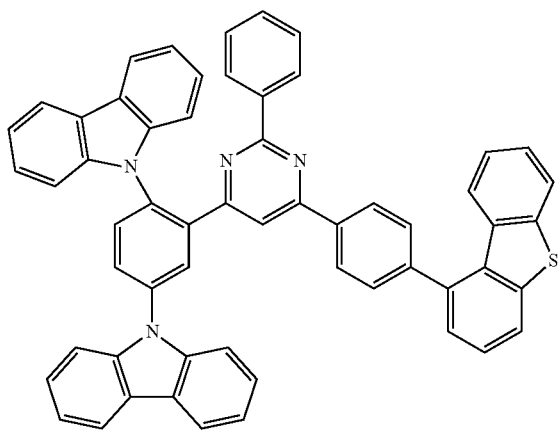

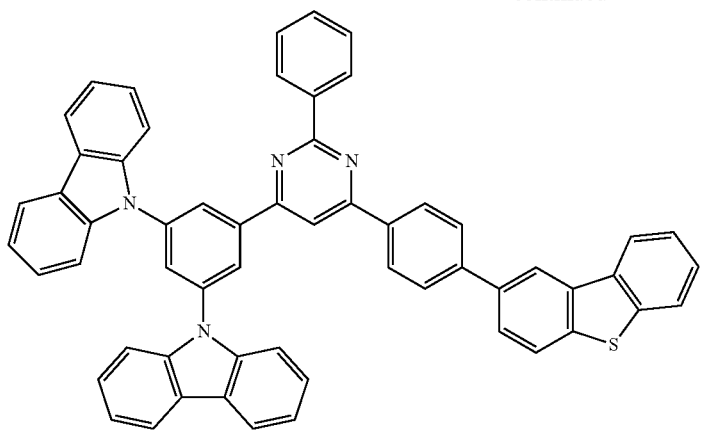
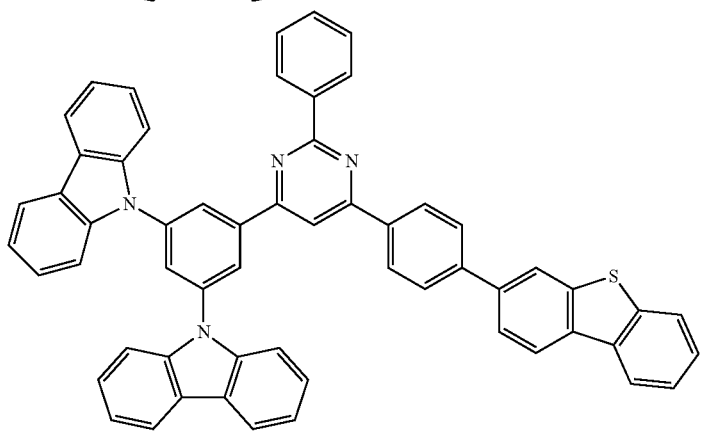
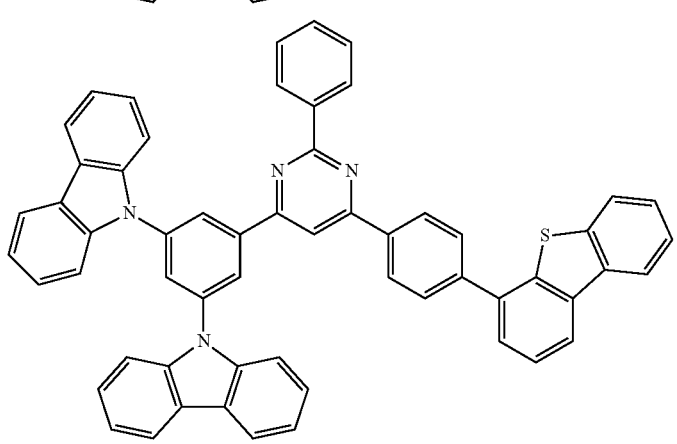
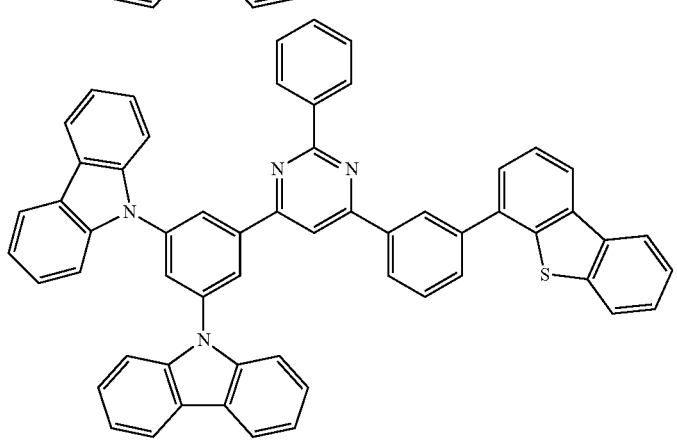

-continued
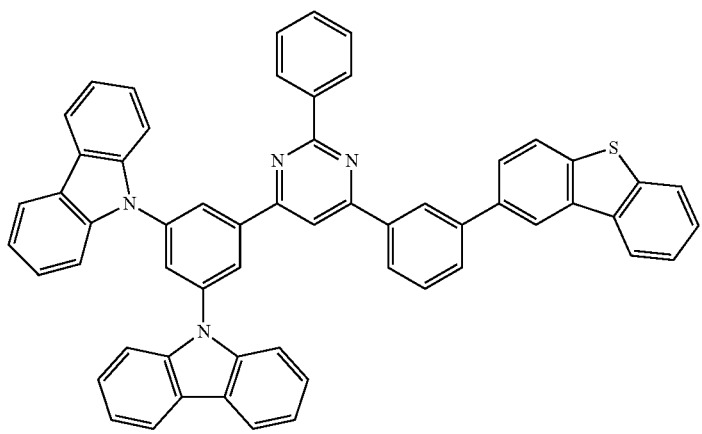
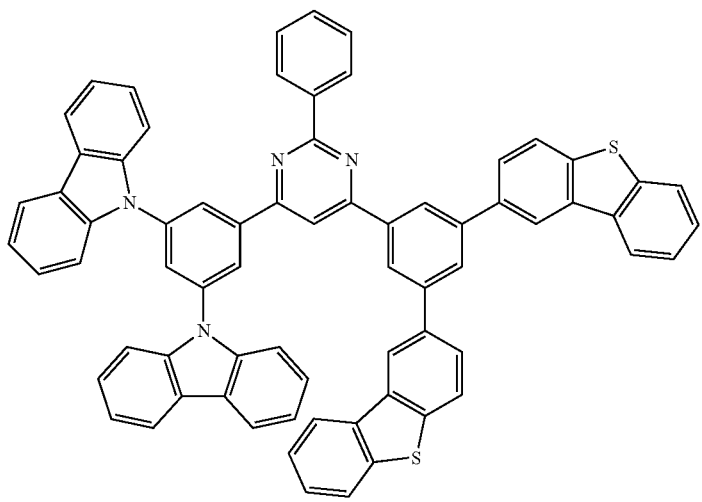
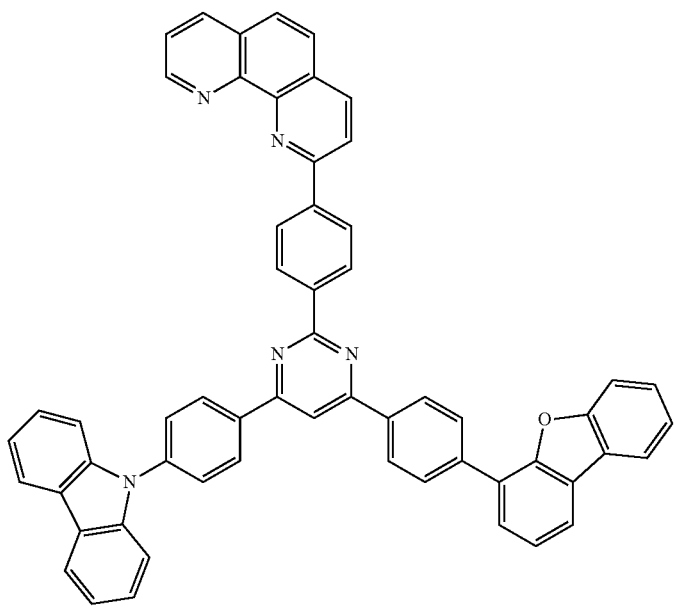

[Formula 24]
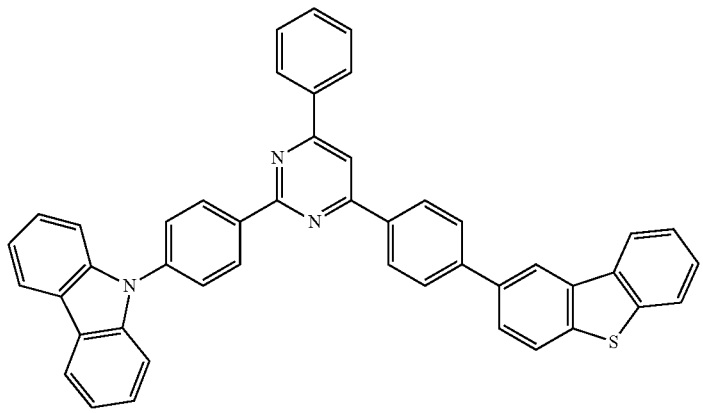
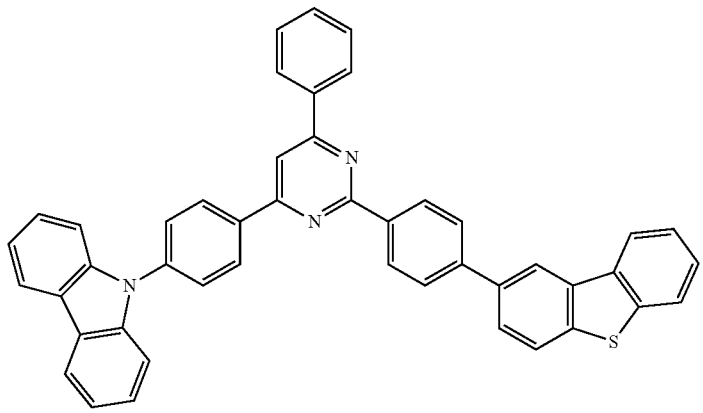
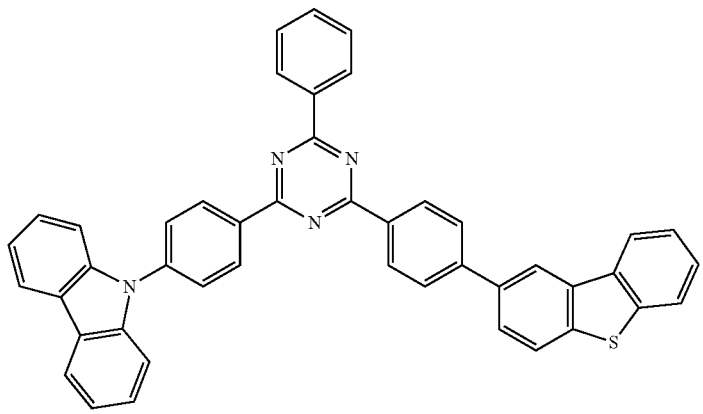
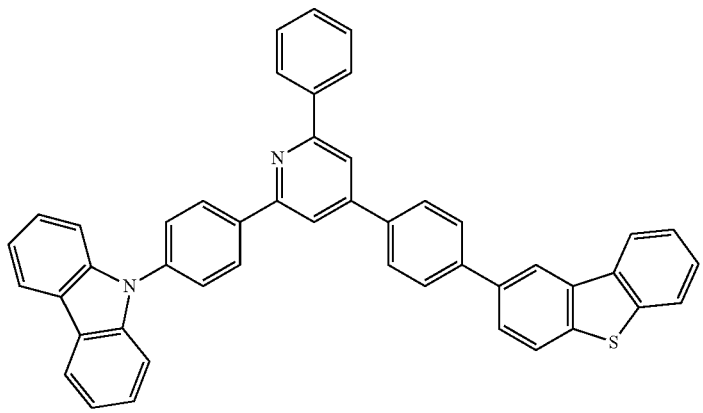

-continued
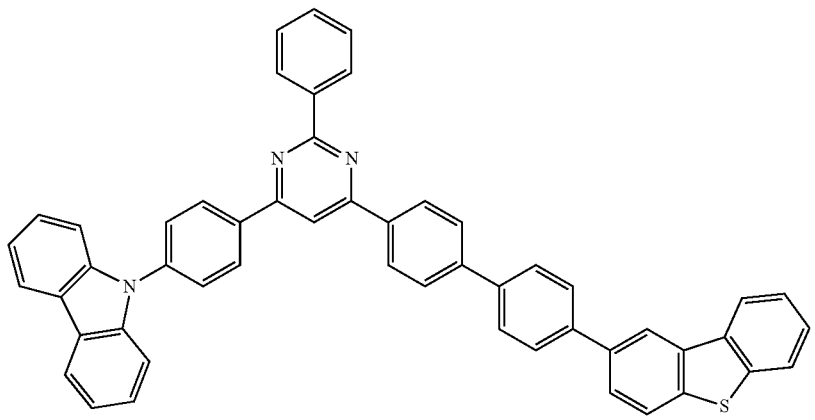
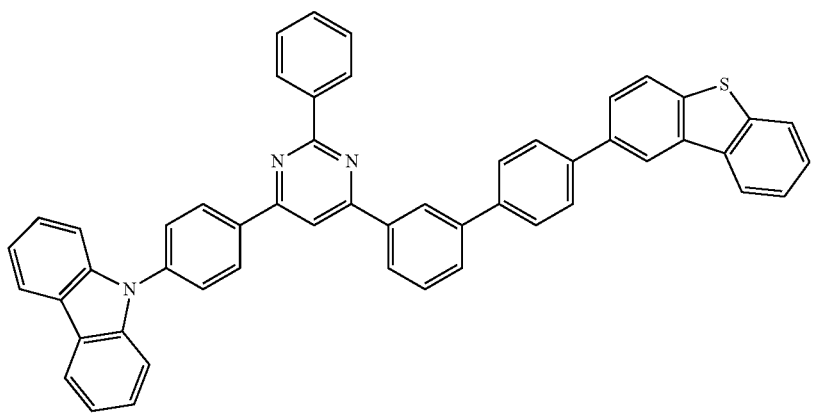
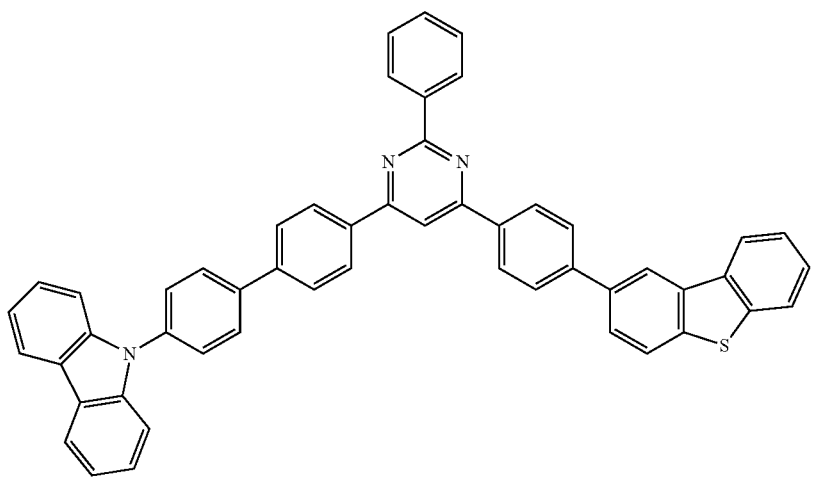

-continued
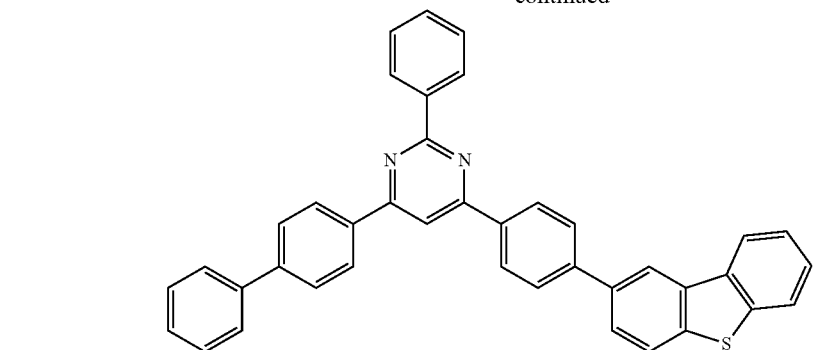
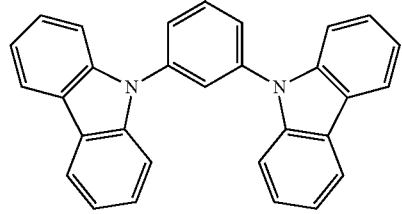
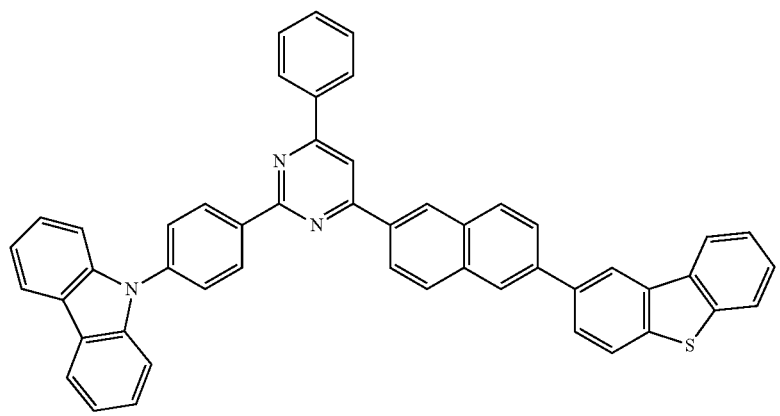
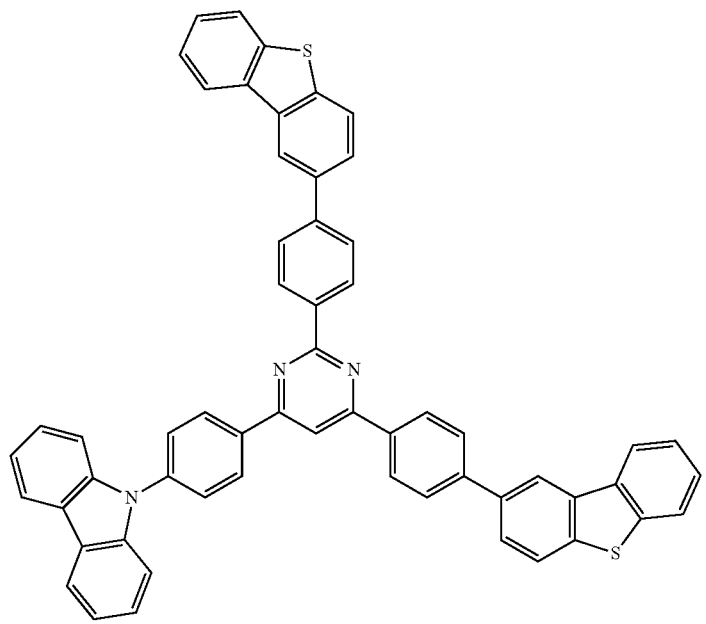

-continued
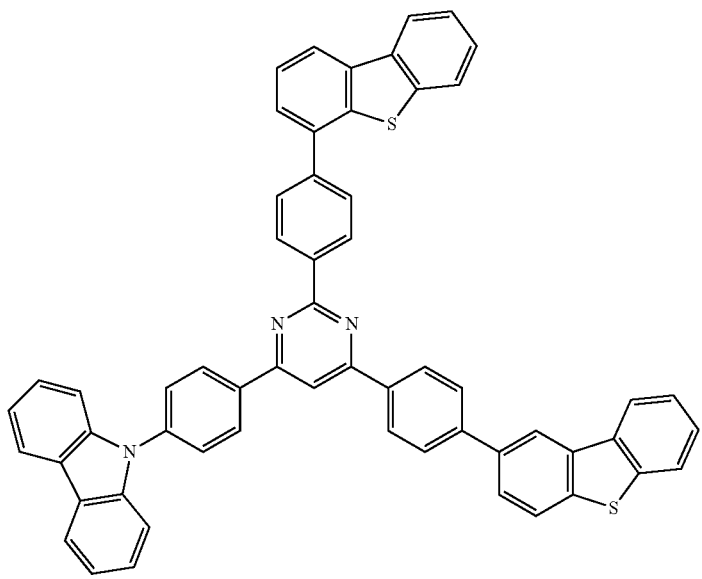
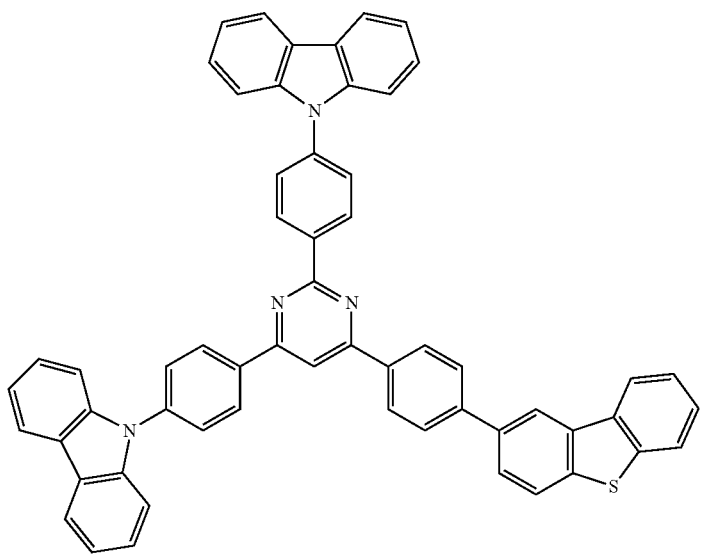

-continued
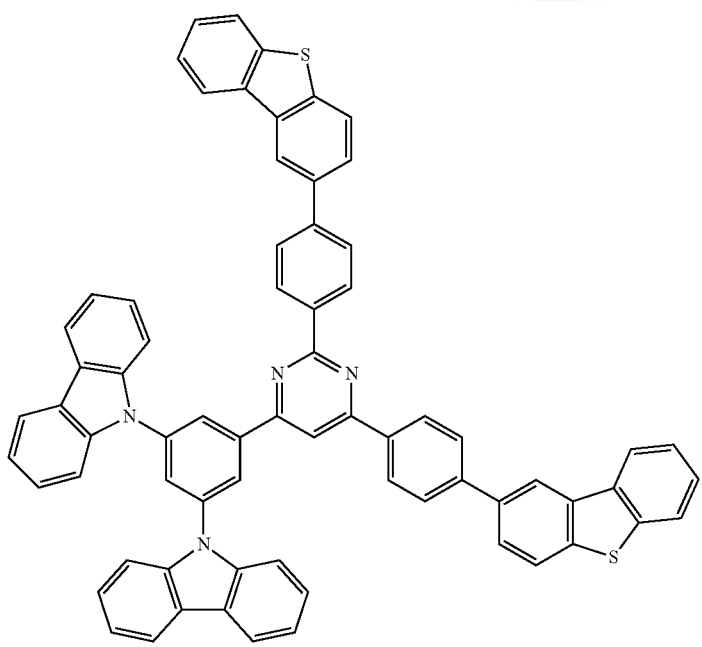
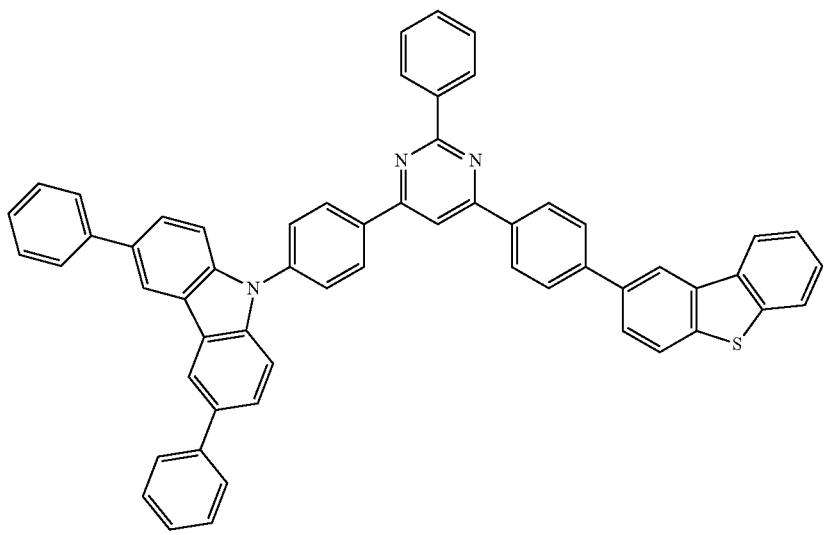
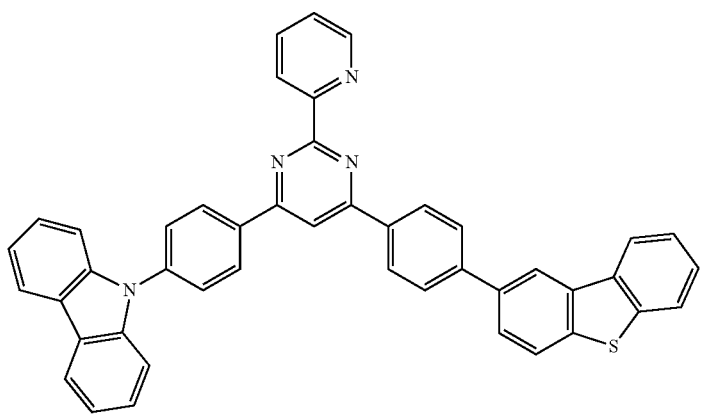

-continued
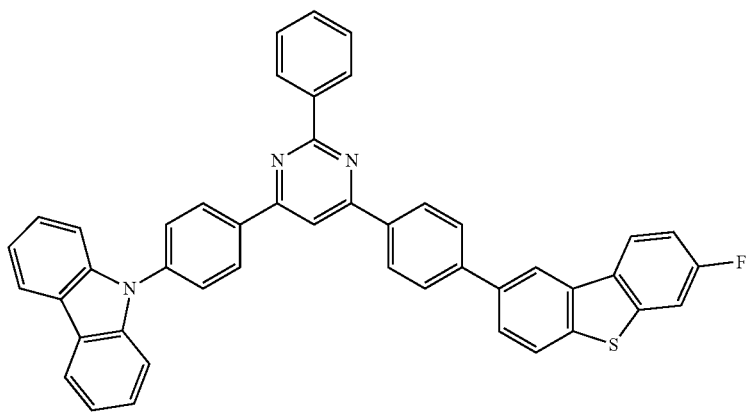
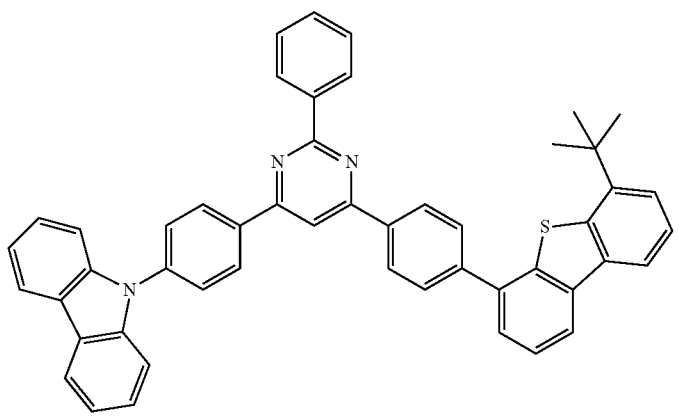
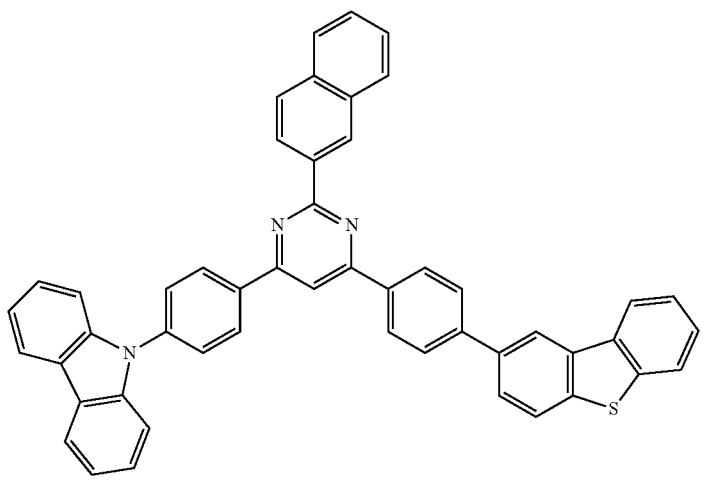

[Formula 25]
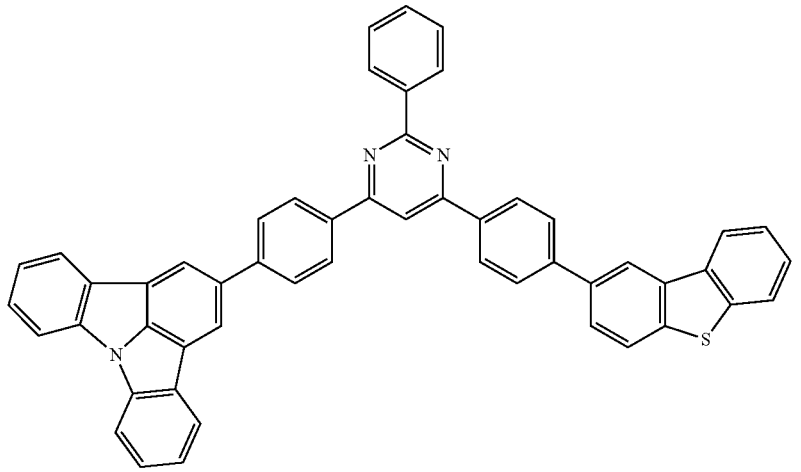
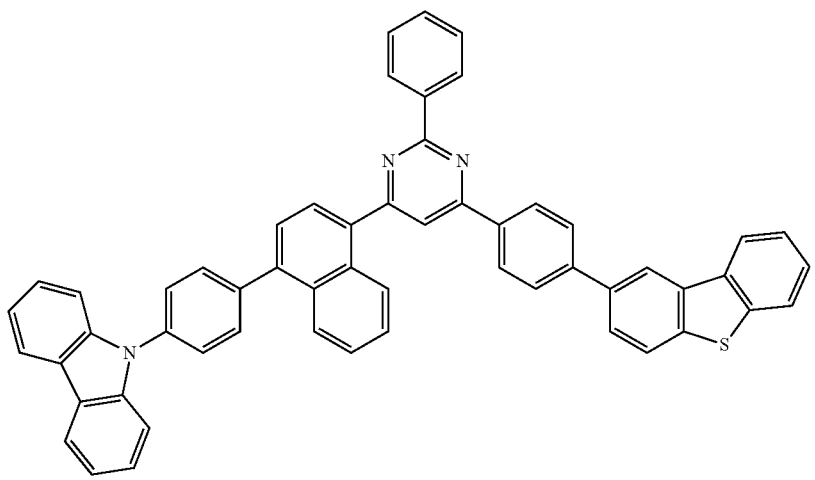
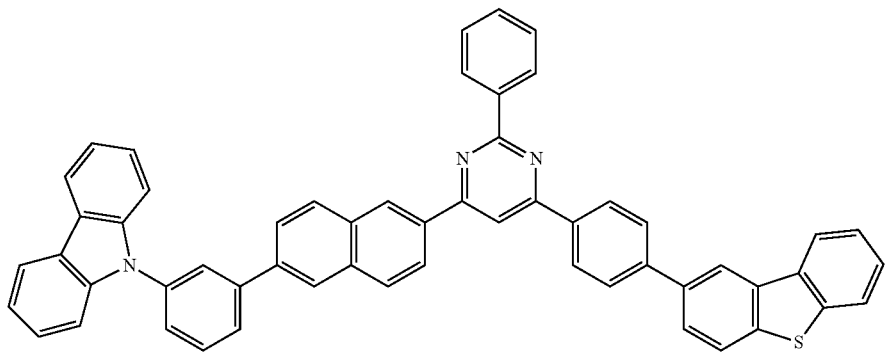
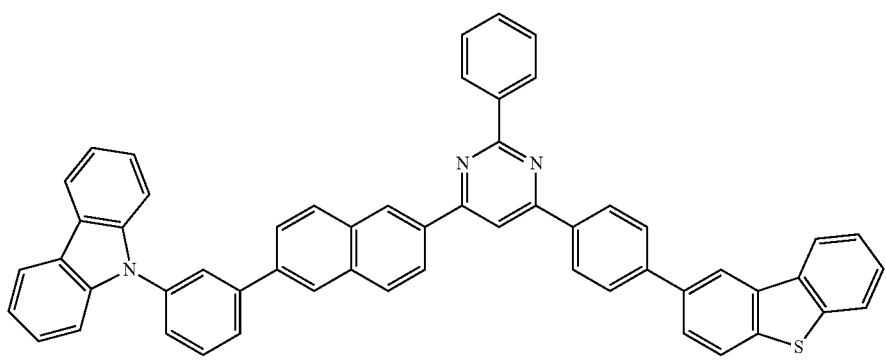

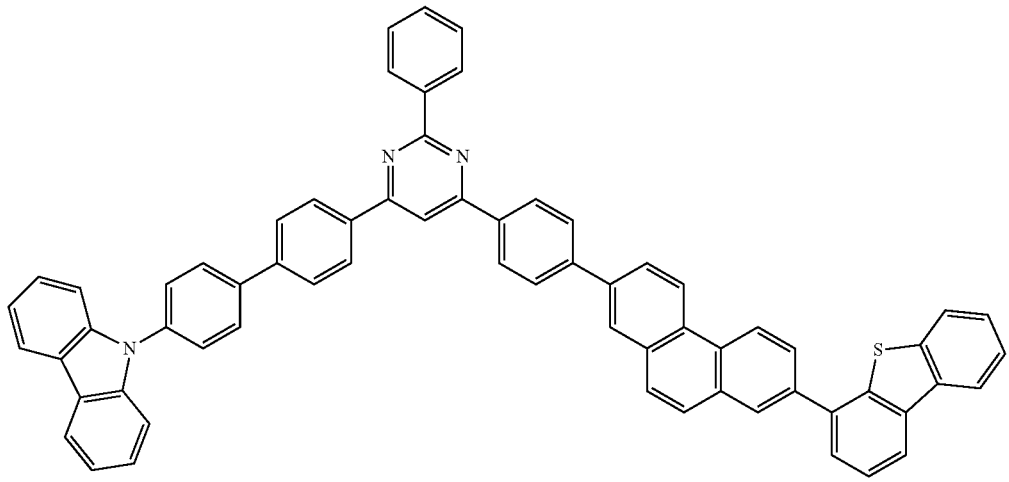

-continued
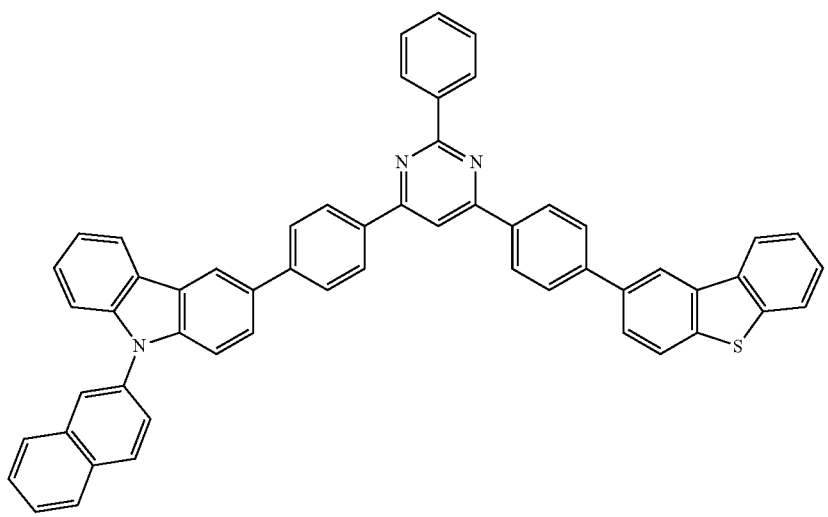
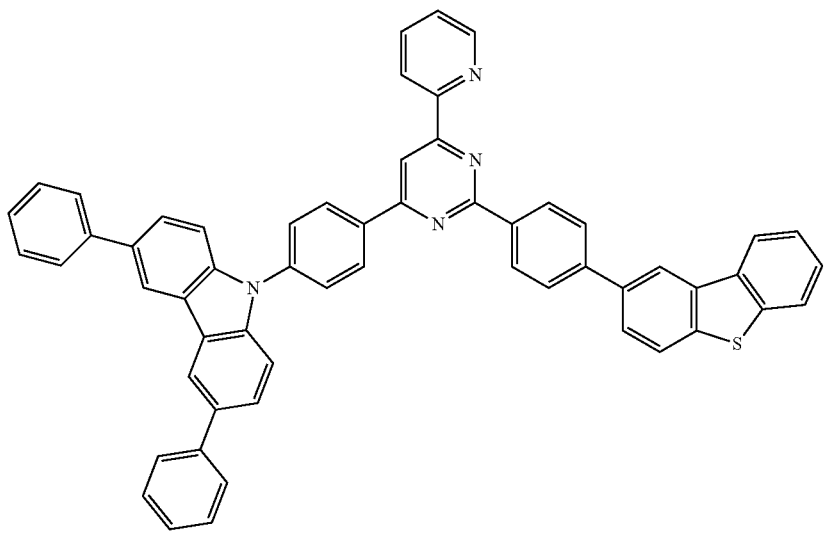
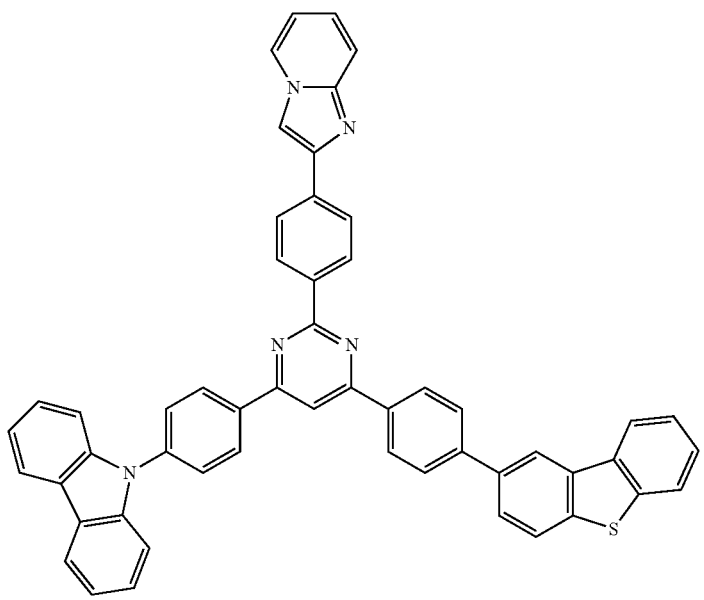

-continued
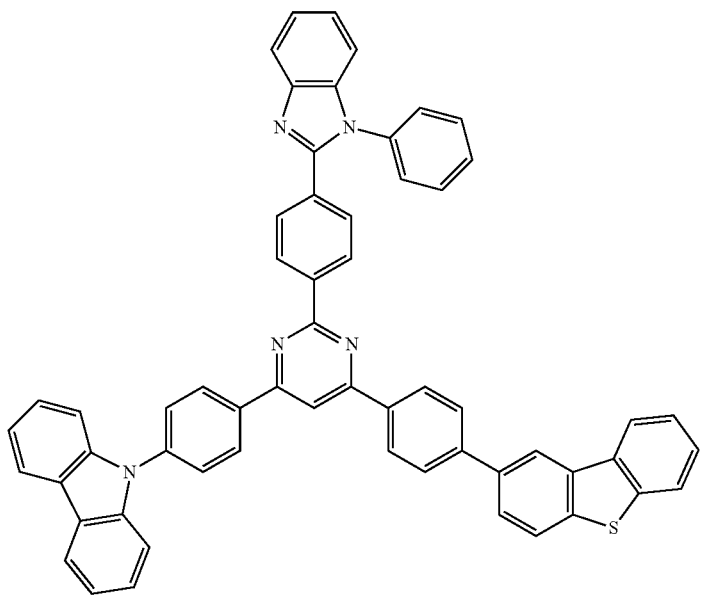
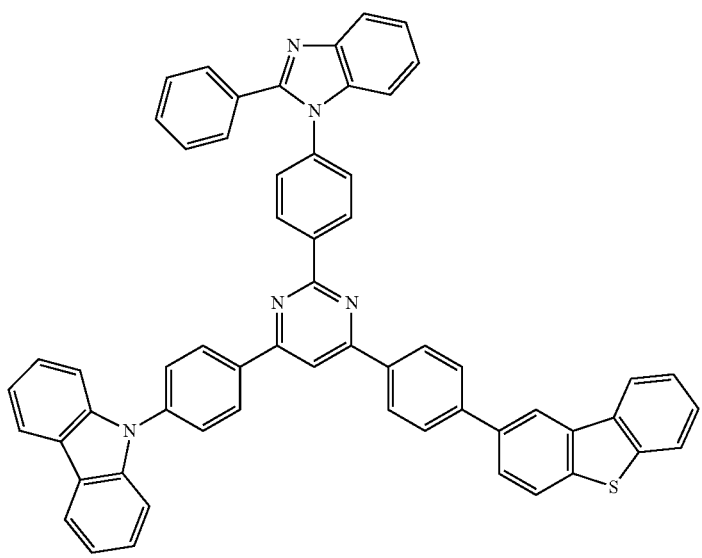

-continued
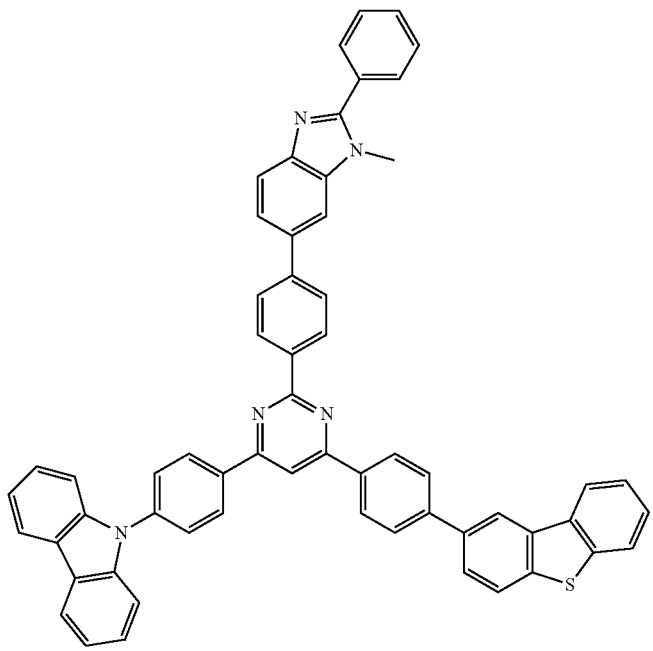
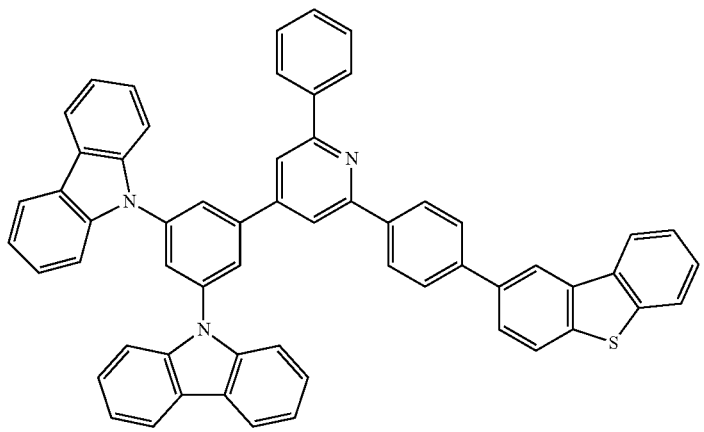
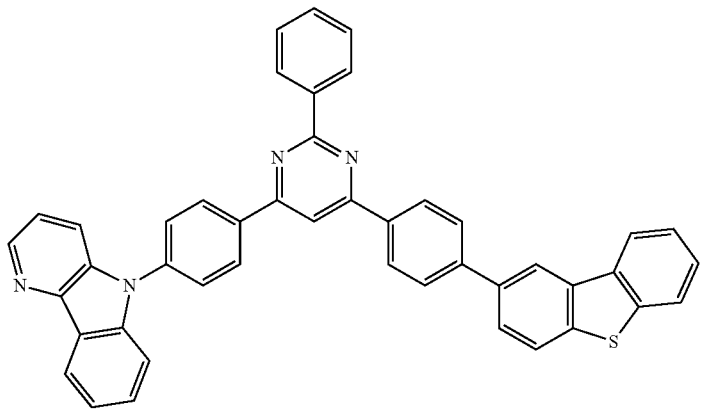

-continued
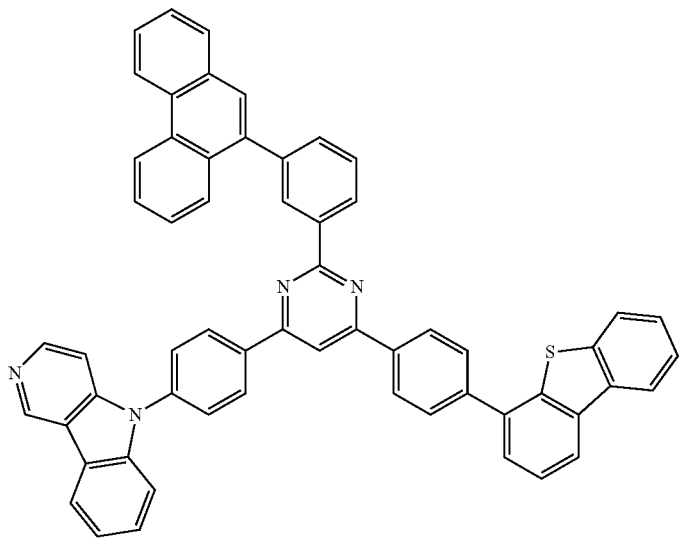
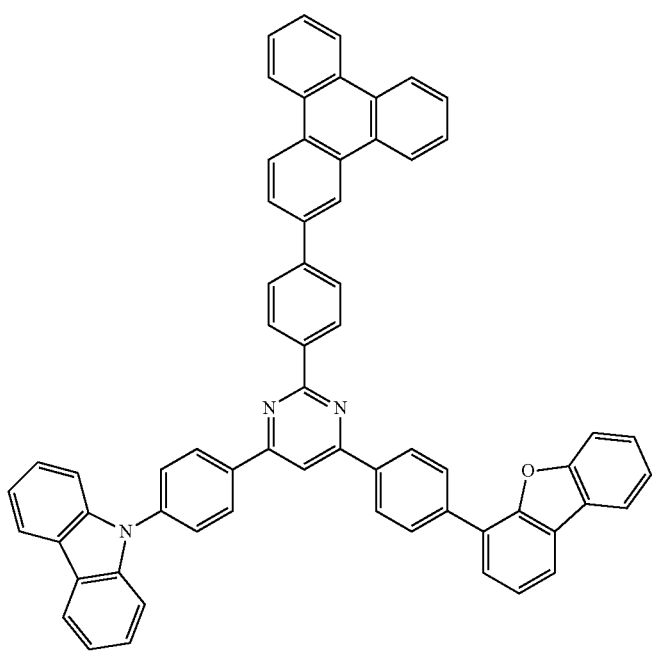

-continued
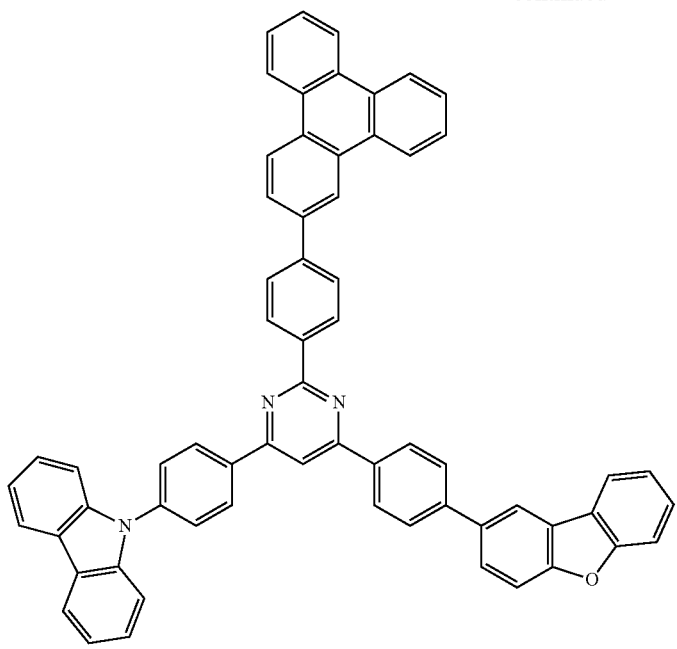
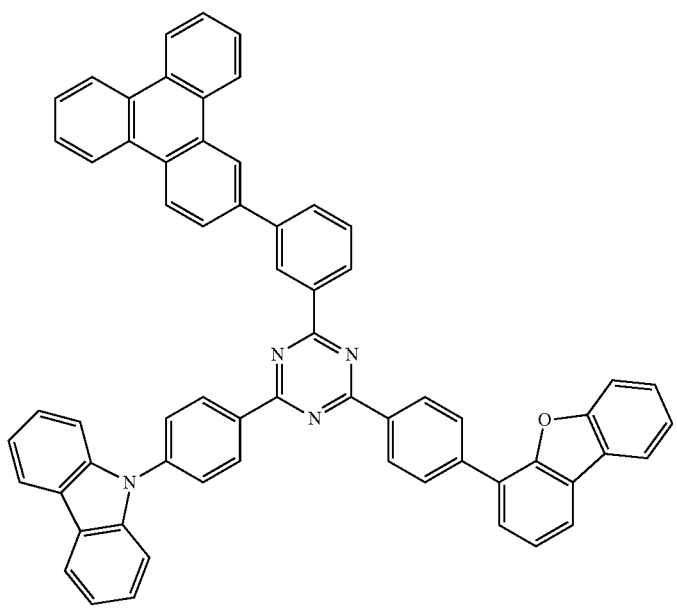
[Formula 26]
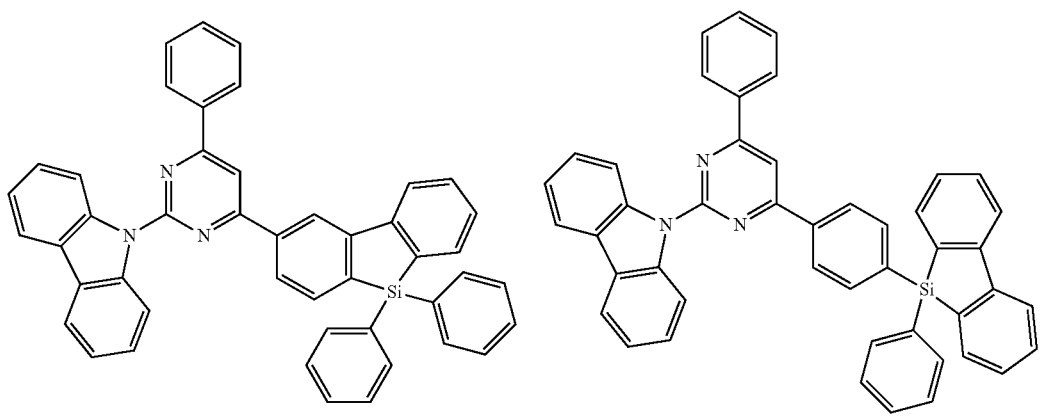

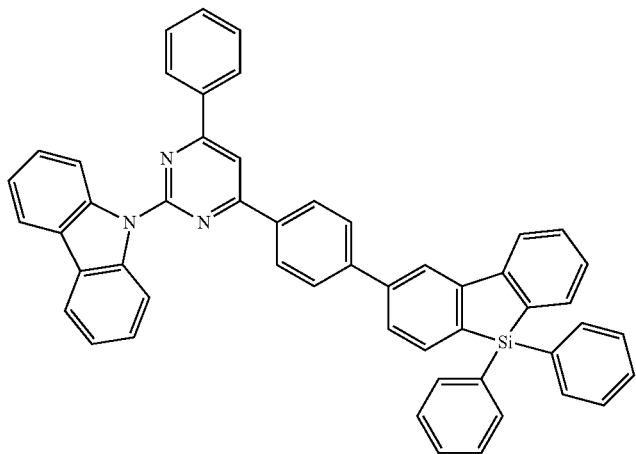
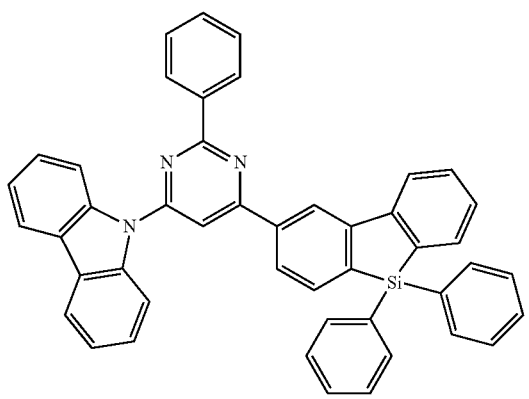
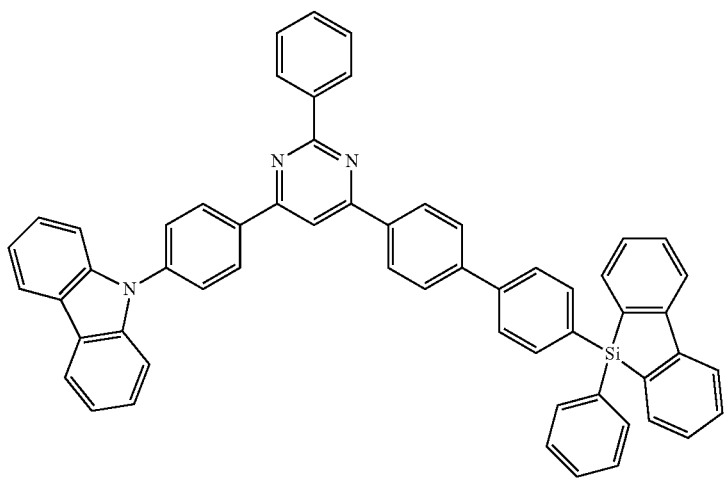

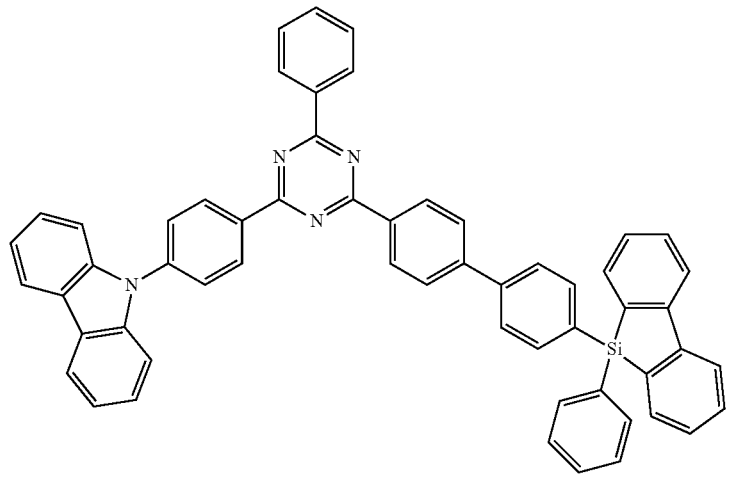
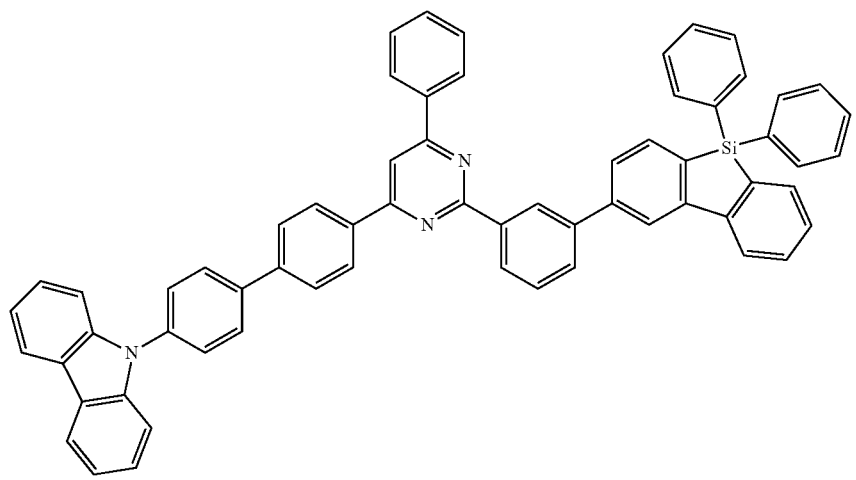
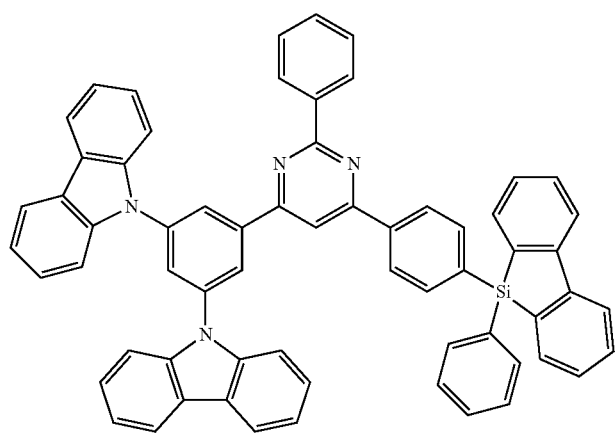

-continued
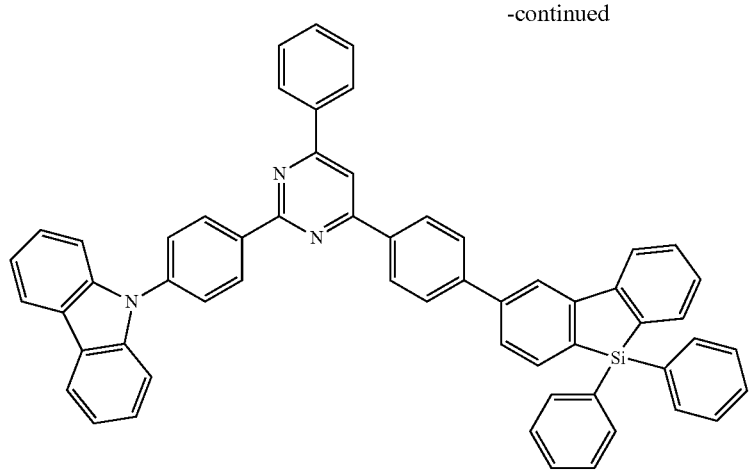
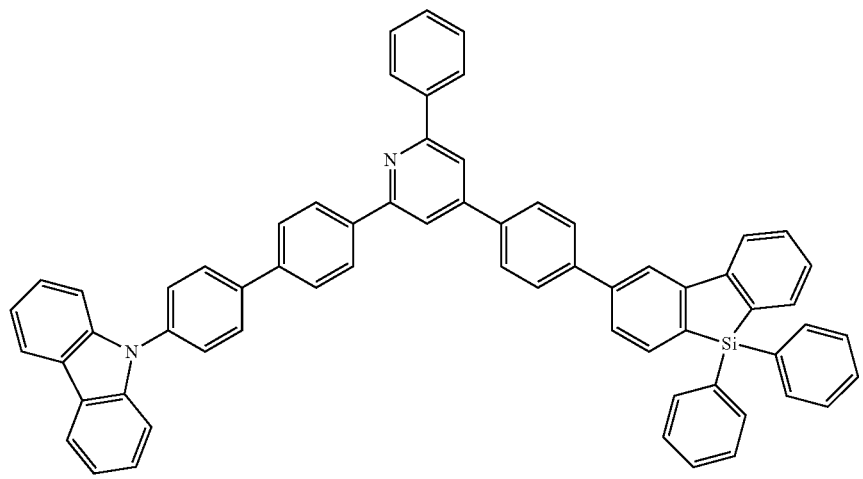
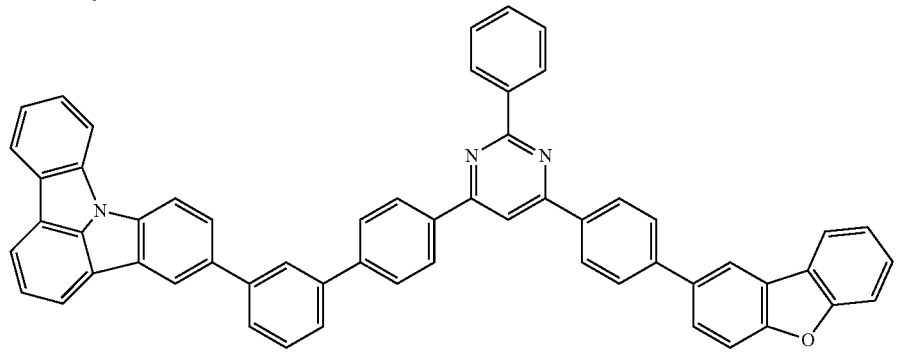
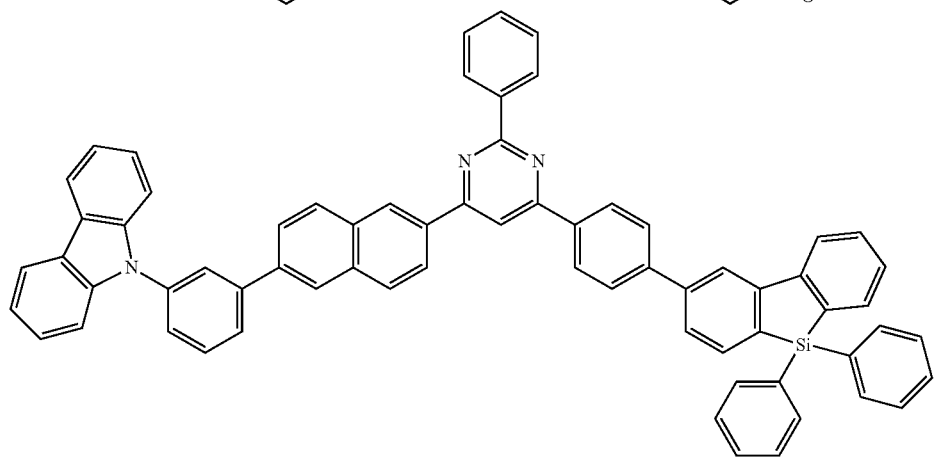

-continued
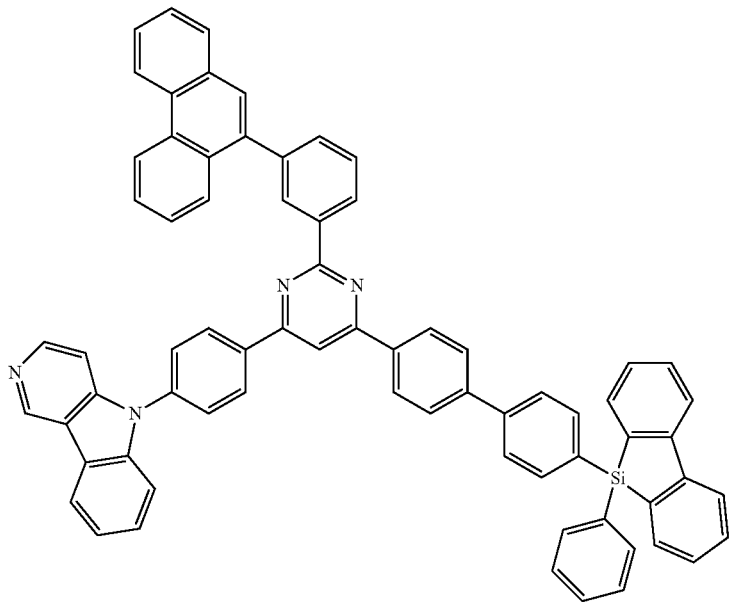
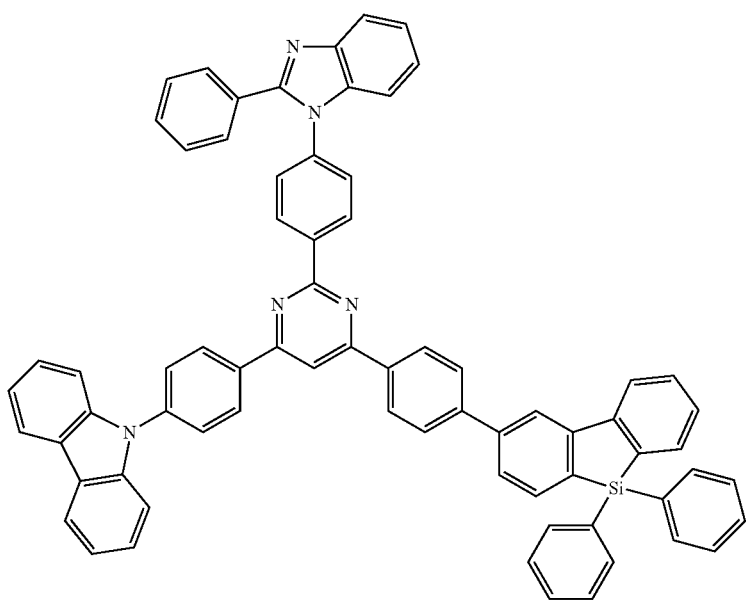

-continued
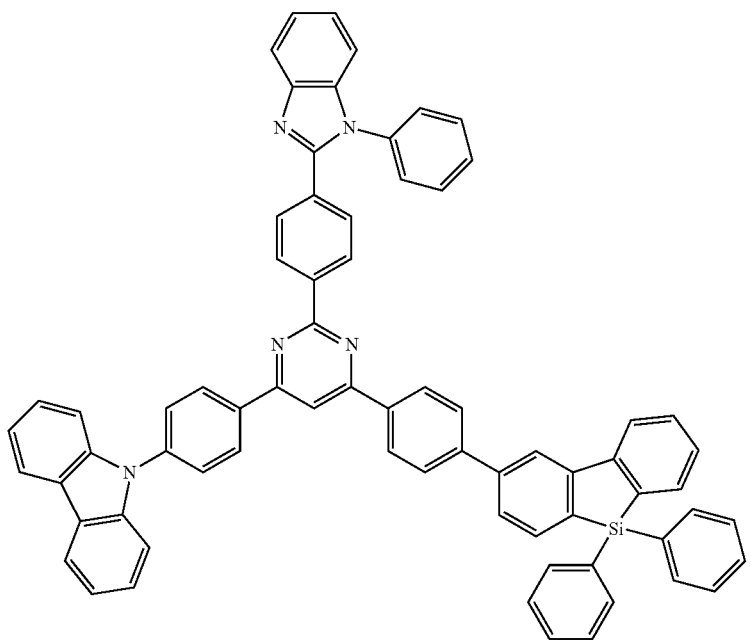
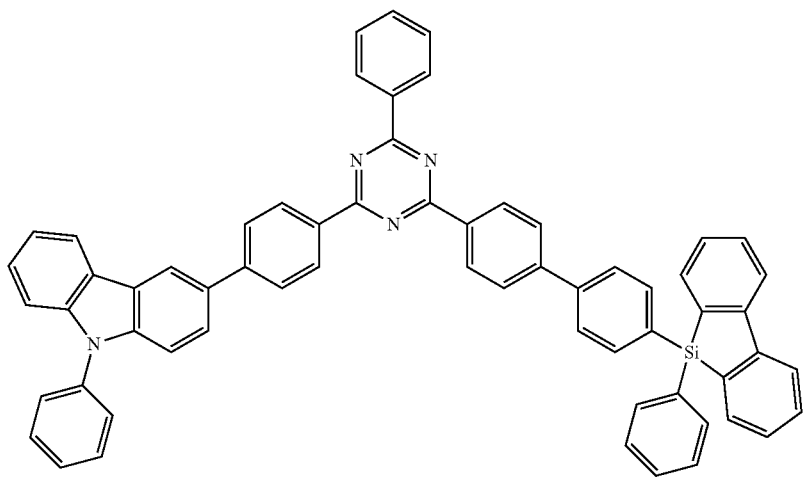
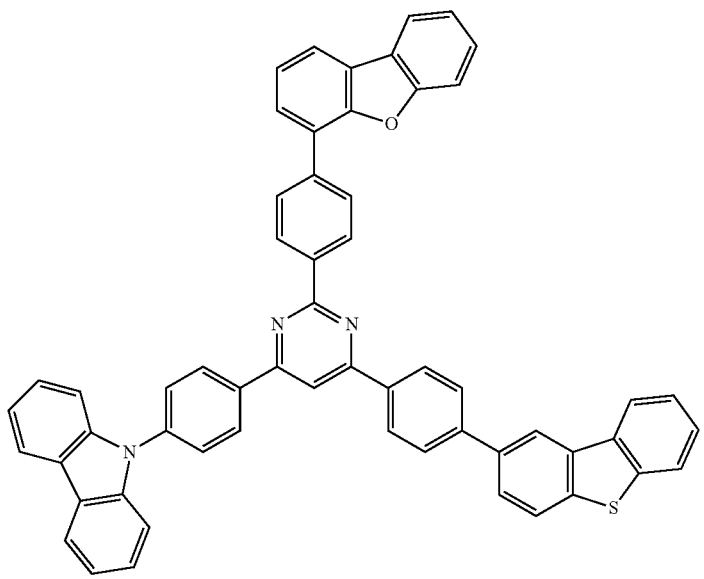

-continued
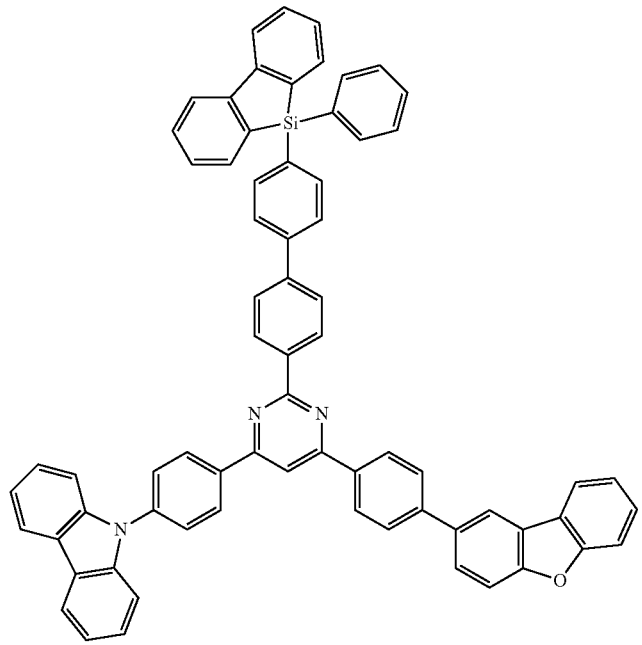
[Formula 27]
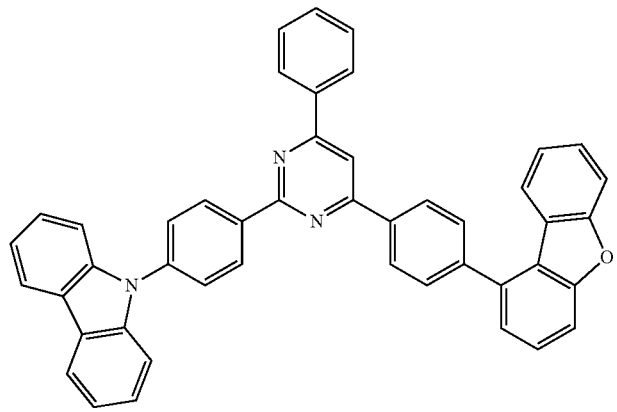
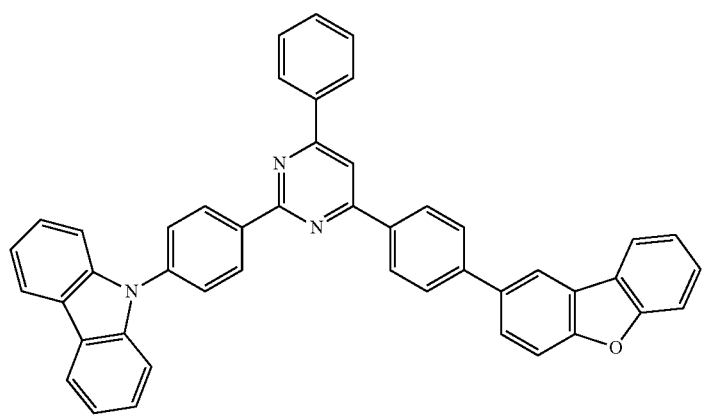

-continued
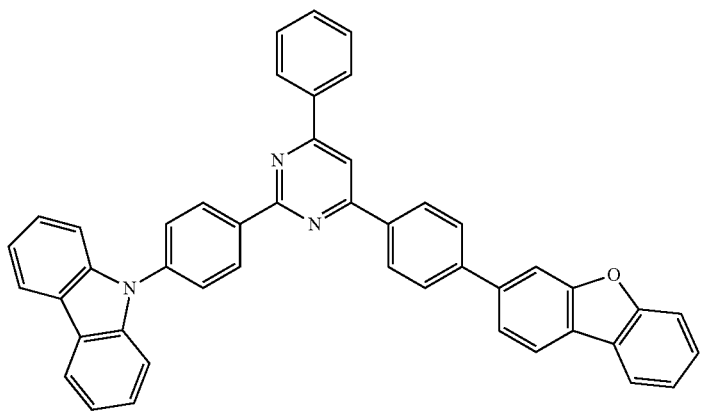

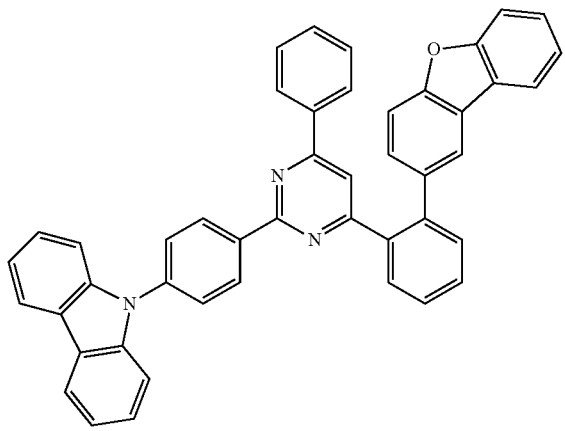
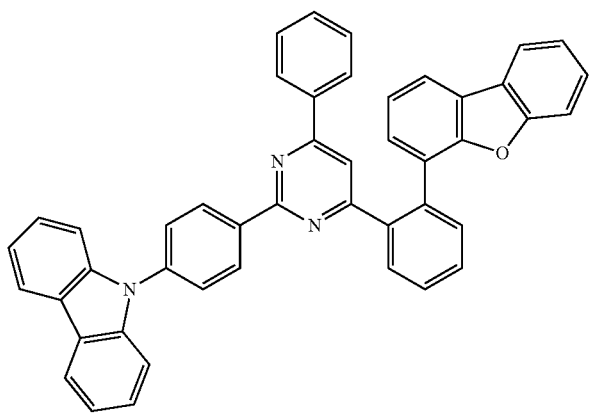
[Formula 28]
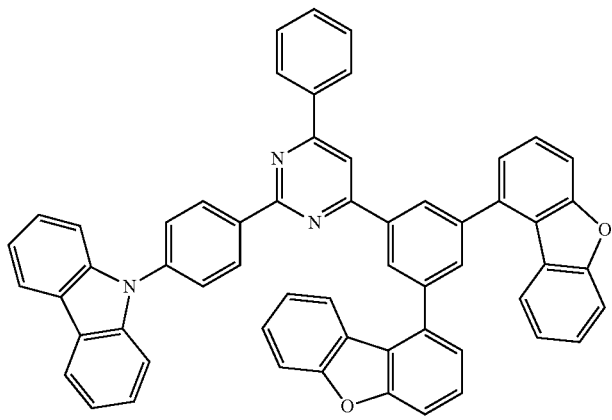

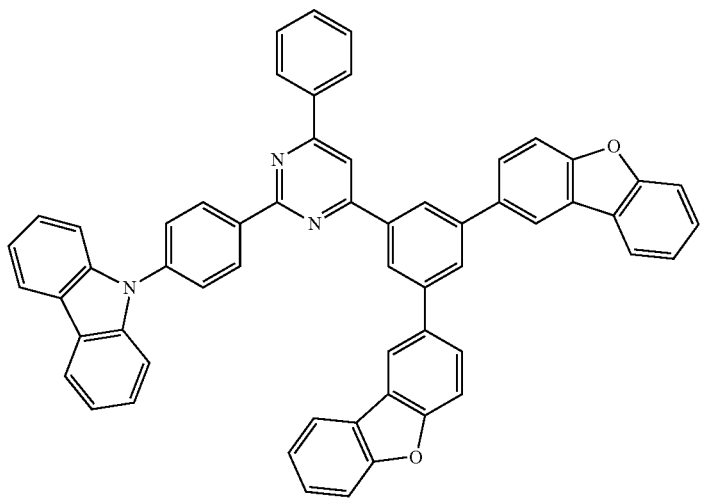
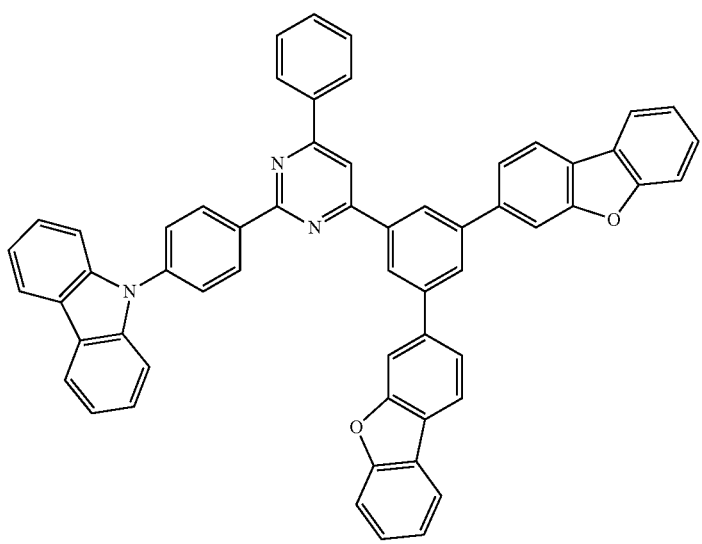
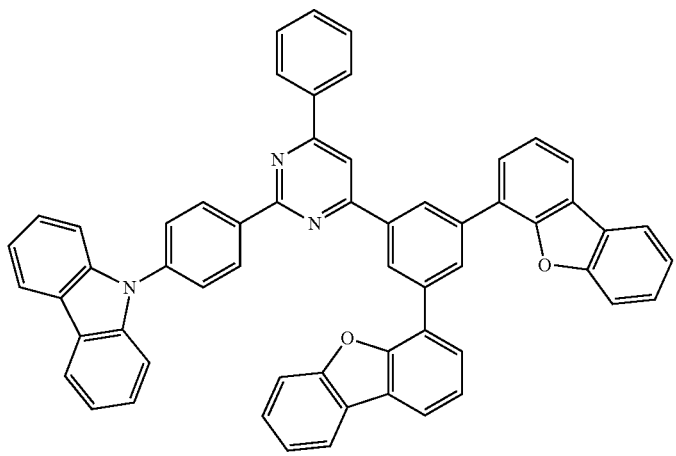

-continued
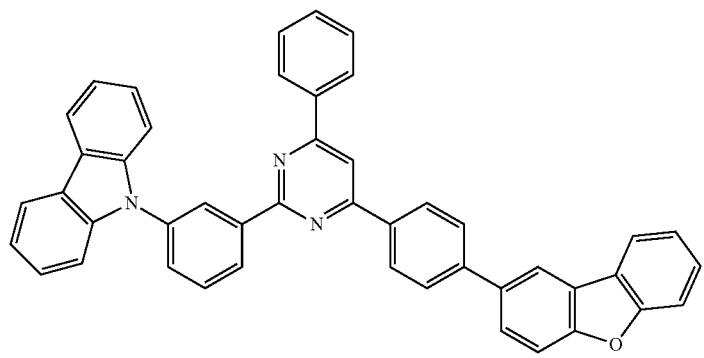
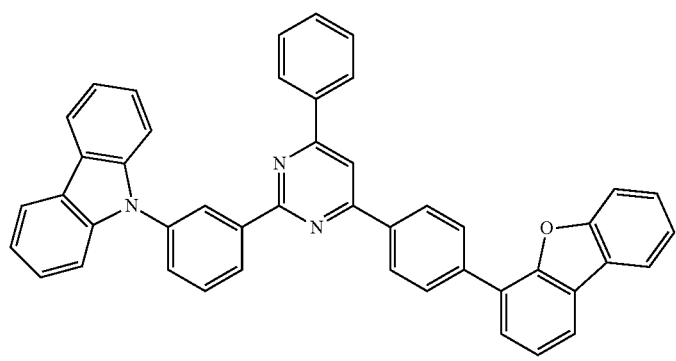
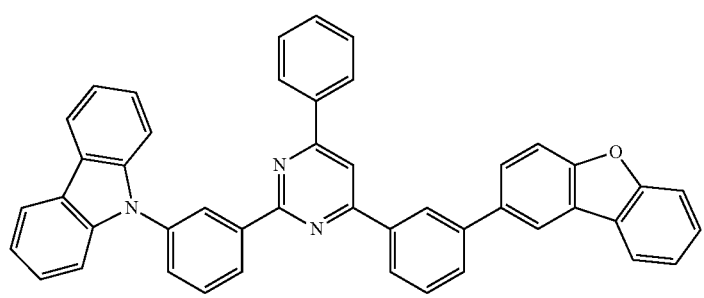
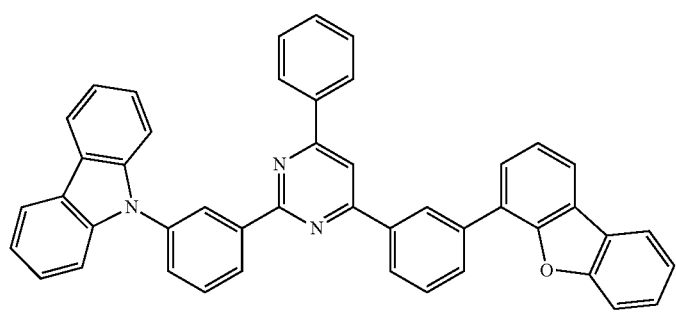
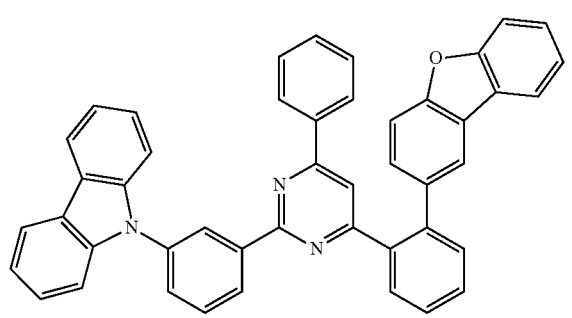

-continued
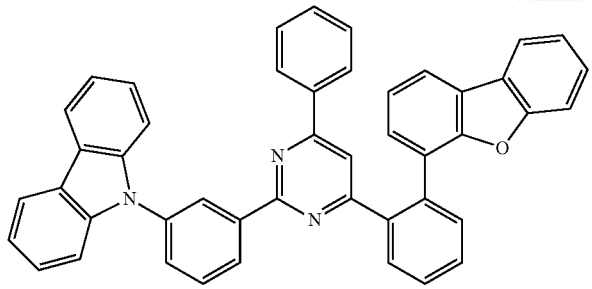
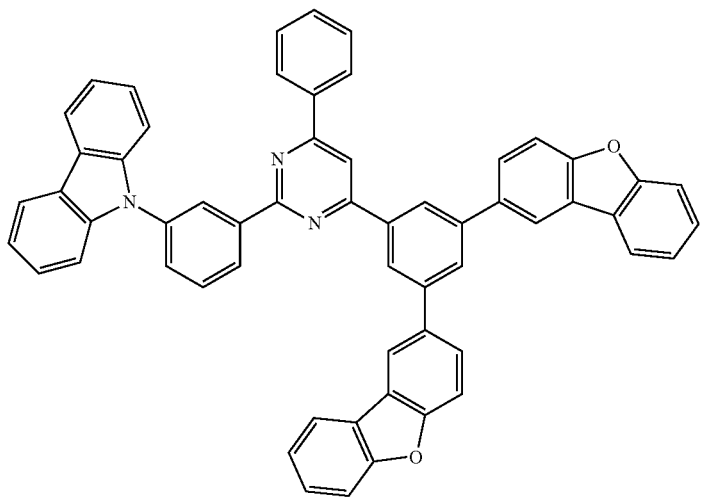
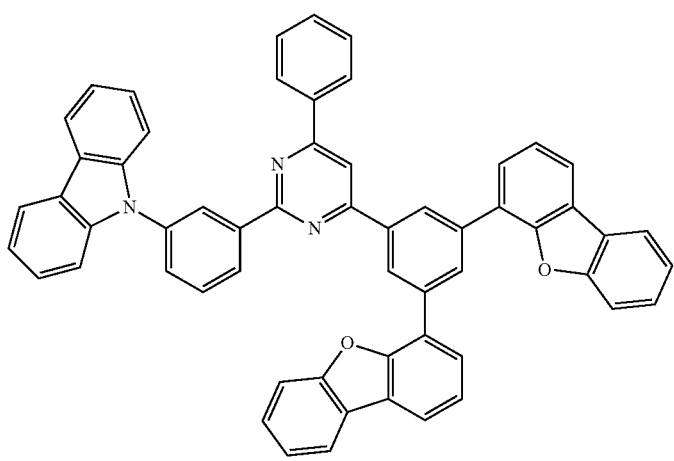
[Formula 29]
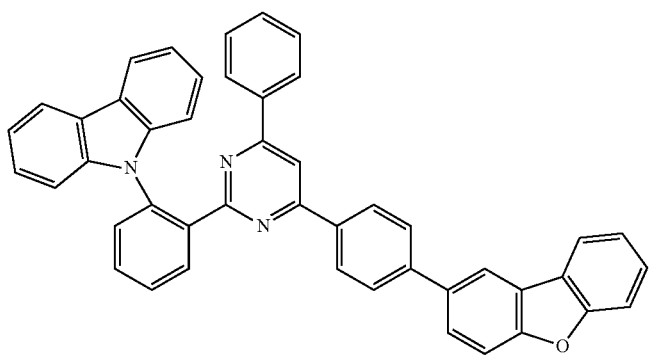

-continued
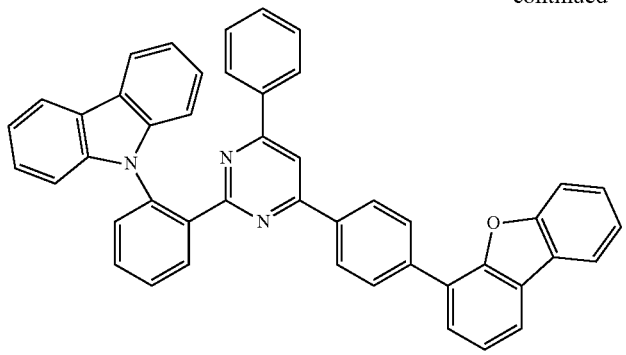
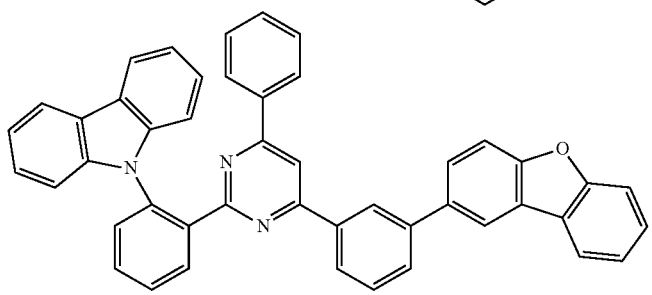
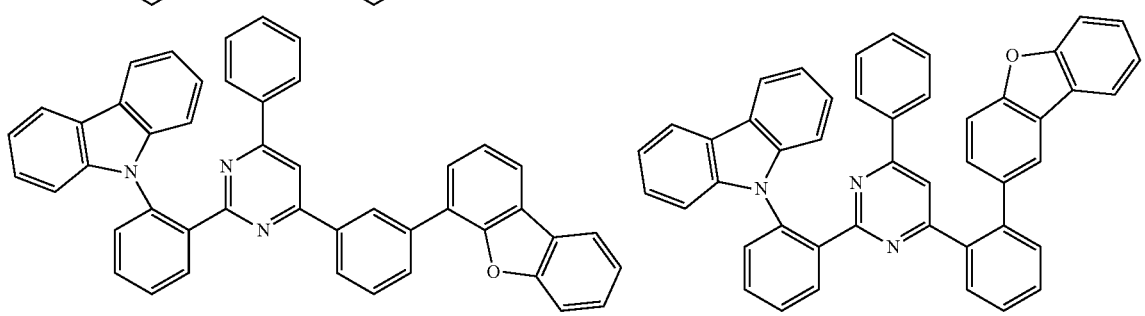
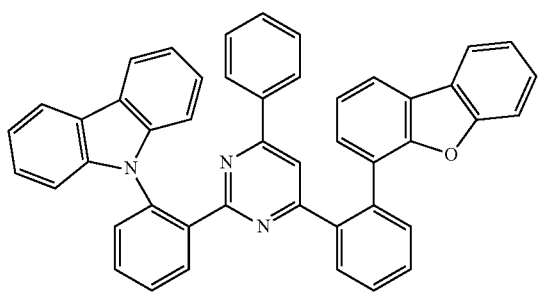
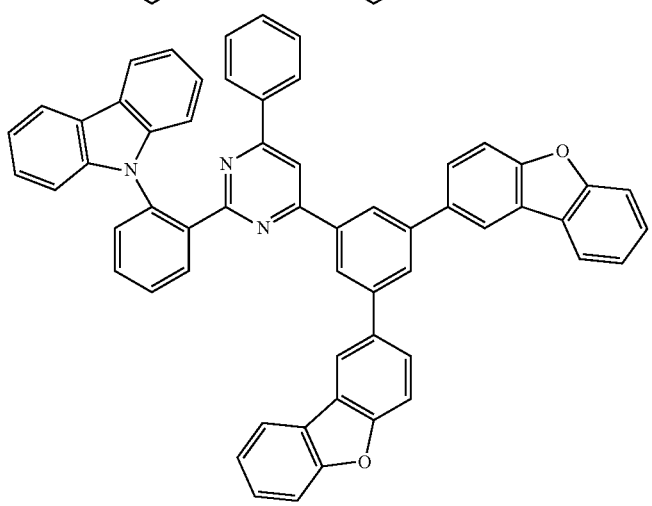

-continued
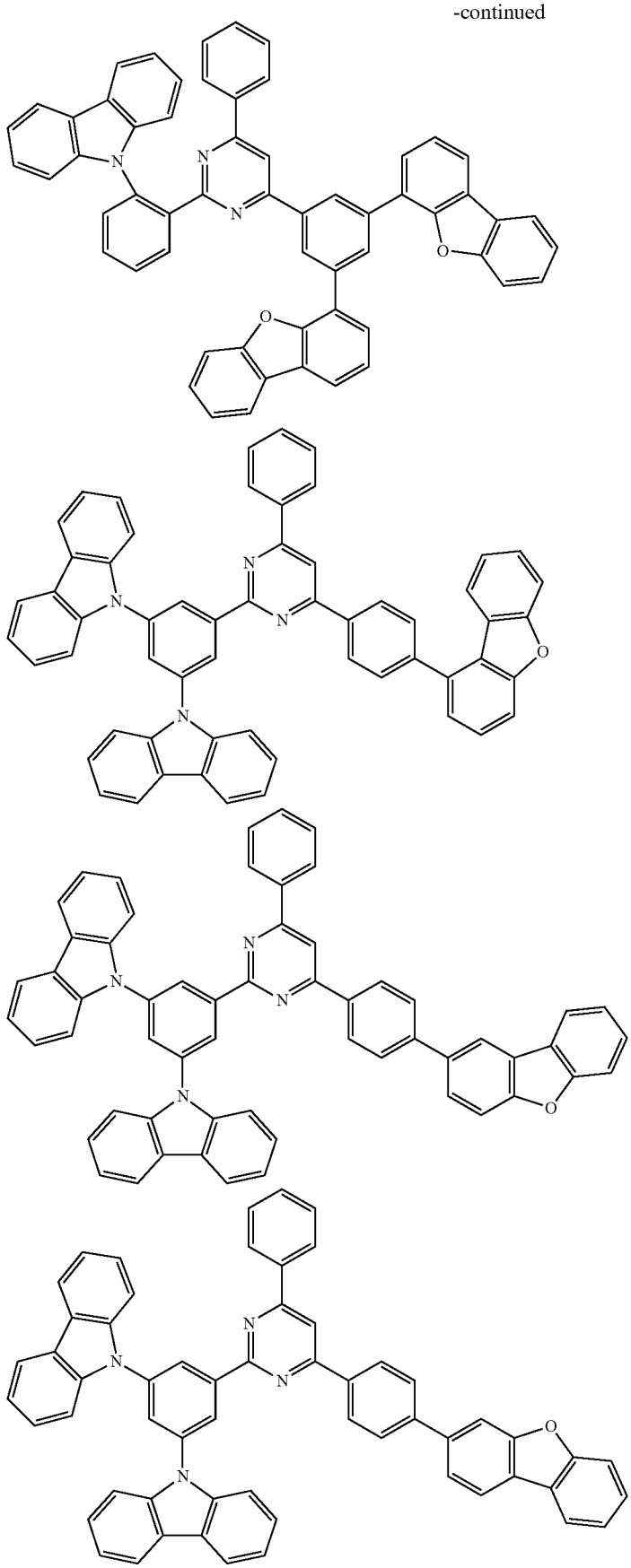

-continued
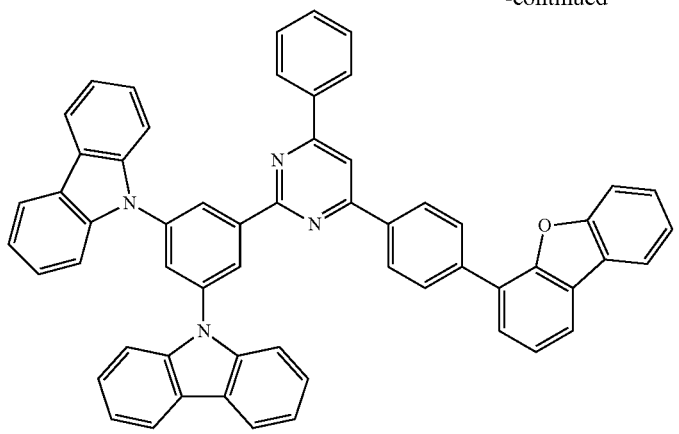
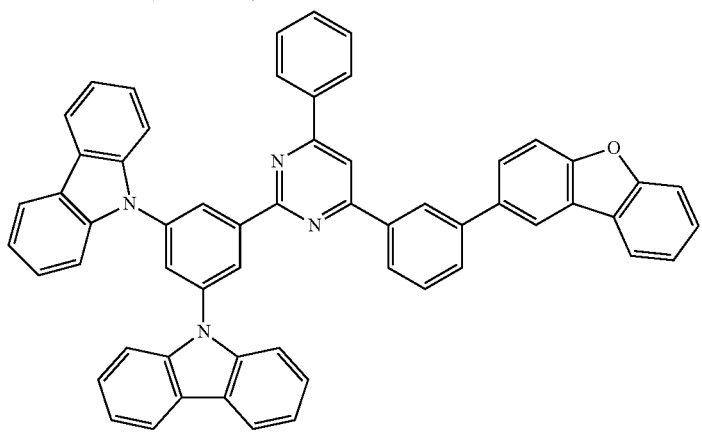
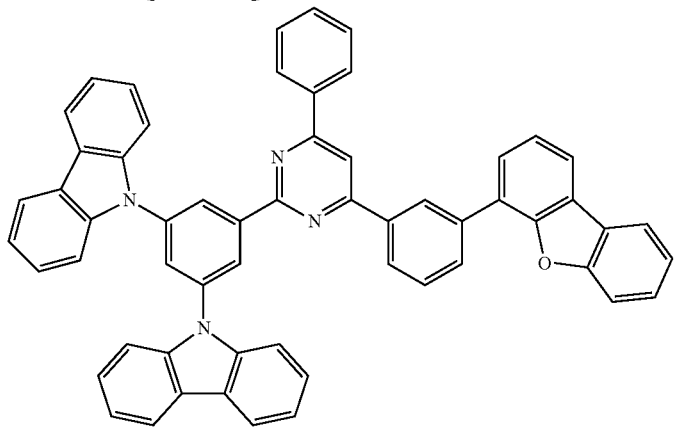
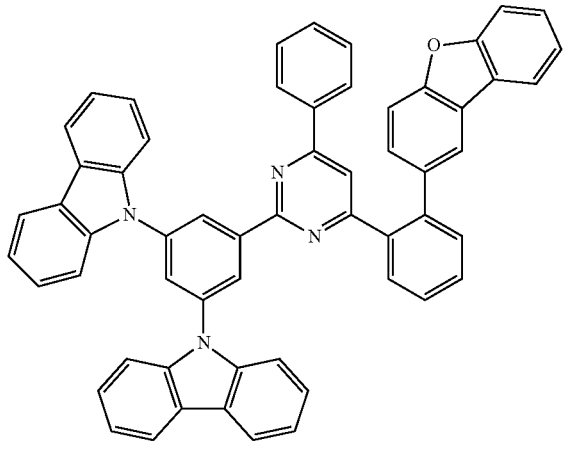

-continued
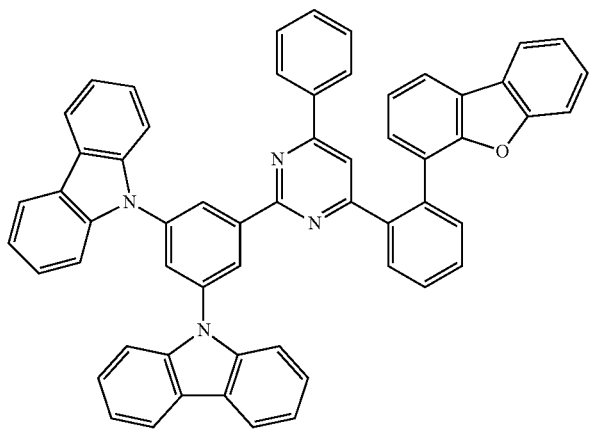
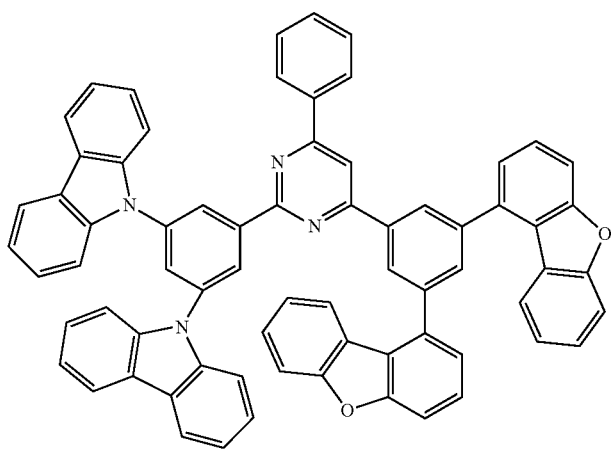
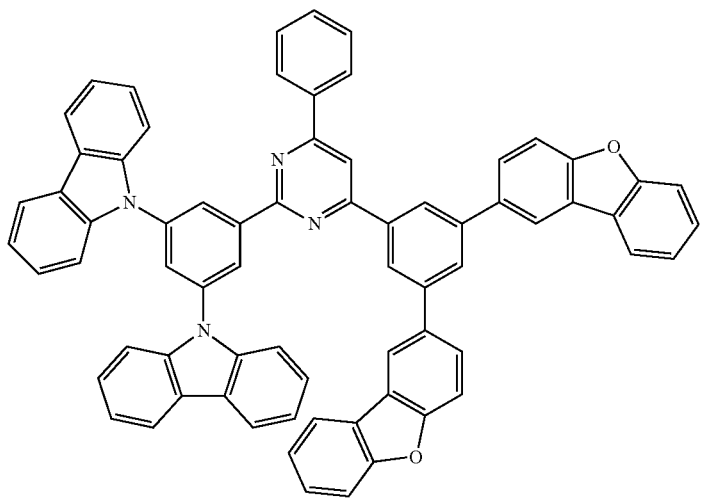

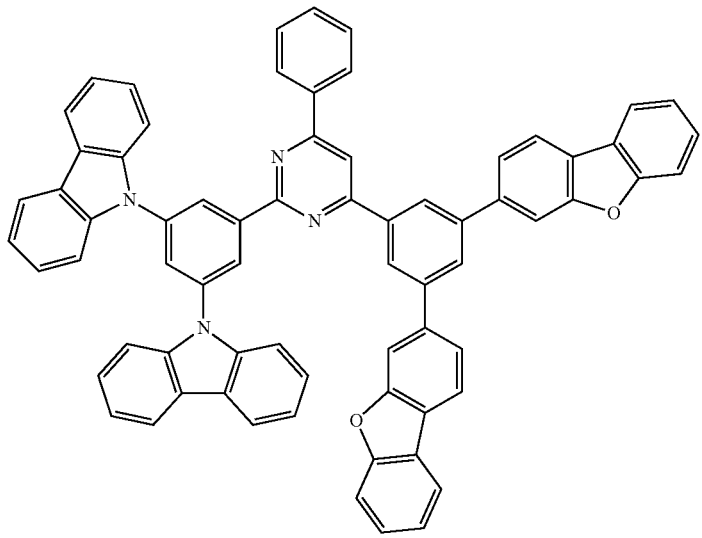
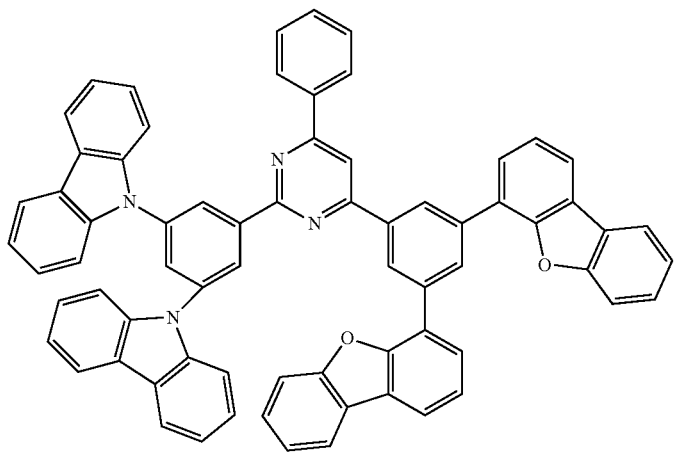
[Formula 31]
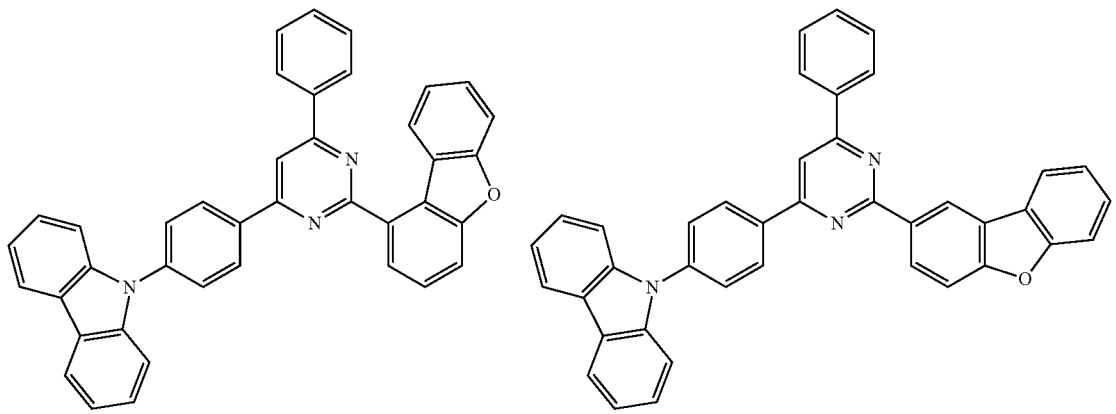

-continued
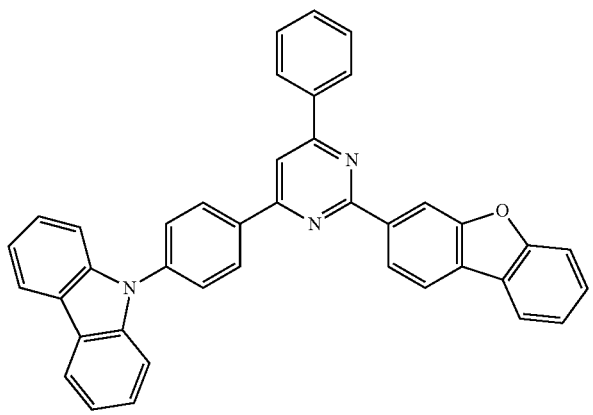
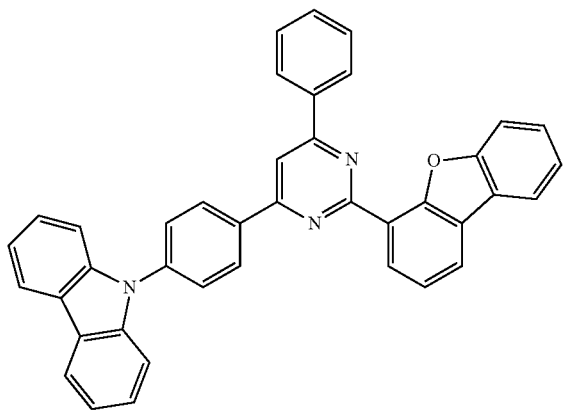
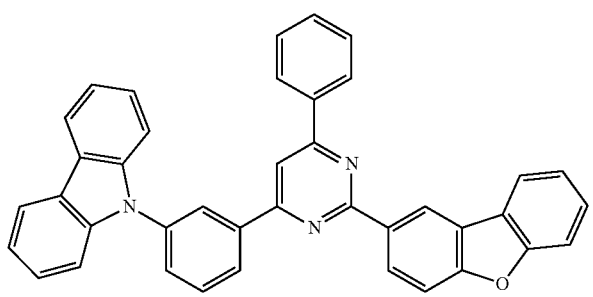
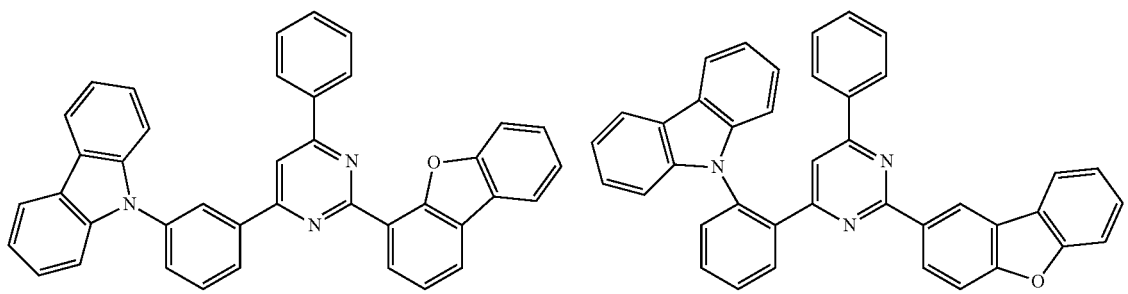

179 180
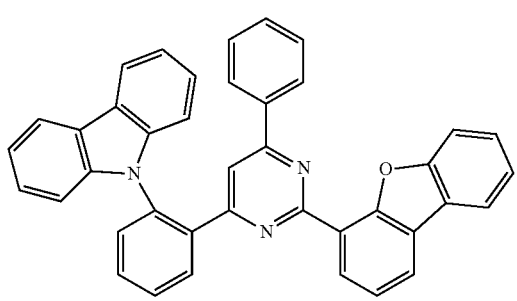
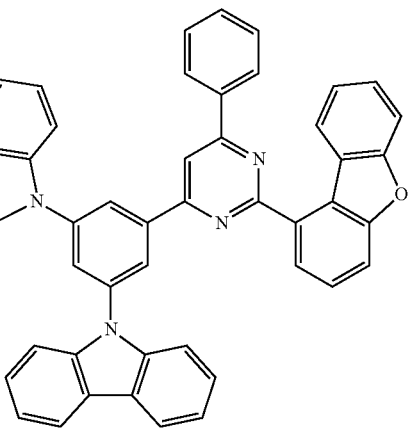
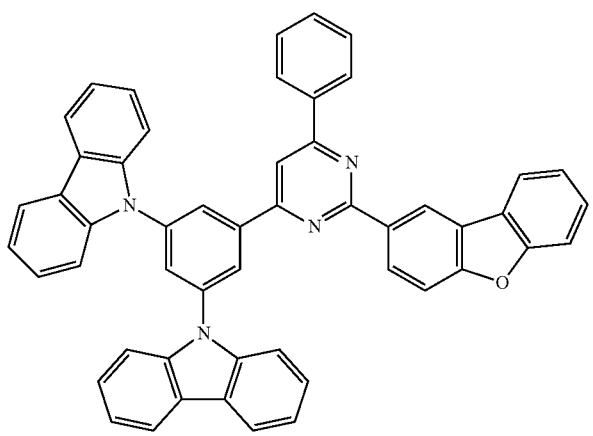
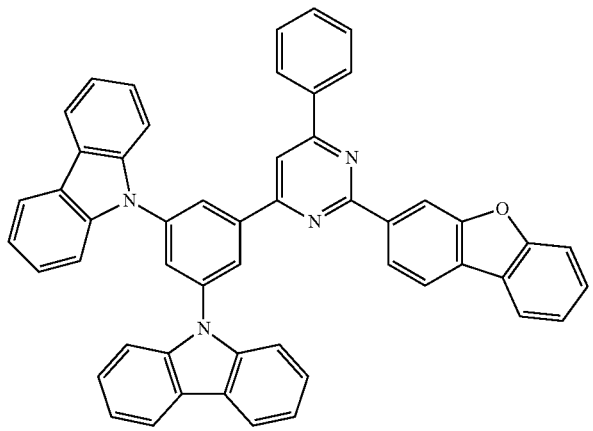
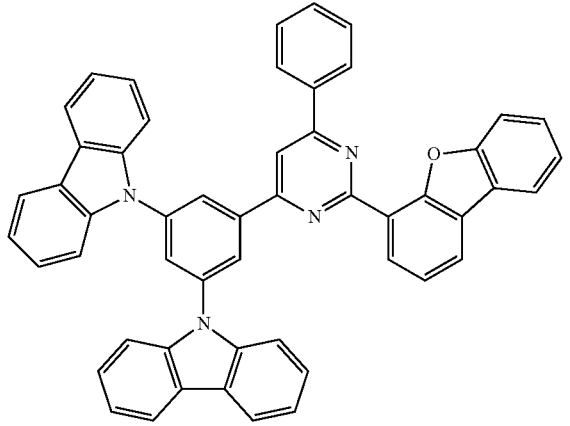

[Formula 32]
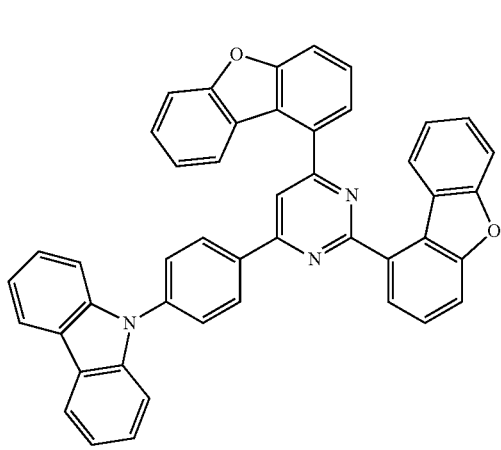
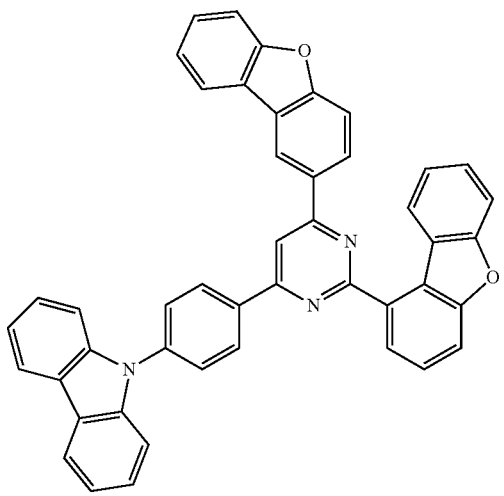
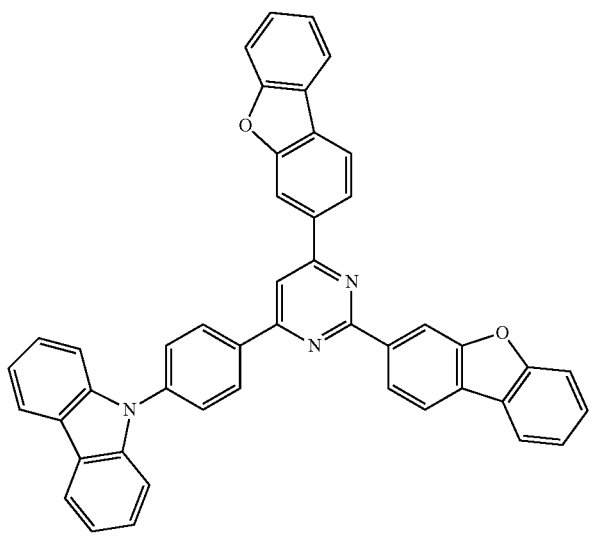
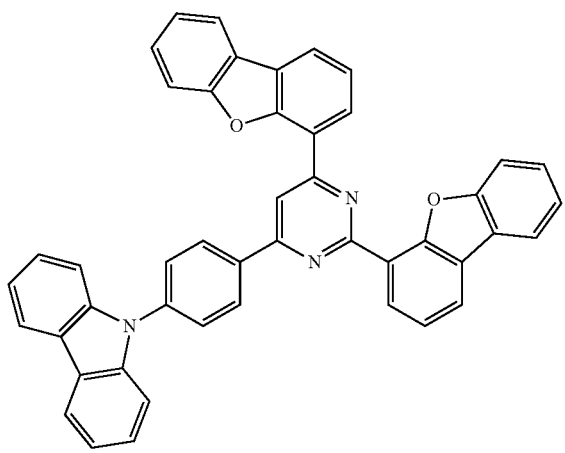

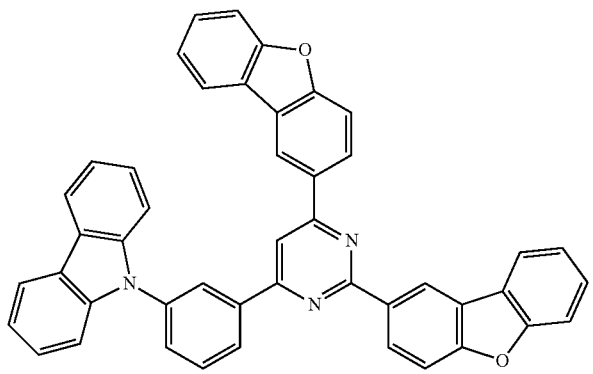
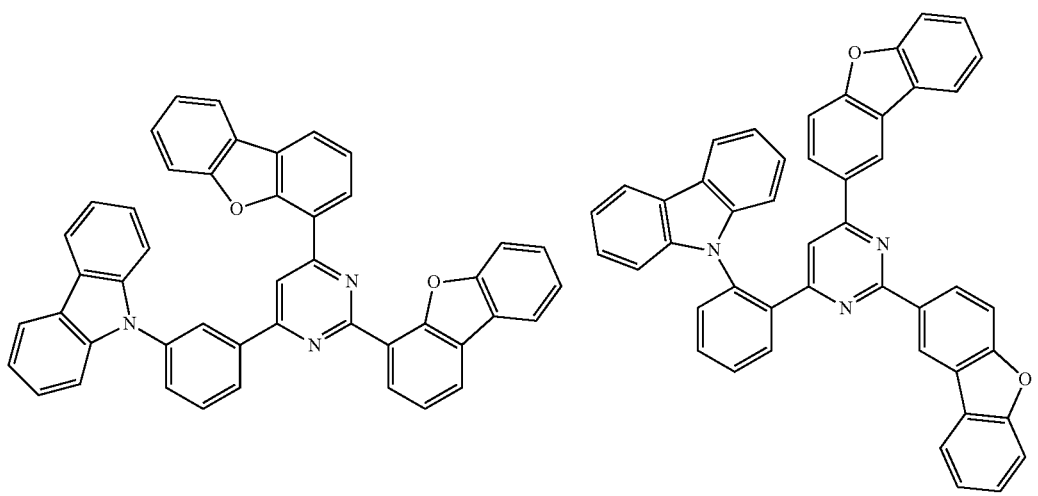
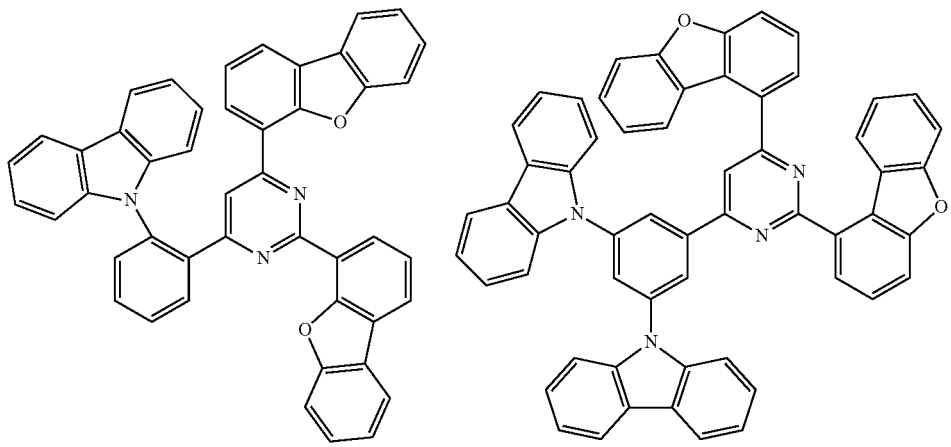

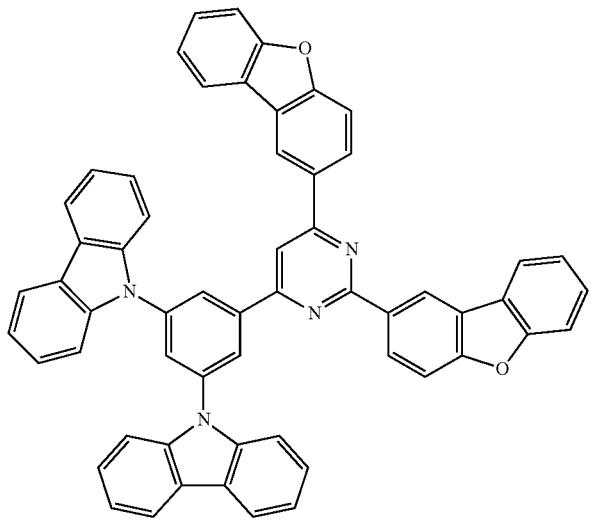
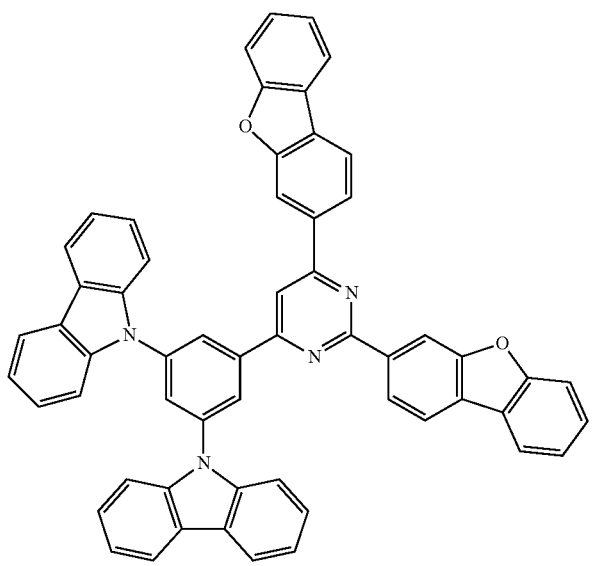
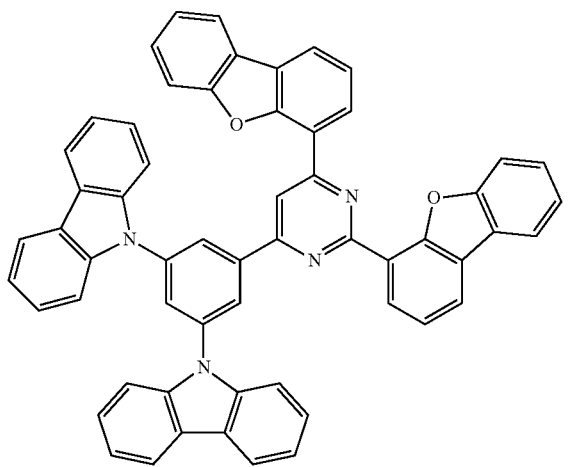

[Formula 33]
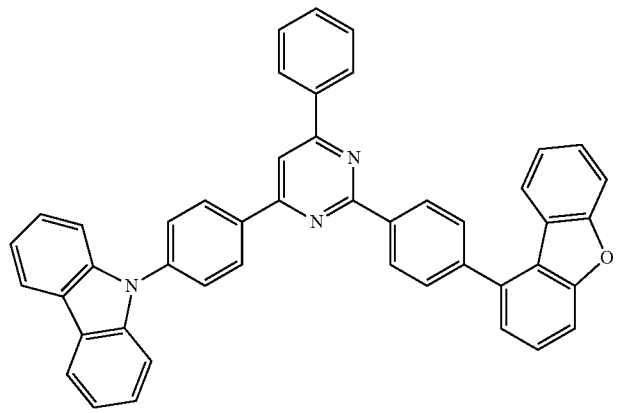
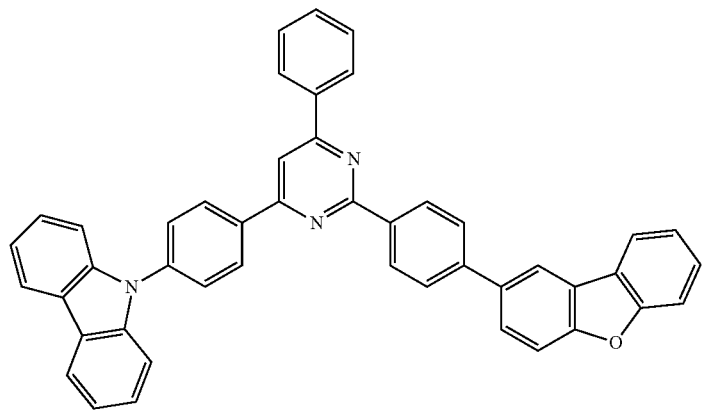
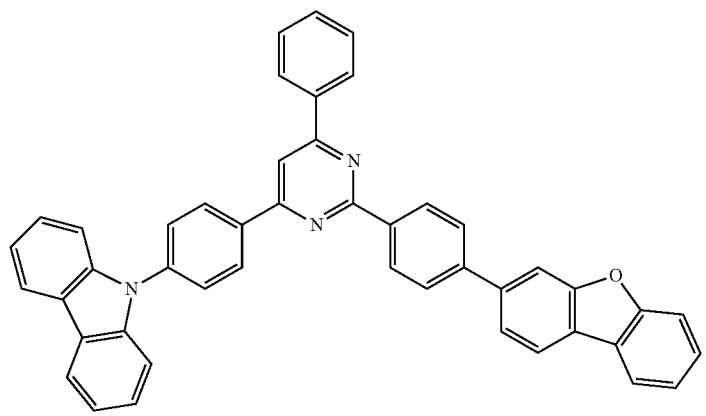
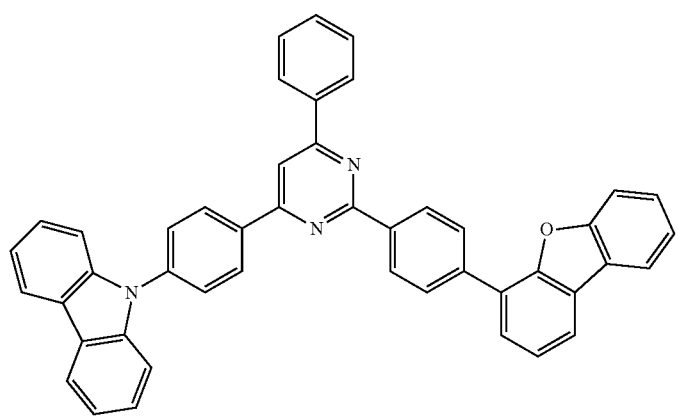

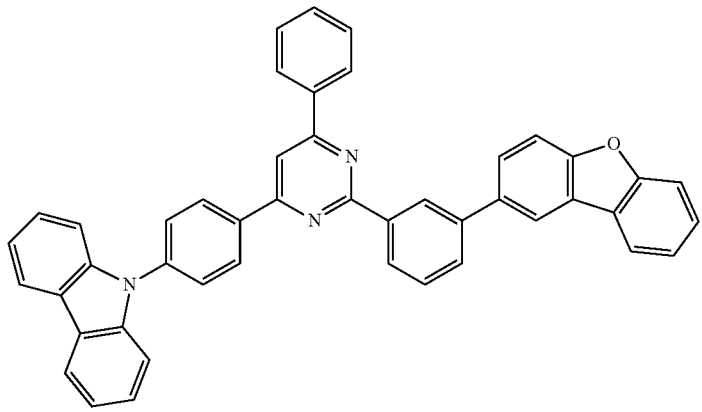
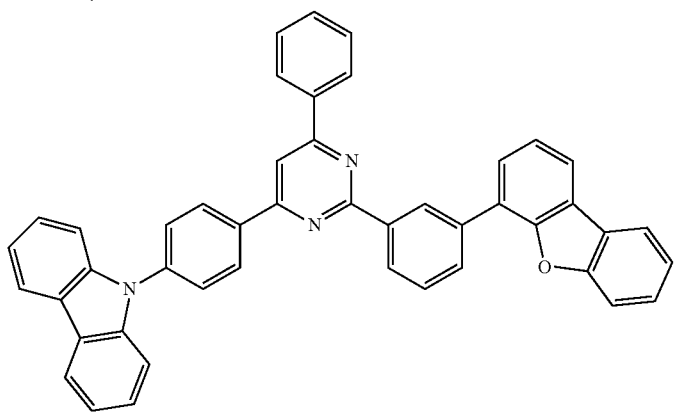
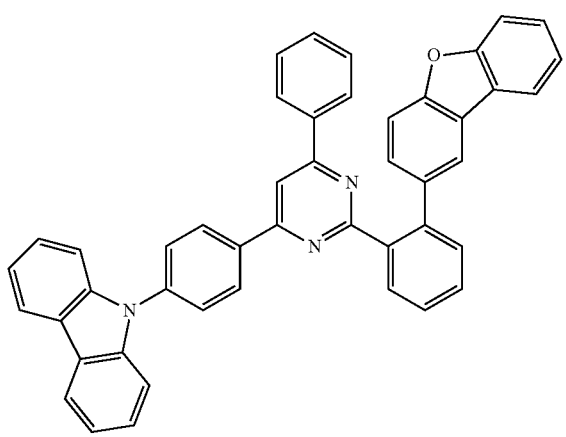
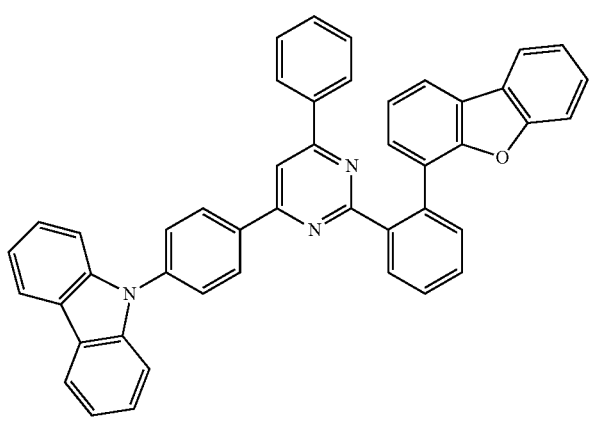

[Formula 34]
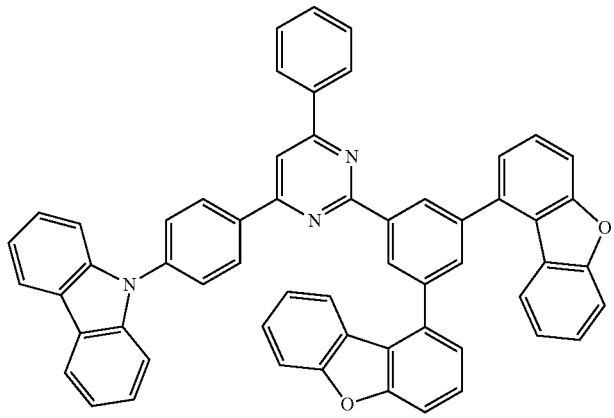
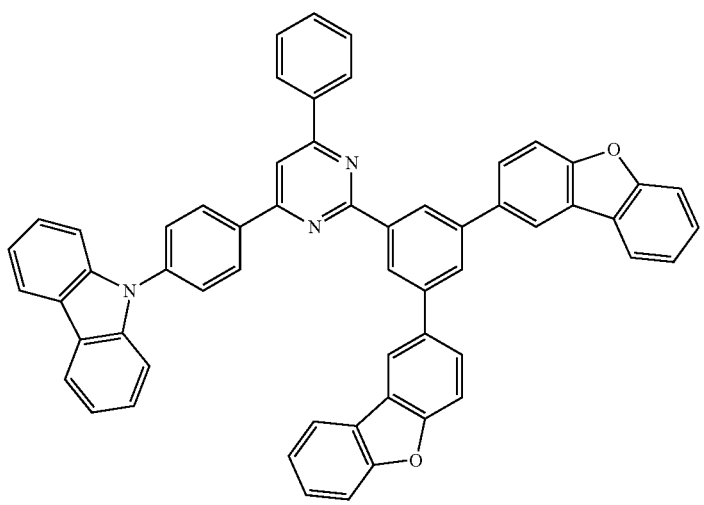
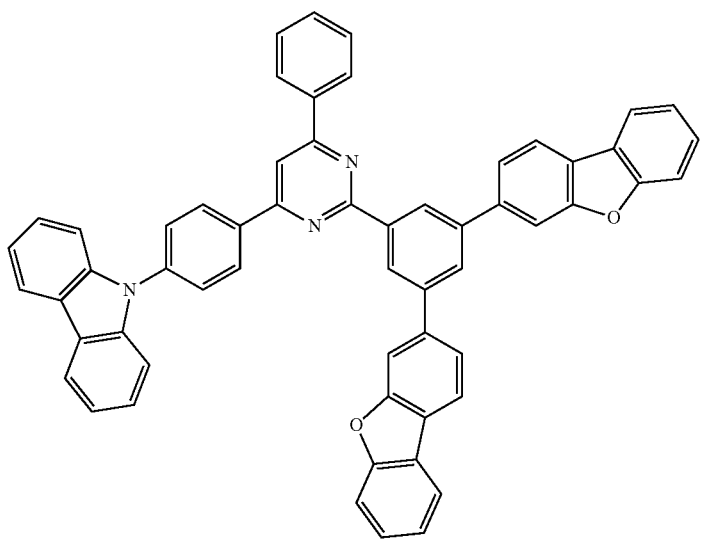

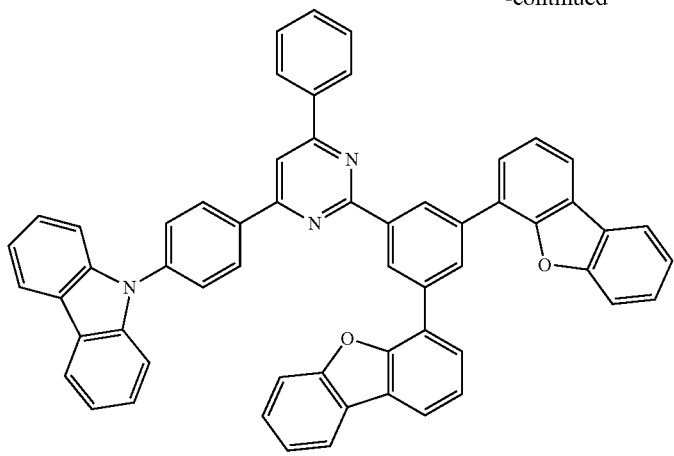
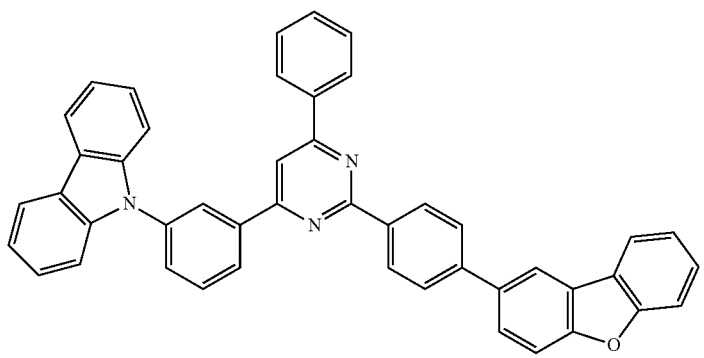
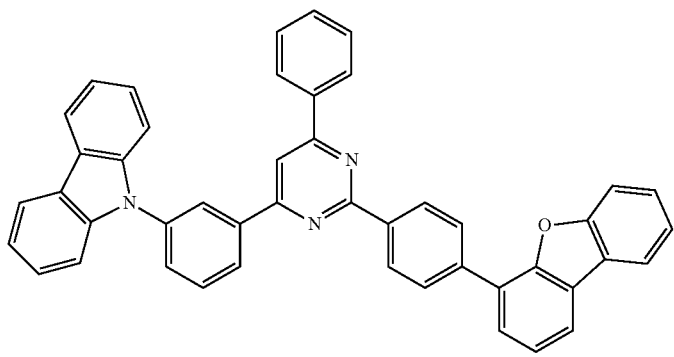
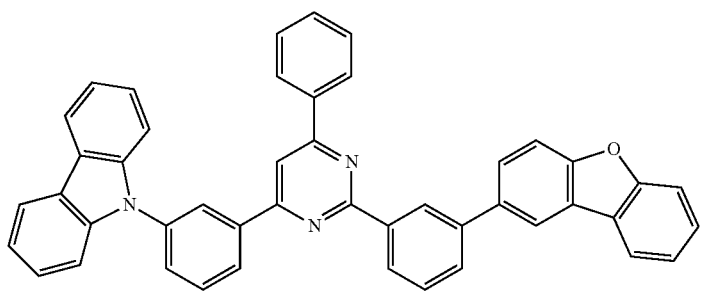

-continued
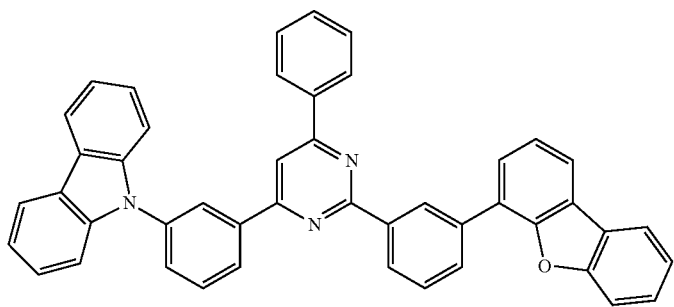
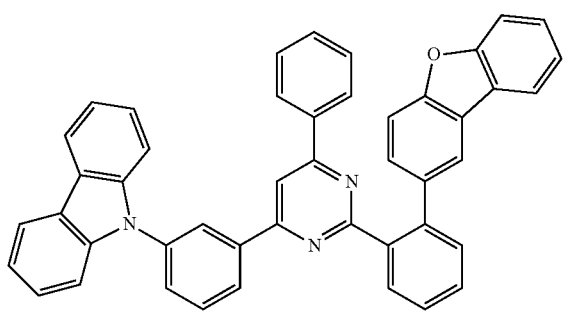
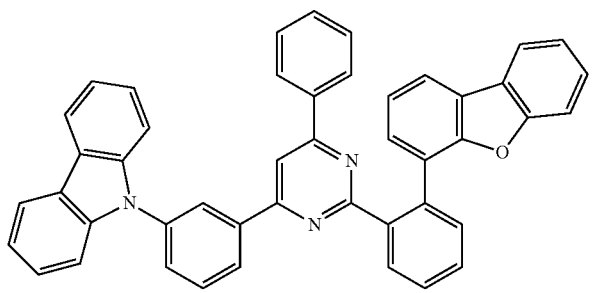
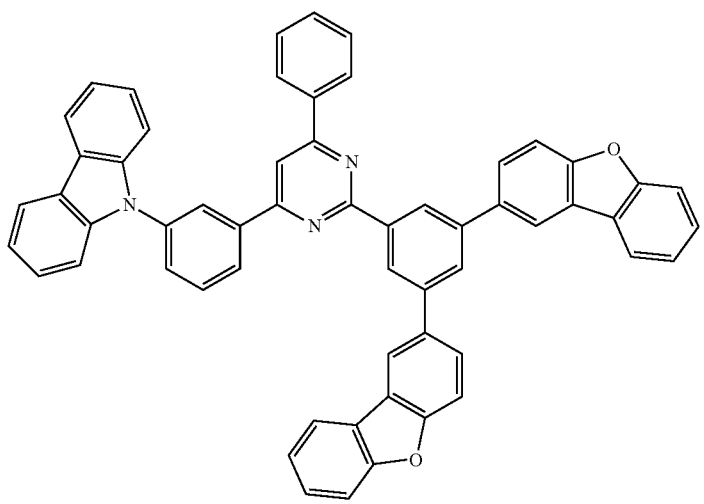

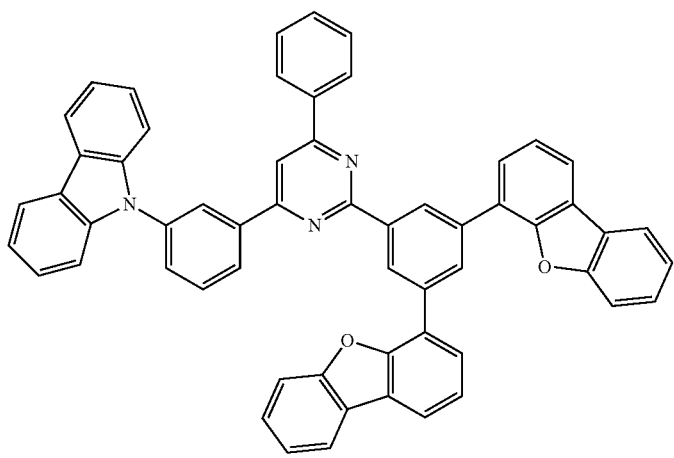
[Formula 35]
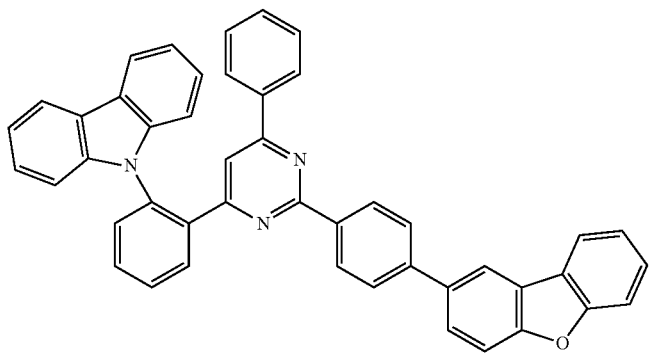
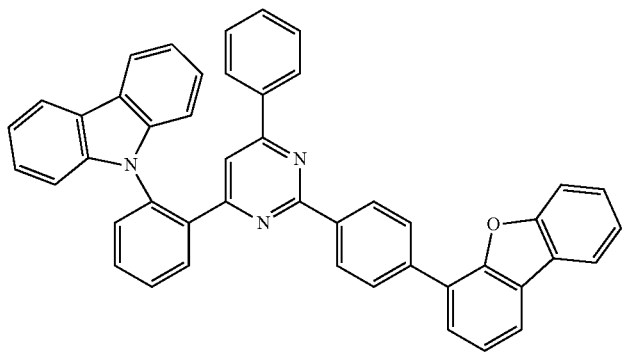
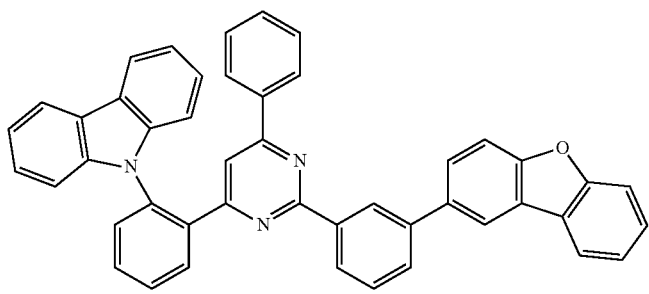

-continued
199
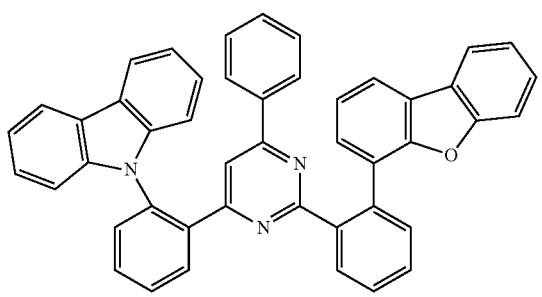
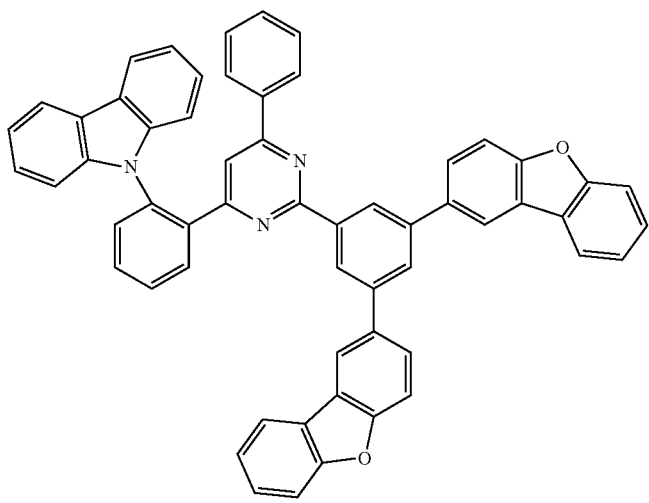
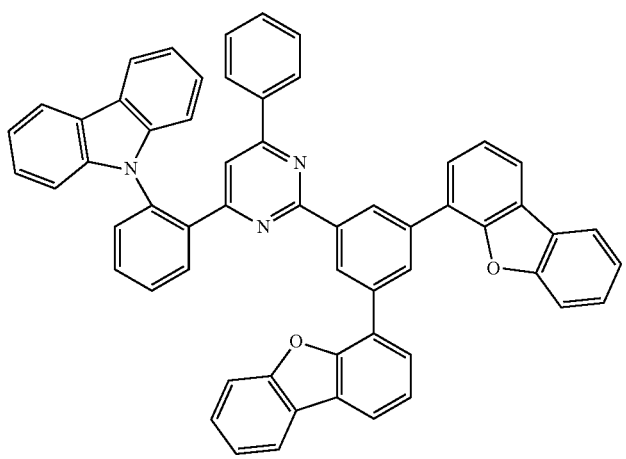
200
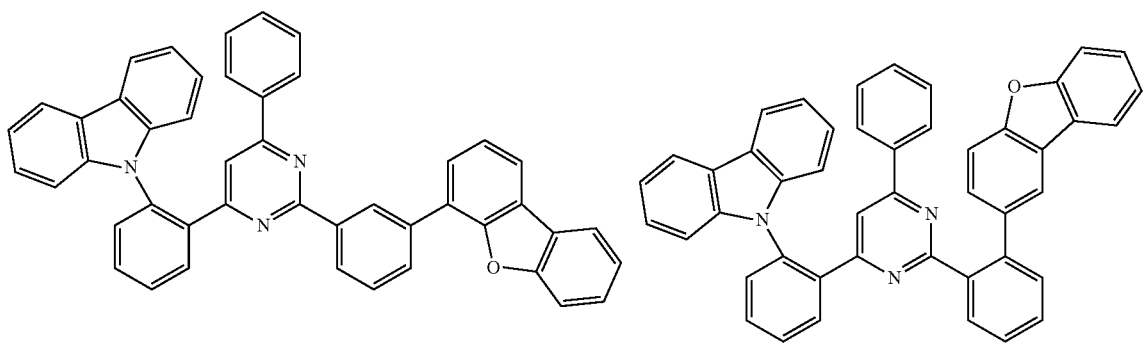

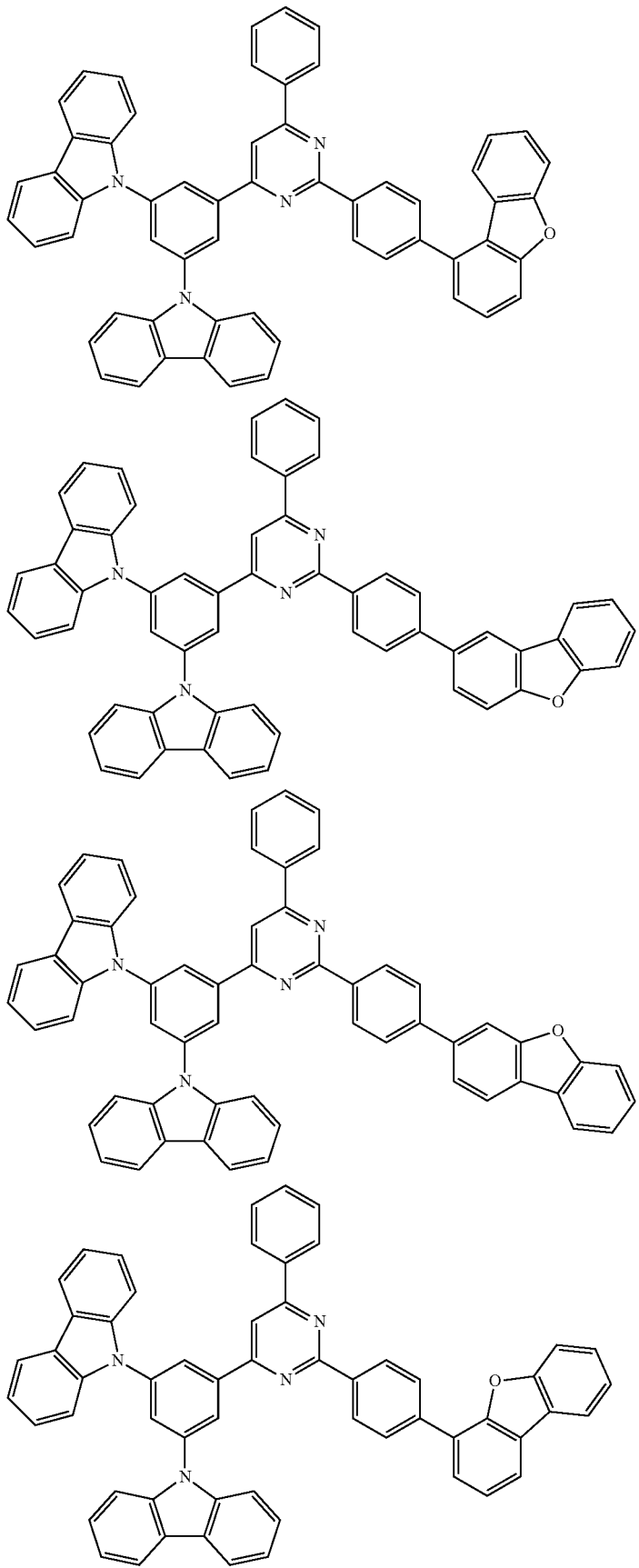

[Formula 36]
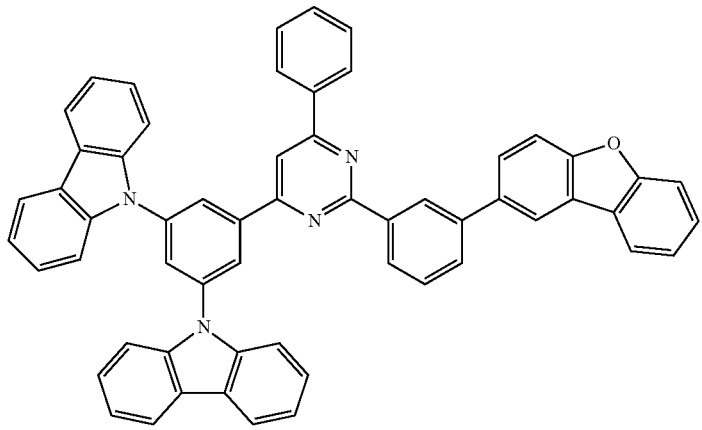
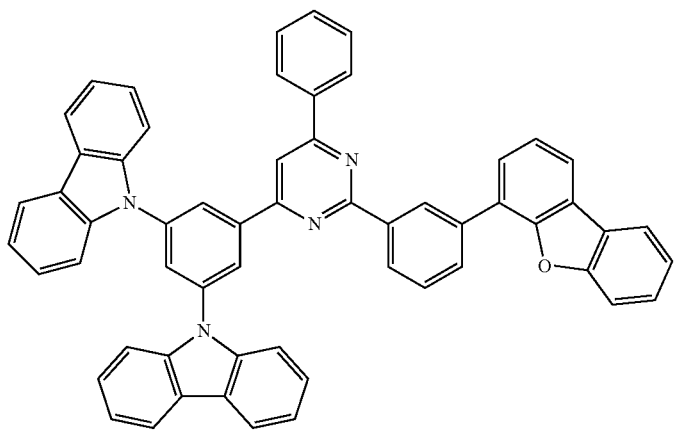
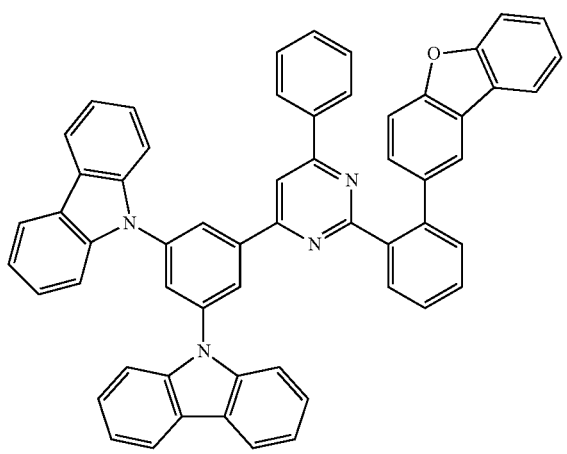

-continued
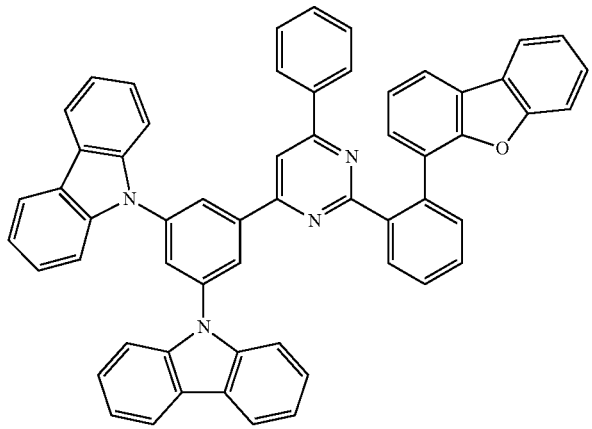
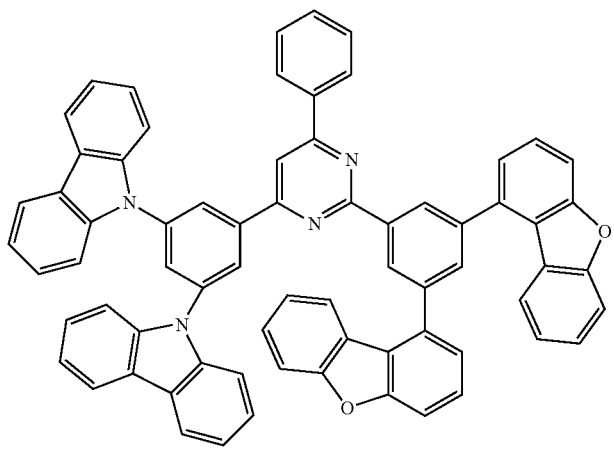
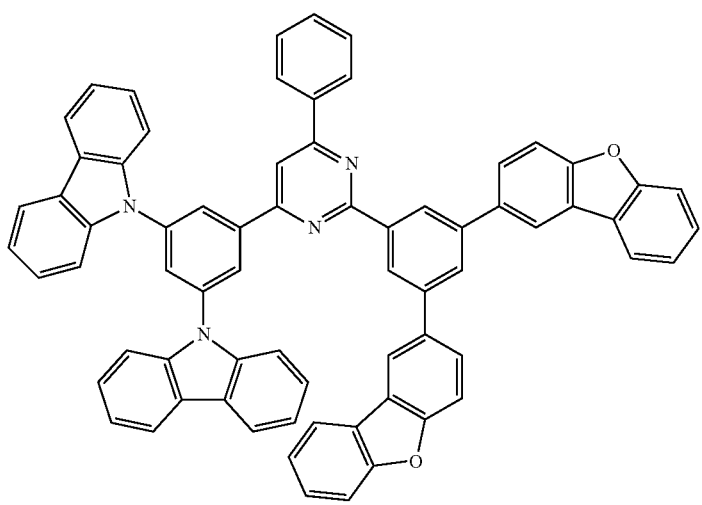

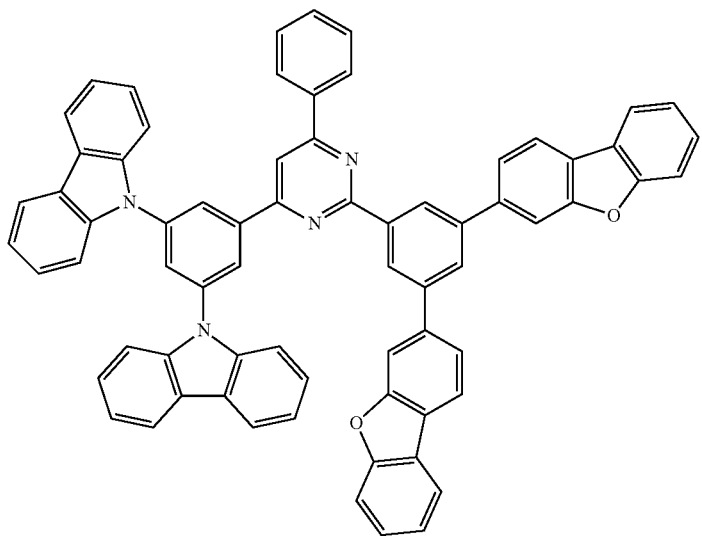
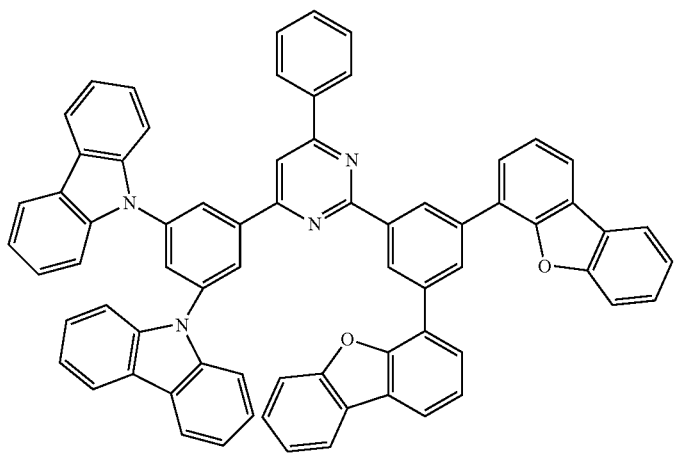
[Formula 37]
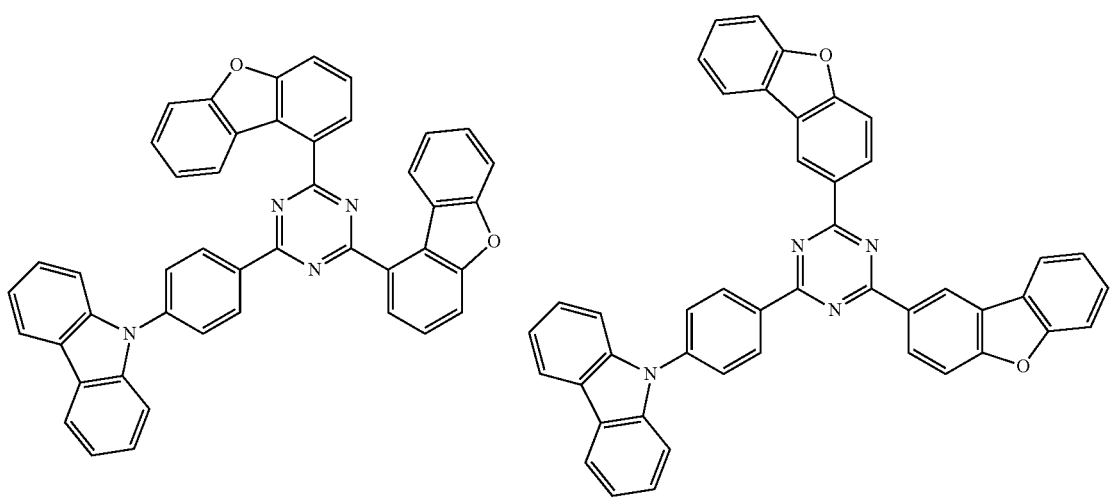

-continued
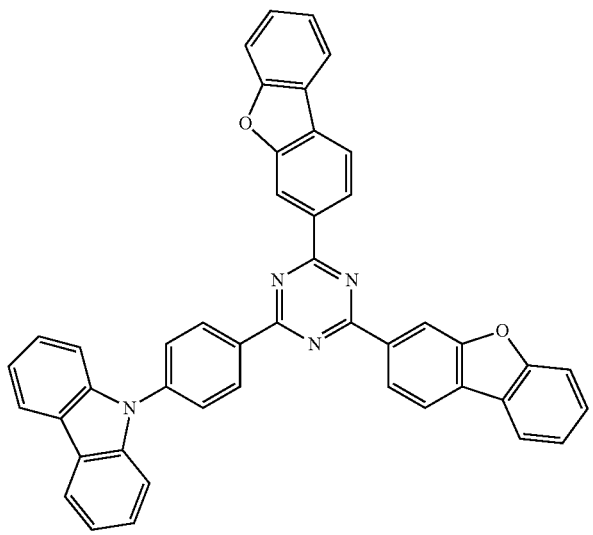
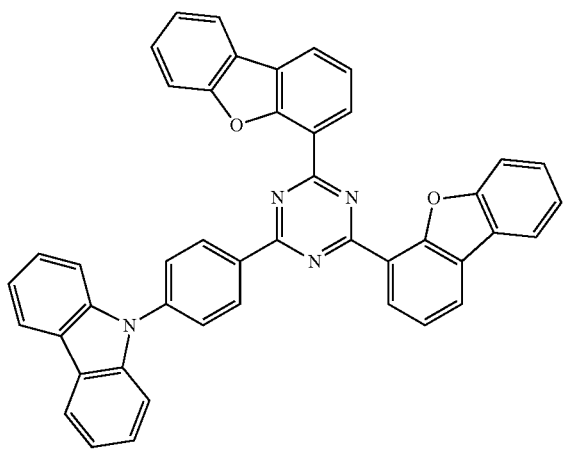
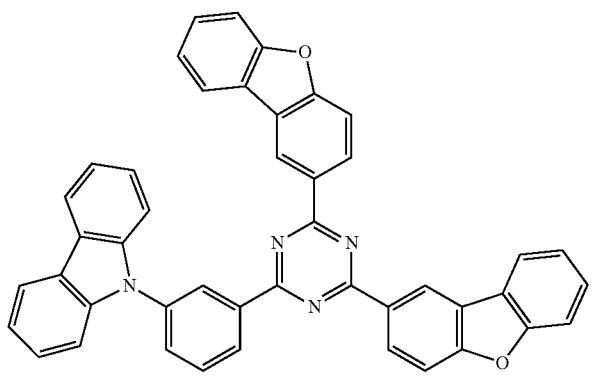

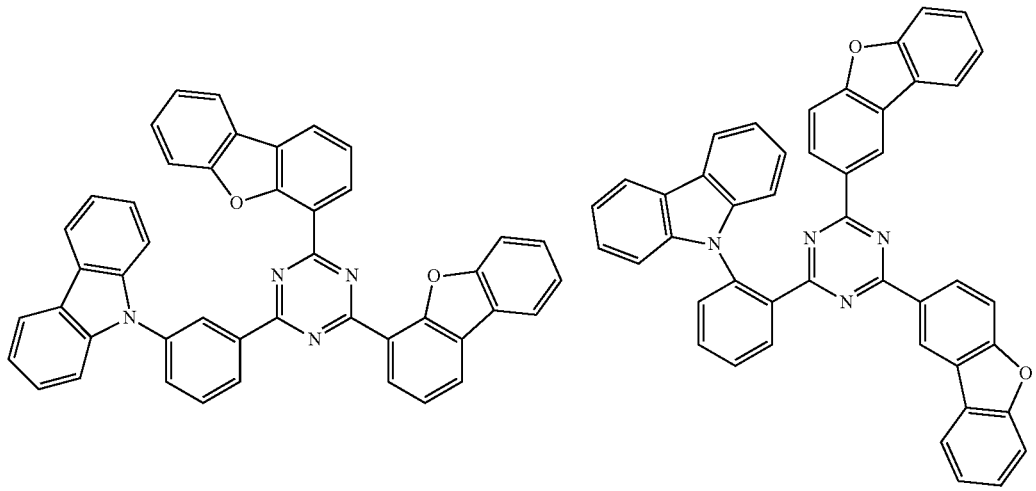
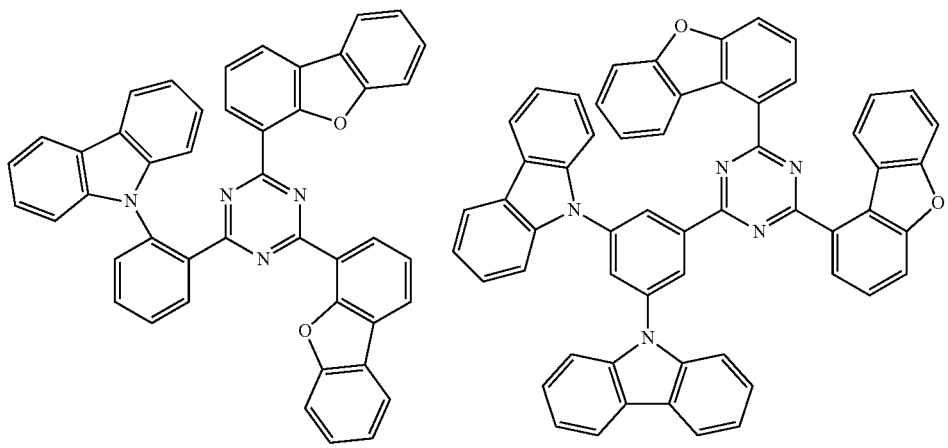
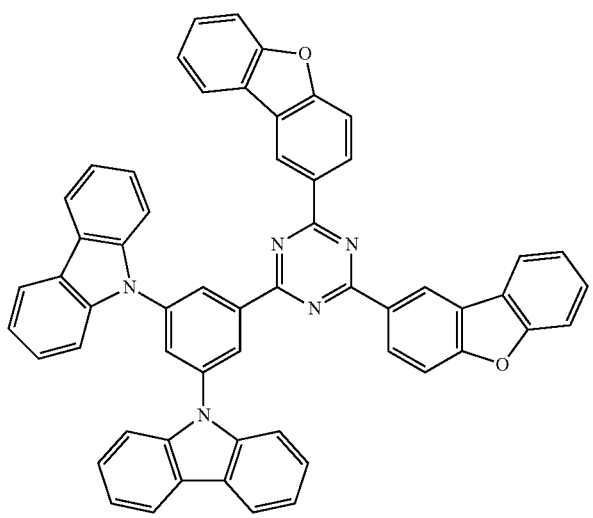

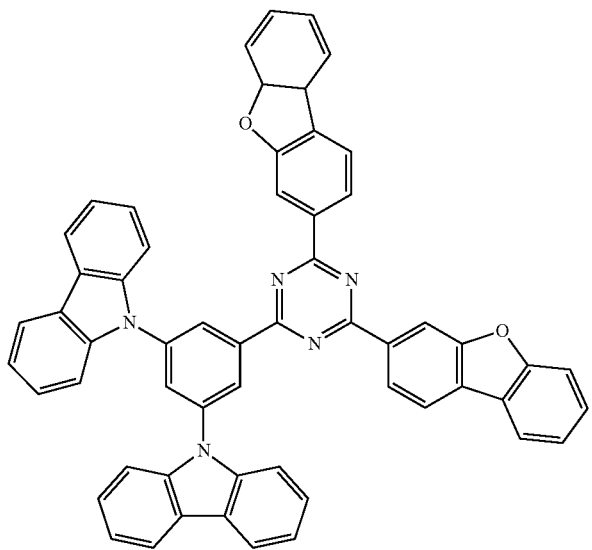
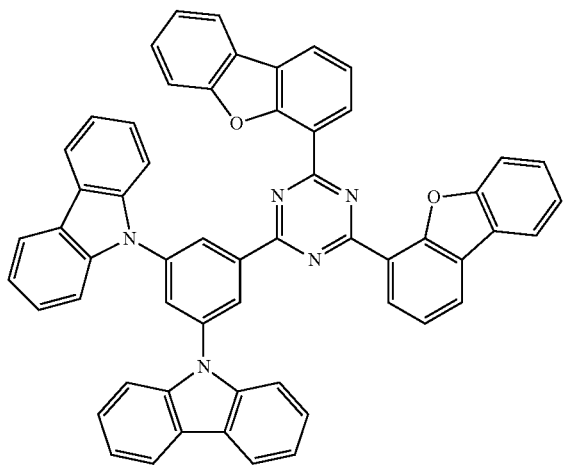
[Formula 38]
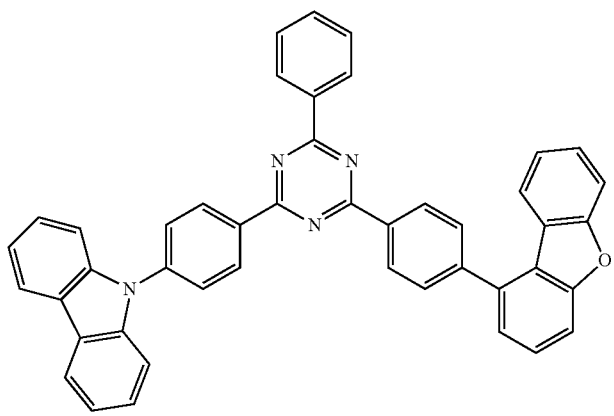

-continued
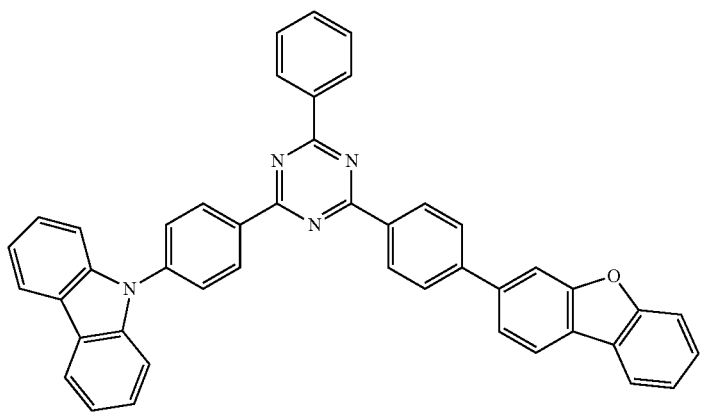
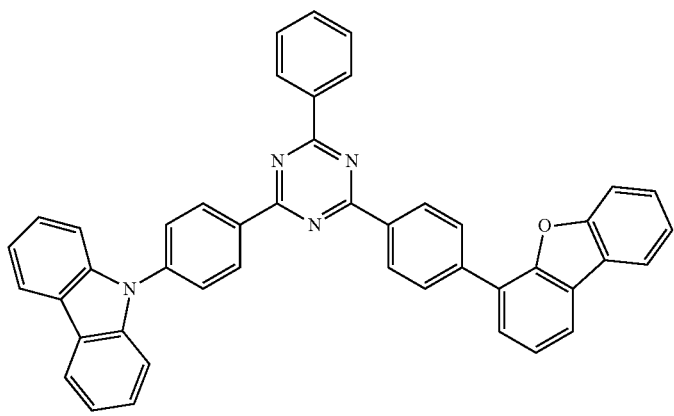
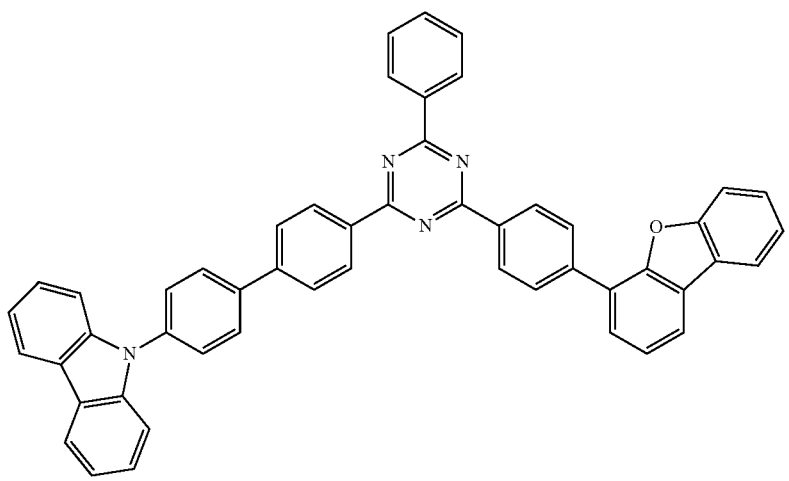
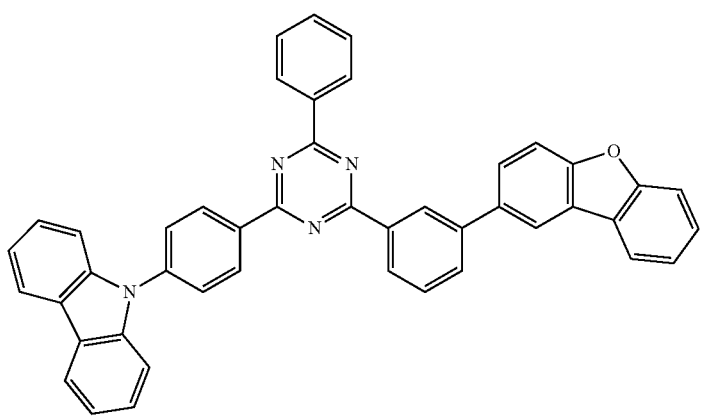

-continued
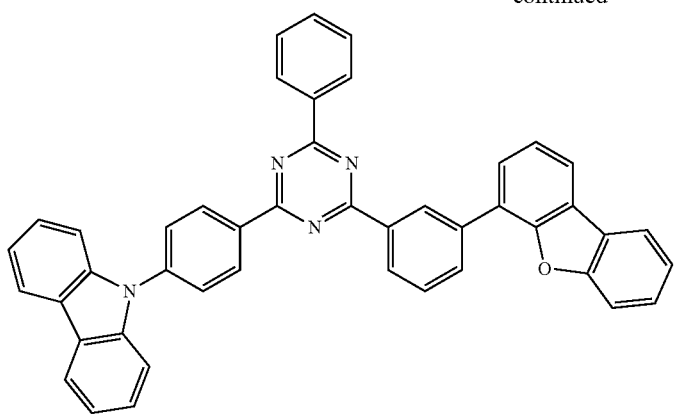
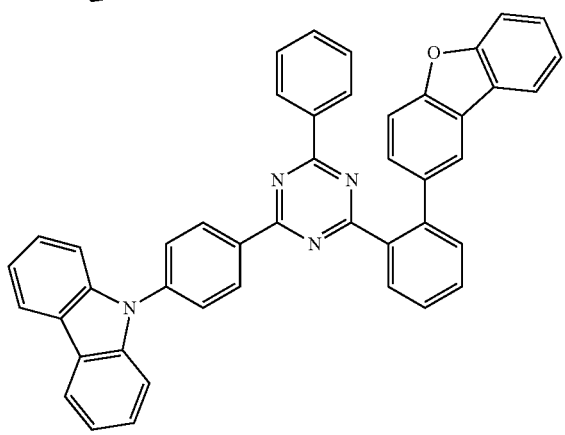
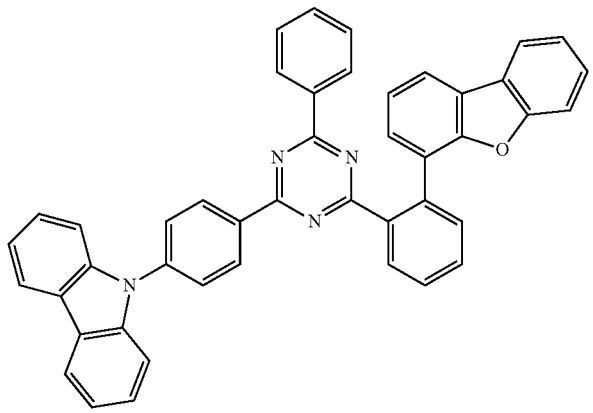
[Formula 39]
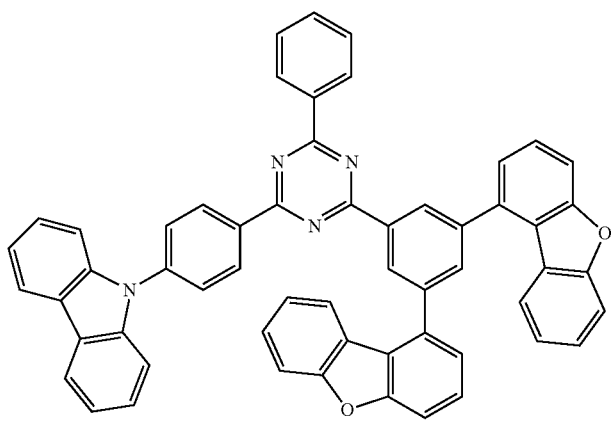

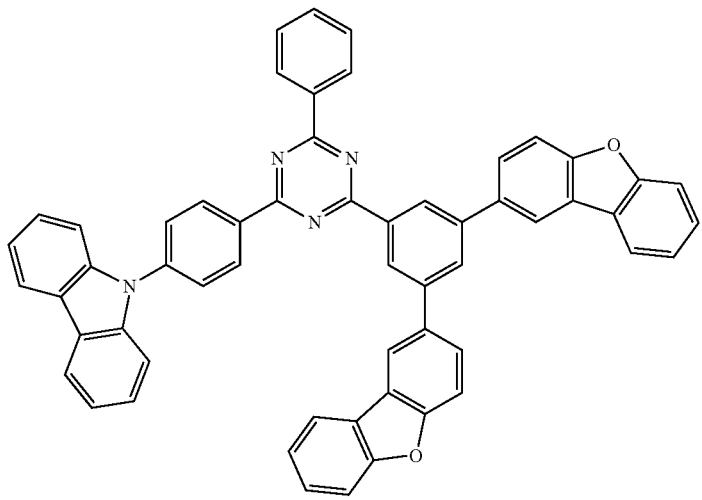
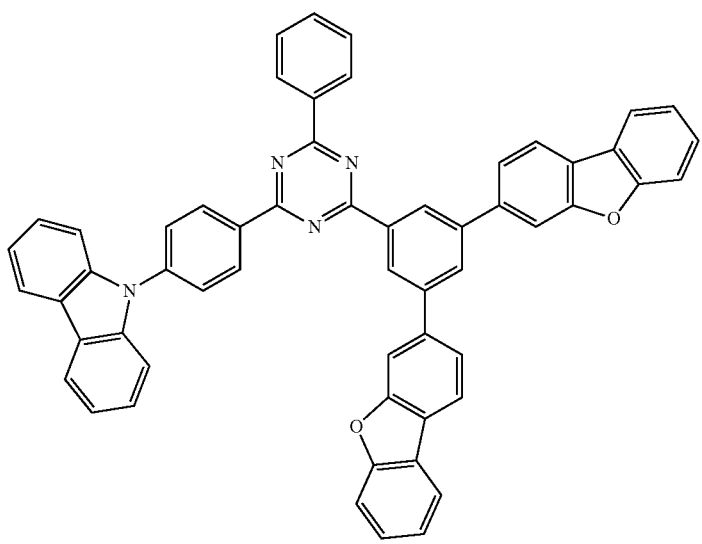
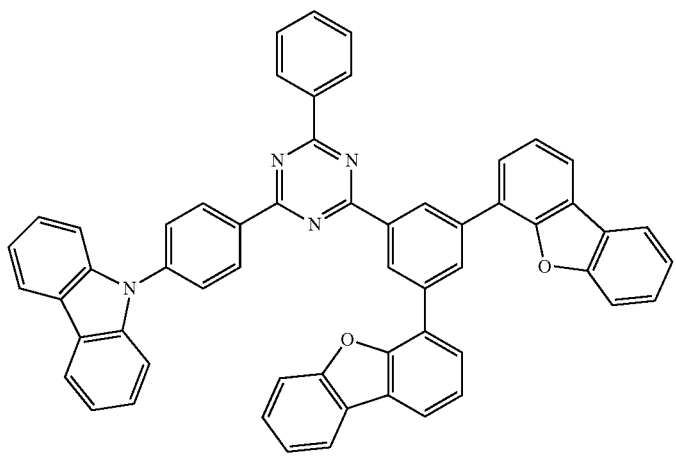

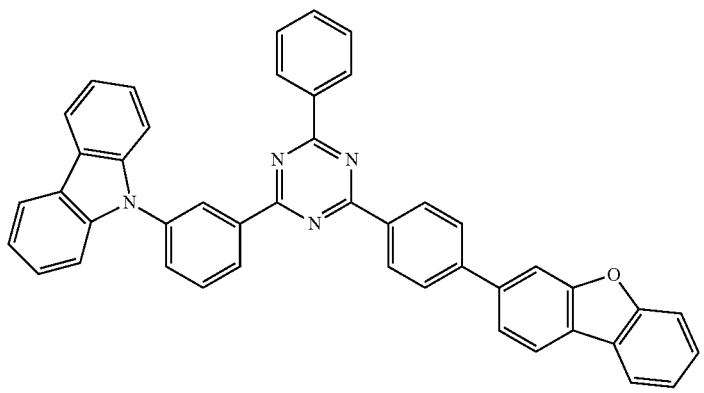
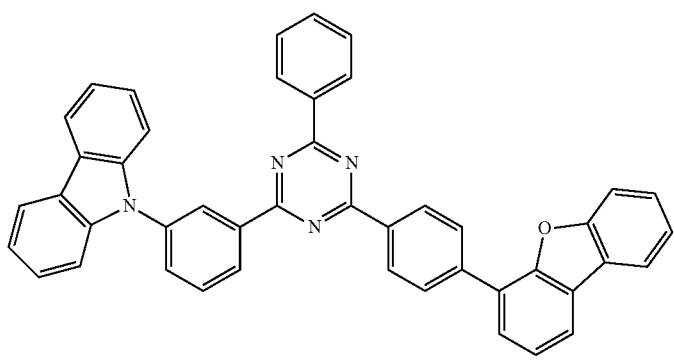
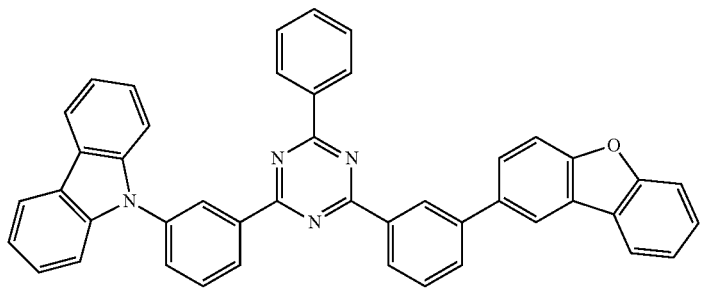
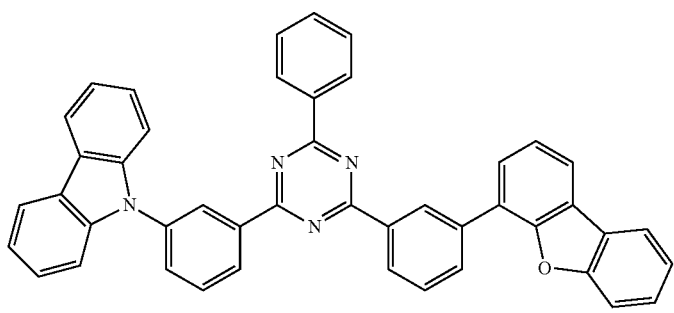
[Formula 40]
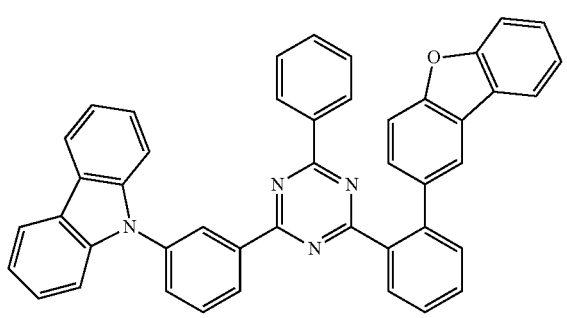

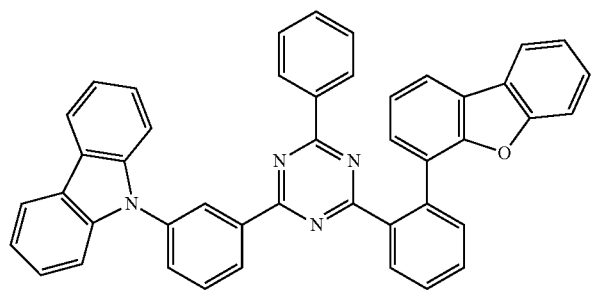
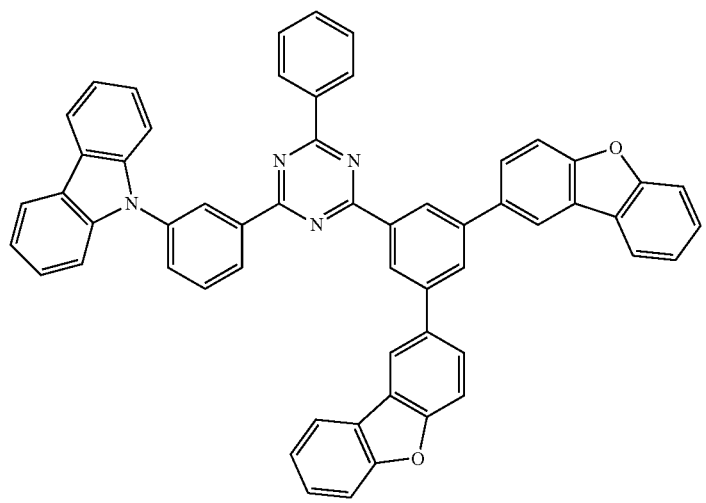
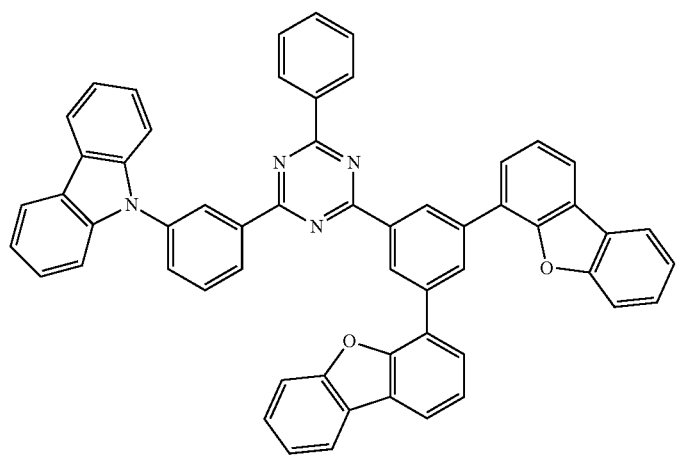
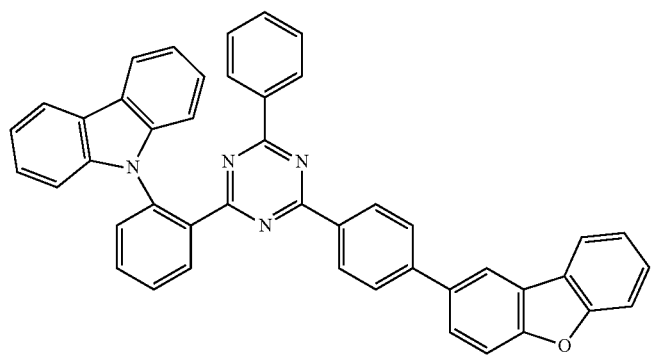

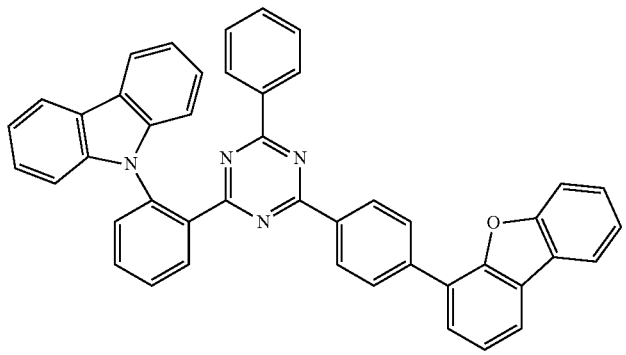
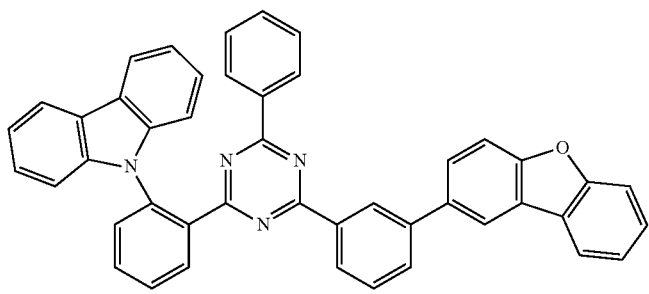
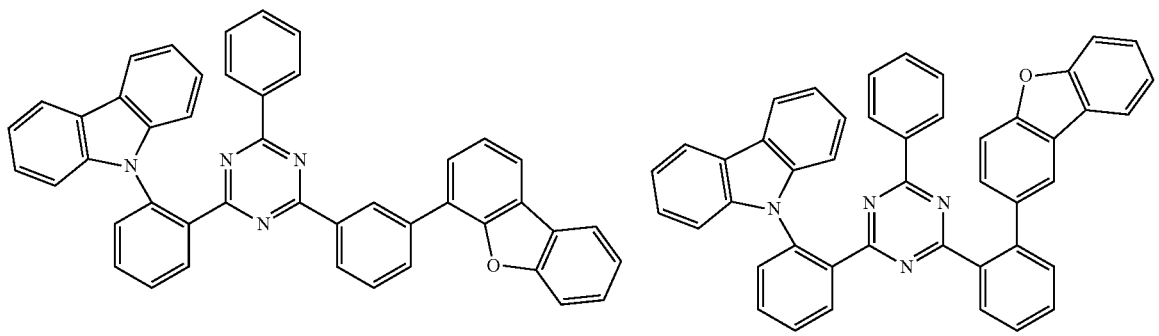
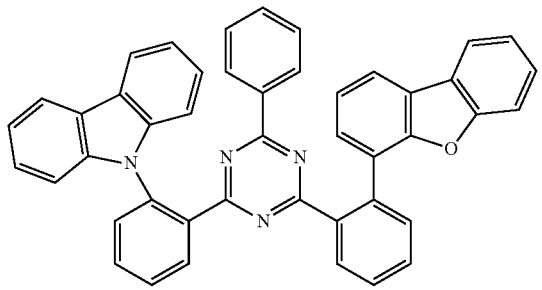

-continued
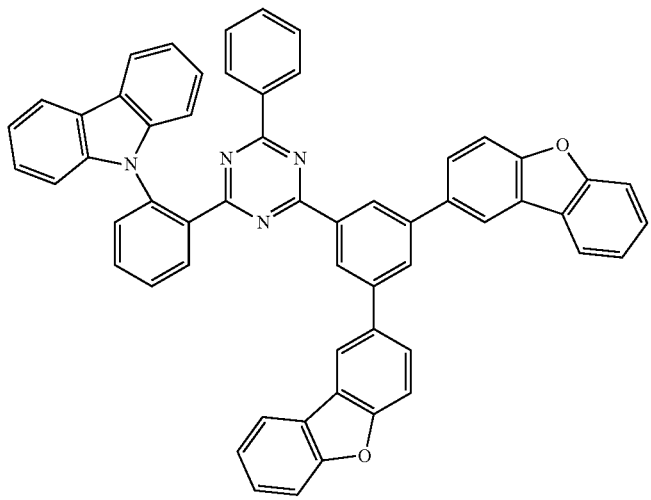
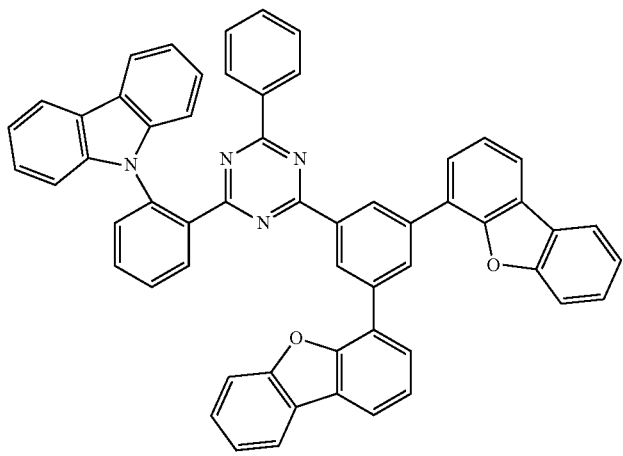
[Formula 41]
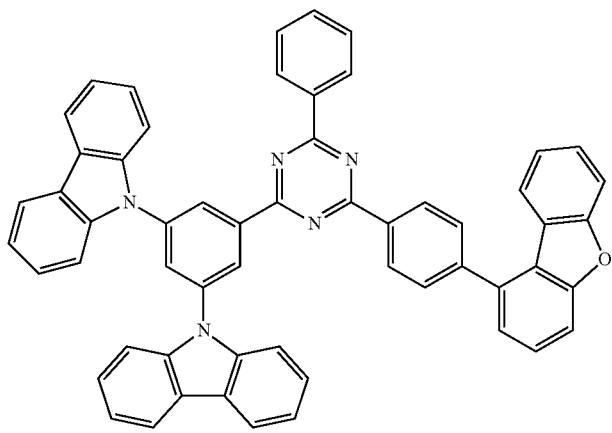

-continued
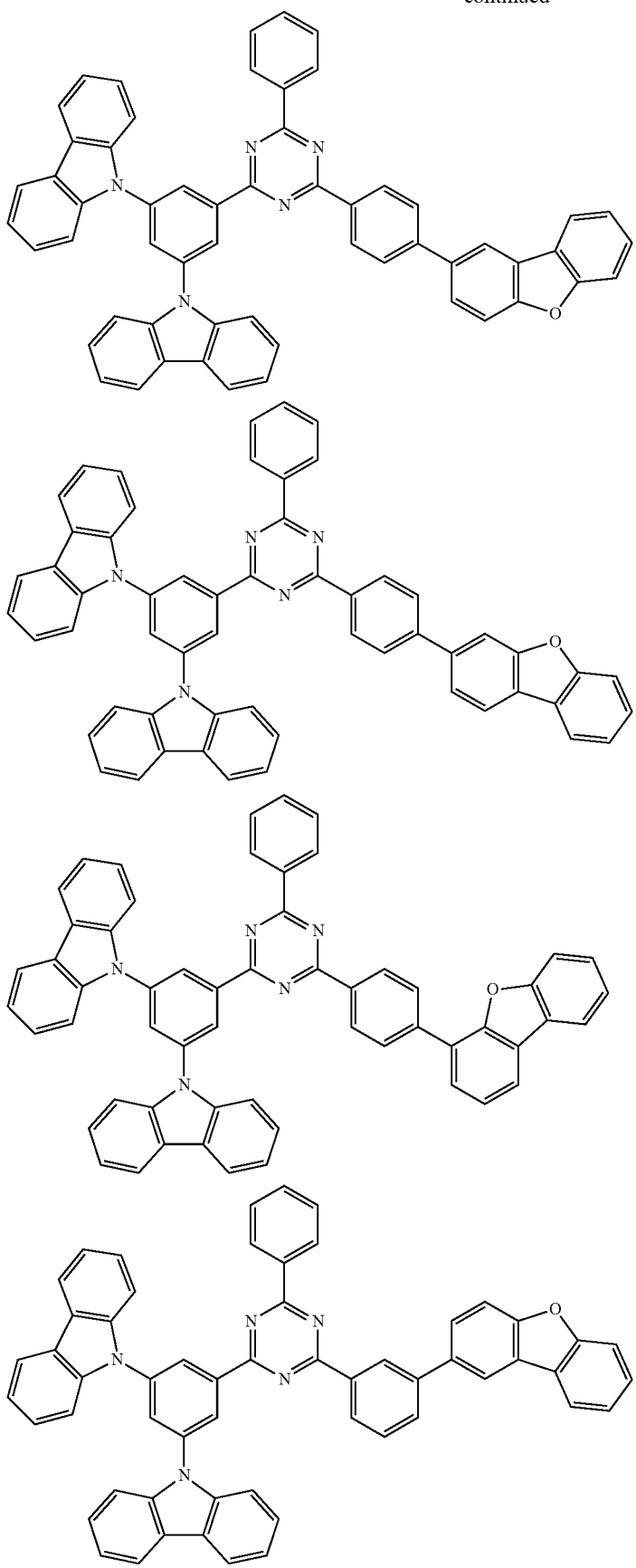

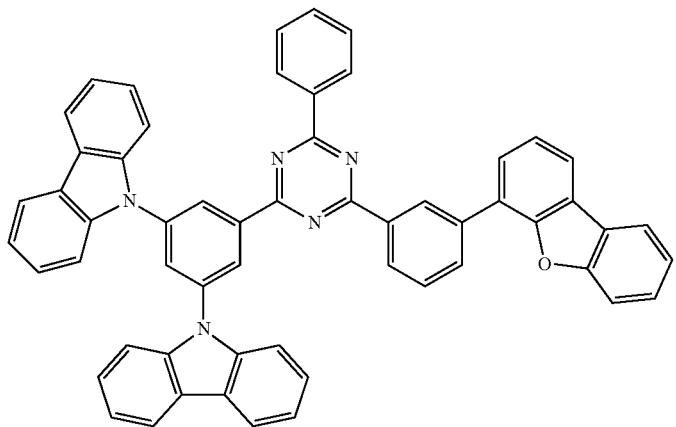
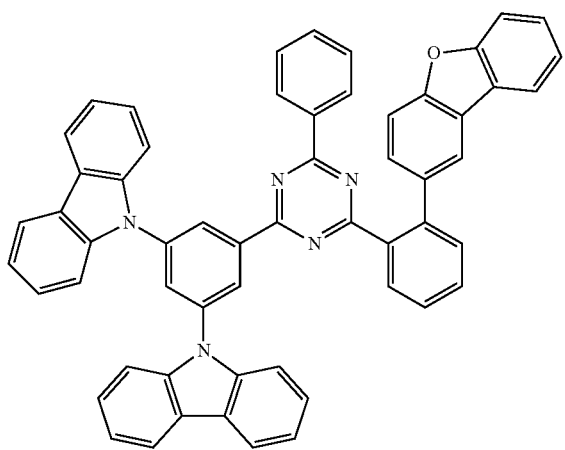
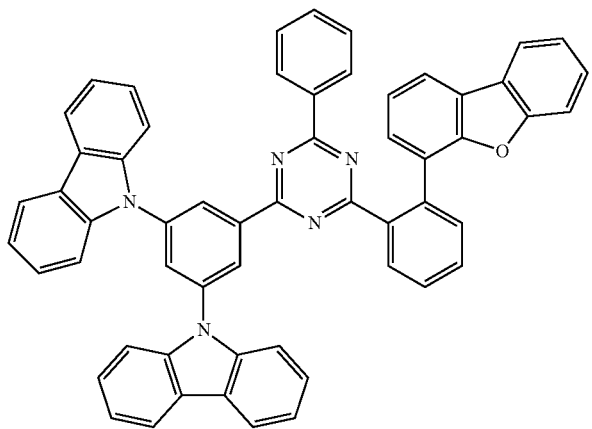

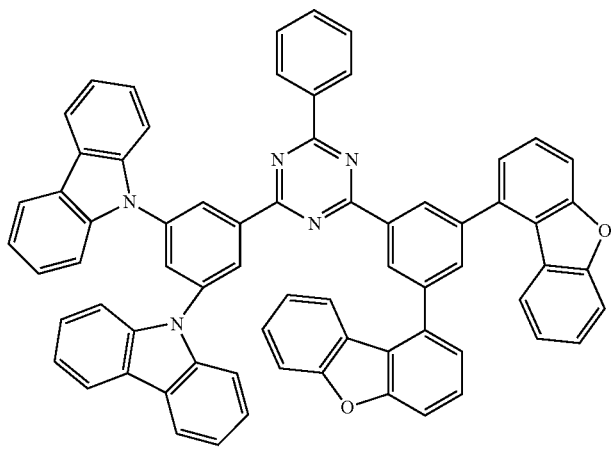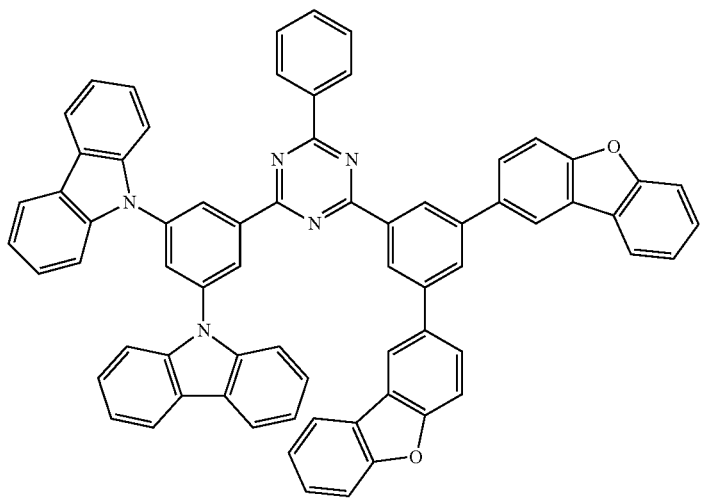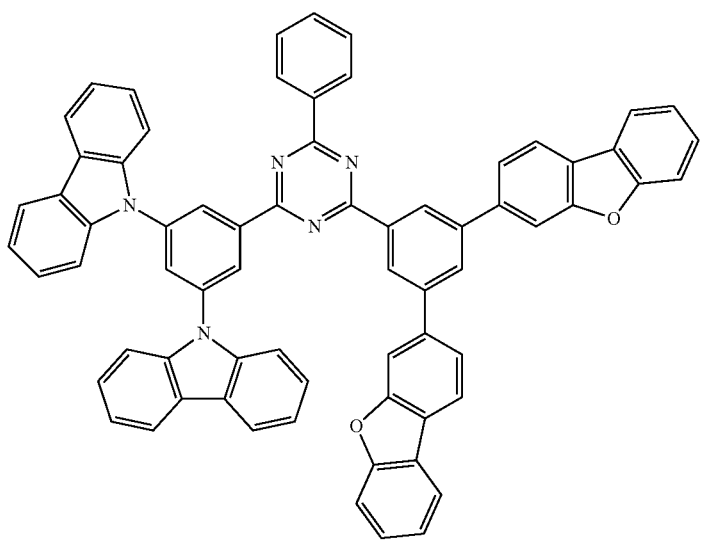

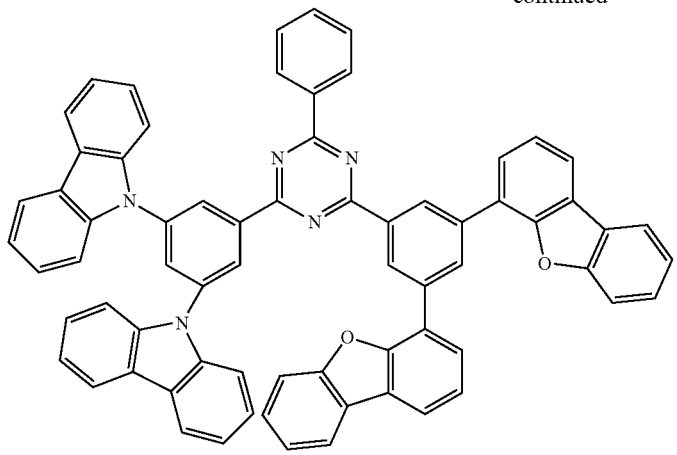

Material for Organic EL Device

The aromatic heterocyclic derivative of the invention is applicable as a material for an organic EL device (an organic-EL-device material). The organic-EL-device material may singularly contain the aromatic heterocyclic derivative of the invention, or may further contain another compound. The organic-EL-device material containing the aromatic heterocyclic derivative of the invention is usable as, for instance, a material for an electron transporting zone and a material for a blocking layer.

In the invention, the electron transporting zone means one of an electron transporting layer, electron injecting layer and blocking layer, or a combination of two or more layers of these layers.

Organic EL Device

First Exemplary Embodiment

The first exemplary embodiment utilizes a TTF phenomenon. The TTF phenomenon will be initially explained below.

Holes and electrons respectively injected from an anode and a cathode are recombined in an emitting layer to generate excitons. As for the spin state, as is conventionally known, singlet excitons account for 25% and triplet excitons account for 75%. In a conventionally known fluorescent device, light is emitted when singlet excitons of 25% are relaxed to the ground state. The remaining triplet excitons of 75% are returned to the ground state without emitting light through a thermal deactivation process. Accordingly, the theoretical limit value of the internal quantum efficiency of a conventional fluorescent device is believed to be 25%.

The behavior of triplet excitons generated within an organic substance has been theoretically examined. According to S. M. Bachilo et al. (J. Phys. Chem. A, 104, 7711 (2000)), assuming that high-order excitons such as quintet excitons are quickly returned to triplet excitons, triplet excitons (hereinafter abbreviated as $^3A^*$) collide with one another with an increase in the density thereof, whereby a reaction shown by the following formula occurs. In the formula, $^1A$ represents the ground state and $^1A^*$ represents the lowest singlet excitons.

$$^3A^* + {}^3A^* \rightarrow (4/9)^1A + (1/9)^1A^* + (13/9)^3A^*$$

In other words, $5\,{}^3A^* \rightarrow 4\,{}^1A + {}^1A^*$, and it is expected that, among triplet excitons initially generated, which account for 75%, one fifth thereof (i.e., 20%) is changed to singlet excitons. Accordingly, the amount of singlet excitons which contribute to emission is 40%, which is a value obtained by adding 15% (75%×(1/5)=15%) to 25%, which is the amount ratio of initially generated singlet excitons. At this time, a ratio of luminous intensity derived from TTF (TTF ratio) relative to the total luminous intensity is 15/40, i.e., 37.5%. Assuming that singlet excitons are generated by collision of initially-generated triplet excitons which account for 75% (i.e., one singlet exciton is generated from two triplet excitons), a significantly high internal quantum efficiency of 62.5% is obtained which is a value obtained by adding 37.5% (75%×(1/2)=37.5%) to 25%, which is the amount ratio of initially generated singlet excitons. At this time, the TTF ratio is 60% (37.5/62.5).

Figure 2:
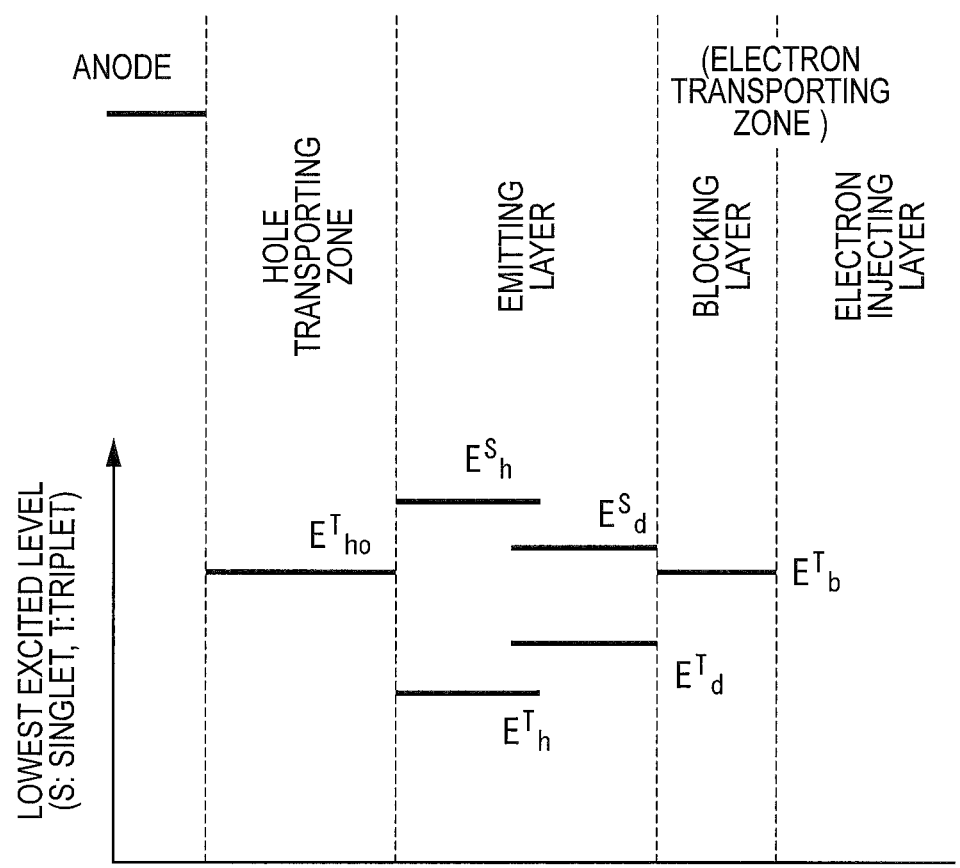
FIG. 2 is a view showing a relationship of energy gaps between layers of the invention.

FIG. 1 is schematic view showing one example of an organic EL device according to the first exemplary embodiment of the invention. FIG. 2 is a schematic view showing a relationship between a triplet energy of the emitting layer and a triplet energy of an electron transporting zone in the organic EL device according to the first exemplary embodiment. In the invention, the triplet energy is referred to as a difference between energy in the lowest triplet state and energy in the ground state. The singlet energy (often referred to as energy gap) is referred to as a difference between energy in the lowest singlet state and energy in the ground state.

An organic EL device 1 shown in FIG. 1 includes an anode 10, a hole transporting zone 60, an emitting layer 20, an electron transporting zone 70 and a cathode 50 in this sequential order. In the organic EL device of the exemplary embodiment, these components are adjacent to each other. In the exemplary embodiment, the electron transporting zone 70 includes a blocking layer 30 and an electron injecting layer 40. The hole transporting zone 60 is preferably interposed between the anode 10 and the emitting layer 20. The hole transporting zone 60 includes at least one of a hole injecting layer and a hole transporting layer. In the invention, a simply-called blocking layer means a layer functioning as a barrier against the triplet energy. Accordingly, the blocking layer functions differently from a hole blocking layer and a charge blocking layer.

The emitting layer includes a host material and a dopant material. The dopant material is preferably a dopant material exhibiting fluorescent emission (hereinafter, also referred to as a fluorescent dopant material). A fluorescent dopant material having a main peak wavelength of 550 nm or less is preferable. A fluorescent dopant material having a main peak wavelength of 500 nm or less is more preferable. A main peak wavelength means a peak wavelength of luminescence spectrum exhibiting a maximum luminous intensity among luminous spectra measured in a toluene solution with a concentration from $10^{-5}$ mol/l to $10^{-6}$ mol/l. The main peak wavelength of 550 nm is substantially equivalent to a green emission. In this wavelength zone, improvement in luminous efficiency of a fluorescent device utilizing the TTF phenomenon is desired. A blue-emitting fluorescent device of 480 nm or less is expected to further improve in luminous efficiency. In a red-emitting fluorescent device of 550 nm or more, a phosphorescent device exhibiting a high internal quantum efficiency has already been at a practical level. Accordingly, improvement in luminous efficiency as a fluorescent device is not desired.

In FIG. 2, the holes injected from the anode are injected to the emitting layer via the hole transporting zone. The electrons injected from the cathode are injected to the emitting layer via the electron injecting layer and the blocking layer. Subsequently, the holes and the electrons are recombined in the emitting layer to generate singlet excitons and triplet excitons. There are two manners as for the occurrence of recombination: recombination may occur either on molecules of the host material or on molecules of the dopant material.

In this exemplary embodiment, as shown in FIG. 2, when the triplet energy of the host material and that of the dopant material are respectively taken as $E^T_h$ and $E^T_d$, a relationship of the following formula (2A) is satisfied.

$$E^T_h < E^T_d \quad (2A)$$

Figure 3:
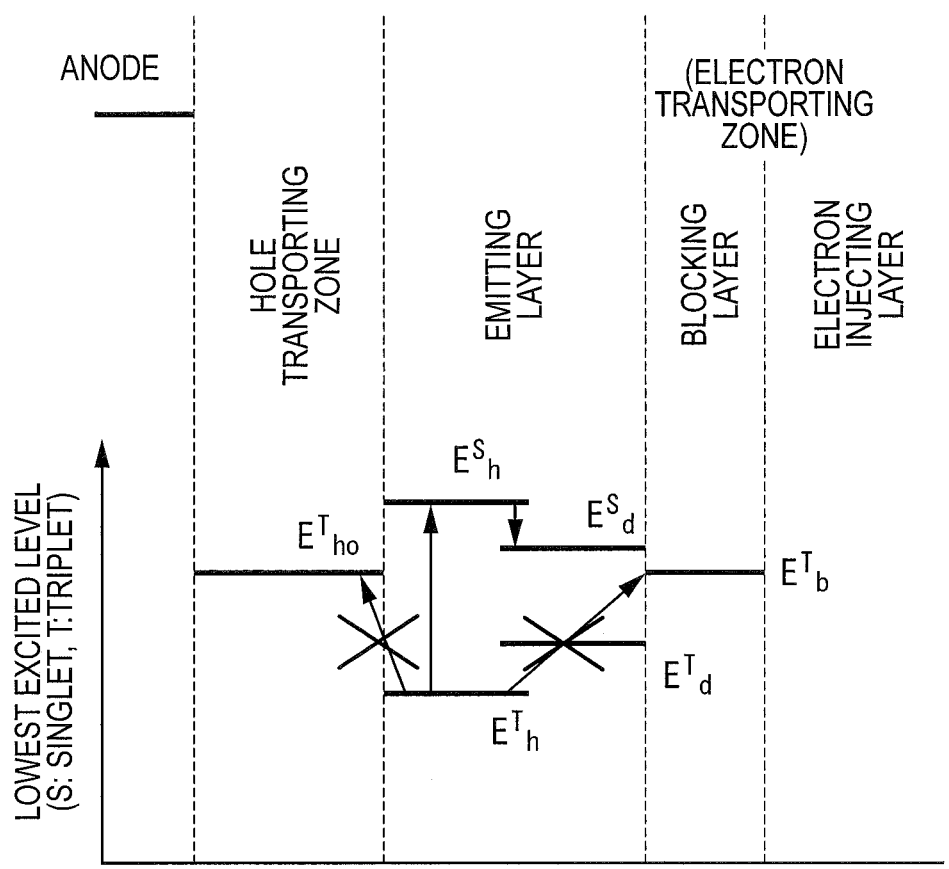
FIG. 3 is a view showing an action based on the relationship of the energy gaps between the layers of the invention.

When this relationship of the formula (2A) is satisfied, triplet excitons generated by recombination on the host do not transfer to the dopant which has a higher triplet energy, as shown in FIG. 3. Triplet excitons generated by recombination on the molecules of the dopant material quickly energy-transfer to the molecules of the host material. In other words, triplet excitons on the host material do not transfer to the dopant material but collide with one another efficiently on the host material to generate singlet excitons by the TTF phenomenon. Further, since the singlet energy $E^S_d$ of the dopant material is smaller than the singlet energy $E^S_h$ of the host material, a relationship of the following formula (2B) is satisfied.

$$E^S_d < E^S_h \quad (2B)$$

Further, since the relationship of the formula (2B) is satisfied, singlet excitons generated by the TTF phenomenon energy-transfer from the host material to the dopant material, thereby contributing to fluorescent emission of the dopant material.

In the dopant material usually used in a fluorescent device, transition from the triplet state to the ground state should be inhibited. In such a transition, triplet excitons are not optically energy-deactivated, but are thermally energy-deactivated. By causing the triplet energy of the host material and the triplet energy of the dopant material to satisfy the above-mentioned relationship, singlet excitons are generated efficiently due to the collision of triplet excitons before they are thermally deactivated, whereby luminous efficiency is improved. As a consequence, luminous efficiency is enhanced.

In the exemplary embodiment, the blocking layer is adjacent to the emitting layer. The blocking layer has a function of preventing triplet excitons generated in the emitting layer to be diffused to an electron transporting zone and confining the triplet excitons within the emitting layer to increase a density of the triplet excitons therein, thereby causing the TTF phenomenon efficiently.

The blocking layer also serves for efficiently injecting the electrons to the emitting layer. When the electron injecting properties to the emitting layer are deteriorated, the density of the triplet excitons is decreased since the electron-hole recombination in the emitting layer is decreased. When the density of the triplet excitons is decreased, the frequency of collision of the triplet excitons is reduced, whereby the TTF phenomenon does not occur efficiently.

In the exemplary embodiment, the blocking layer contains the above-described aromatic heterocyclic derivative of the invention.

The electron injecting layer is interposed between the blocking layer and the cathode. The electron injecting layer facilitates electron injection from the cathode. Specific examples of the electron injecting layer include: an electron injecting layer in which a conventional electron transporting material is layered on at least one of an electron-donating dopant and an organic metal complex; and an electron injecting layer that is provided by doping a blocking-layer material with at least one of the electron-donating dopant material and the organic metal complex near an interface between the electron injecting layer and the cathode.

The electron-donating dopant material may be at least one compound selected from an alkali metal, alkali metal compound, alkaline earth metal, alkaline earth metal compound, rare earth metal, and rare earth metal compound.

The organic metal complex may be at least one compound selected from an organic metal complex including an alkali metal, an organic metal complex including an alkaline earth metal, and an organic metal complex including rare earth metal.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), among which a substance having a work function of 2.9 eV or less is particularly preferable. Among the above, the alkali metal is preferably K, Rb or Cs, more preferably Rb or Cs, the most preferably Cs.

Examples of the alkaline earth metal are calcium (Ca) (work function: 2.9 eV), strontium (Sr) (work function: 2.0 to 2.5 eV), and barium (Ba) (work function: 2.52 eV), among which a substance having a work function of 2.9 eV or less is particularly preferable.

Examples of the rare earth metal are scandium (Sc), yttrium (Y), cerium (Ce), terbium (Tb) and ytterbium (Yb), among which a substance having a work function of 2.9 eV or less is particularly preferable.

Since the above preferable metals have particularly high reducibility, addition of a relatively small amount of the metals to an electron injecting zone can enhance luminance intensity and lifetime of the organic EL device.

Examples of the alkali metal compound are an alkali oxide such as lithium oxide ($Li_2O$), cesium oxide ($Cs_2O$) or potassium oxide ($K_2O$), an alkali halide such as lithium fluoride (LiF), sodium fluoride (NaF), cesium fluoride (CsF) or potassium fluoride (KF), among which lithium fluoride (LiF), lithium oxide ($Li_2O$) and sodium fluoride (NaF) are preferable.

Examples of the alkaline earth metal compound are barium oxide (BaO), strontium oxide (SrO), calcium oxide (CaO) and a mixture thereof, i.e., $Ba_xSr_{1-x}O$ (0<x<1), $Ba_xCa_{1-x}O$ (0<x<1), among which BaO, SrO and CaO are preferable.

Examples of the rare earth metal compound are ytterbium fluoride (YbF$_3$), scandium fluoride (ScF$_3$), scandium oxide (ScO$_3$), yttrium oxide (Y$_2$O$_3$), cerium oxide (Ce$_2$O$_3$), gadolinium fluoride (GdF$_3$) and terbium fluoride (TbF$_3$), among which YbF$_3$, ScF$_3$ and TbF$_3$ are preferable.

The alkali metal complex is not particularly limited, as long as at least one of alkali metal ion, alkaline earth metal ion and rare earth metal ion is contained therein as metal ion. The ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The electron-donating dopant material and the organic metal complex are added to preferably form a layer or an island pattern in an interfacial region. The layer or the island pattern of the electron-donating dopant material and the organic metal complex is preferably formed by simultaneously depositing an organic substance (an emitting material and an electron injecting material) for forming the interfacial region while depositing at least one of the electron-donating dopant material and the organic metal complex by resistance heating deposition, thereby dispersing at least one of the electron-donating dopant material and the organic metal complex in the organic substance. A dispersion concentration in a molar ratio of the organic substance relative to the electron-donating dopant and/or organic metal complex is 100:1 to 1:100, preferably 5:1 to 1:5.

When at least one of the electron-donating dopant and the organic metal complex forms a layer, the emitting material or the electron injecting material for forming the organic layer of the interfacial region is initially layered, and at least one of the electron-donating dopant and the organic metal complex is subsequently deposited singularly thereon by resistance heating deposition to form a preferably 0.1 nm to 15 nm thick layer.

When at least one of the electron-donating dopant and the organic metal complex forms an island pattern, the emitting material or the electron injecting material for forming the organic layer of the interfacial region is initially formed in an island pattern, and at least one of the electron-donating dopant and the organic metal complex is subsequently deposited singularly thereon by resistance heating deposition to form a preferably 0.05 nm to 1 nm thick island.

A molar ratio of the main component relative to at least one of the electron-donating dopant material and the organic metal complex in the organic EL device of this exemplary embodiment is preferably 5:1 to 1:5, more preferably 2:1 to 1:2.

A compound other than the electron-donating dopant material and the organic metal complex, which is used in the electron injecting layer, is exemplified by a compound represented by a formula (EIL-1) below.

[Formula 42]

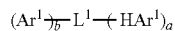

(EIL-1)

In the formula (EIL-1), HAr$^1$ is a substituted or unsubstituted nitrogen-containing heterocyclic group, which preferably has the following structures.

[Formula 43]

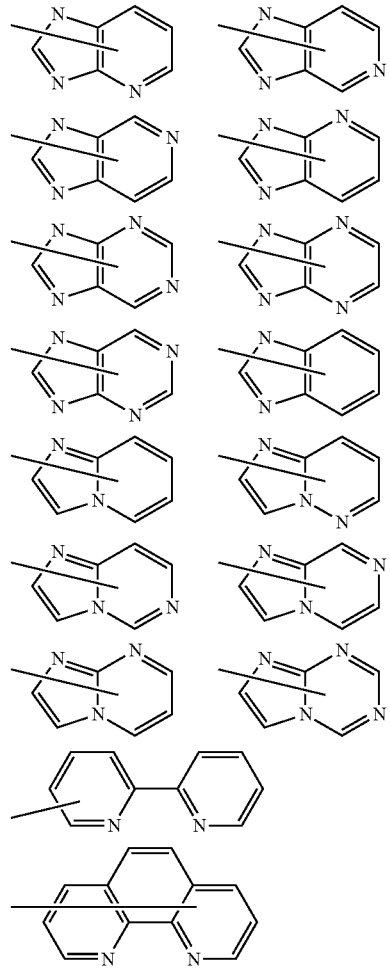

Examples of a substituent for HAr$^1$ in the formula (EIL-1) are a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkylsilyl group having 3 to 20 carbon atoms, a substituted or unsubstituted arylsilyl group having 8 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 ring carbon atoms, and a substituted or unsubstituted heterocyclic group having 5 to 30 ring atoms.

In the formula (EIL-1), Ar$^1$ is a substituted or unsubstituted fused ring group having 10 to 30 ring carbon atoms, which preferably has the following fused ring structures.

[Formula 44]

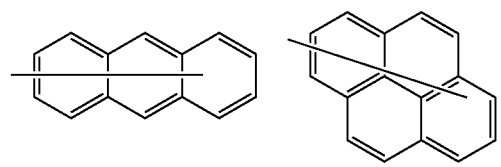

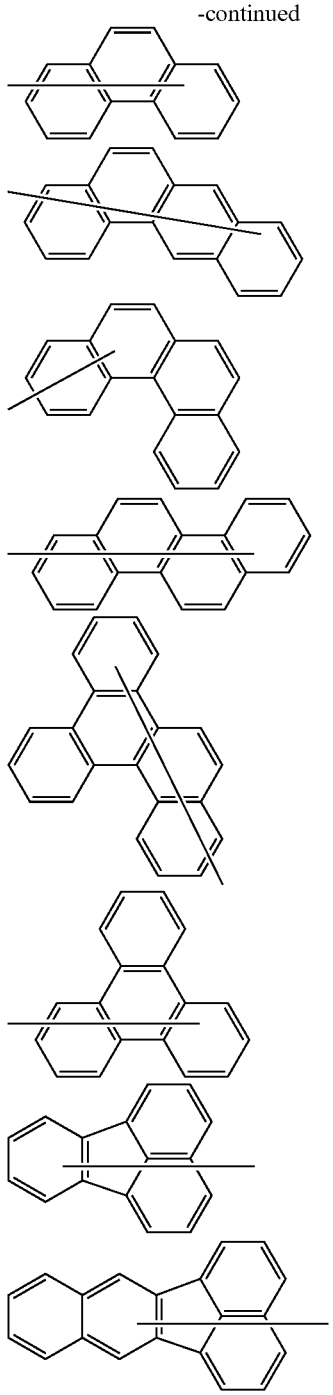

Examples of a substituent for Ar¹ in the formula (EIL-1) are a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkylsilyl group having 3 to 20 carbon atoms, a substituted or unsubstituted arylsilyl group having 8 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 ring carbon atoms, and a substituted or unsubstituted heterocyclic group having 5 to 30 ring atoms.

In the formula (EIL-1), $L^1$ represents a single bond, a substituted or unsubstituted a+b valent hydrocarbon ring group having 6 to 30 ring carbon atoms, a substituted or unsubstituted a+b valent heterocyclic group having 5 to 30 ring atoms, a substituted or unsubstituted hydrocarbon ring group having 6 to 30 ring carbon atoms, and an a+b valent group formed by bonding a plurality of substituted or unsubstituted heterocyclic groups having 5 to 30 ring atoms.

Examples of a substituent for $L^1$ in the formula (EIL-1) are a fluorine atom, a cyano group, a substituted or unsubstituted alkylsilyl group having 3 to 20 carbon atoms, a substituted or unsubstituted arylsilyl group having 8 to 30 carbon atoms, a substituted or unsubstituted aryl group having 6 to 30 ring carbon atoms, and a substituted or unsubstituted heterocyclic group having 5 to 30 ring atoms.

In the formula (EIL-1), a is an integer of 1 to 3, preferably 1.

In the formula (EIL-1), b is an integer of 1 to 3, preferably 1.

A compound used in the electron injecting layer is exemplified by a compound represented by a formula (EIL-2) below.

[Formula 45]

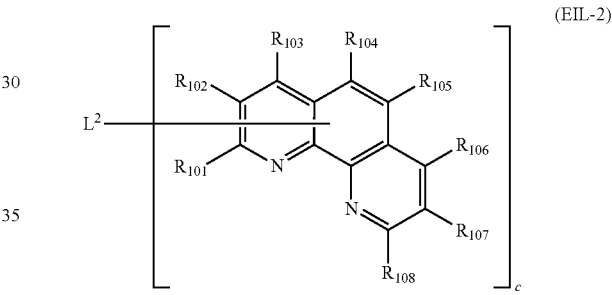

In the formula (EIL-2), one of $R_{101}$ to $R_{108}$ is bonded to $L_2$ by a single bond and the rest of $R_{101}$ to $R_{108}$ are a hydrogen atom or a substituent.

Examples of a substituent for $R_{101}$ to $R_{108}$ in the formula (EIL-2) are the same as those in the formula (EIL-1), among which an alkyl group having 1 to 20 carbon atoms and an aryl group having 6 to 30 ring carbon atoms are preferable.

In the formula (EIL-2), $L^2$ represents a single bond or a linking group. The linking group is a c-valent aromatic hydrocarbon group or a c-valent group having a structure represented by the following formula (EIL-2-1).

[Formula 46]

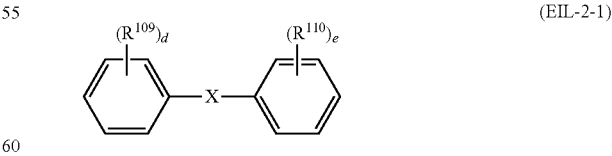

In the formula (EIL-2-1), $R^{109}$ to $R^{110}$ are a hydrogen atom or a substituent.

In the formula (EIL-2-1), d and e are each independently an integer of 1 to 5.

In the formula (EIL-2-1), X has a structure selected from those represented by the following formulae.

[Formula 47]

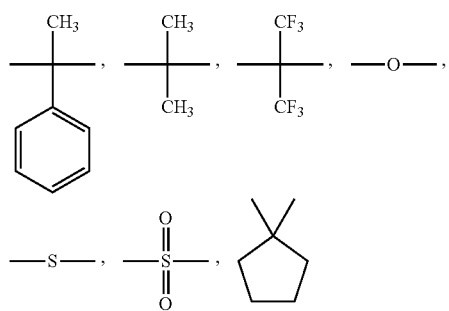

In the formula (EIL-2), c is an integer of 2 to 4, preferably 2.

Among the compound represented by the formula (EIL-2), a compound that is bonded to $L^2$ at $R_{101}$ and is represented by the following formula (EIL-2-2) is preferable.

[Formula 48]

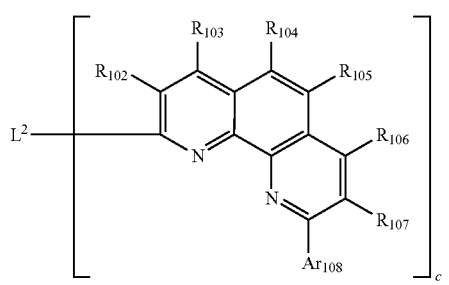

(EIL-2-2)

In the formula (EIL-2-2), $R_{102}$ to $R_{107}$ are a hydrogen atom or a substituent, preferably a hydrogen atom In the formulae (EIL-2-2), c and $L^2$ each are the same as c and $L^2$ in the formula (EIL-2).

In the formula (EIL-2-2), c is preferably 2.

In the formula (EIL-2-2), $L^2$ is preferably a substituted or unsubstituted phenylene group or a substituted or unsubstituted naphthylene group.

In the formula (EIL-2-2), $Ar_{108}$ is a hydrogen atom, alkyl group having 1 to 20 carbon atoms, or a substituted or unsubstituted aryl group having 6 to 30 ring carbon atoms, more preferably a methyl group, t-butyl group, substituted or unsubstituted phenyl group, or substituted or unsubstituted naphthyl group.

It is preferable to adjust a relationship between an affinity of the host material and that of the dopant material as described below, in order to efficiently cause the TTF phenomenon. Hereinafter, the affinity of the host material is described as $A_h$, the affinity of the dopant material as $A_d$, ionization potential of the host material as $I_h$ and ionization potential of the dopant material as $I_d$.

Now, the relationship will be described according to the following cases.

[1] Case of $A_h > A_d$

[2] Case of $A_h < A_d$

[3] Case Where Dopant Material Satisfying $A_h < A_d$ And Dopant Material Satisfying $A_h > A_d$ Coexist

[1] Case of $A_h > A_d$

A case where a relationship of $A_h > A_d$ is satisfied will be described. The dopant material used in this exemplary embodiment is a dopant material exhibiting fluorescent emission of a main peak wavelength of 550 nm or less (hereinafter occasionally referred to as a fluorescent dopant having a main peak wavelength of 550 nm or less). The dopant material exhibits a relatively large energy gap. Accordingly, when the relationship of $A_h > A_d$ is satisfied, a relationship of $I_h > I_d$ is simultaneously satisfied. Consequently, the dopant material easily functions as a hole trap.

Figure 4:
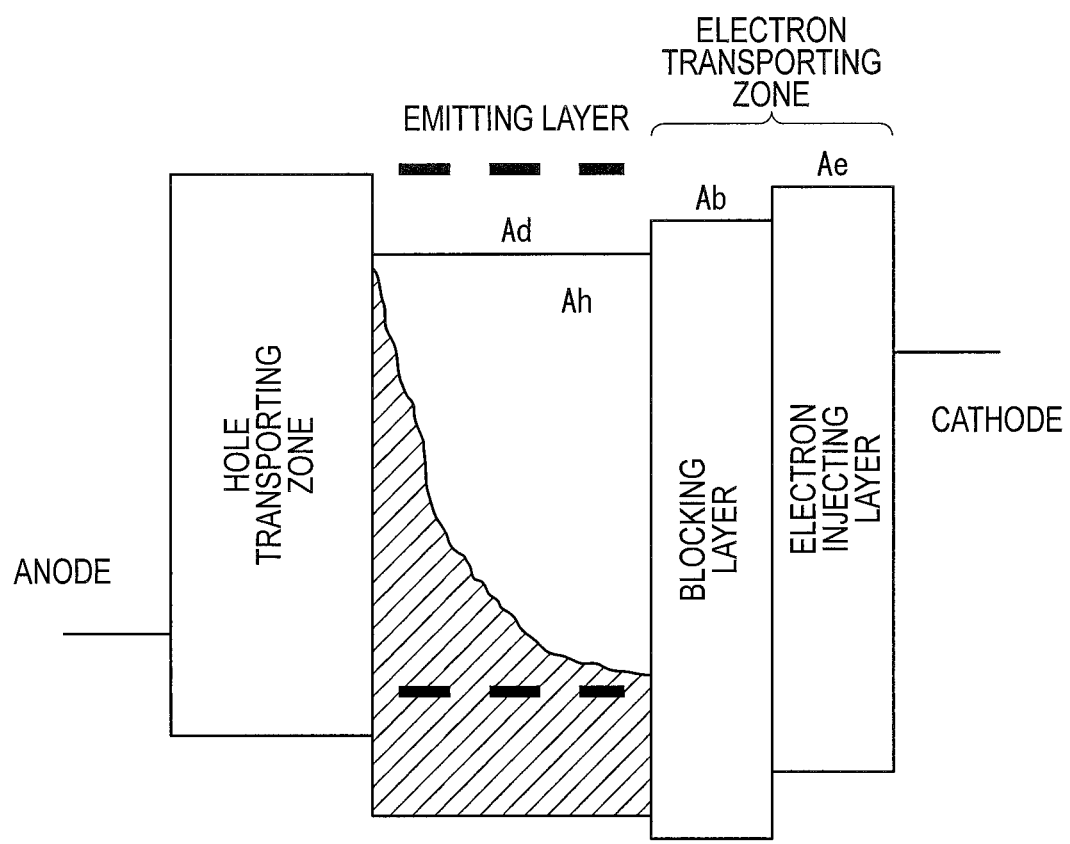
FIG. 4 is an energy band diagram showing a case where an affinity of a host material (Ah)>an affinity of a dopant material (Ad) is satisfied.

For instance, FIG. 4 shows an Ip-Af relationship of the host material and the dopant material in the emitting layer in the above case. In FIG. 4, a shaded area in the emitting layer shows an exciton-density distribution. The same applies to FIGS. 5 to 7. FIG. 4 shows the relationship in the case of $A_h > A_b > A_e$.

When a gap in ionization potential between the host material and the dopant material becomes large, the dopant material is likely to have a hole-trapping property, whereby triplet excitons are generated not only on the molecules of the host material but directly on the molecules of the dopant material. Consequently, the triplet excitons generated directly on the dopant material are increased. When a relationship of $E^T_h < E^T_d$ is satisfied, triplet exciton energy on the molecules of the dopant material is transferred onto the molecules of the host material by Dexter energy transfer, resulting in that all the triplet excitons gather on the host material. As a result, the TTF phenomenon occurs efficiently.

In the exemplary embodiment, it is preferable that the hole transporting layer is adjacent to the emitting layer in the hole transporting zone and a triplet energy $E^T_{ho}$ of the hole transporting layer is larger than a triplet energy $E^T_h$ of the host material.

When the dopant material has a hole-trapping property, the holes injected from the hole transporting zone to the emitting layer are trapped by the dopant material. Accordingly, recombination often occurs in the emitting layer near the anode. A typically-known hole transporting material used for the hole transporting zone often exhibits a larger triplet energy than the host material. Accordingly, diffusion of the triplet excitons on holes-side has not been a problem.

However, even though recombinations often occur near the anode, the triplet exciton density in the interface of the electron transporting zone cannot be ignored. Even under such conditions, highly efficient recombinations can be achieved by increasing the triplet energy of the blocking layer.

Other factors to determine recombination areas are a carrier mobility, ionization potential, affinity and film thickness of each of the hole transporting zone and the electron transporting zone. For instance, when the film thickness of the hole transporting zone is thicker than that of the electron transporting zone, an amount of the electrons injected to the emitting layer is relatively decreased. As a result, the recombination areas are shifted near the electron transporting zone. In such a case, when the blocking layer having a large triplet energy as in the invention is used, the TTF phenomenon can be efficiently induced.

The host material and the dopant material that satisfy the above relationship in the affinity are selected from, for instance, the following compounds (see JP-A-2010-50227 (Japanese Patent Application No. 2008-212102) and the like).

The host material is an anthracene derivative and a polycyclic aromatic skeleton-containing compound, preferably the anthracene derivative.

The dopant material is at least one compound selected from the group consisting of a pyrene derivative, aminoanthracene derivative, aminochrysene derivative and aminopyrene derivative.

Examples of preferable combinations of the host material and the dopant material are the anthracene derivative as the host material and at least one compound selected from the group consisting of a pyrene derivative, aminoanthracene derivative, aminochrysene derivative and aminopyrene derivative as the dopant material.

The aminoanthracene derivative is exemplified by a compound represented by a formula (20A) below.

[Formula 49]

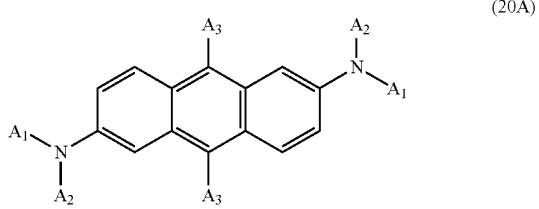

(20A)

In the formula (20A), $A_1$ and $A_2$ independently represent a substituted or unsubstituted aliphatic hydrocarbon group having 1 to 6 carbon atoms, substituted or unsubstituted aromatic hydrocarbon group having 6 to 20 ring carbon atoms, or substituted or unsubstituted heterocyclic aromatic hydrocarbon group having 5 to 19 ring atoms and containing nitrogen, sulfur or oxygen atom.

$A_3$ independently represents a substituted or unsubstituted aliphatic hydrocarbon group having 1 to 6 carbon atoms, substituted or unsubstituted aromatic hydrocarbon group having 6 to 20 ring carbon atoms, substituted or unsubstituted heterocyclic aromatic hydrocarbon group having 5 to 19 ring atoms, or a hydrogen atom. The heterocyclic aromatic hydrocarbon group includes nitrogen, sulfur or oxygen atom.

The aminochrysene derivative is exemplified by a compound represented by a formula (20B) below.

[Formula 50]

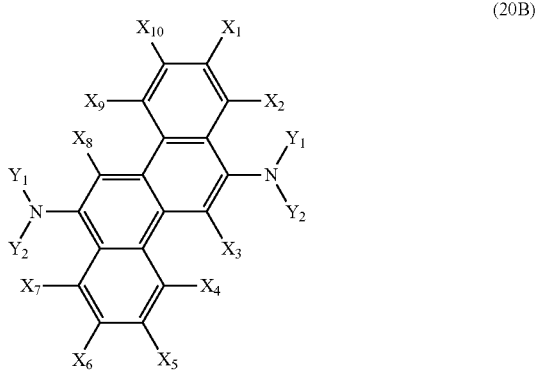

(20B)

In the formula (20B), $X_1$ to $X_{10}$ each are a hydrogen atom or a substituent. $Y_1$ and $Y_2$ each are a substituent.

$X_1$ to $X_{10}$ are preferably a hydrogen atom. $Y_1$ and $Y_2$ are preferably a substituted or unsubstituted aromatic ring having 6 to 30 ring carbon atoms. The substituent of the aromatic ring is preferably an alkyl group having 1 to 6 carbon atoms. The aromatic ring is preferably an aromatic ring having 6 to 10 ring carbon atoms or a phenyl group.

The aminopyrene derivative is exemplified by a compound represented by the following formula (20C).

[Formula 51]

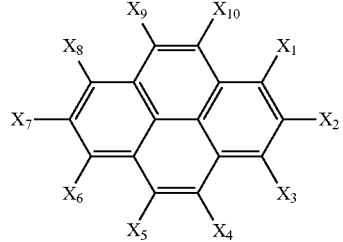

(20C)

In the formula (20C), $X_1$ to $X_{10}$ each represent a hydrogen atom or a substituent, with a proviso that $X_3$ and $X_8$ or $X_2$ and $X_7$ each represent —$NY_1Y_2$ ($Y_1$ and $Y_2$: substituents). When $X_3$ and $X_8$ each represent —$NY_1Y_2$, it is preferable that $X_{2,4,5,7,9,10}$ represent a hydrogen atom, $X_1$ and $X_6$ represent a hydrogen atom, alkyl group or cycloalkyl group. When $X_2$ and $X_7$ each represent —$NY_1Y_2$, it is preferable that $X_{1,3-6,8-10}$ are a hydrogen atom. $Y_1$ and $Y_2$ are preferably a substituted or unsubstituted aromatic ring, e.g., a phenyl group and a naphthyl group. The substituent of the aromatic ring is exemplified by an alkyl group having 1 to 6 carbon atoms.

The anthracene derivative is preferably a compound represented by the formula (20D).

In the formula (20D), $Ar^{11}$ and $Ar^{12}$ each independently represent a substituted or unsubstituted monocyclic group having 5 to 30 ring atoms, a substituted or unsubstituted fused ring group having 10 to 30 ring atoms, or a group provided by combining the above monocyclic group and the above fused ring group.

The monocyclic group in the formula (20D) is a group consisting of a ring structure without a fused structure.

The monocyclic group has 5 to 30 ring atoms, preferably 5 to 20 ring atoms. Examples of the monocyclic group are: an aromatic group such as a phenyl group, biphenyl group, terphenyl group, and quarterphenyl group; and a heterocyclic group such as a pyridyl group, pyrazyl group, pyrimidyl group, triazinyl group, furyl group, and thienyl group. Among the monocyclic group, a phenyl group, biphenyl group and terphenyl group are preferable.

The fused ring group in the formula (20D) is a group provided by fusing two or more ring structures.

The fused ring group has 10 to 30 ring atoms, preferably 10 to 20 ring atoms. Examples of the fused ring group are: a fused aromatic ring group such as a naphthyl group, phenanthryl group, anthryl group, chrysenyl group, benzanthryl group, benzophenanthryl group, triphenylenyl group, benzochrysenyl group, indenyl group, fluorenyl group, 9,9-dimethylfluorenyl group, benzofluorenyl group, dibenzofluoranthenyl group, fluoranthenyl group, and benzofluoranthenyl group; and a fused heterocyclic group such as a benzofuranyl group, benzothiophenyl group, indolyl group, dibenzofuranyl group, dibenzothiophenyl group, carbazolyl group, quinolyl group, and phenanthrolinyl group. Among the fused ring group, a naphthyl group, phenanthryl group, anthryl group, 9,9-dimethylfluorenyl group, fluoranthenyl group, benzanthryl group, dibenzothiophenyl group, dibenzofuranyl group and carbazolyl group are preferable.

The group provided by combining the monocyclic group and the fused ring group in the formula (20D) is exemplified by a group combined by sequentially bonding a phenyl group, a naphthyl group and a phenyl group to the anthracene ring.

Examples of each of the alkyl group, silyl group, alkoxy group, aryloxy group, aralkyl group and halogen atom for $R^{101}$ to $R^{108}$ in the formula (20D) are the same as those described in relation to $R_1$ of the formula (1). Examples of the cycloalkyl group are the same as the above. The same description as the above also applies to these substituents in the case of "substituted or unsubstituted."

Preferable examples of the substituents (in the case of "substituted or unsubstituted" for $Ar^{11}$, $Ar^{12}$ and $R^{101}$ to $R^{108}$ in the formula (20D) are a monocyclic group, fused ring group, alkyl group, cycloalkyl group, silyl group, alkoxy group, cyano group, and a halogen atom (particularly, fluorine). The monocyclic group and fused ring group are particularly preferable. Specific preferable examples of the substituent are the same as those of each of the groups in the formulae (20D) and (1).

[2] Case of $A_h < A_d$

Using the combination of the host material and the dopant material which allows $A_h < A_d$, the advantageous effects of the blocking layer provided within the electron transporting zone is exhibited outstandingly, whereby improvement in efficiency due to the TTF phenomenon can be attained. Description will be given in the following cases of [2-1] and [2-2]. In general, an organic material has a broadening of a LUMO level in a range larger than the measured affinity level by approximately 0.2 eV.

[2-1] Case where Difference Between $A_d$ and $A_h$ is Smaller than 0.2 eV

Figure 5:
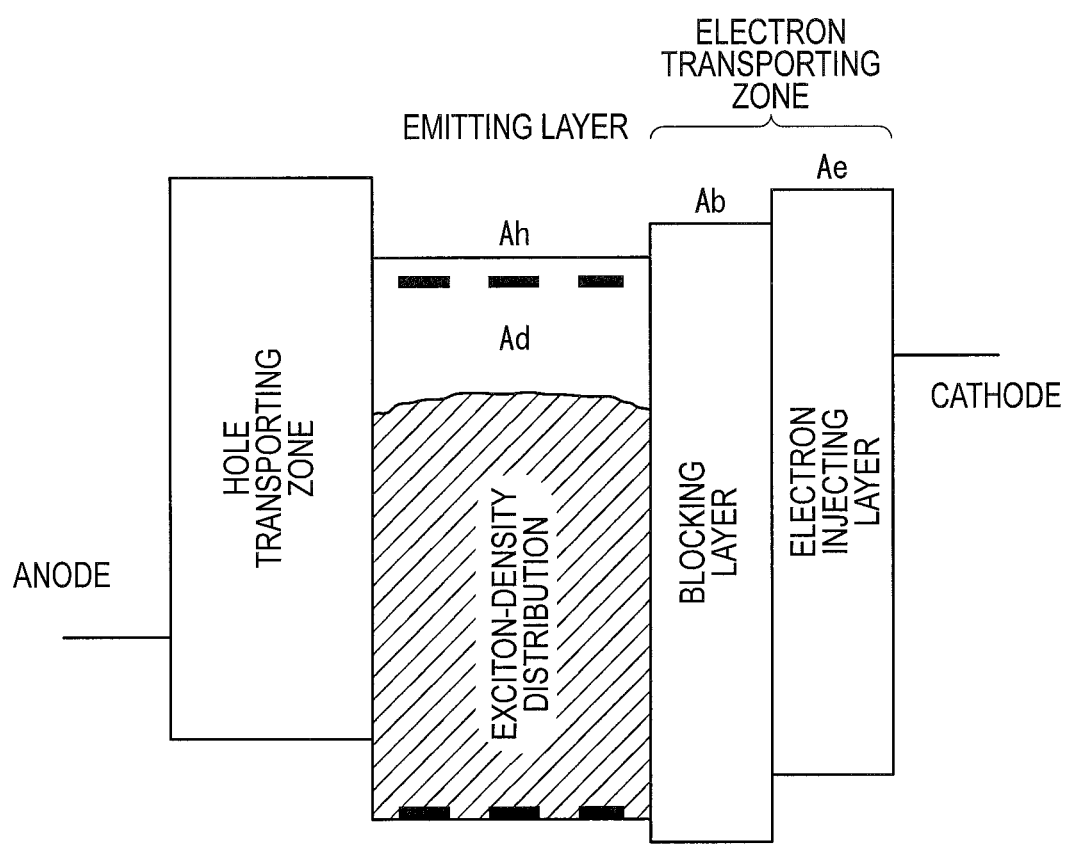
FIG. 5 is an energy band diagram showing a case where Ah<Ad is satisfied and a difference between Ah and Ad is less than 0.2 eV.

FIG. 5 shows one example of an energy band diagram in this case. Dotted lines in the emitting layer show an energy level of the dopant material. As shown in FIG. 5, when a difference between $A_d$ and $A_h$ is smaller than 0.2 eV, the LUMO level of the dopant material is included in the range of the broadening of the LUMO level of the host material, so that the electrons carried within the emitting layer is unlikely to be trapped by the dopant material. In other words, the dopant material is unlikely to exhibit an electron-trapping property. Moreover, the dopant of the exemplary embodiment is a wide-gap fluorescent dopant material having a main peak wavelength of 550 nm or less. When the relationship of $A_h < A_d$ is satisfied, since the difference between $A_h$ and $A_d$ is approximately 0.2 eV, a difference between the ionization potential of the host material and the ionization potential of the dopant material is reduced. As a result, the dopant material does not tend to exhibit a outstanding hole-trapping property. FIG. 5 shows the relationship in the case of $A_h > A_b > A_e$.

In other words, the dopant material in this case does not tend to exhibit an outstanding trapping property for both electrons and holes. In this case, as shown by the shaded area of the emitting layer in FIG. 5, the electron-hole recombinations occur mainly on the molecule of the host material in the broad whole area in the emitting layer, thereby generating 25% of singlet excitons and 75% of triplet excitons mainly on the molecule of the host material. Energy of the singlet excitons generated on the host material is transferred to the dopant material by Forster energy transfer to contribute to a fluorescent emission of the molecule of the dopant material. On the other hand, the transfer direction of the energy of triplet excitons depends on the triplet energy relationship of the host material and the dopant material. When the relationship is $E^T_h > E^T_d$, the triplet excitons generated on the host material are transferred to a dopant material which exists in the vicinity by the Dexter energy transfer. A concentration of the dopant material in the emitting layer of a fluorescent device is typically as low as at a few mass % to approximately 20 mass %. Accordingly, triplet excitons which have transferred to the dopant material collide with one another less frequently, resulting in a less possibility of occurrence of the TTF phenomenon. However, when the relationship of $E^T_h < E^T_d$ is satisfied as in this exemplary embodiment, since the triplet excitons are present on the molecules of the host material, the frequency of collision is increased, so that the TTF phenomenon easily and efficiently occur.

In the exemplary embodiment, the blocking layer is adjacent to the emitting layer. Since the triplet energy $E^T_h$ of the blocking layer is set to be larger than the triplet energy $E^T_h$ of the host material, the triplet excitons are prevented from dispersing into the electron transporting zone, so that the TTF phenomenon can occur efficiently in the emitting layer.

[2-2] Case where Difference Between $A_d$ and $A_h$ is Larger than 0.2 eV

Figure 6:
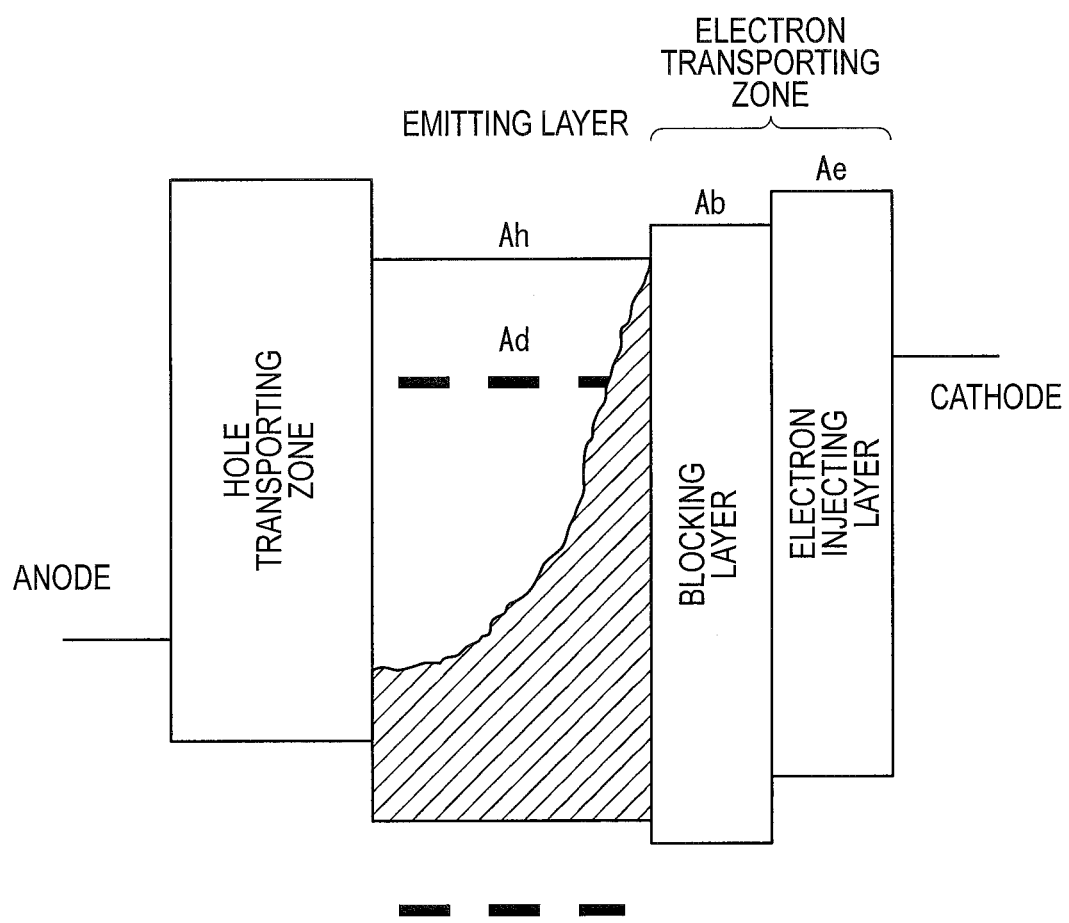
FIG. 6 is an energy band diagram showing a case where Ah<Ad is satisfied and a difference between Ah and Ad is more than 0.2 eV.

FIG. 6 shows one example of an energy band diagram in this case. The difference in affinity between the dopant material and the host material is increased, so that a LUMO level of the dopant material is present at a position further higher than the LUMO level broadening of the host material. Accordingly, the dopant material is more likely to exhibit a significant electron-trapping property. Electrons trapped by the dopant material are recombined with holes after the holes are transferred from the host material to the dopant material. In other words, unlike the condition shown in FIG. 5, the electrons and the holes are recombined in a pair not only on the molecules of the host material but also on the molecules of the dopant material. As a result, triplet excitons are generated not only on the molecules of the host material but also directly on the molecules of the dopant material. Under such conditions, when the relationship of $E^T_h < E^T_d$ is satisfied as in this exemplary embodiment, the triplet excitons generated directly on the dopant material also gather on the host material by Dexter energy transfer, so that the TTF phenomenon occurs efficiently.

When the affinities satisfy the above-mentioned relationship, the possibility of trapping of electrons by the dopant material is increased in the vicinity of the interface between the emitting layer and the blocking layer. As a result, recombinations occur frequently in the vicinity of the interface between the emitting layer and the blocking layer. In this case, the efficiency of confining triplet excitons by the blocking layer is increased as compared with the case mentioned in [2-1], resulting in an increase in density of triplet excitons at the interface between the emitting layer and the blocking layer. FIG. 6 shows the relationship in the case of $A_h > A_b > A_e$.

The host and the dopant that satisfy the above relationship in the $A_h < A_d$ can be selected from, for instance, the following compounds (see JP-A-2010-50227 (Japanese Patent Application No. 2008-212102) and the like).

Examples of the host material are an anthracene derivative and a polycyclic aromatic skeleton-containing compound, preferably an anthracene derivative.

Examples of the dopant material are a fluoranthene derivative, pyrene derivative, arylacetylene derivative, fluorene derivative, boron complex, perylene derivative, oxadiazole derivative and anthracene derivatives, preferably fluoranthene derivative, pyrene derivative, and boron complex, more preferably fluoranthene derivative and boron complex. As for the combination of the host material and the dopant material, it is preferable that the host material is an anthracene derivative and the dopant material is a fluoranthene derivative or a boron complex.

The fluoranthene derivative is specifically exemplified by the following compound.

[Formula 52]

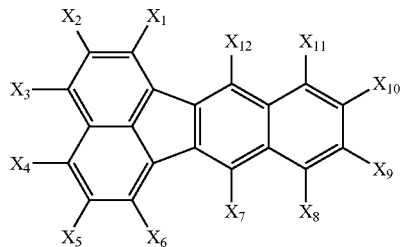

(30A)

In the formula (30A), $X_1$ to $X_{12}$ each represent a hydrogen atom or a substituent. Preferably, in the compound, $X_1$ to $X_2$, $X_4$ to $X_6$ and $X_8$ to $X_{11}$ are a hydrogen atom, and $X_3$, $X_7$ and $X_{12}$ are a substituted or unsubstituted aryl group having 5 to 50 ring atoms. Preferably, in the compound, $X_1$ to $X_2$, $X_4$ to $X_6$ and $X_8$ to $X_{11}$ are a hydrogen atom, $X_3$, $X_7$ and $X_{12}$ are a substituted or unsubstituted aryl group having 5 to 50 ring atoms. $X_3$ is —$Ar_1$—$Ar_2$, in which $Ar_1$ is a substituted or unsubstituted arylene group having 5 to 50 ring atoms, and $Ar_2$ is a substituted or unsubstituted aryl group having 5 to 50 ring atoms.

More preferably, in the compound, $X_1$ to $X_2$, $X_4$ to $X_6$ and $X_8$ to $X_{11}$ are a hydrogen atom and $X_7$ and $X_{12}$ are a substituted or unsubstituted aryl group having 5 to 50 ring atoms. $X_3$ is —$Ar_1$—$Ar_2$—$Ar_3$, in which $Ar_1$ and $Ar_3$ are each a substituted or unsubstituted arylene group having 5 to 50 ring atoms, and $Ar_2$ is a substituted or unsubstituted aryl group having 5 to 50 ring atoms.

The boron complex is specifically exemplified by the following compound.

[Formula 53]

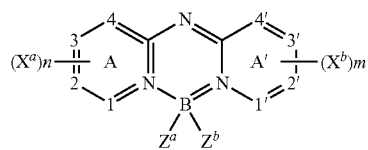

(30B)

In the formula (30B), A and A' represent an independent azine ring system corresponding to a six-membered aromatic ring containing one or more nitrogen. $X^a$ and $X^b$ represent independently-selected substituents, which are bonded together to form a fused ring for the ring A or the ring A'. The fused ring contains an aryl or heteroaryl substituent. m and n independently represent 0 to 4. $Z^a$ and $Z^b$ each represent an independently-selected halide. 1, 2, 3, 4, 1', 2', 3' and 4' each represent an independently-selected carbon atom or nitrogen atom.

Desirably, the azine ring is preferably a quinolinyl ring or isoquinolinyl ring in which all of 1, 2, 3, 4, 1', 2', 3' and 4' are carbon atoms, m and n each are 2 or more, and $X^a$ and $X^b$ are a substituent having 2 or more carbon atoms that combine with each other to form an aromatic ring. $Z^a$ and $Z^b$ are desirably fluorine atoms.

The anthracene derivatives as the host material in the case of [2] are the same as those described in the above "[1] Case of $A_h > A_d$."

Figure 7:
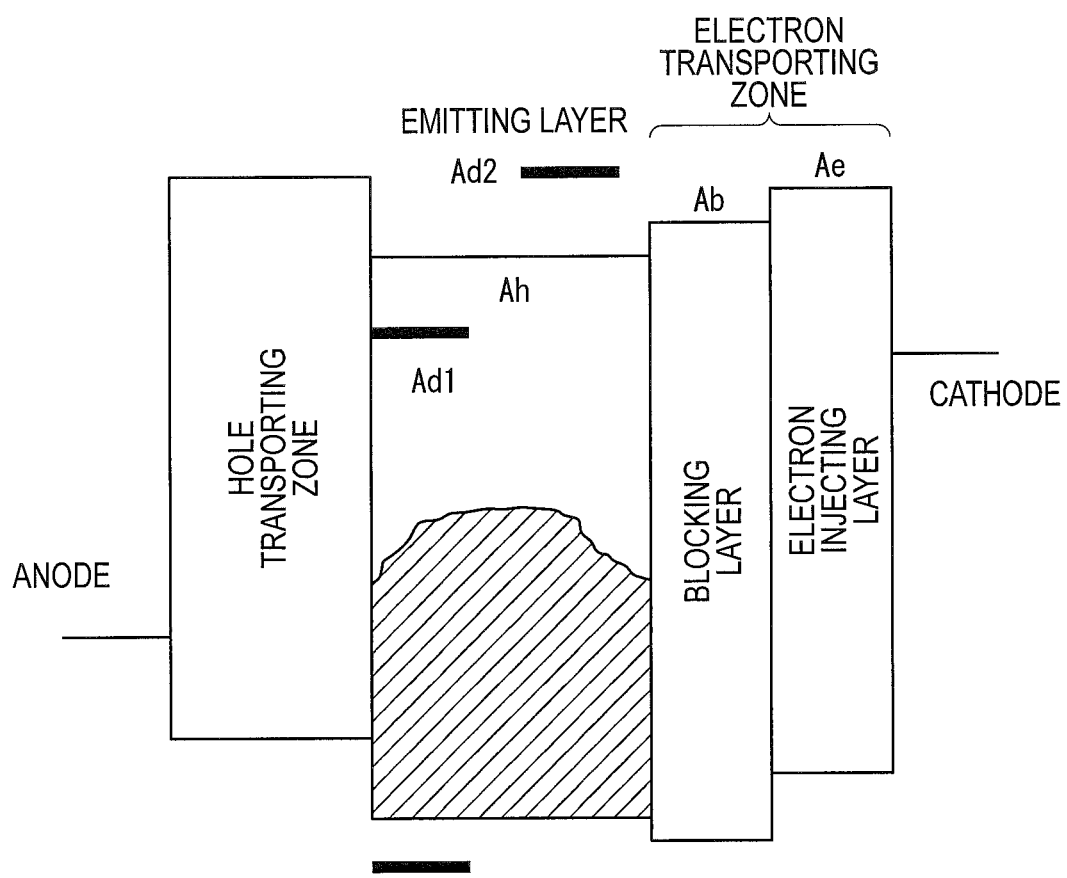
FIG. 7 is an energy band diagram showing a case where a dopant material satisfying Ah<Ad and a dopant material satisfying Ah>Ad coexist.

[3] Case where Dopant Material Satisfying $A_h < A_d$ and Dopant Material Satisfying $A_h > A_d$ Coexist FIG. 7 shows one example of an energy band diagram when a dopant material satisfying $A_h < A_d$ and a dopant material satisfying $A_h > A_d$ are both contained in the emitting layer. In such a case, both electrons and holes are trapped properly, whereby recombination occurs in the entire region of the emitting layer. Accordingly, recombination occurs frequently also on the cathode side. By providing a blocking layer that has a large triplet energy, the TTF phenomenon occurs efficiently. FIG. 7 shows the relationship in the case of $A_h > A_b > A_e$.

In the exemplary embodiment, the density of excitons is large in the interface between the emitting layer and the blocking layer. In this case, holes which do not contribute to recombination in the emitting layer are injected in the blocking layer with a high probability. Accordingly, as the material to be used in the blocking layer, among the above-mentioned aromatic heterocyclic derivatives, one having an excellent oxidation resistance is preferable The blocking-layer material desirably exhibits a reversible oxidation process in a cyclic voltammetry measurement.

The emitting layer may contain two or more fluorescent dopant materials of which the main peak wavelength is 550 nm or less. When the emitting layer contains two or more fluorescent dopant materials, the affinity $A_d$ of at least one dopant material is equal to or larger than the affinity $A_h$ of the host material, and the triplet energy $E^T_d$ of this dopant material is larger than the triplet energy $E^T_h$ of the host material. For instance, the affinity $A_d$ of at least one of the rest of the dopant materials may be smaller than the affinity $A_h$ of the host material. Containing such two kinds of dopant materials means containing both of a dopant material satisfying $A_h < A_d$ and a dopant material satisfying $A_h > A_d$ as described above. Efficiency can be significantly improved by providing the blocking layer having a large triplet energy.

Examples of the dopant material having the affinity $A_d$ that is smaller than the affinity $A_h$ of the host material are a pyrene derivative, aminoanthracene derivative, aminochrysene derivative, and aminopyrene derivative.

In addition to the above-mentioned host materials, dibenzofuran compounds disclosed in WO05/113531 and JP2005-314239, fluorene compounds disclosed in WO02/14244, and benzanthracene compounds disclosed in WO08/145,239 can be used.

In addition to the above-mentioned dopant materials, pyrene compounds disclosed in JP2004-204238, WO05/108348, WO04/83162, WO09/84512, KR10-2008-79956, KR10-2007-115588 and KR10-2010-24894, chrysene compounds disclosed in WO04/44088, and anthracene compounds disclosed in WO07/21117 can be used.

Preferably, the host material and the dopant material are each a compound formed by bonding of ring structures or single atoms (including bonding of a ring structure and a single atom), in which the bonding is a single bond. A compound having a carbon-carbon double bond in the part other than the ring structure thereof is not preferable The reason thereof is that the triplet energies generated on the host material and the dopant material are used for the structural change of the double bond, without being used for a TTF phenomenon.

Forming Method of Each Layer of Organic EL Device

For forming each layer of the organic EL device in the exemplary embodiment, any methods of dry film-forming such as vacuum deposition, sputtering, plasma or ion plating and wet film-forming such as spin coating, dipping, flow coating or ink jet are applicable.

In the wet film-forming method, a material for forming each layer is dissolved or dispersed in an appropriate solvent such as ethanol, chloroform, tetrahydrofuran or dioxane to form a thin film, in which any solvent is usable.

As a solution suitable for the wet film-forming method, an organic EL material-containing solution that contains the aromatic amine derivative of the invention (organic-EL-device material) and a solvent is usable.

In any organic thin-film layer, a resin and an additive suitable for improving film formability and preventing pin holes on a film may be used.

Film Thickness of Each Layer of Organic EL Device

A film thickness is not particularly limited, but needs to be set in an appropriate range. When the film thickness is too large, a large applied voltage is required for obtaining emission at a certain level, which deteriorates efficiency. When the film thickness is too small, pin holes and the like generate, which causes insufficient luminescence intensity even when an electric field is applied A film thickness of the blocking layer is preferably 20 nm or less. A film thickness of each of other layers is typically preferably in a range of 5 nm to 10 μm, more preferable in a range of 10 nm to 0.2 μm.

Second Exemplary Embodiment

Figure 8:
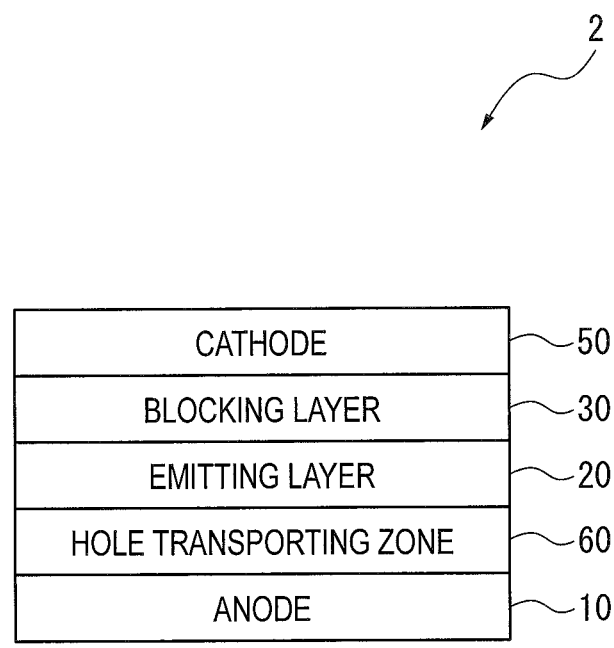
FIG. 8 is a view showing an example of an organic EL device according to a second exemplary embodiment.

FIG. 8 shows an example of an organic EL device 2 according to a second exemplary embodiment.

The organic EL device according to the second exemplary embodiment does not necessarily include an electron injecting layer. The organic EL device 2 according to the second exemplary embodiment includes the anode 10, hole transporting zone 60, emitting layer 20, electron transporting zone (blocking layer 30 in the second exemplary embodiment) and cathode 50 in this sequential order. In the organic EL device of the exemplary embodiment, these layers are adjacent to each other.

The blocking layer 30 of the organic EL device 2 also includes the aromatic heterocyclic derivative represented by the formula (1) in the same manner as in the first exemplary embodiment. Other layers of the organic EL device 2 are also provided in the same manner as in the first exemplary embodiment.

Third Exemplary Embodiment

Figure 9:
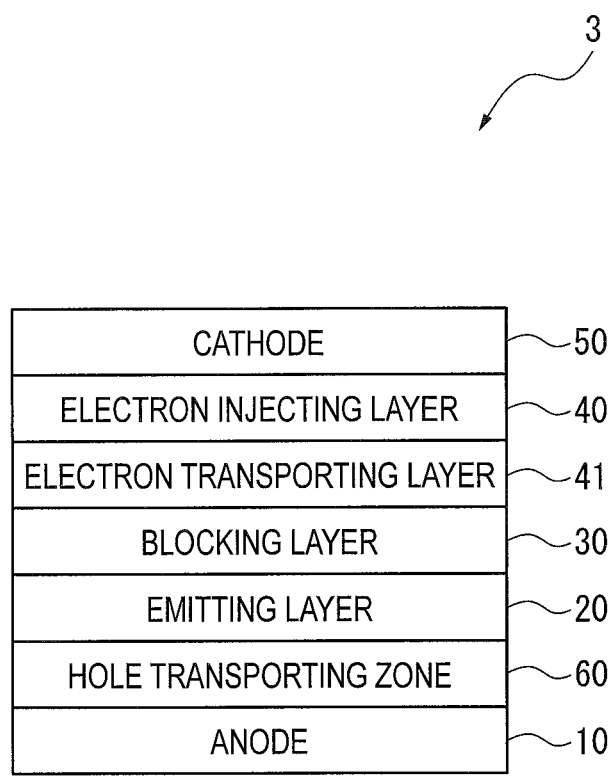
FIG. 9 is a view showing an example of an organic EL device according to a third exemplary embodiment.

FIG. 9 shows an example of an organic EL device 3 according to a third exemplary embodiment.

The organic EL device 3 according to the third exemplary embodiment may include the electron injecting layer between the electron transporting layer and the cathode. The organic EL device 3 according to the third exemplary embodiment shown in FIG. 9 includes the anode 10, hole transporting zone 60, emitting layer 20, electron transporting zone (blocking layer 30, electron transporting layer 41 and electron injecting layer 40 in the third exemplary embodiment) and cathode 50 in this sequential order. In the exemplary embodiment, these layers are adjacent to each other.

In the organic EL device 3, at least one of the electron injecting layer 40 and the electron transporting layer 41 preferably includes the above-described aromatic heterocyclic derivative of the invention. The materials described above in relation to the electron injecting layer and known electron transporting materials are usable as a material to be contained in the electron transporting layer 41. Moreover, the electron injecting layer 40 and the electron injecting layer 41 may further contain another material in addition to the above aromatic heterocyclic derivative of the invention.

The blocking layer 30 of the organic EL device 3 also includes the aromatic heterocyclic derivative represented by the formula (1), in the same manner as in the first exemplary embodiment. Other layers of the organic EL device 3 are also provided in the same manner as in the first exemplary embodiment.

Fourth Exemplary Embodiment

The organic EL device according to a fourth exemplary embodiment may have a tandem device configuration in which at least two organic layer units including emitting layers are provided. An intermediate layer (intermediate conductive layer, charge generation layer or CGL) is interposed between the two emitting layers. An electron transporting zone can be provided in each unit. At least one emitting layer is a fluorescent emitting layer and the unit including the emitting layer satisfies the above-mentioned requirements.

Figure 10:
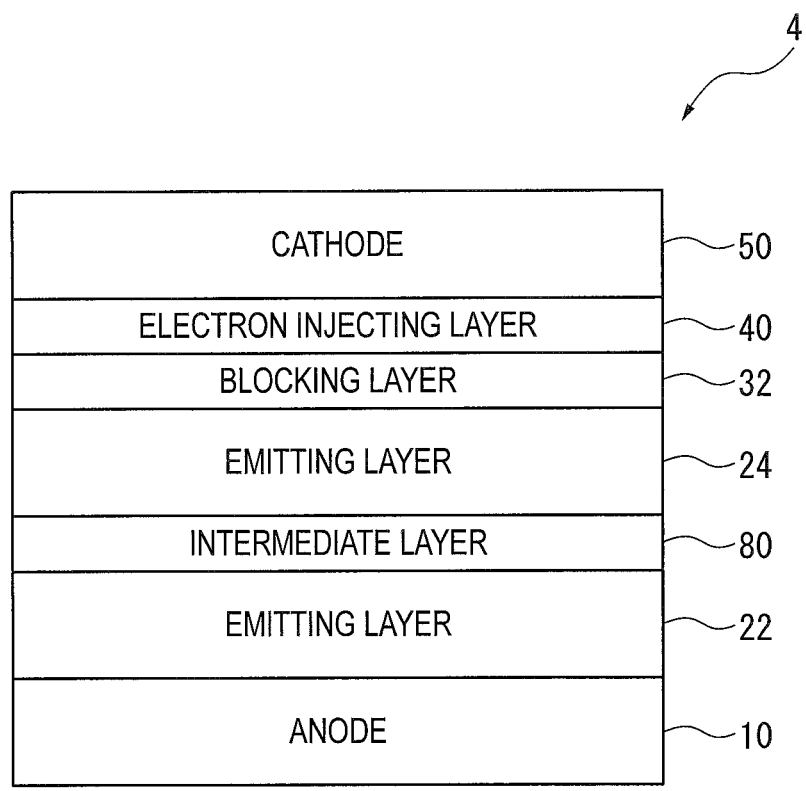
FIG. 10 is a view showing an example of an organic EL device according to a fourth exemplary embodiment.

FIG. 10 shows an example of an organic EL device according to the fourth exemplary embodiment.

An organic EL device 4 includes the anode 10, emitting layers 22 and 24 and cathode 50 in this sequential order. An intermediate layer 80 is interposed between the emitting layers 22 and 24. A blocking layer 32 is adjacent to the emitting layer 24. The electron injecting layer 40 is interposed between the blocking layer 32 and the cathode 50. The blocking layer 32, the electron injecting layer 40 and the emitting layer 24 are respectively a blocking layer, an electron injecting layer and a fluorescent emitting layer which satisfy the requirements of the invention. The other emitting layer may be either a fluorescent emitting layer or a phosphorescent emitting layer. Another blocking layer and another electron injecting layer are provided adjacent to the emitting layer 22 in sequential order. These blocking layer and electron injecting layer and the emitting layer 22 may be respectively used as the blocking layer, the electron injecting layer, and the fluorescent emitting layer which satisfy the requirements of the invention.

In the fourth exemplary embodiment, the blocking layer 32 and the electron injecting layer 40 correspond to the electron transporting zone.

At least one of an electron transporting zone and hole transporting zone may be interposed between the two emitting layers 22 and 24. Three or more emitting layers may be provided, and two or more intermediate layers may be provided. When three or more emitting layers are present, an intermediate layer may or may not be present between all of the emitting layers.

The intermediate layer is a layer including at least one of the intermediate conductive layer and the charge generation layer, or at least one of the intermediate conductive layer and the charge generation layer. The intermediate layer serves as a source for supplying electrons or holes to be injected in an emitting unit. In addition to charges injected from a pair of electrodes, charges supplied from the intermediate layer are injected into the emitting unit. Accordingly, by providing the intermediate layer, luminous efficiency (current efficiency) relative to injected current is improved.

Examples of the intermediate layer include a metal, metal oxide, mixture of metal oxides, composite oxide, and electron-accepting organic compound. Examples of the metal are preferably Mg, Al, and a film formed by co-evaporating Mg and Al. Examples of the metal oxide include ZnO, $WO_3$, $MoO_3$ and $MoO_2$. Examples of the mixture of the metal oxides include ITO, IZO (Registered Trademark), and ZnO:Al. Examples of the electron-accepting organic compound include an organic compound having a CN group as a substituent. The organic compound having a CN group is preferably a triphenylene derivative, tetracyanoquinodimethane derivative and indenofluorene derivative. The triphenylene derivative is preferably hexacyanohexaazatriphenylene. The tetracyanoquinodimethane derivative is preferably tetrafluoroquinodimethane and dicyanoquinodimethane. The indenofluorene derivative is preferably a compound disclosed in WO2009/011327, WO2009/069717, or WO2010/064655. The electron accepting substance may be a single substance, or a mixture with other organic compounds.

In order to easily accept the electrons from the charge generation layer, at least one of an electron-donating dopant represented by an alkali metal and the organic metal complex is preferably doped in the vicinity of an interface of the charge generation layer in the electron transporting layer. Examples of the electron-donating dopant and the organic metal complex are the same as the above examples of those in first exemplary embodiment. Examples of the compounds used for the electron-donating dopant and the organic metal complex are compounds disclosed in Patent Application Number PCT/JP2010/003434.

Fifth Exemplary Embodiment

In a fifth exemplary embodiment, the anode, a plurality of emitting layers, the electron transporting zone that includes the blocking layer adjacent to one of the emitting layers and the electron injecting layer adjacent to the blocking layer, and the cathode are provided in this sequential order. A charge blocking layer is provided between two emitting layers of the plurality of the emitting layers. The emitting layers in contact with the charge blocking layer are fluorescent emitting layers. The fluorescent emitting layer, and the blocking layer and the electron injecting layer in the electron transporting zone satisfy the above requirements.

As a configuration of a suitable organic EL device according to the fifth exemplary embodiment, there can be given a configuration as disclosed in Japanese Patent No. 4134280, US Patent Publication US2007/0273270A1 and International Publication WO2008/023623A1. Specifically, the configuration in which the anode, a first emitting layer, the charge blocking layer, a second emitting layer and the cathode are sequentially layered, and the electron-transporting zone having the blocking layer and the electron injecting layer for preventing diffusion of triplet excitons is further provided between the second emitting layer and the cathode. Here, the charge blocking layer means a layer to control the carrier injection to the emitting layer and the carrier balance between electrons and holes injected in the emitting layer by providing an energy barrier of a HOMO level or a LUMO level between adjacent emitting layers.

Figure 11:
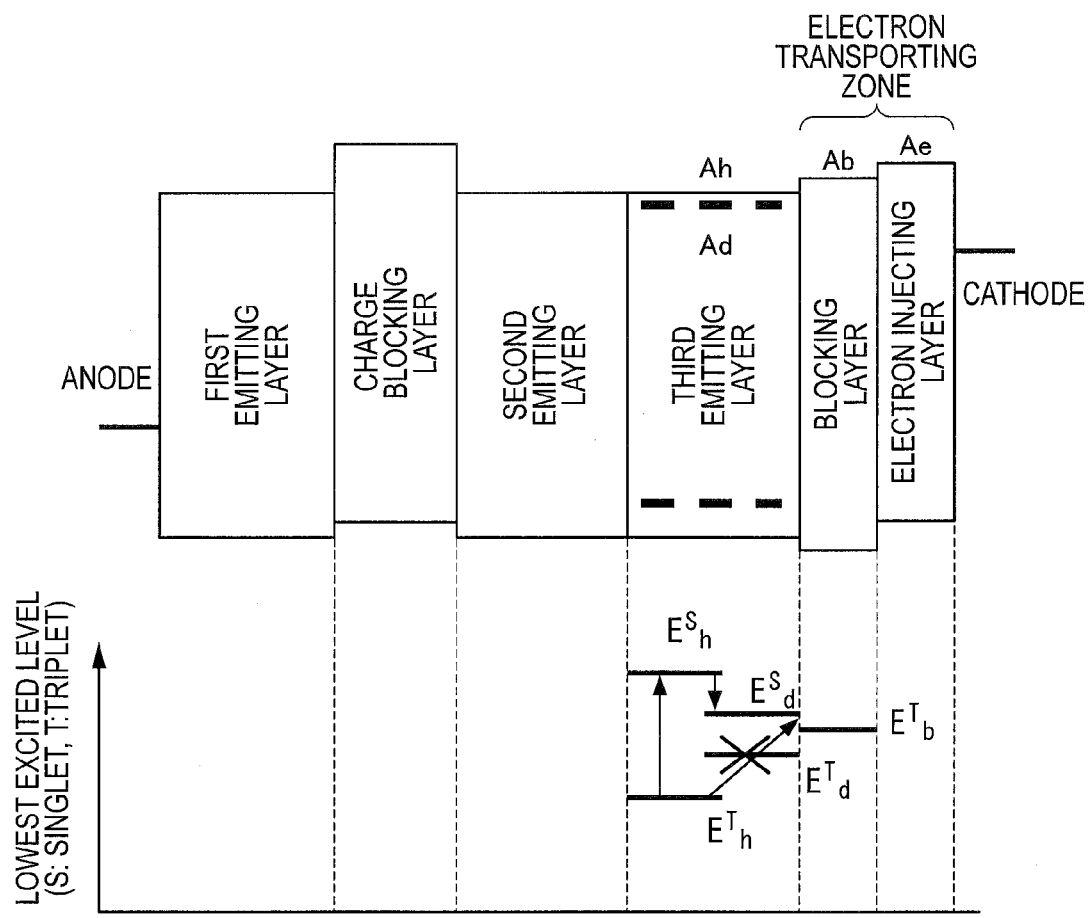
FIG. 11 is a view showing an example of an organic EL device according to a fifth exemplary embodiment.

Specific examples of such a configuration are given below.

anode/first emitting layer/charge blocking layer/second emitting layer/electron transporting zone/cathode anode/first emitting layer/charge blocking layer/second emitting layer/third emitting layer/electron transporting zone/cathode It is preferable that a hole transporting zone is provided between the anode and the first emitting layer in the same manner as in other embodiments FIG. 11 shows one example of an organic EL device according to the fifth exemplary embodiment. An upper view in FIG. 11 shows a device configuration, and the HOMO and LUMO energy levels of each layer. A lower view in FIG. 11 shows a relationship between energy gaps of the third emitting layer and the blocking layer. The upper view in FIG. 11 shows the relationship in the case of $A_h > A_b > A_e$.

The organic EL device includes the anode, first emitting layer, second emitting layer, third emitting layer, electron transporting zone, and cathode in sequential order. A charge blocking layer is interposed between the first and second emitting layers. The electron transporting zone is formed of the blocking layer. This blocking layer and third emitting layer are the blocking layer and the fluorescent emitting layer that satisfy the requirements of the invention. The first and second emitting layers may be either a fluorescent emitting layer or a phosphorescent emitting layer.

The device of the fifth exemplary embodiment is suitable as a white emitting device. The device can be a white emitting device by adjusting the emission colors of the first emitting layer, second emitting layer and third emitting layer. Moreover, the device can be a white emitting device by arranging only the first emitting layer and the second emitting layer and adjusting the emission colors of these two emitting layers. In this case, the second emitting layer is a fluorescent emitting layer satisfying the requirements of the invention.

In particular, by using a hole transporting material as the host material in the first emitting layer, by adding a fluorescent emitting dopant material of which the main peak wavelength is larger than 550 nm, by using an electron transporting material as the host material in the second emitting layer (and the third emitting layer), and by adding a fluorescent emitting dopant material of which the main peak wavelength is equal to or smaller than 550 nm, it is possible to achieve a white emitting device that exhibits a higher luminous efficiency as compared with conventional white emitting devices, even though all of them are entirely formed of fluorescent materials.

Reference is made particularly to a hole transporting layer which is adjacent to the emitting layer. In order to allow the TTF phenomenon to occur effectively, it is preferable that the triplet energy of the hole transporting material is larger than the triplet energy of the host material, when the triplet energy of the hole transporting material and that of the host material are compared.

Sixth Exemplary Embodiment

In a sixth exemplary embodiment, a blue pixel, a green pixel and a red pixel are arranged in parallel on a substrate. Of the three color pixels, at least one of the blue pixel and the green pixel has the configuration of the first exemplary embodiment or second exemplary embodiment.

Figure 12:
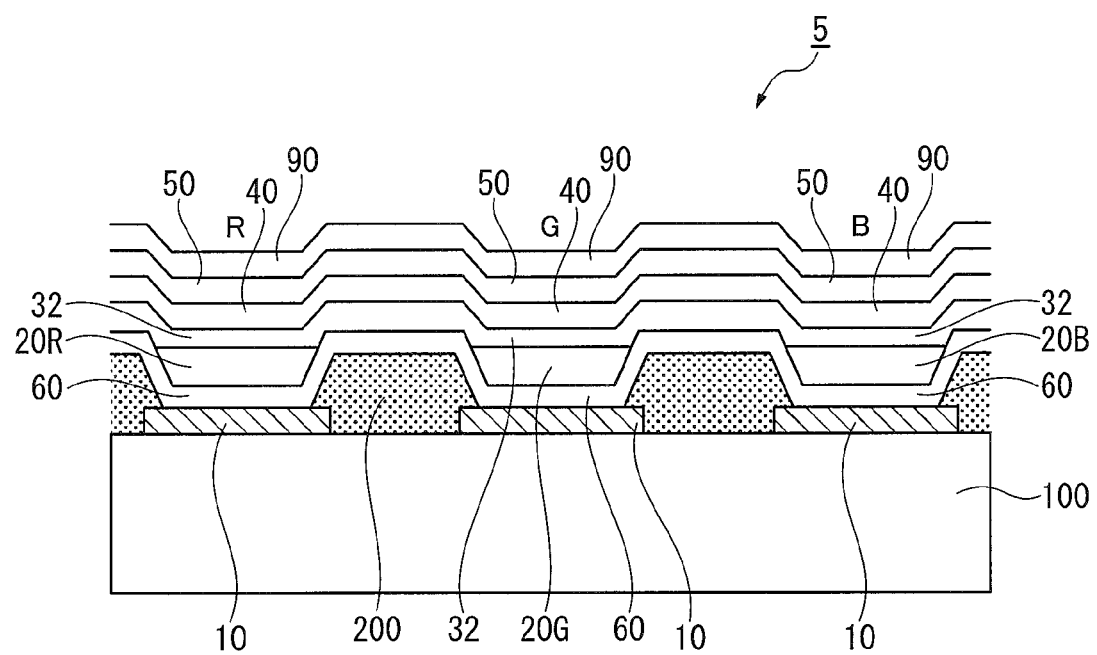
FIG. 12 is a view showing an example of an organic EL device according to a sixth exemplary embodiment.

FIG. 12 shows an example of an organic EL device according to the sixth exemplary embodiment.

In a top-emission type organic EL device 5 shown in FIG. 12, a blue pixel B, a green pixel G and a red pixel R are arranged in parallel on a common substrate 100.

The blue pixel B includes the anode 10, the hole transporting zone 60, a blue emitting layer 20B, the blocking layer 32, the electron injecting layer 40, the cathode 50, and a protection layer 90 on the substrate 100 in this sequential order.

The green pixel G includes the anode 10, the hole transporting zone 60, a green emitting layer 20G, the blocking layer 32, the electron injecting layer 40, the cathode 50, and the protection layer 90 on the substrate 100 in this sequential order.

The red pixel R includes the anode 10, the hole transporting zone 60, a red emitting layer 20R, the blocking layer 32, the electron injecting layer 40, the cathode 50, and the protection layer 90 on the substrate 100 in this sequential order.

An insulating film 200 is formed between the anodes of adjacent pixels so as to keep the insulation between the pixels. The electron transporting zone is formed of the blocking layer 32 and the electron injecting layer 40.

In the organic EL device 5, the blocking layer is provided as a common blocking layer for the blue pixel B, the red pixel R and the green pixel G.

The advantageous effects brought by the blocking layer are outstanding comparing to the luminous efficiency conventionally attained in a blue fluorescent device. In a green fluorescent device and a red fluorescent device, similar advantageous effects, such as confining triplet energies in the emitting layer, can be attained, and improvement in luminous efficiency can also be expected.

On the other hand, in a phosphorescent emitting layer, it is possible to attain the advantageous effects of confining triplet energies in the emitting layer, and as a result, diffusion of triplet energies is prevented, thereby contributing to improvement in luminous efficiency of a phosphorescent dopant material.

The hole transporting zone is formed of, for instance, a hole transporting layer, or a combination of a hole transporting layer and a hole injecting layer. A common hole transporting zone may be provided or different hole transporting zones may be provided for the blue pixel B, the red pixel R and the green pixel G. Typically, the hole transporting zones respectively have a configuration suited to the color of emitted light.

The configuration of the organic layer formed of the emitting layers 20B, G and R and the blocking layer is not limited to that shown in the figure and is changeable appropriately.

The host material and dopant material as described above can be used in the sixth exemplary embodiment. In particular, the host material and dopant material for each color emitting layer will be described below.

A green emitting layer is preferably formed of the following host material and dopant material.

The host material is preferably a fused aromatic ring derivative. As the fused aromatic ring derivative, an anthracene derivative, pyrene derivative and the like are more preferable in view of luminous efficiency and luminous lifetime.

The host material is exemplified by a heterocycle-containing compound. Examples of the heterocycle-containing compound are a carbazole derivative, dibenzofuran derivative, ladder-type furan compound and pyrimidine derivative.

The dopant material is not limited so long as it functions as a dopant, but an aromatic amine derivative is preferable in view of luminous efficiency and the like. As the aromatic amine derivative, a fused aromatic ring derivative having a substituted or unsubstituted arylamino group is preferable. Examples of such a compound are pyrene, anthracene and chrysene having an arylamino group.

A styrylamine compound is also preferable as the dopant material. Examples of the styrylamine compound are styrylamine, styryldiamine, styryltriamine and styryltetraamine. Here, the styrylamine means a compound in which a substituted or unsubstituted arylamine is substituted with at least one arylvinyl group. The arylvinyl group may be substituted with a substituent such as an aryl group, silyl group, alkyl group, cycloalkyl group, or arylamino group, which may have a further substituent.

Furthermore, as the dopant material, a boron complex and a fluoranthene compound are preferable. A metal complex is also preferable as the dopant material. The metal complex is exemplified by an iridium complex or platinum complex.

A red emitting layer is preferably formed of the following host material and dopant material. The host material is preferably a fused aromatic ring derivative. As the fused aromatic ring derivative, a naphthacene derivative, pentacene derivative and the like are more preferable in view of luminous efficiency and luminous lifetime.

The host material is exemplified by a fused polycyclic aromatic compound. Examples of the fused polycyclic aromatic compound are a naphthalene compound, phenanthrene compound and fluoranthene compound.

The dopant material is preferably an aromatic amine derivative. As the aromatic amine derivative, a fused aromatic ring derivative having a substituted or unsubstituted arylamino group is preferable. Such a compound is exemplified by periflanthene having an arylamino group.

A metal complex is also preferable as the dopant material. The metal complex is exemplified by an iridium complex or platinum complex.

The organic EL device of the sixth exemplary embodiment is manufactured in the following manner.

On a substrate, an APC (Ag—Pd—Cu) layer as a silver alloy layer (reflective layer) and a transparent conductive layer such as a zinc oxide (IZO) film and a tin oxide film are sequentially formed. Next, by a typical lithographic technology, this conductive material layer is patterned by etching using a mask with a resist pattern, thereby forming an anode. Then, by the spin coating method, an insulating film formed of a photosensitive resin such as a polyimide is formed by coating on the anode. Thereafter, the resulting film is exposed, developed and cured to allow the anode to be exposed, whereby the anodes for a blue emitting region, a green emitting region and a red emitting region are patterned.

There are three types of electrodes, i.e. an electrode for the red pixel, an electrode for the green pixel and an electrode for a blue pixel. They respectively correspond to the blue emitting region, the green emitting region and the red emitting region, and respectively correspond to the anode. After conducting cleaning for 5 minutes in isopropyl alcohol, a UV ozone cleaning is conducted for 30 minutes. When the hole injecting layer and the hole transporting layer are formed thereafter, the hole injecting layer is layered over the entire surface of the substrate, and the hole transporting layer is layered thereon. Emitting layers are formed so as to be correspondingly arranged to the positions of the anode for the red pixel, the anode for the green pixel and the anode for the blue pixel When vacuum evaporation method is used, the blue emitting layer, the green emitting layer and the red emitting layer are finely patterned by using a shadow mask.

Next, a blocking layer is layered over the entire surface. Subsequently, an electron injecting layer is layered over the entire surface. Thereafter, Mg and Ag are formed into a film by evaporation, thereby forming a semi-transparent cathode formed of an Mg—Ag alloy.

As for the other members used in the sixth exemplary embodiment, such as the substrate, the anode, the cathode, the hole injecting layer and the hole transporting layer, known members disclosed in PCT/JP2009/053247, PCT/JP2008/073180, U.S. patent application Ser. No. 12/376,236, U.S. patent application Ser. No. 11/766,281, U.S. patent application Ser. No. 12/280,364 or the like can be appropriately selected and used.

It is preferable that the hole transporting layer include an aromatic amine derivative represented by any one of the following formulae (a-1) to (a-5).

[Formula 54]

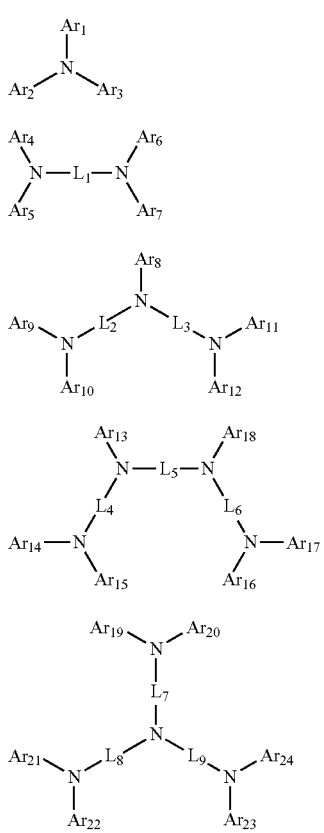

In the formulae (a-1) to (a-5), $Ar_1$ to $Ar_{24}$ are independently a substituted or unsubstituted aryl group having 6 to 50 ring carbon atoms, or a substituted or unsubstituted heteroaryl group having 5 to 50 ring atoms.

$L_1$ to $L_9$ are independently a substituted or unsubstituted arylene group having 6 to 50 ring carbon atoms or a substituted or unsubstituted heteroarylene group having 5 to 50 ring atoms.

Examples of a substituent which $Ar_1$ to $Ar_{24}$ and $L_1$ to $L_9$ may have include a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 50 ring carbon atoms, a heteroaryl group having 5 to 50 ring atoms, a halogen atom, and a cyano group. Adjacent substituents may be bonded to each other to form a saturated or unsaturated divalent group forming a ring.

At least one of the above $Ar_1$ to $Ar_{24}$ is preferably a substituent represented by the following formula (a-6) or (a-7).

[Formula 55]

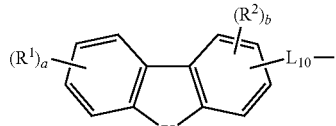

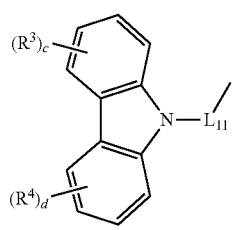

In the formula (a-6), X is an oxygen atom, sulfur atom or N—Ra. Ra is a linear or branched alkyl group having 1 to 15 carbon atoms, a cycloalkyl group having 3 to 15 ring carbon atoms, an aryl group having 6 to 50 ring carbon atoms or a heteroaryl group having 5 to 50 ring atoms.

$L_{10}$ is a single bond, a substituted or unsubstituted arylene group having 6 to 50 ring carbon atoms, or a substituted or unsubstituted heteroarylene group having 5 to 50 ring atoms.

In the formula (a-7), $L_{11}$ is a substituted or unsubstituted arylene group having 6 to 50 ring carbon atoms, or a substituted or unsubstituted heteroarylene group having 5 to 50 ring atoms.

In the formulae (a-6) and (a-7), $R^1$ to $R^4$ are independently a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 14 ring carbon atoms, a heteroaryl group having 5 to 50 ring atoms, a halogen atom, or a cyano group. Adjacent ones of a plurality of $R^1$ to $R^4$ may be bonded to each other to form a ring.

a, c and d are each an integer of 0 to 4.

b is an integer of 0 to 3.

The compound represented by the formula (a-1) is preferably a compound represented by the following formula (a-8).

[Formula 56]

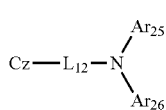

In the formula (a-8), Cz is a substituted or unsubstituted carbazolyl group.

$L_{12}$ is a substituted or unsubstituted arylene group having 6 to 50 ring carbon atoms, or a substituted or unsubstituted heteroarylene group having 5 to 50 ring atoms.

$Ar_{25}$ and $Ar_{26}$ are independently a substituted or unsubstituted aryl group having 6 to 50 ring carbon atoms or a substituted or unsubstituted heteroaryl group having 5 to 50 ring atoms.

The compound represented by the formula (a-8) is preferably a compound represented by the following formula (a-9).

[Formula 57]

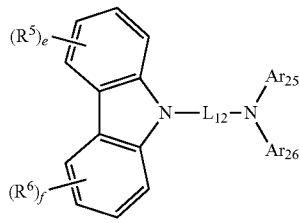

(a-9)

In the formula (a-9), $R^5$ and $R^6$ are independently a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 14 ring carbon atoms, a heteroaryl group having 5 to 50 ring atoms, a halogen atom, or a cyano group. Adjacent ones of a plurality of $R^5$ and $R^6$ may be bonded to each other to form a ring.

e and f are each an integer of 0 to 4.

$L_{12}$, $Ar_{25}$ and $Ar_{26}$ are the same as $L_{12}$, $Ar_{25}$ and $Ar_{26}$ in the formula (a-8).

The compound represented by the formula (a-9) is preferably a compound represented by the following formula (a-10).

[Formula 58]

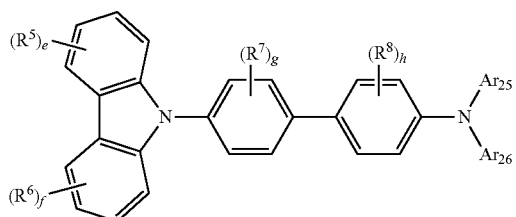

(a-10)

In the formula (a-10), $R^7$ and $R^8$ are independently a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 14 ring carbon atoms, a heteroaryl group having 5 to 50 ring atoms, a halogen atom, or a cyano group. Adjacent ones of the plurality of $R^5$ and $R^6$ may be bonded to each other to form a ring.

g and h are each an integer of 0 to 4.

$R^5$, $R^6$, e, f, $Ar_{25}$ and $Ar_{26}$ are the same as $R^5$, $R^6$, e, f, $Ar_{25}$ and $Ar_{26}$ in the formula (a-9).)

Seventh Exemplary Embodiment

An organic EL device according to a seventh exemplary embodiment may include an electron transporting layer in place of the blocking layer 30 as the electron transporting zone in the organic EL device 2 according to the second exemplary embodiment shown in FIG. 8. Specifically, the organic EL device (not shown) according to the seventh exemplary embodiment includes the anode 10, hole transporting zone 60, emitting layer 20, electron transporting layer and the cathode 50 in this sequential order. The electron transporting layer may further contain another material in addition to the aromatic heterocyclic derivative of the invention. In the seventh exemplary embodiment, the emitting layer 20 preferably contains a phosphorescent dopant material as the dopant material.

Other layers of the organic EL device in the exemplary embodiment are also provided in the same manner as in the first and second exemplary embodiments.

EXAMPLE(S)

Examples of the invention will be described below. However, the invention is not limited by these Examples.

Synthesis of Compound(s)

Synthesis Example 1 (Synthesis of Compound 9)

A synthesis scheme of a compound 9 is shown below

[Formula 59]

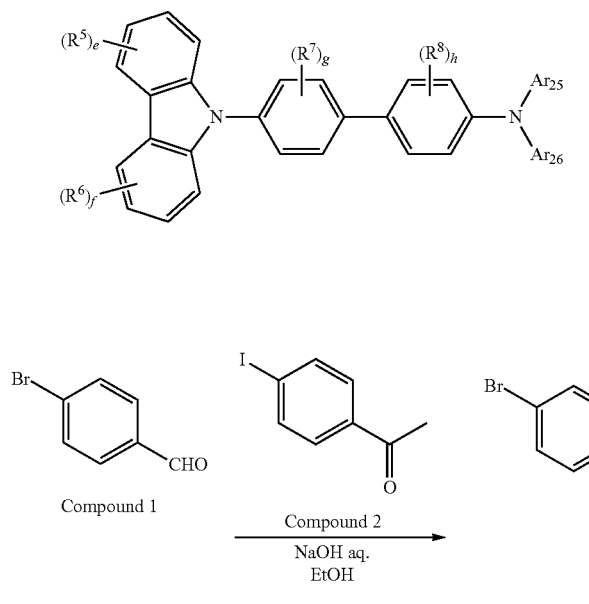

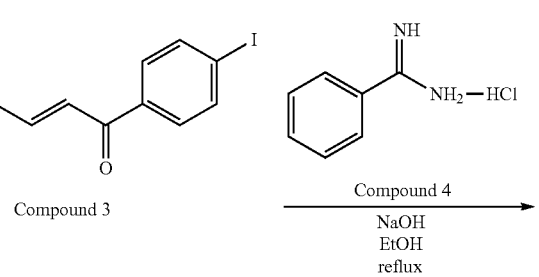

-continued

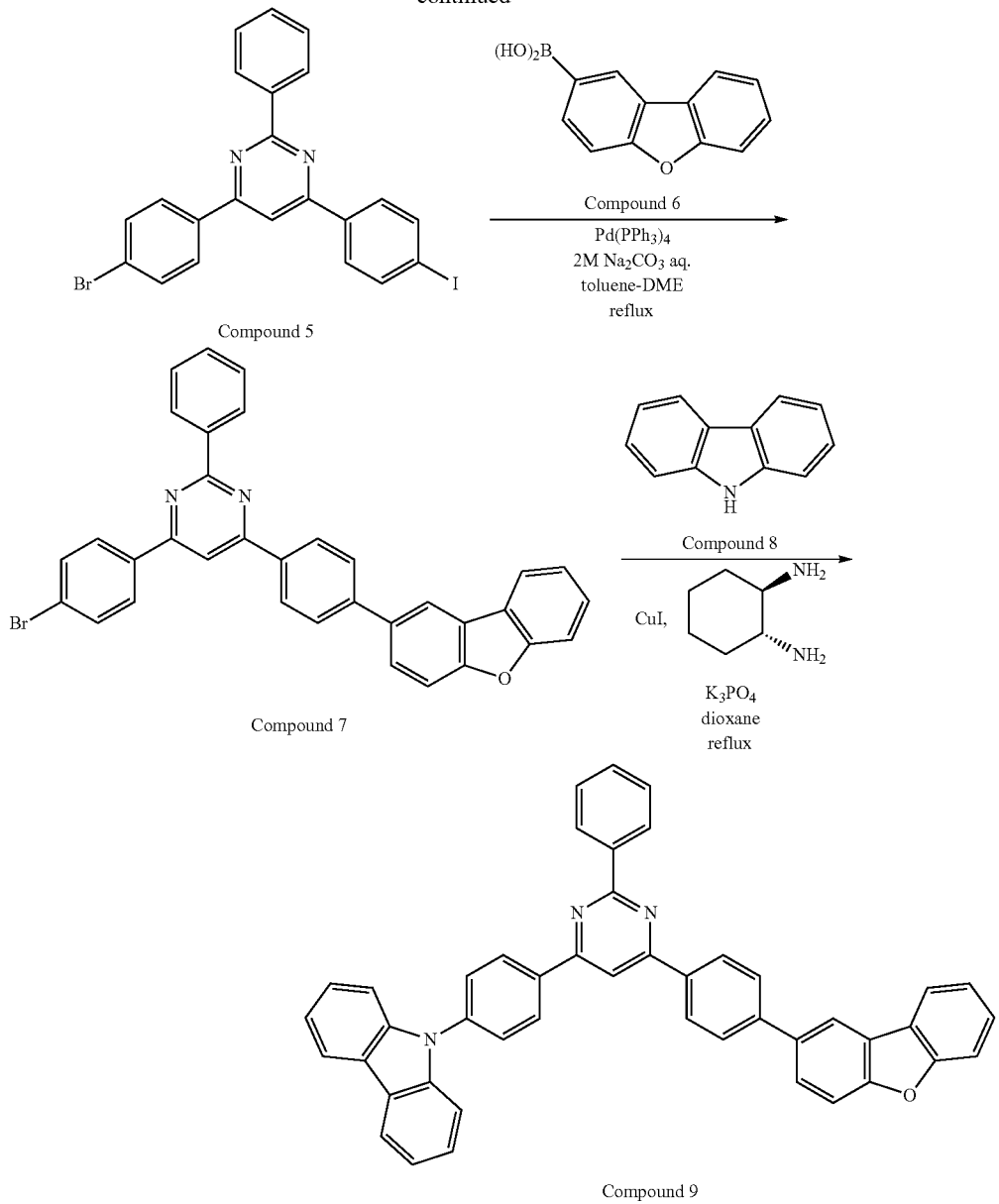

Compound 9

(1) Synthesis of Compound 5

4-bromobenzaldehyde (compound 1) (19 g, 100 mmol), 4'-iodoacetophenone (compound 2) (25 g, 100 mmol), sodium hydroxide (7.4 g, 185 mmol), ethanol (500 mL), and water (37 mL) were mixed and intensively stirred for seven hours at the room temperature. A precipitated solid was separated by filtration. After the obtained solid was suspended and washed in methanol, the solid was dried under reduced pressure to obtain a compound 3 (40 g) as a white solid.

Next, the compound 3 (40 g), benzamidine hydrochloride (compound 4) (15 g, 97 mmol) and sodium hydroxide (7.7 g, 193 mmol) were added in ethanol (1000 mL) and heated to reflux for eight hours.

After the reaction, a precipitated solid was separated by filtration and purified by silica-gel column chromatography (eluent: toluene). Further, the obtained solid was suspended and washed in a mixture solvent of hexane and toluene (4:1) at the room temperature to obtain a compound 5 (12 g, a yield of 23%) as a white solid.

(1-2) Synthesis of Compound 7

The compound 5 (5.0 g, 9.7 mmol) and a compound 6 (2.1 g, 9.7 mmol) were dissolved in toluene (150 mL) and 1,2-dimethoxyethane (100 mL), to which tetrakis(triphenyl-phosphine)palladium(0) (0.2 g, 0.2 mmol) and an aqueous solution of 2M sodium carbonate (15 mL) were added. The obtained solution was heated to reflux for 15 hours.

After the reaction, the reactant solution was cooled down to the room temperature and extracted with toluene. The obtained organic phase was sequentially washed with water and saturated saline and dried with sodium sulfate to distill the solvent under vacuum. Toluene was added to the residue. The obtained mixture was heated to reflux, thereby dissolving the residue. The mixture was cooled in air to precipitate crystals. The crystals were separated by filtration. After being washed with toluene, the crystals were dried under reduced pressure to obtain a compound 7 (3.7 g, a yield of 62%) as a light-yellow solid.

(1-3) Synthesis of Compound 9

Under argon atmosphere, the compound 7 (3.3 g, 6.0 mmol), carbazole (compound 8) (1.2 g, 7.2 mmol), copper iodide(I) (0.34 g, 1.8 mmol), and tripotassium phosphate (1.3 g, 6.0 mmol) were suspended in 1,4-dioxane (18 mL), to which trans-1,2-diaminocyclohexane (0.2 mL, 1.8 mmol) was added. The obtained mixture was heated to reflux for 20 hours.

After the reaction, the reactant solution was distilled under vacuum. After the obtained residue was added with toluene (100 mL) and heated to reflux, a precipitated solid was separated by filtration with Celite. The obtained filtrate was condensed under reduced pressure. The obtained residue was added with toluene (30 mL) and heated to reflux, whereby the residue was dissolved. The mixture was cooled in air to precipitate crystals. The crystals were separated by filtration. After being washed with toluene, the crystals were dried under reduced pressure to obtain a compound 9 (2.7 g, a yield of 70%) as a white solid. By FD-MS (Field Desorption Mass Spectrometry) analysis, the obtained compound was identified to be the compound 9.

Synthesis Example 2 (Synthesis of Compound 15)

A synthesis scheme of a compound 15 is shown below.

[Formula 60]

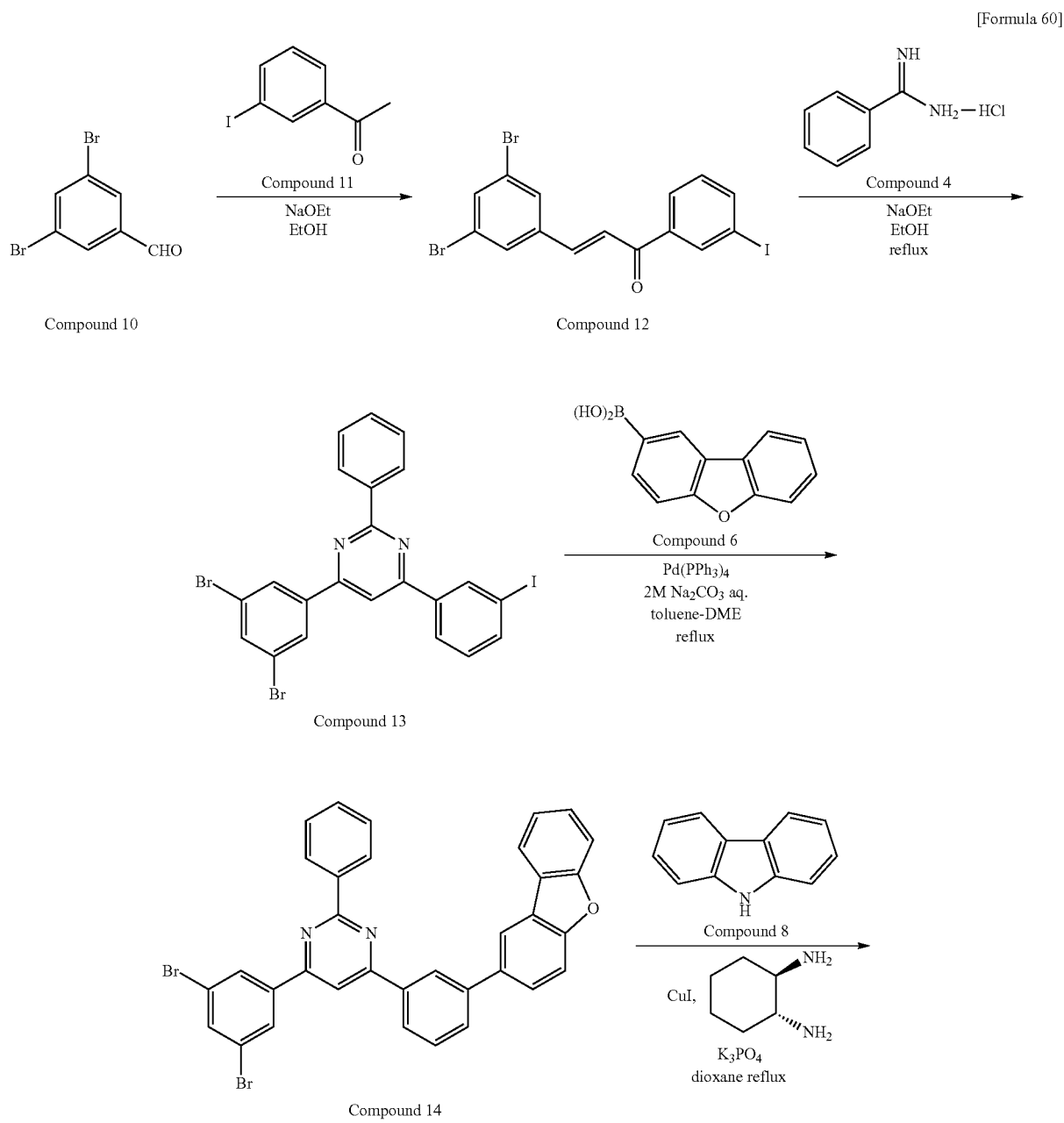

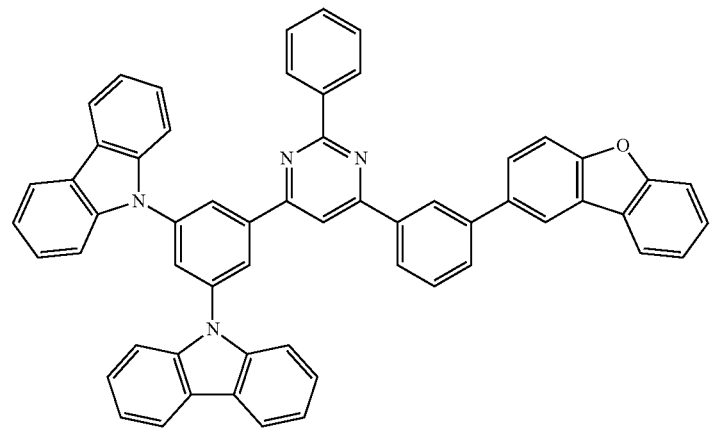

Compound 15

(2-1) Synthesis of Compound 13

3,5-dibromobenzaldehyde (compound 10) (15 g, 57 mmol) and 3'-iodoacetophenone (compound 11) (14 g, 57 mmol) were dissolved in ethanol (400 mL), into which a solution obtained by dissolving sodium ethoxide (7.2 g, 105 mmol) in ethanol (100 mL) was dropped. The obtained solution was stirred for seven hours at the room temperature.

After the reaction, the reactant solution was cooled down to the room temperature. A precipitated solid was separated by filtration. After the obtained solid was washed in ethanol, the solid was dried under reduced pressure to obtain a compound 12 (28 g) as a light-yellow solid.

Next, the compound 12 (28 g), benzamidine hydrochloride (compound 4) (9.2 g, 59 mmol) and sodium hydroxide (7.0 g, 112 mmol) were added in ethanol (500 mL) and heated with stirring for eight hours under reflux.

After the reaction, a precipitated solid was separated by filtration and purified by silica-gel column chromatography (eluent: toluene). Further, the obtained solid was suspended and washed in a mixture solvent of hexane and toluene (4:1) at the room temperature to obtain a compound 13 (9.1 g, a yield of 27%) as a light-yellow solid.

(2-2) Synthesis of Compound 14

A compound 14 (4.3 g, a yield of 89%) was obtained as a white solid according to the same method except for using the compound 13 (4.5 g, 7.6 mmol) in place of the compound 5 in (1-2) of synthesis of the compound 9.

(2-3) Synthesis of Compound 15

A compound 15 (3.3 g, a yield of 79%) was obtained as a white solid according to the same method except for using the compound 14 (3.3 g, 5.2 mmol) in place of the compound 7, using 2.4 molar equivalent of the compound 8 relative to the compound 14, and using 2 molar equivalent of tripotassium phosphate relative to the compound 14 in (1-3) of synthesis of the compound 9. By FD-MS analysis, the obtained compound was identified to be the compound 15.

Synthesis Example 3 (Synthesis of Compound 19)

A synthesis scheme of a compound 19 is shown below.

[Formula 61]

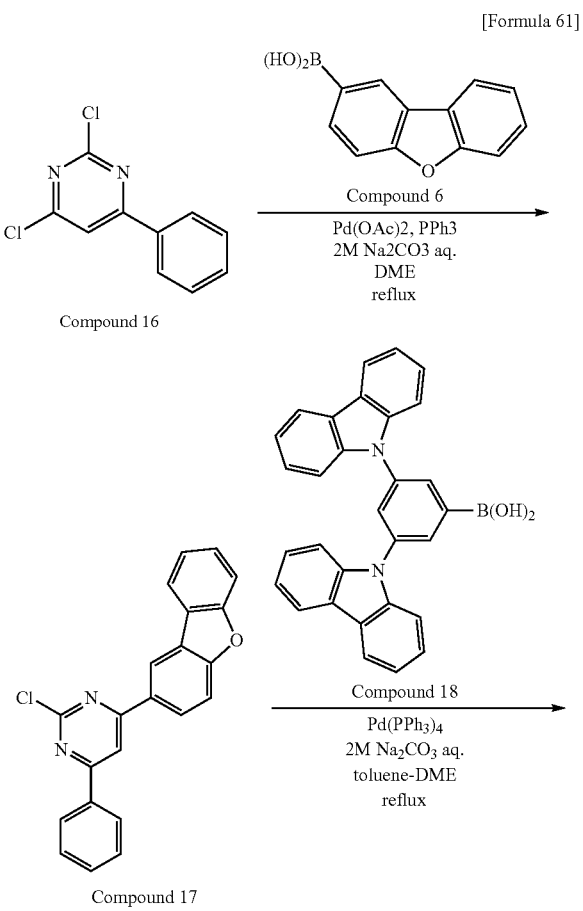

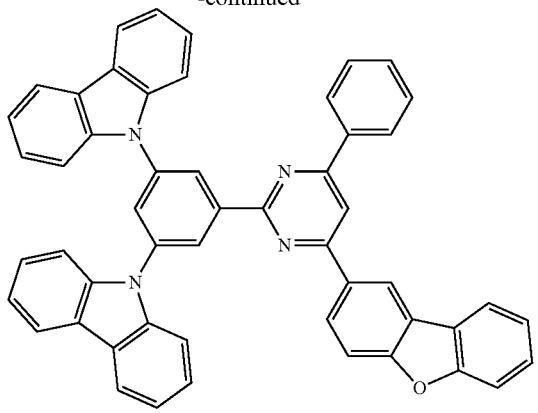

Compound 19

(3-1) Synthesis of Compound 17

The compound 16 (4.0 g, 18 mmol), the compound 6 (3.6 g, 18 mmol), palladium acetate(II) (0.2 g, 0.8 mmol), and triphenylphosphine (0.4 g, 1.6 mmol) were suspended in 1,2-dimethoxyethane (100 mL), to which an aqueous solution of 2M sodium carbonate (26 mL) was added. The obtained solution was heated to reflux for seven hours.

After the reaction, the reactant solution was condensed under reduced pressure. The obtained solid was separated by filtration and washed with water and methanol, and was suspended and washed with 1,2-dimethoxyethane to obtain a compound 17 (4.0 g, a yield of 63%) as a yellow-brown solid.

(3-2) Synthesis of Compound 19

A compound 19 (6.5 g, a yield of 80%) was obtained as a white solid according to the same method except for using the compound 17 (4.0 g, 11 mmol) in place of the compound 5 and using the compound 18 (4.8 g, 11 mmol) in place of the compound 6 in (1-2) of synthesis of the compound 9. By FD-MS (Field Desorption Mass Spectrometry) analysis, the obtained compound was identified to be the compound 19.

Synthesis Example 4 (Synthesis of Compound 25)

A synthesis scheme of a compound 25 is shown below.

[Formula 62]

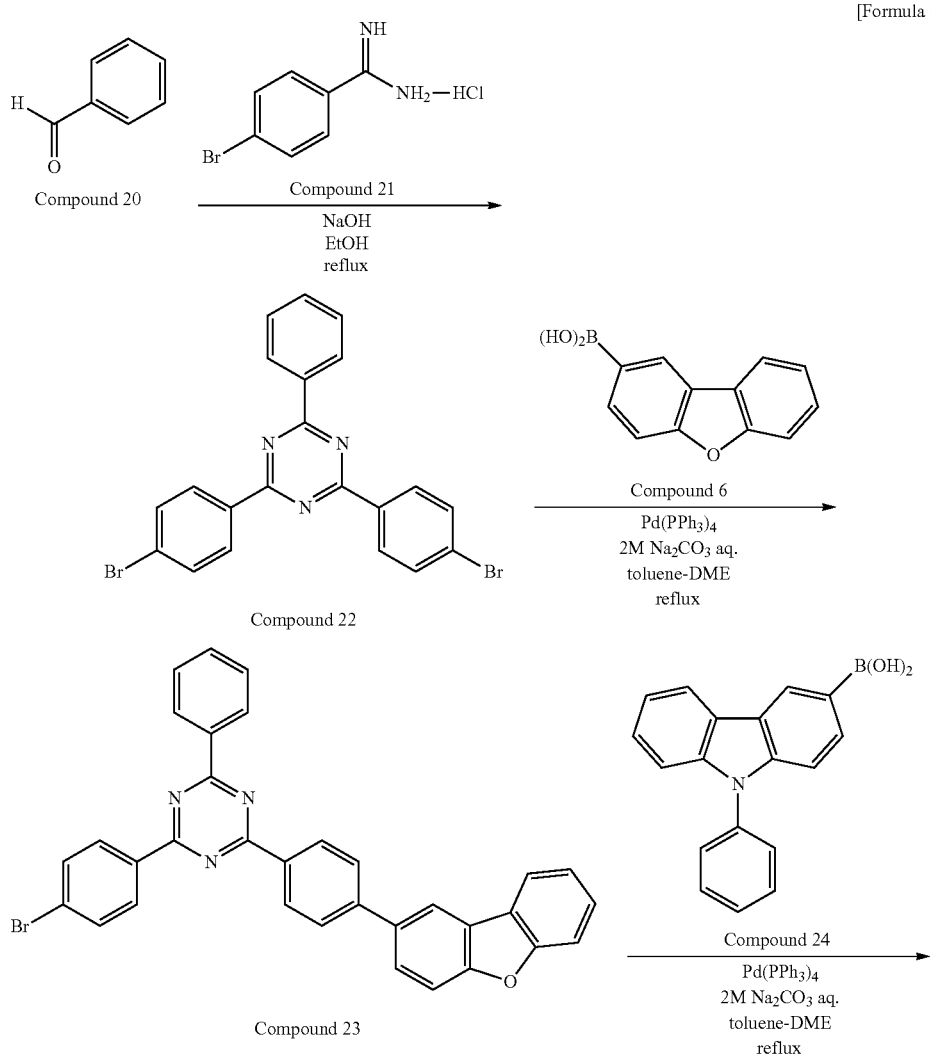

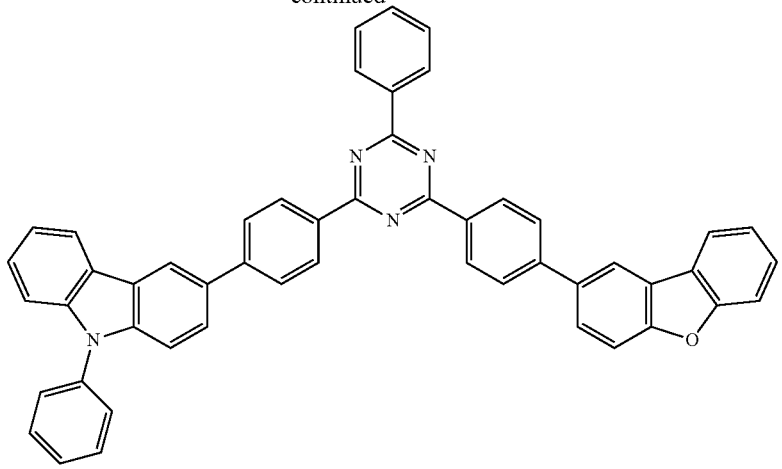

Compound 25

(4-1) Synthesis of Compound 22

A compound 22 (9.4 g, a yield of 32%) was obtained as a white solid according to the same method except for using the compound 20 (7.7 g, 72 mmol) in place of the compound 3 and using the compound 21 in place of the compound 4 at 2 molar equivalent of the compound 21 relative to the compound 20 in the second step of (1-1) of synthesis of the compound 9.

(4-2) Synthesis of Compound 23

A compound 23 (7.5 g, a yield of 63%) was obtained as a white solid according to the same method except for using the compound 22 (10 g, 21 mmol) in place of the compound 5 in (1-2) of synthesis of the compound 9.

(4-3) Synthesis of Compound 25

A compound 25 (3.9 g, a yield of 76%) was obtained as a white solid according to the same method except for using the compound 23 (4.0 g, 7.2 mmol) in place of the compound 5 and using the compound 24 (2.3 g, 7.9 mmol) in place of the compound 6 in (1-2) of synthesis of the compound 9. By FD-MS (Field Desorption Mass Spectrometry) analysis, the obtained compound was identified to be the compound 25.

Synthesis Example 5 (Synthesis of Compound 31)

A synthesis scheme of a compound 31 is shown below.

[Formula 63]

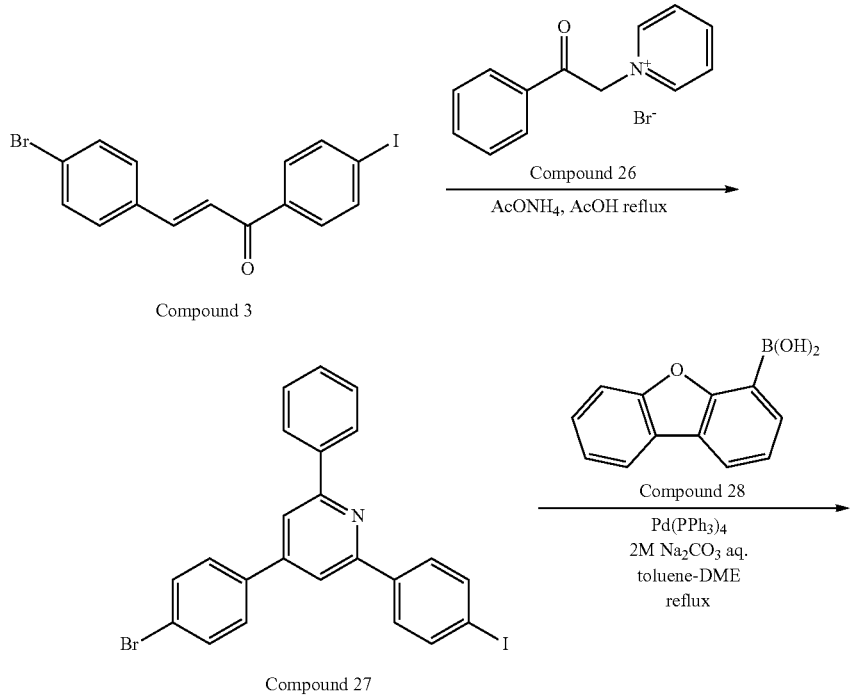

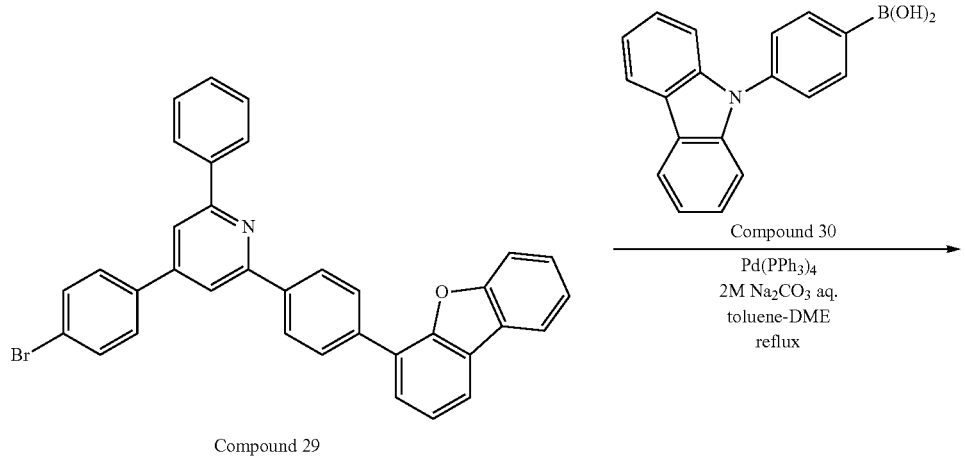

Compound 29

Compound 30

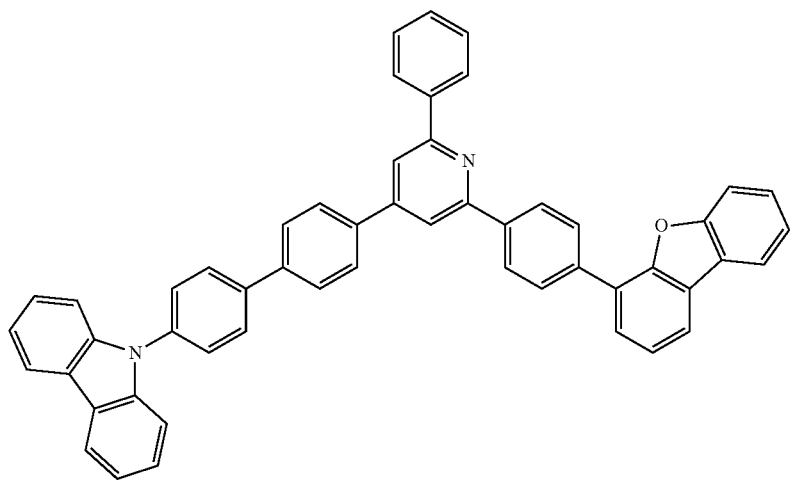

Compound 31

(5-1) Synthesis of Compound 27

The compound 3 (15 g, 36 mmol), 1-phenacylpyridinium bromide (compound 26) (10 g, 36 mmol), ammonium acetate (22 g, 288 mmol) were suspended in acetic acid (31 mL) and heated to reflux for 12 hours. After the reaction, the reactant solution was cooled down to the room temperature, added with water and extracted with toluene. The obtained organic phase was sequentially washed with 10-mass %-aqueous sodium hydroxide and saturated saline, dried with sodium sulfate to distill the solvent under vacuum. Ethanol was added to a residue. The obtained mixture was heated to reflux, thereby dissolving the residue. The mixture was cooled in air to precipitate crystals. The crystals were separated by filtration. After being washed with ethanol, the crystals were dried under reduced pressure to obtain a compound 27 (15 g, a yield of 78%) as a light-yellow solid.

(5-2) Synthesis of Compound 29

A compound 29 (3.8 g, a yield of 70%) was obtained as a white solid according to the same method except for using the compound 27 (5.0 g, 10 mmol) in place of the compound 5 and using the compound 28 (2.1 g, 10 mmol) in place of the compound 6 in (1-2) of synthesis of the compound 9.

(5-3) Synthesis of Compound 31

A compound 31 (3.9 g, a yield of 80%) was obtained as a white solid according to the same method except for using the compound 29 (3.8 g, 6.9 mmol) in place of the compound 5 and using the compound 30 (2.0 g, 6.9 mmol) in place of the compound 6 in (1-2) of synthesis of the compound 9. By FD-MS (Field Desorption Mass Spectrometry) analysis, the obtained compound was identified to be the compound 31.

Synthesis Example 6 (Synthesis of Compound 35)

A synthesis scheme of a compound 35 is shown below.

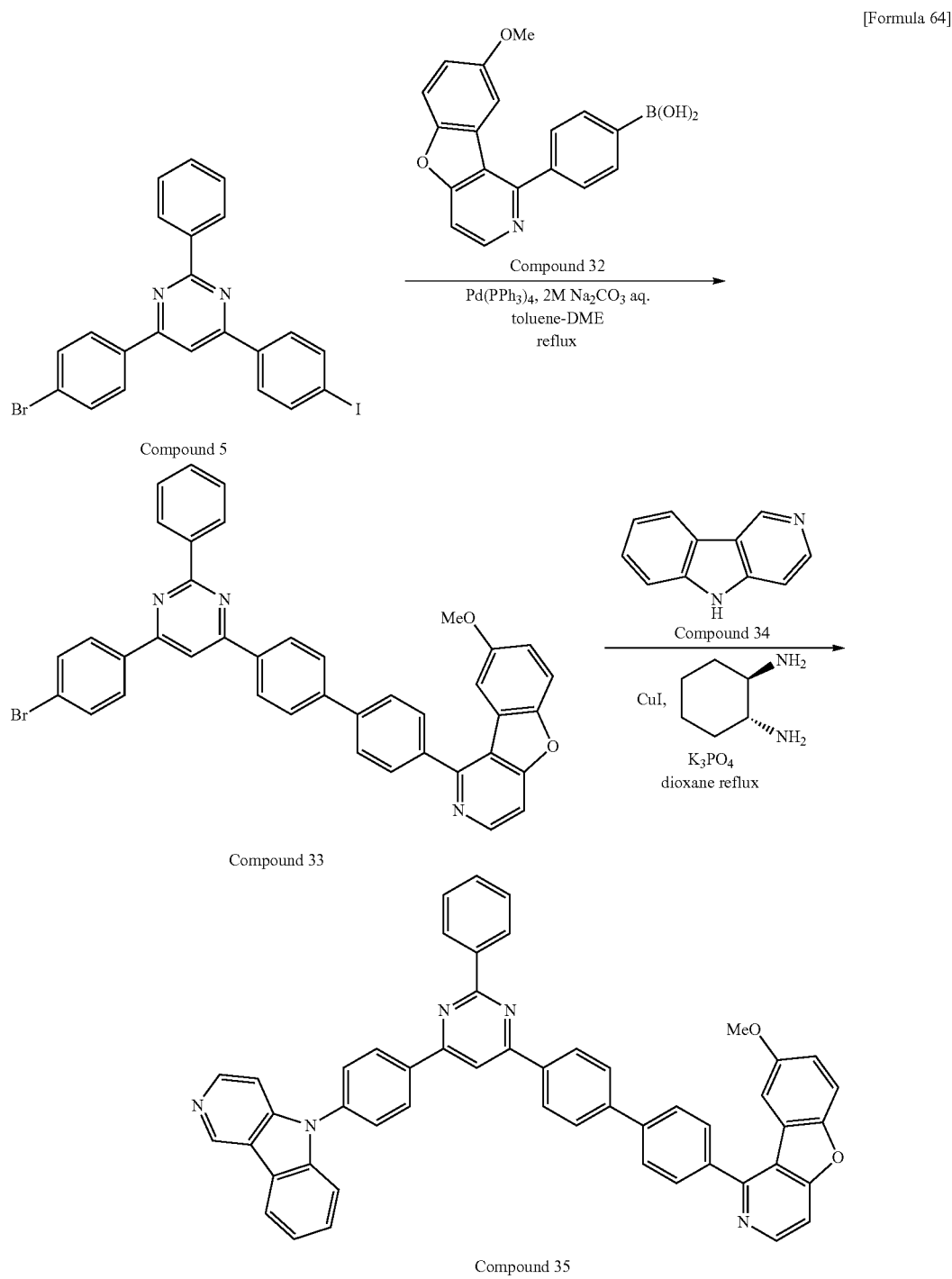

[Formula 64]

(6-1) Synthesis of Compound 33

A compound 33 (4.6 g, a yield of 72%) was obtained as a white solid according to the same method except for using the compound 32 (3.1 g, 9.7 mmol) in place of the compound 6 in (1-2) of synthesis of the compound 9.

(6-2) Synthesis of Compound 35

A compound 35 (3.2 g, a yield of 62%) was obtained as a white solid according to the same method except for using the compound 33 (4.6 g, 7.0 mmol) in place of the compound 7 and using the compound 34 (1.4 g, 8.4 mmol) in place of the compound 8 in (1-3) of synthesis of the compound 9. By FD-MS analysis, the obtained compound was identified to be the compound 35.

Synthesis Example 7 (Synthesis of Compound 38)

A synthesis scheme of a compound 38 is shown below.

(7-2) Synthesis of Compound 38

A compound 38 (3.5 g, a yield of 82%) was obtained as a white solid according to the same method except for using

[Formula 65]

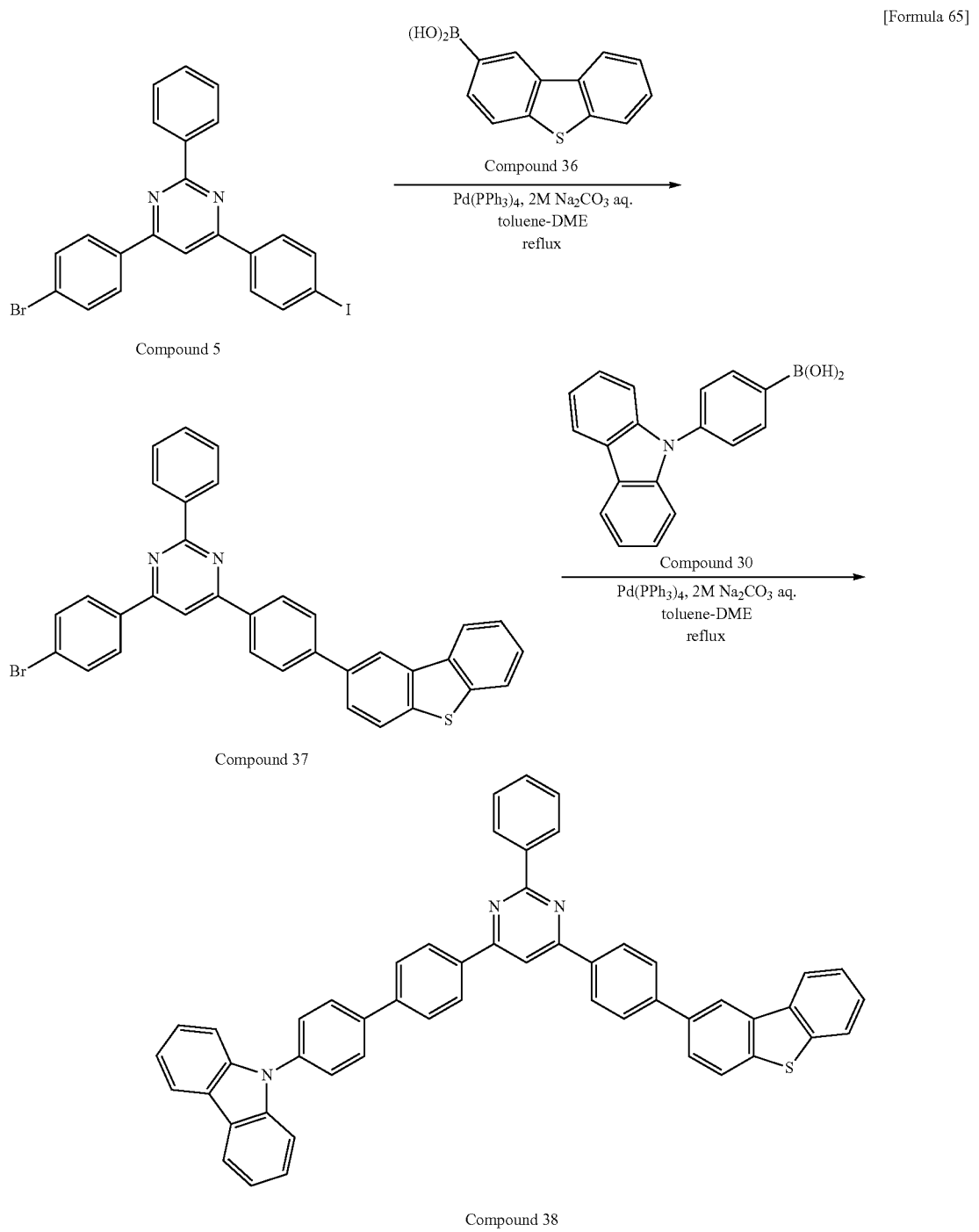

(7-1) Synthesis of Compound 37

A compound 37 (3.3 g, a yield of 75%) was obtained as a white solid according to the same method except for using the compound 36 (1.8 g, 7.8 mmol) in place of the compound 6 in (1-2) of synthesis of the compound 9.

the compound 37 (3.3 g, 5.8 mmol) in place of the compound 5 and using the compound 30 (1.4 g, 5.8 mmol) in place of the compound 6 in (1-2) of synthesis of the compound 9. By FD-MS (Field Desorption Mass Spectrometry) analysis, the obtained compound was identified to be the compound 38.

Synthesis Example 8 (Synthesis of Compound 42)
A synthesis scheme of a compound 42 is shown below.

the compound 11 (25 g, 102 mmol) in place of the compound 2 in (1-1) of synthesis of the compound 9.

[Formula 66]

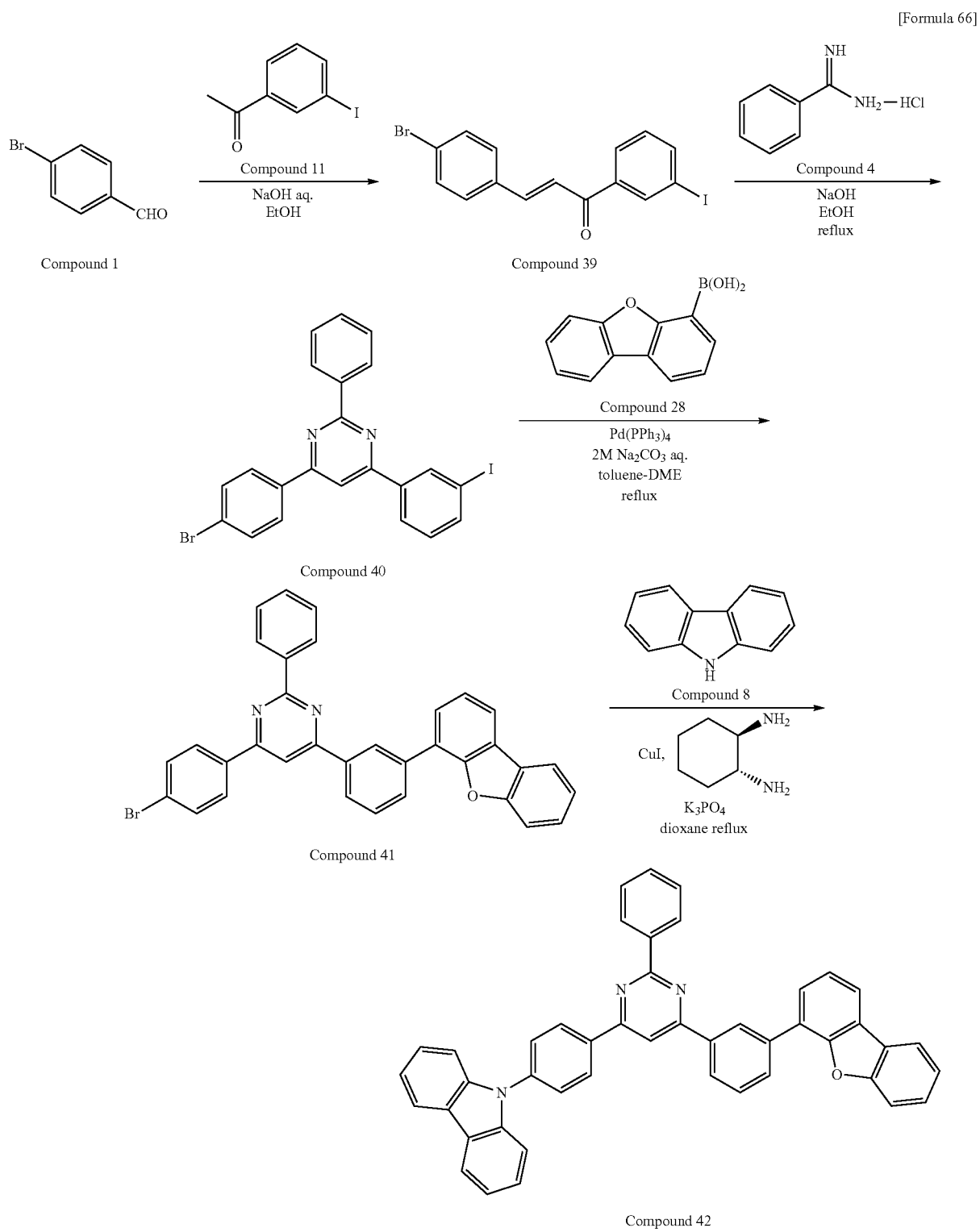

(8-1) Synthesis of Compound 40

A compound 40 (12 g, a yield of 28%) was obtained as a white solid according to the same method except for using (8-2) Synthesis of Compound 41

A compound 41 (5.5 g, a yield of 85%) was obtained as a yellow solid according to the same method except for using the compound 40 (6.0 g, 12 mmol) in place of the compound 5 and using the compound 28 (2.4 g, 11 mmol) in place of the compound 6 in (1-2) of synthesis of the compound 9.

(8-3) Synthesis of Compound 42

A compound 42 (1.8 g, a yield of 21%) was obtained as a white solid according to the same method except for using the compound 41 (5.5 g, 10 mmol) in place of the compound 7 in (1-3) of synthesis of the compound 9. By FD-MS analysis, the obtained compound was identified to be the compound 42.

Synthesis Example 9 (Synthesis of Compound 47)

A synthesis scheme of a compound 47 is shown below.

[Formula 67]

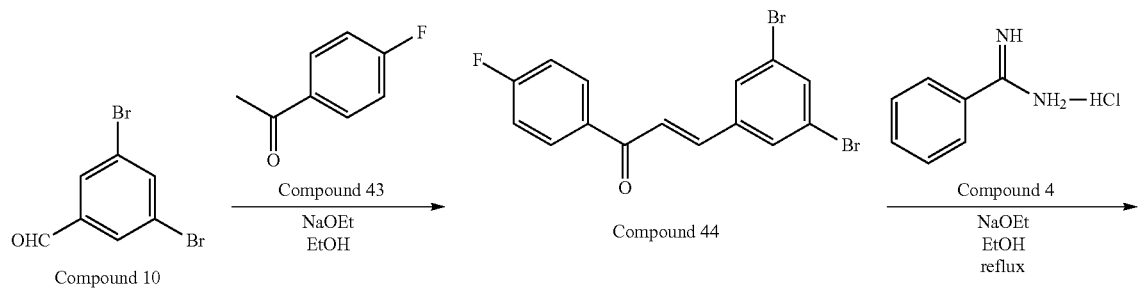

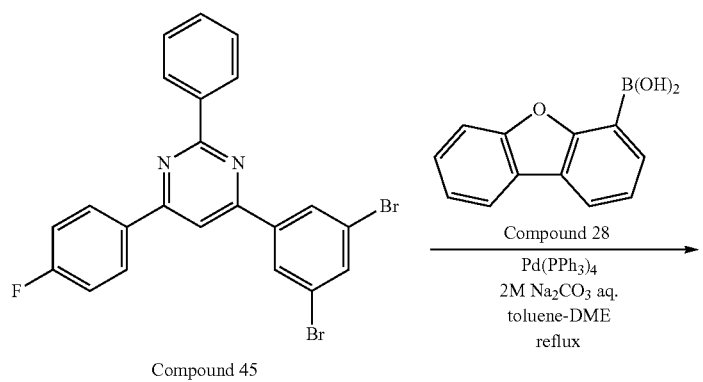

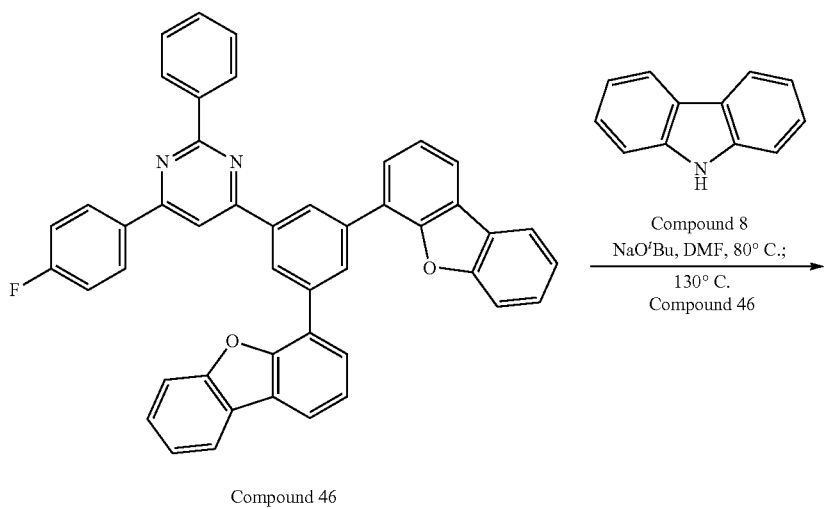

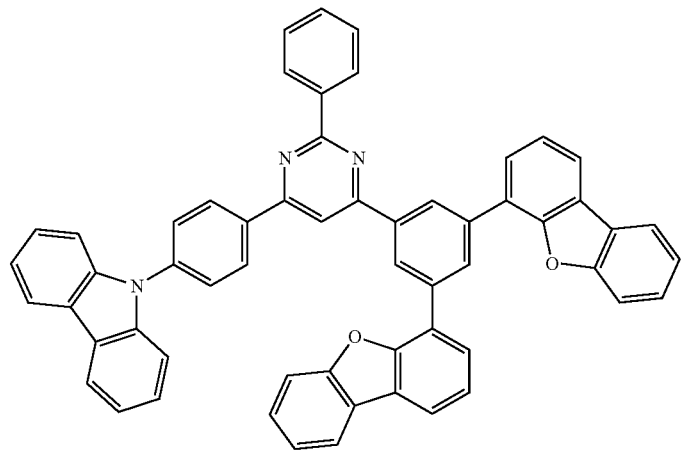

Compound 47

(9-1) Synthesis of Compound 45

A compound 45 (7.7 g, a yield of 28%) was obtained as a light-yellow solid according to the same method except for using the compound 43 (7.9 g, 57 mmol) in place of the compound 11 in (2-1) of synthesis of the compound 15.

(9-2) Synthesis of Compound 46

A compound 46 (9.1 g, a yield of 87%) was obtained as a light-yellow solid according to the same method except for using the compound 45 (7.7 g, 16 mmol) in place of the compound 5 and using the compound 28 (7.1 g, 33 mmol) in place of the compound 6 in (1-2) of synthesis of the compound 9.

(9-3) Synthesis of Compound 47

Under argon atmosphere, sodium t-butoxide (0.98 g, 10 mmol) was added to a solution of the compound 8 (1.3 g, 7.5 mmol) in anhydrous N,N-dimethylformamide solution and was stirred for one hour at 80 degrees C. The compound 46 (4.5 g, 6.8 mmol) was further added thereto. The obtained mixture was stirred for three hours at 130 degrees C. After the reaction, the reaction solution was cooled down to the room temperature, added with methanol and separated by filtration. The obtained crude substance was washed with toluene and dried under reduced pressure to obtain a compound 47 (2.8 g, a yield of 50%) as a white solid. By FD-MS analysis, the obtained compound was identified to be the compound 47.

Synthesis Example 10 (Synthesis of Compound 48)

A synthesis scheme of a compound 48 is shown below.

[Formula 68]

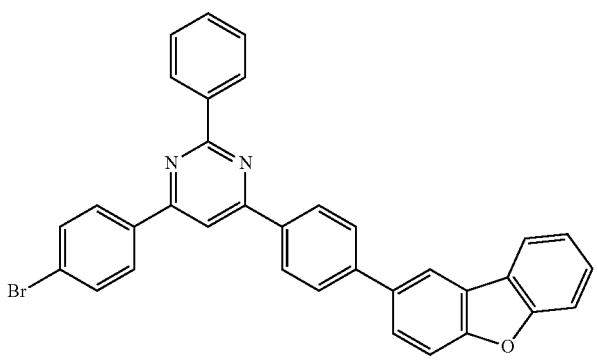

Compound 7

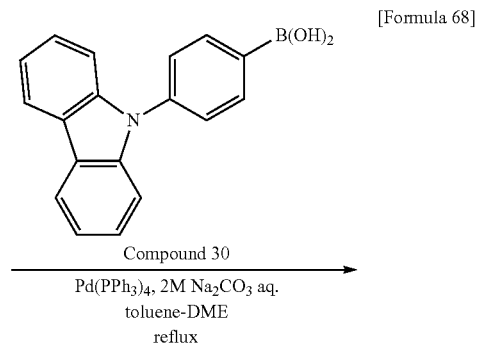

Compound 30

Pd(PPh$_3$)$_4$, 2M Na$_2$CO$_3$ aq.
toluene-DME
reflux

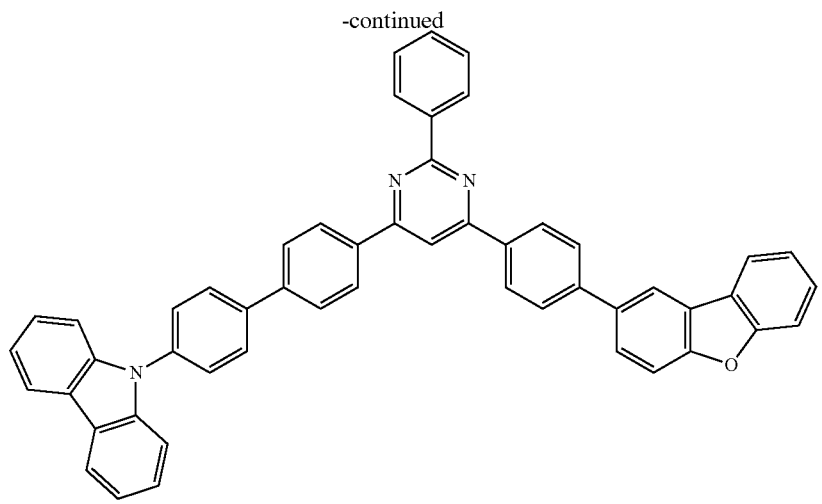

Compound 48

(10-1) Synthesis of Compound 48

A compound 48 (2.2 g, a yield of 63%) was obtained as a white solid according to the same method except for using the compound 7 (2.7 g, 4.9 mmol) in place of the compound 5 and using the compound 30 (1.7 g, 5.9 mmol) in place of the compound 6 in (1-2) of synthesis of the compound 9. By FD-MS analysis, the obtained compound was identified to be the compound 48.

Synthesis Example 11 (Synthesis of Compound 50)

A synthesis scheme of a compound 50 is shown below

[Formula 69]

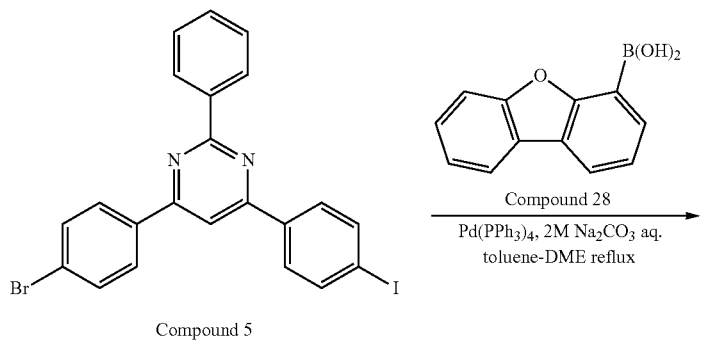

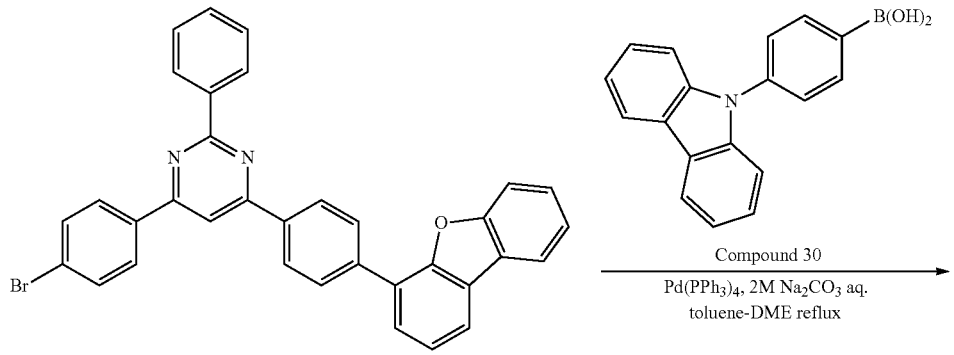

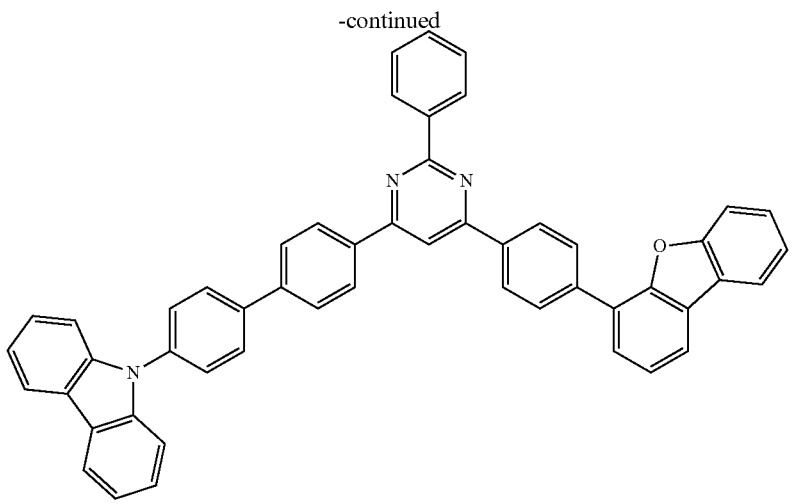

Compound 50

(11-1) Synthesis of Compound 49

A compound 49 (5.4 g, a yield of 52%) was obtained as a white solid according to the same method except for using the compound 28 (4.0 g, 19 mmol) in place of the compound 6 in (1-2) of synthesis of the compound 9.

(11-2) Synthesis of Compound 50

A compound 50 (4.2 g, a yield of 89%) was obtained as a white solid according to the same method except for using the compound 49 (3.7 g, 6.6 mmol) in place of the compound 5 and using the compound 30 (2.4 g, 7.9 mmol) in place of the compound 6 in (1-2) of synthesis of the compound 9. By FD-MS analysis, the obtained compound was identified to be the compound 50.

Manufacturing of Organic EL Device

Example 1

A glass substrate (size: 25 mm×75 mm×0.7 mm thick, manufactured by Geomatec Co., Ltd.) having an ITO transparent electrode (anode) was ultrasonic-cleaned in isopropyl alcohol for five minutes, and then UV/ozone-cleaned for 30 minutes.

After the glass substrate having the transparent electrode line was cleaned, the glass substrate was mounted on a substrate holder of a vacuum evaporation apparatus. Initially, a compound HI-1 was deposited on a surface of the glass substrate where the transparent electrode line was provided in a manner to cover the transparent electrode, thereby forming a 5-nm thick HI-1 film of the compound HI-1. The HI-1 film serves as a hole injecting layer.

After the film formation of the HI-1 film, a compound HT-1 was deposited on the HI-1 film to form an 80-nm thick HT-1 film. The HT-1 film serves as a hole transporting layer.

After the film formation of the HT-1 film, a compound HT-2 was deposited on the HT-1 film to form a 15-nm thick HT-2 film. The HT-2 film serves as a second hole transporting layer.

Then, a compound BH-1 (host material) and a compound BD-1 (dopant material) (mass ratio of BH-1 to BD-1 was 20:1) were co-deposited on the HT-2 film to form a 25-nm thick emitting layer.

The compound 9 was deposited on this emitting layer to form a 20-nm thick blocking layer.

Further, ET-1 (electron transporting material) was deposited on the blocking layer to form a 5-nm thick electron injecting layer.

LiF was deposited on the electron injecting layer to form a 1-nm thick LiF film.

Metal (Al) was deposited on the LiF film to form an 80-nm thick metal cathode, thereby manufacturing an organic EL device of Example 1.

Structures of compounds used in Example 1 are shown below.

[Formula 70]

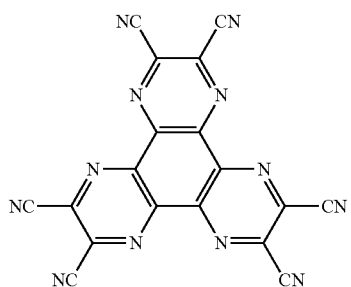

HI-1

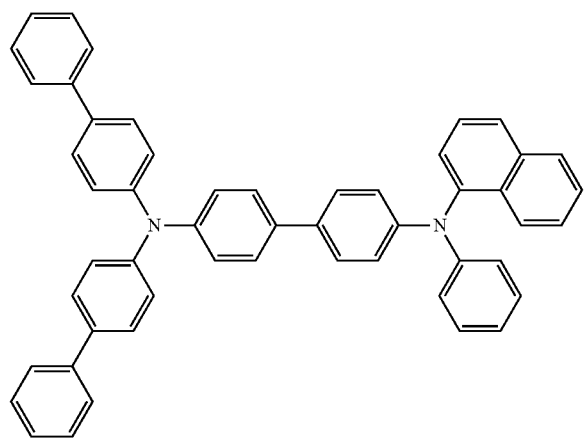

HT-1

HT-2

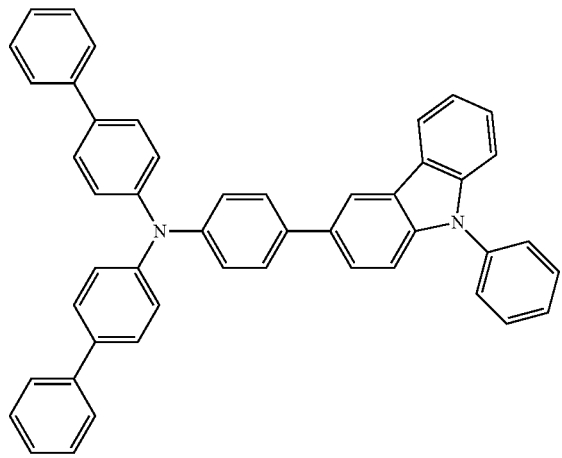

BH-1

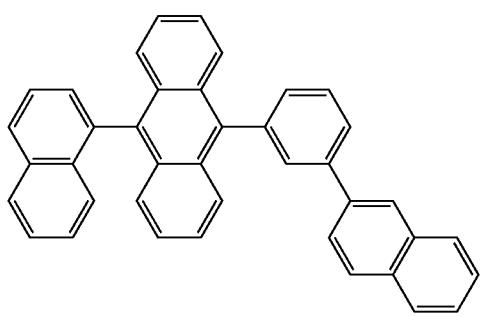

BD-1

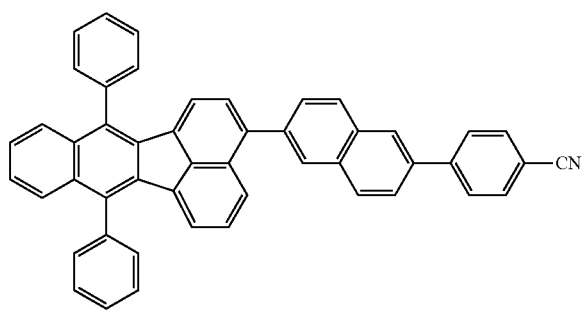

ET-1

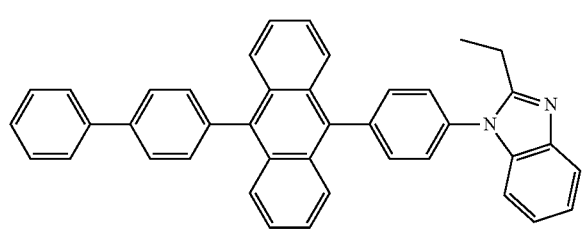

Examples 2 to 4 and Comparative 1

In Examples 2 to 4 and Comparative 1, organic EL devices were manufactured in the same manner as in the Example 1 except for using materials shown in Table 1. A structure of BCP used in Example 1 is shown below.

[Formula 71]

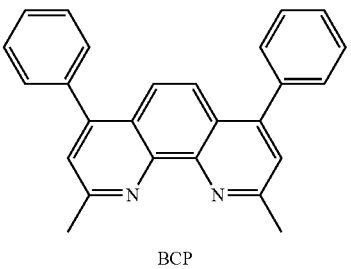

BCP

Device Evaluation

The manufactured organic EL devices were evaluated as below. The results are shown in Table 1.

Initial Performance

A voltage was applied on the organic EL devices such that a current density was 10 mA/cm², where a value (V) of the voltage was measured. EL spectra were measured with a spectral radiance meter (CS-1000, manufactured by Konica Minolta Inc.). Chromaticity $CIE_x$, $CIE_y$, current efficiency L/J (cd/A), and external quantum efficiency EQE (%) were calculated from the obtained spectral-radiance spectra.

Measurement of TTF Ratio

A ratio of luminous intensities derived from TTF relative to the total emission can be increased by satisfying a predetermined relationship in triplet energy among the host material, the dopant material and the blocking-layer material, thereby enabling a fluorescent device to exhibit a high efficiency unattainable by a typically known fluorescent device.

The ratio of luminous intensities derived from TTF is measurable by a transitional EL method. The transitional EL method is for measuring attenuation behavior (transitional property) of EL emission after a DC voltage applied on the device is removed. EL luminous intensities are classified into a luminescence component from singlet excitons generated in the first recombination and a luminescence component from singlet excitons generated through the TTF phenomenon. Since lifetime of the singlet excitons is very short at a nano-second order, EL emission is rapidly attenuated after the removal of the DC voltage.

On the other hand, since the TTF phenomenon provides emission from singlet excitons generated through long-life triplet excitons, EL emission is gradually attenuated. Thus, since there is a large difference in time between emission from the singlet excitons and emission from the triplet excitons, a luminous intensity derived from TTF is obtainable. Specifically, the luminous intensity can be determined by the following method.

Figure 13:
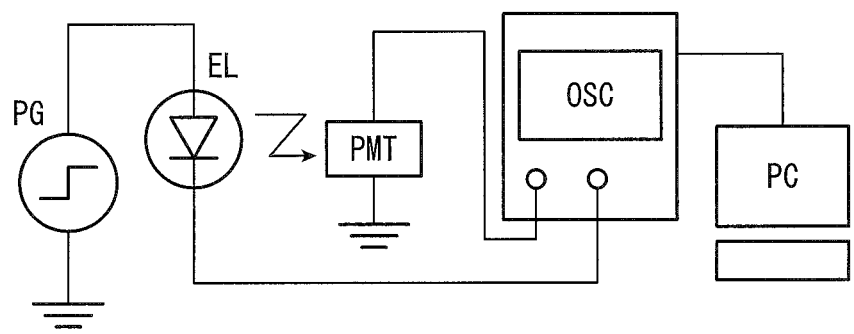
FIG. 13 shows a measurement system of a transitional EL waveform.

Transitional EL waveform is measured as follows (see FIG. 13). Pulse voltage waveform outputted from a voltage pulse generator (PG) is applied on an EL device. The applied voltage waveform is loaded in an oscilloscope (OSC). When pulse voltage is applied on the EL device, the EL device generates pulse emission. This emission is loaded in the oscilloscope (OSC) through a photomultiplier (PMT). The voltage waveform and the pulse emission are synchronized and loaded in a personal computer (PC).

The ratio of luminous intensity derived from TTF is determined as follows based on analysis of the transitional EL waveform.

The attenuation behavior of the luminous intensity based on the TTF phenomenon is modeled by solving a rate equation of the attenuation behavior of the triplet excitons.

Time attenuation of a triplet exciton density $n_T$ within the emitting layer can be represented by the following rate equation using an attenuation speed α due to the lifetime of the triplet excitons and an attenuation speed γ caused by collision of the triplet excitons.

$$\frac{dn_T}{dt} = -\alpha \cdot n_T - \gamma \cdot n_T^2 \quad \text{[Numerical Formula 1]}$$

When the above differential equation is approximately solved, the following formula is obtained. Herein, $I_{TTF}$ represents a luminous intensity derived from TTF. A is a constant. Thus, when the transitional EL emission is based on TTF, inverse square roots of the luminous intensities are shown by a linear approximation. The measured transitional EL waveform data is fit in the following approximate equation to obtain the constant A. Herein, a luminous intensity $1/A^2$ at the time t=0 when the DC voltage is removed is defined as the ratio of luminous intensity derived from TTF.

$$\frac{1}{\sqrt{I_{TTF}}} \propto A + \gamma \cdot t \quad \text{[Numerical Formula 2]}$$

Figure 14A:
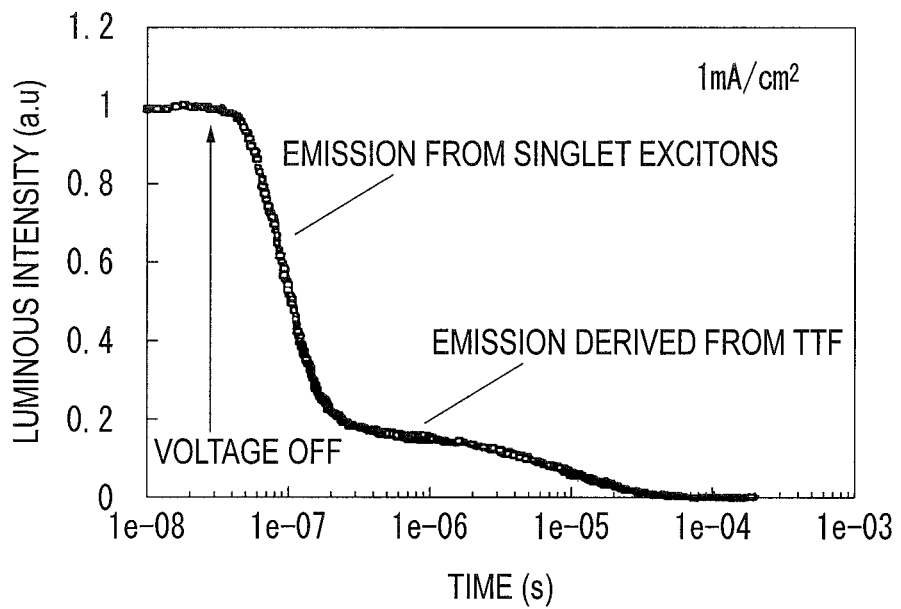
FIG. 14A shows a measurement method of a ratio of luminous intensities derived from TTF and is a graph showing time-varying luminous intensities of the organic EL device.
Figure 14B:
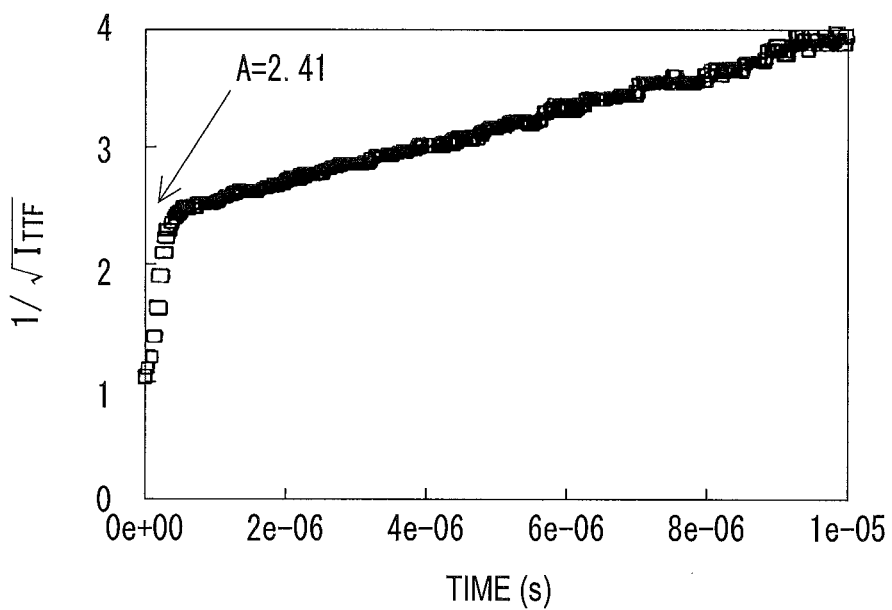
FIG. 14B shows a measurement method of a ratio of luminous intensities derived from TTF and is a graph showing time-varying inverse square root of luminous intensities.

A graph of FIG. 14A shows a measurement example where a predetermined DC voltage is applied on the organic EL device and then the DC voltage is removed and shows time-varying luminous intensities of the EL device. The DC voltage was removed at the time of about $3 \times 10^{-8}$ seconds in the graph of FIG. 14A. In the graph, the luminous intensity when the voltage is removed is defined as 1. After rapid attenuation before the elapse of about $2 \times 10^{-7}$ seconds after the voltage removal, a gradual attenuation component appears. In the graph of FIG. 14B, the voltage removal time is a starting point and the inverse square root of luminous intensity before the elapse of $10^{-5}$ seconds after voltage removal is plotted. The graph is found to be linearly well approximated. A value at an intersection A of the ordinate axis and the linear line extended to the starting point is 2.41. Accordingly, the ratio of luminous intensity derived from the TTF obtained from the transitional EL waveform is $1/2.41^2 = 0.17$, which means that 17% of the total luminous intensities was derived from TTF.

The luminous intensity is preferably fitted in a linear line by the method of least squares. In this case, the luminous intensity before the elapse of $10^{-5}$ seconds is preferably fitted.

Voltage pulse waveform (pulse width: 500 micro second, frequency: 20 Hz, voltage: equivalent to 0.1 to 100 mA/cm²) output from a pulse generator 8114A (manufactured by Agilent Technologies) was applied. EL emission was input in a photomultiplier R928 (manufactured by HAMAMATSU PHOTONICS K.K.). The pulse voltage waveform and the EL emission were synchronized and loaded in an oscilloscope 2440 (manufactured by Tektronix) to obtain a transitional EL waveform. The transitional EL waveform was analyzed to determine a TTF ratio.

The organic EL device in Example was electrically conducted at the room temperature. The pulse voltage was removed at the time of about $3 \times 10^{-8}$ seconds.

The TTF ratio was calculated from the graph in which the voltage removal time was a starting point and the inverse square root of luminous intensity before the elapse of $1.5 \times 10^{-5}$ seconds after voltage removal was plotted. In other Examples and Comparative, the measurement was conducted in the same manner The results are shown in Table 1.

TABLE 1

| | Blocking Layer Material | Current Density (mA/cm²) | Voltage (V) | Chromaticity CIE | | L/J (cd/A) | EQE (%) | TTF Ratio (%) |
|---|---|---|---|---|---|---|---|---|
| | | | | x | y | | | |
| Example 1 | Compound 9 | 10 | 3.70 | 0.143 | 0.127 | 10.68 | 9.76 | 34 |
| Example 2 | Compound 15 | 10 | 3.89 | 0.142 | 0.126 | 8.91 | 8.22 | 31 |
| Example 3 | Compound 42 | 10 | 3.59 | 0.142 | 0.141 | 11.09 | 9.47 | 30 |
| Example 4 | Compound 48 | 10 | 3.63 | 0.142 | 0.133 | 9.29 | 8.24 | 29 |
| Comp. 1 | BCP | 10 | 4.30 | 0.144 | 0.128 | 8.43 | 7.65 | 25 |

The organic EL devices of Examples 1 to 4, in which the aromatic heterocyclic compound of the invention was used in the blocking layer, exhibited a higher TTF ratio, a higher luminous efficiency and a higher external quantum efficiency than the organic EL device of Comparative 1. In addition, the drive voltage was lower than that in Comparative 1.

The invention claimed is:

1. An aromatic heterocyclic derivative of formula (1):

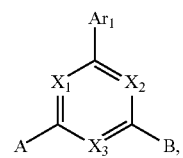

(1)

wherein:
X₁ is a nitrogen atom;
X₂ and X₃ are each a nitrogen atom or CR₁;
R₁ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms;

A is represented by formula (2):

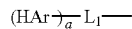
(2)

wherein:
HAr is represented by formula (3);
a is an integer of 1 to 5;
when a is 1, $L_1$ is a single bond or a divalent linking group;
when a is in a range of 2 to 5, $L_1$ is a trivalent to hexavalent linking group and HAr is the same or different;
the linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups; and
the groups to be mutually bonded are mutually the same or different,

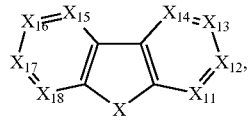
(3)

wherein:
$X_{11}$ to $X_{18}$ each independently represent a nitrogen atom, $CR_{13}$ or a carbon atom to be bonded to $L_1$ by a single bond;
$Y_1$ represents an oxygen atom, a sulfur atom, or $SiR_{11}R_{12}$, with a proviso that the atom bonded to $L_1$ is one of the carbon atoms at $X_{11}$ to $X_{18}$,
$R_{11}$ and $R_{12}$ represent the same as $R_1$ of formula (1);
$R_{11}$ and $R_{12}$ are the same or different;
$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms;
a plurality of $R_{13}$ are the same or different; adjacent ones of $R_{13}$ are optionally bonded to each other to form a ring; and B is represented by formula (4):

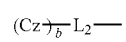
(4)

wherein:
Cz is represented by a formula (5) or (6);
b is an integer of 1 to 5;
when b is 1 and Cz is represented by formula (5), $L_2$ is a single bond or a divalent linking group;
when b is 1 and Cz is represented by formula (6), $L_2$ is a divalent linking group;
when b is in a range of 2 to 5, $L_2$ is a trivalent to hexavalent linking group and Cz is the same or different;
the linking group is a substituted or unsubstituted aryl group having 6 to 30 ring carbon atoms, a substituted or unsubstituted heterocyclic group having 5 to 30 ring atoms, or a divalent or trivalent residue derived from any one of groups provided by bonding two or three of the above groups; and
the groups to be mutually bonded are mutually the same or different,

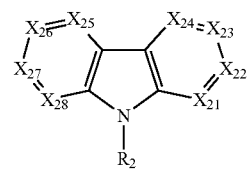
(5)

wherein:
$R_2$ represents the same as $R_1$ of formula (1);
one of $X_{21}$ to $X_{28}$ is a carbon atom to be bonded to $L_2$ by a single bond and each of the rest of $X_{21}$ to $X_{28}$ is a nitrogen atom or $CR_{21}$; and
$R_{21}$ represents the same as $R_{13}$ of the formula (3), with a proviso that, when at least one of $X_{21}$ and $X_{28}$ is $CR_{21}$, $R_2$ is optionally bonded to one of $R_{21}$ to form a ring, or alternatively, N is optionally directly bonded to one of $R_{21}$ to form a ring,

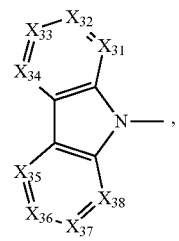
(6)

wherein:
$X_{31}$ to $X_{38}$ each are a nitrogen atom or $CR_{31}$;
$R_{31}$ represents the same as $R_{13}$ of formula (3); and
a nitrogen atom at a position 9 is bonded to $L_2$ by a single bond; and
$Ar_1$ represents a substituted or unsubstituted aryl group having 6 to 30 ring carbon atoms, wherein the substituent of $Ar_1$ is at least one selected from the group consisting of an aryl group, alkyl group, alkenyl group, alkynyl group, alkylsilyl group, arylsilyl group, alkoxy group, halogenated alkoxy group, aralkyl group, aryloxy group, halogen atom, cyano group, hydroxyl group, nitro group, and carboxy group.

2. The aromatic heterocyclic derivative according to claim 1, wherein, in formula (3), one of $X_{13}$ and $X_{16}$ or one of $X_{11}$ and $X_{18}$ is a carbon atom to be bonded to $L_1$ by a single bond.

3. The aromatic heterocyclic derivative according to claim 1, wherein, in formula (2), a is an integer of 1 to 3.

4. The aromatic heterocyclic derivative according to claim 1, wherein, in formula (2), a is 1 or 2.

5. The aromatic heterocyclic derivative according to claim 1, wherein, in formula (2), a is 1 and $L_1$ is a linking group, and the linking group is a divalent residue of a substituted or unsubstituted aryl group having 6 to 30 ring carbon atoms or a divalent residue of a substituted or unsubstituted heterocyclic group having 5 to 30 ring atoms.

6. The aromatic heterocyclic derivative according to claim 1, wherein, in formula (2), a is 2 and $L_1$ is a linking group, and the linking group is a trivalent residue of a substituted or unsubstituted aryl group having 6 to 30 ring carbon atoms or a trivalent residue of a substituted or unsubstituted heterocyclic group having 5 to 30 ring atoms.

7. The aromatic heterocyclic derivative according to claim 1, wherein, in formula (4), b is an integer of 1 to 3.

8. The aromatic heterocyclic derivative according to claim 1, wherein, in formula (4), b is 1 or 2.

9. The aromatic heterocyclic derivative according to claim 1, wherein, in formula (4), b is 1 and $L_2$ is a linking group, and the linking group is a divalent residue of a substituted or unsubstituted aryl group having 6 to 30 ring carbon atoms or a divalent residue of a substituted or unsubstituted heterocyclic group having 5 to 30 ring atoms.

10. The aromatic heterocyclic derivative according to claim 1, wherein, in formula (4), b is 2 and $L_2$ is a trivalent residue of a substituted or unsubstituted aryl group having 6 to 30 ring carbon atoms or a trivalent residue of a substituted or unsubstituted heterocyclic group having 5 to 30 ring atoms.

11. The aromatic heterocyclic derivative according to claim 1, wherein, in formula (3), $Y_1$ is an oxygen atom or a sulfur atom.

12. The aromatic heterocyclic derivative according to claim 1, wherein, in formula (3), $Y_1$ is an oxygen atom or a sulfur atom, one of $X_{11}$ to $X_{18}$ is a carbon atom to be bonded to $L_1$ by a single bond, and the rest of $X_{11}$ to $X_{18}$ are $CR_{13}$.

13. The aromatic heterocyclic derivative according to claim 1, wherein, in formula (1), two or three of $X_1$ to $X_3$ are nitrogen atoms.

14. The aromatic heterocyclic derivative according to claim 1, wherein at least one of $L_1$ in formula (2) and $L_2$ in formula (4) is a divalent or trivalent residue derived from one of benzene, biphenyl, terphenyl, naphthalene and phenanthrene.

15. A material for an organic electroluminescence device comprising: the aromatic heterocyclic derivative according to claim 1.

16. The material for an organic electroluminescence device according to claim 15, wherein the material is used for a blocking layer.

17. An organic electroluminescence device comprising:
an anode;
an emitting layer;
an electron transporting zone; and
a cathode in this sequential order,
wherein the electron transporting zone comprises the aromatic heterocyclic derivative according to claim 1.

18. The organic electroluminescence device according to claim 17, wherein the electron transporting zone comprises a blocking layer, and the blocking layer comprises the aromatic heterocyclic derivative.

19. The organic electroluminescence device according to claim 18, wherein at least one of an electron injecting layer and an electron transporting layer is provided between the blocking layer and the cathode and comprises at least one of an electron-donating dopant material and an organic metal complex.

20. The organic electroluminescence device according to claim 19, wherein the electron-donating dopant material is at least one selected from the group consisting of alkali metal, alkaline earth metal, rare earth metal, oxide of alkali metal, halide of alkali metal, oxide of alkaline earth metal, halide of alkaline earth metal, oxide of rare earth metal, and halide of rare earth metal, and
wherein the organic metal complex is at least one selected from an organic metal complex including an alkali metal, an organic metal complex including an alkaline earth metal, and an organic metal complex including rare earth metal.

21. The organic electroluminescence device according to claim 17, wherein the emitting layer is adjacent to the electron transporting zone.

22. The organic electroluminescence device according to claim 17, wherein the emitting layer comprises an anthracene derivative represented by formula (20D):

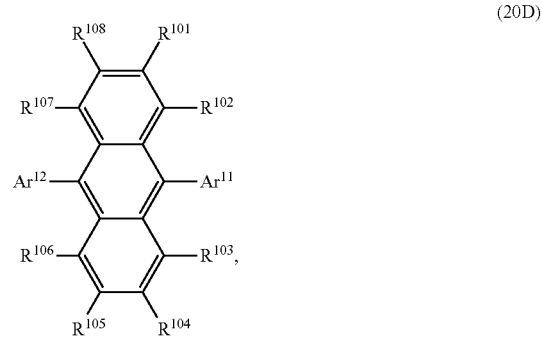

(20D)

wherein:
$Ar^{11}$ and $Ar^{12}$ each independently represent a substituted or unsubstituted monocyclic group having 5 to 30 ring atoms, a substituted or unsubstituted fused ring group having 10 to 30 ring atoms, or a group provided by combining the monocyclic group and the fused ring group; and
$R^{101}$ to $R^{108}$ each independently represent a hydrogen atom, a halogen atom, a cyano group, a substituted or unsubstituted monocyclic group having 5 to 30 ring atoms, a substituted or unsubstituted fused ring group having 10 to 30 ring atoms, a group provided by combining the monocyclic group and the fused ring group, a substituted or unsubstituted alkyl group having 1 to 30 carbon atoms, a substituted or unsubstituted cycloalkyl group having 3 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, or a substituted or unsubstituted silyl group.

23. The organic electroluminescence device according to claim 17, wherein the emitting layer comprises a dopant material that exhibits fluorescent emission having a main peak wavelength of 500 nm or less.

* * * * *

UNITED STATES PATENT AND TRADEMARK OFFICE
CERTIFICATE OF CORRECTION

PATENT NO. : 9,847,501 B2
APPLICATION NO. : 14/358043
DATED : December 19, 2017
INVENTOR(S) : Sayaka Mizutani et al.

It is certified that error appears in the above-identified patent and that said Letters Patent is hereby corrected as shown below:

In the Claims

Column 290, Lines 40-50, formula (1), " 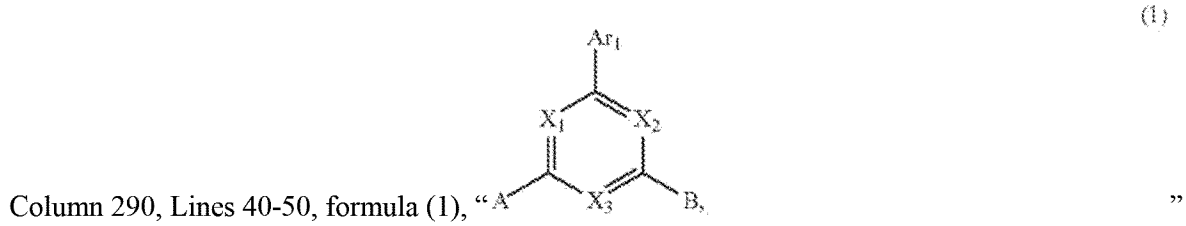 "

should read -- 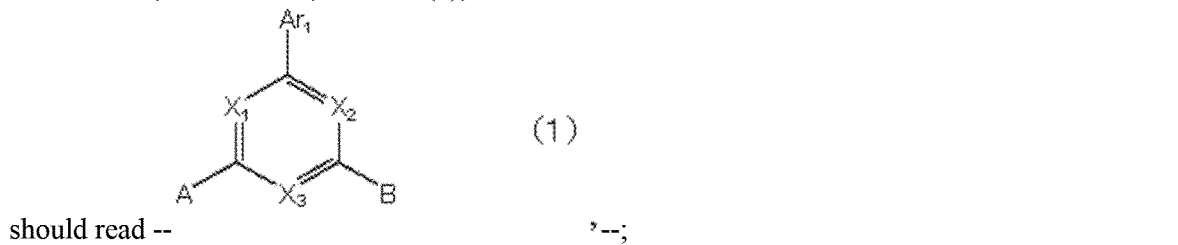 --;

Column 291, Lines 30-35, formula (3),

" 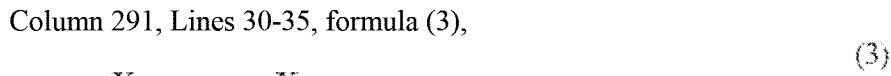 " should read

-- 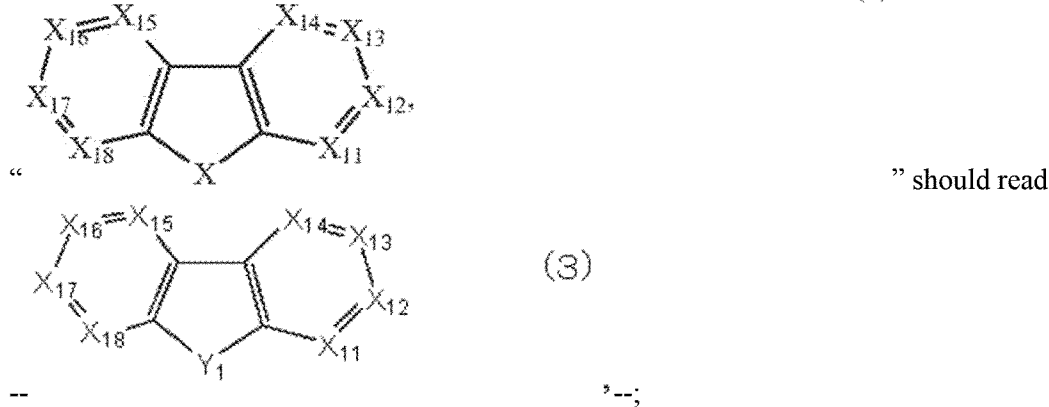 --;

Signed and Sealed this
Sixteenth Day of April, 2019

Andrei Iancu
*Director of the United States Patent and Trademark Office*

CERTIFICATE OF CORRECTION (continued)
U.S. Pat. No. 9,847,501 B2

Column 292, Line 45, formula (6), " 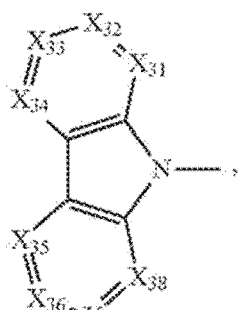 "

should read -- 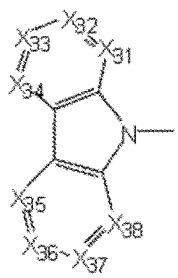 --; and

Column 294, Line 35, formula (20D), " 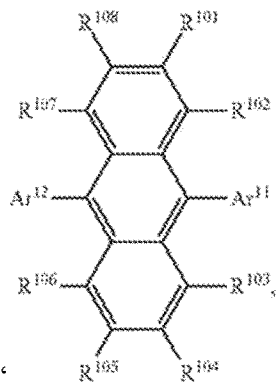 " should read -- 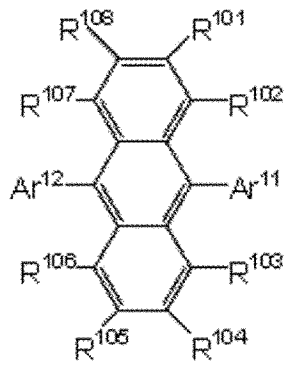 --.